United States Patent
Theunissen et al.

(10) Patent No.: US 12,123,019 B2
(45) Date of Patent: Oct. 22, 2024

(54) USES OF KINASE INHIBITORS FOR INDUCING AND MAINTAINING PLURIPOTENCY

(71) Applicants: Whitehead Institute for Biomedical Research, Cambridge, MA (US); Dana-Farber Cancer Institute, Inc., Boston, MA (US)

(72) Inventors: Thorold W Theunissen, Belmont, MA (US); Nathanael S. Gray, Boston, MA (US); Rudolf Jaenisch, Brookline, MA (US)

(73) Assignees: Whitehead Institute for Biomedical Research, Cambridge, MA (US); Dana-Farber Cancer Institute, Inc., Boston, MA (US)

(*) Notice: Subject to any disclaimer, the term of this patent is extended or adjusted under 35 U.S.C. 154(b) by 813 days.

(21) Appl. No.: 17/071,627

(22) Filed: Oct. 15, 2020

(65) Prior Publication Data
US 2021/0230538 A1 Jul. 29, 2021

Related U.S. Application Data

(63) Continuation of application No. 15/318,533, filed as application No. PCT/US2015/036692 on Jun. 19, 2015, now abandoned.

(60) Provisional application No. 62/045,337, filed on Sep. 3, 2014, provisional application No. 62/014,674, filed on Jun. 19, 2014.

(51) Int. Cl.
C12N 5/0735 (2010.01)
C12N 5/074 (2010.01)

(52) U.S. Cl.
CPC ......... *C12N 5/0606* (2013.01); *C12N 5/0696* (2013.01); *C12N 2501/11* (2013.01); *C12N 2501/115* (2013.01); *C12N 2501/165* (2013.01); *C12N 2501/727* (2013.01); *C12N 2501/999* (2013.01)

(58) Field of Classification Search
CPC .......................... C12N 5/0606; C12N 5/0696; C12N 2501/11; C12N 2501/115; C12N 2501/165; C12N 2501/727; C12N 2501/999
See application file for complete search history.

(56) References Cited

U.S. PATENT DOCUMENTS

| | | |
|---|---|---|
| 6,057,117 A | 5/2000 | Harrison et al. |
| 6,153,618 A | 11/2000 | Schultz et al. |
| 6,417,185 B1 | 7/2002 | Goff et al. |
| 6,489,344 B1 | 12/2002 | Nuss et al. |
| 6,608,063 B2 | 8/2003 | Nuss et al. |
| 6,784,336 B2 | 8/2004 | Eggan et al. |
| 7,482,367 B2 | 1/2009 | Aikawa et al. |
| 7,491,829 B2 | 2/2009 | Laird et al. |
| 8,637,311 B2 | 1/2014 | Mandalam et al. |
| 8,709,718 B1 | 4/2014 | Thomas et al. |
| 8,748,179 B2 | 6/2014 | Egusa et al. |
| 2001/0034051 A1 | 10/2001 | Nuss et al. |
| 2002/0156087 A1 | 10/2002 | Nuss et al. |
| 2004/0077707 A1 | 4/2004 | Desai et al. |
| 2004/0092535 A1 | 5/2004 | Barsanti et al. |
| 2004/0138273 A1 | 7/2004 | Wagman et al. |
| 2004/0209878 A1 | 10/2004 | Guzi et al. |
| 2005/0026914 A1 | 2/2005 | Buchanan et al. |
| 2005/0054663 A1 | 3/2005 | Bennett et al. |
| 2006/0030000 A1 | 2/2006 | Alitalo et al. |
| 2006/0089369 A1 | 4/2006 | Nuss et al. |
| 2006/0258686 A1 | 11/2006 | Cheresh et al. |
| 2008/0058340 A1 | 3/2008 | Maderna et al. |
| 2008/0255133 A1 | 10/2008 | Vernier et al. |
| 2009/0227608 A1 | 9/2009 | Donato et al. |
| 2009/0246198 A1 | 10/2009 | Dong et al. |
| 2009/0275606 A1 | 11/2009 | Chikkanna et al. |
| 2010/0041137 A1 | 2/2010 | Smith et al. |
| 2010/0249152 A1 | 9/2010 | Schenone et al. |
| 2012/0264218 A1 | 10/2012 | Lin et al. |

(Continued)

FOREIGN PATENT DOCUMENTS

| | | |
|---|---|---|
| WO | WO 2001/066697 A2 | 9/2001 |
| WO | WO 2002/085909 A1 | 10/2002 |

(Continued)

OTHER PUBLICATIONS

Tamm et al. "Differential effects on cell motility, embryonic stem cell self-renewal and senescence by diverse Src kinase family inhibitors." Exp Cell Res.Feb. 15, 2012;318(4):336-49. (Year: 2012).*
Eum et al. "Differential inhibitory effects of two Raf-targeting drugs, sorafenib and PLX4720, on the growth of multidrug-resistant cells." Mol Cell Biochem.Jan. 2013;372(1-2):65-74. (Year: 2013).*
Gilmartin et al. "Distinct concentration-dependent effects of the polo-like kinase 1-specific inhibitor GSK461364A, including differential effect on apoptosis."Cancer Res.Sep. 1, 2009;69(17):6969-77. (Year: 2009).*

(Continued)

*Primary Examiner* — Titilayo Moloye
(74) *Attorney, Agent, or Firm* — Wolf, Greenfield & Sacks, P.C.

(57) ABSTRACT

The present disclosure provides compounds of any one of Formulae (A) to (L). The present disclosure also provides compositions, uses, and methods that include or involve a compound described herein, a serine/threonine-protein kinase B-Raf (BRAF) inhibitor, an epidermal growth factor receptor (EGFR) inhibitor, a vascular endothelial growth factor 1 (VEGFR1) inhibitor, a fibroblast growth factor receptor 1 (FGFR1) inhibitor, or a combination thereof. The compounds, compositions, uses, and methods are useful in changing the pluripotency state of a vertebrate cell to a more naïve state.

7 Claims, 76 Drawing Sheets
Specification includes a Sequence Listing.

(56) References Cited

U.S. PATENT DOCUMENTS

| | | | |
|---|---|---|---|
| 2013/0040949 A1* | 2/2013 | Gray | C07D 401/12 514/300 |
| 2013/0040972 A1 | 2/2013 | Manley | |
| 2013/0059385 A1 | 3/2013 | Li et al. | |
| 2013/0196437 A1 | 8/2013 | Stankewicz et al. | |
| 2013/0273651 A1 | 10/2013 | Gold et al. | |
| 2014/0315301 A1 | 10/2014 | Hanna et al. | |
| 2017/0114323 A1 | 4/2017 | Theunissen et al. | |

FOREIGN PATENT DOCUMENTS

| | | |
|---|---|---|
| WO | WO 2003/011287 A1 | 2/2003 |
| WO | WO 2003/049739 A1 | 6/2003 |
| WO | WO 2003/073843 A2 | 9/2003 |
| WO | WO 2005/039485 A2 | 5/2005 |
| WO | WO 2007/002325 A1 | 1/2007 |
| WO | WO 2007/002433 A1 | 1/2007 |
| WO | WO 2007/096259 A1 | 8/2007 |
| WO | WO 2008/020206 A2 | 2/2008 |
| WO | WO 2008/021389 A2 | 2/2008 |
| WO | WO 2008/024724 A1 | 2/2008 |
| WO | WO 2008/024725 A1 | 2/2008 |
| WO | WO 2008/055236 A2 | 5/2008 |
| WO | WO 2008/067481 A1 | 6/2008 |
| WO | WO 2008/078086 A1 | 7/2008 |
| WO | WO 2008/089459 A1 | 7/2008 |
| WO | WO 2008/101840 A1 | 8/2008 |
| WO | WO 2008/120004 A1 | 10/2008 |
| WO | WO 2008/124085 A2 | 10/2008 |
| WO | WO 2008/125820 A1 | 10/2008 |
| WO | WO 2009/013462 A1 | 1/2009 |
| WO | WO 2009/018233 A1 | 2/2009 |
| WO | WO 2009/018238 A1 | 2/2009 |
| WO | WO 2009/074827 A2 | 6/2009 |
| WO | WO 2009/093008 A1 | 7/2009 |
| WO | WO 2009/093009 A1 | 7/2009 |
| WO | WO 2009/093013 A1 | 7/2009 |
| WO | WO 2009/111277 A1 | 9/2009 |
| WO | WO 2009/111278 A2 | 9/2009 |
| WO | WO 2009/111279 A1 | 9/2009 |
| WO | WO 2009/111280 A1 | 9/2009 |
| WO | WO 2009/129246 A2 | 10/2009 |
| WO | WO 2009/129938 A1 | 10/2009 |
| WO | WO 2009/153554 A1 | 12/2009 |
| WO | WO 2010/003022 A1 | 1/2010 |
| WO | WO 2010/003025 A1 | 1/2010 |
| WO | WO 2010/051933 A2 | 5/2010 |
| WO | WO 2010/051935 A2 | 5/2010 |
| WO | WO 2010/105082 A1 | 9/2010 |
| WO | WO 2010/105110 A1 | 9/2010 |
| WO | WO 2010/124290 A2 | 10/2010 |
| WO | WO 2010/138377 A1 | 12/2010 |
| WO | WO 2010/145197 A1 | 12/2010 |
| WO | WO 2011/025927 A1 | 3/2011 |
| WO | WO 2011/107608 A1 | 9/2011 |
| WO | WO 2012/087965 A2 | 6/2012 |
| WO | WO 2012/146724 A2 | 11/2012 |
| WO | WO 2013/030216 A1 | 3/2013 |
| WO | WO 2013/030365 A1 | 3/2013 |
| WO | WO 2013/030367 A1 | 3/2013 |
| WO | WO 2013/042731 A1 | 3/2013 |
| WO | WO 2013/159103 A1 | 10/2013 |
| WO | WO 2014/011881 A2 | 1/2014 |
| WO | WO 2014/068035 A1 | 5/2014 |

OTHER PUBLICATIONS

Sutherland et al. "LIF-dependent survival of embryonic stem cells is regulated by a novel palmitoylated Gab1 signalling protein." J Cell Sci (2018) 131 (18): j (Year: 2018).*

Su et al. "Treatment with progesterone attenuates proliferation of endometrial polyps (EP) via regulation of expression of miR-320b and its target gene, MCL1."Arch Med Sci 2023;19(6): 1934-1939 (Year: 2023).*

International Search Report and Written Opinion for Application No. PCT/US2015/036692, mailed Nov. 27, 2015.

International Preliminary Report on Patentability for Application No. PCT/US2015/036692, mailed Dec. 29, 2016.

Bao et al, Epigenetic reversion of post-implantation epiblast to pluripotent embryonic stem cells. Nature. Oct. 29, 2009;461(7268):1292-5. doi: 10.1038/nature08534.

Berge et al, Pharmaceutical salts. J Pharm Sci. Jan. 1977;66(1):1-19.

Brambrink et al, Sequential expression of pluripotency markers during direct reprogramming of mouse somatic cells. Cell Stem Cell. Feb. 7, 2008;2(2):151-9. doi:10.1016/j.stem.2008.01.004.

Breitkreutz et al., The Novel, Orally Available Multi-Kinase Inhibitor BAY 73-4506 in Multiple Myeloma. Blood. Nov. 16, 2008;112(11):2766. doi: 10.1182/blood.V112.11.2766.2766.

Brons et al, Derivation of pluripotent epiblast stem cells from mammalian embryos. Nature. Jul. 12, 2007;448(7150):191-5. Epub Jun. 27, 2007.

Chan et al, Induction of a human pluripotent state with distinct regulatory circuitry that resembles preimplantation epiblast. Cell Stem Cell. Dec. 5, 2013;13(6):663-75. doi: 10.1016/j.stem.2013.11.015.

Chen et al, Optimal timing of inner cell mass isolation increases the efficiency of human embryonic stem cell derivation and allows generation of sibling cell lines. Cell Stem Cell. Feb. 6, 2009;4(2):103-6. doi:10.1016/j.stem.2008.12.001.

Chen et al, Robust self-renewal of rat embryonic stem cells requires fine-tuning of glycogen synthase kinase-3 inhibition. Stem Cell Reports. Aug. 22, 2013;1(3):209-17. doi: 10.1016/j.stemcr.2013.07.003. eCollection 2013.

Costa et al, A method for genetic modification of human embryonic stem cells using electroporation. Nat Protoc. 2007;2(4):792-6.

Faddah et al, Single-cell analysis reveals that expression of nanog is biallelic and equally variable as that of other pluripotency factors in mouse ESCs. Cell Stem Cell. Jul. 3, 2013;13(1):23-9. doi: 10.1016/j.stem.2013.04.019.

Gafni et al, Derivation of novel human ground state naive pluripotent stem cells. Nature. Dec. 12, 2013;504(7479):282-6. doi: 10.1038/nature12745. Epub Oct. 30, 2013. Erratum in: Nature. Apr. 30, 2015;520(7549):710.

Guo et al, Klf4 reverts developmentally programmed restriction of ground state pluripotency. Development. Apr. 2009;136(7):1063-9. doi: 10.1242/dev.030957. Epub Feb. 18, 2009.

Guo et al., Requirement of B-Raf, C-Raf, and A-Raf for the growth and survival of mouse embryonic stem cells. Exp Cell Res. Nov. 1, 2013;319(18):2801-11. doi: 10.1016/j.yexcr.2013.09.006. Epub Sep. 16, 2013.

Hall et al, Oct4 and LIF/Stat3 additively induce Krüppel factors to sustain embryonic stem cell self-renewal. Cell Stem Cell. Dec. 4, 2009;5(6):597-609. doi: 10.1016/j.stem.2009.11.003.

Hanna et al, Human embryonic stem cells with biological and epigenetic characteristics similar to those of mouse ESCs. Proc Natl Acad Sci U S A. May 18, 2010;107(20):9222-7. doi: 10.1073/pnas.1004584107. Epub May 4, 2010.

Hanna et al, Metastable pluripotent states in NOD-mouse-derived ESCs. Cell Stem Cell. Jun. 5, 2009;4(6):513-24. doi:10.1016/j.stem.2009.04.015. Epub May 7, 2009. Erratum in: Cell Stem Cell. Jul. 2, 2009;5(1):124. Cell Stem Cell. May 7, 2015;16(5):566-7.

Hanna et al, Pluripotency and cellular reprogramming: facts, hypotheses, unresolved issues. Cell. Nov. 12, 2010;143(4):508-25. doi:10.1016/j.cell.2010.10.008.

Hayashi et al, Dynamic equilibrium and heterogeneity of mouse pluripotent stem cells with distinct functional and epigenetic states. Cell Stem Cell. Oct. 9, 2008;3(4):391-401. doi: 10.1016/j.stem.2008.07.027.

Hirano et al, Human and mouse induced pluripotent stem cells are differentially reprogrammed in response to kinase inhibitors. Stem Cells Dev. May 20, 2012;21(8):1287-98. doi: 10.1089/scd.2011.0283. Epub Oct. 18, 2011.

Hockemeyer et al, A drug-inducible system for direct reprogramming of human somatic cells to pluripotency. Cell Stem Cell. Sep. 11, 2008;3(3):346-53. doi:10.1016/j.stem.2008.08.014.

(56) References Cited

OTHER PUBLICATIONS

Hockemeyer et al., Genetic engineering of human pluripotent cells using TALE nucleases. Nat Biotechnol. Jul. 7, 2011;29(8):731-4. doi: 10.1038/nbt.1927.
Hough et al, A continuum of cell states spans pluripotency and lineage commitment in human embryonic stem cells. PLoS One. Nov. 5, 2009;4(11):e7708. doi: 10.1371/journal.pone.0007708.
Ilic et al, Derivation of hESC from intact blastocysts. Curr Protoc Stem Cell Biol. Jun. 2007;Chapter 1:Unit 1A.2. doi:10.1002/9780470151808.sc01a02s1.
Itzkovitz et al, Single-molecule transcript counting of stem-cell markers in the mouse intestine. Nat Cell Biol. Nov. 27, 2011;14(1):106-14. doi:10.1038/ncb2384.
Kelly et al., DNA microarray analyses of genes regulated during the differentiation of embryonic stem cells. Mol Reprod Dev. Jun. 2000;56(2):113-23. doi: 10.1002/(SICI)1098-2795(200006)56:2<113::AID-MRD1>3.0.CO;2-Q.
Lengner et al, Derivation of pre-X inactivation human embryonic stem cells under physiological oxygen concentrations. Cell. May 28, 2010;141(5):872-83. doi: 10.1016/j.cell.2010.04.010. Epub May 13, 2010.
Ludwig et al, Defined, feeder-independent medium for human embryonic stem cell culture. Curr Protoc Stem Cell Biol. Sep. 2007;Chapter 1:Unit 1C.2. doi:10.1002/9780470151808.sc01c02s2.
Mandal et al, Reprogramming human fibroblasts to pluripotency using modified mRNA. Nat Protoc. Mar. 2013;8(3):568-82. doi: 10.1038/nprot.2013.019.
Marks et al, The transcriptional and epigenomic foundations of ground state pluripotency. Cell. Apr. 27, 2012;149(3):590-604. doi: 10.1016/j.cell.2012.03.026.
Martello et al, Identification of the missing pluripotency mediator downstream of leukaemia inhibitory factor. EMBO J. Oct. 2, 2013;32(19):2561-74. doi: 10.1038/emboj.2013.177. Epub Aug. 13, 2013.
Martin et al., Novel 2-aminopyrimidine carbamates as potent and orally active inhibitors of Lck: synthesis, SAR, and in vivo antiinflammatory activity. J Med Chem. Aug. 10, 2006;49(16):4981-91. doi: 10.1021/jm060435i.
Meek et al, Tuning of β-catenin activity is required to stabilize self-renewal of rat embryonic stem cells. Stem Cells. Oct. 2013;31(10):2104-15. doi:10.1002/stem.1466.
Melichar et al, Comparative study of hematopoietic differentiation between human embryonic stem cell lines. PLoS One. 2011;6(5):e19854. doi: 10.1371/journal.pone.0019854. Epub May 16, 2011.
Mitalipova et al, Isolation and characterization of human embryonic stem cells. Methods Mol Biol. 2006;331:55-76.
Morrison et al, Regulatory mechanisms in stem cell biology. Cell. Feb. 7, 1997;88(3):287-98.
Najm et al, Isolation of epiblast stem cells from preimplantation mouse embryos. Cell Stem Cell. Mar. 4, 2011;8(3):318-25. doi: 10.1016/j.stem.2011.01.016.
Nazor et al, Recurrent variations in DNA methylation in human pluripotent stem cells and their differentiated derivatives. Cell Stem Cell. May 4, 2012;10(5):620-34. doi:10.1016/j.stem.2012.02.013.
Nichols et al, Naive and primed pluripotent states. Cell Stem Cell. Jun. 5, 2009;4(6):487-92. doi: 10.1016/j.stem.2009.05.015.
Osafune et al, Marked differences in differentiation propensity among human embryonic stem cell lines. Nat Biotechnol. Mar. 2008;26(3):313-5. doi:10.1038/nbt1383. Epub Feb. 17, 2008.
Reubinoff et al, Embryonic stem cell lines from human blastocysts: somatic differentiation in vitro. Nat Biotechnol. Apr. 2000;18(4):399-404. Erratum in: Nat Biotechnol May 2000;18(5):559.
Schmöle et al., Novel indolylmaleimide acts as GSK-3beta inhibitor in human neural progenitor cells. Bioorg Med Chem. Sep. 15, 2010;18(18):6785-95. doi: 10.1016/j.bmc.2010.07.045. Epub Jul. 25, 2010.

Shimuzu et al., Dual inhibition of Src and GSK3 maintains mouse embryonic stem cells, whose differentiation is mechanically regulated by Src signaling. Stem Cells. Jul. 2012;30(7):1394-404. doi: 10.1002/stem.1119.
Si-Tayeb et al, Highly efficient generation of human hepatocyte-like cells from induced pluripotent stem cells. Hepatology. Jan. 2010;51(1):297-305. doi:10.1002/hep.23354. Erratum in: Hepatology. Mar. 2010;51(3):1094.
Silva et al, Capturing pluripotency. Cell. Feb. 22, 2008;132(4):532-6. doi: 10.1016/j.cell.2008.02.006.
Silva et al, Nanog is the gateway to the pluripotent ground state. Cell. Aug. 21, 2009;138(4):722-37. doi: 10.1016/j.cell.2009.07.039.
Silva et al, Promotion of reprogramming to ground state pluripotency by signal inhibition. PLoS Biol. Oct. 21, 2008;6(10):e253. doi: 10.1371/journal.pbio.0060253.
Soldner et al, Generation of isogenic pluripotent stem cells differing exclusively at two early onset Parkinson point mutations. Cell. Jul. 22, 2011;146(2):318-31. doi: 10.1016/j.cell.2011.06.019. Epub Jul. 14, 2011. Erratum in: Cell. Aug. 19, 2011;146(4):659.
Soldner et al, Parkinson's disease patient-derived induced pluripotent stem cells free of viral reprogramming factors. Cell. Mar. 6, 2009;136(5):964-77. doi: 10.1016/j.cell.2009.02.013.
Tesar et al, New cell lines from mouse epiblast share defining features with human embryonic stem cells. Nature. Jul. 12, 2007;448(7150):196-9. Epub Jun. 27, 2007.
Theunissen et al, Nanog overcomes reprogramming barriers and induces pluripotency in minimal conditions. Curr Biol. Jan. 11, 2011;21(1):65-71. doi: 10.1016/j.cub.2010.11.074. Epub Dec. 30, 2010.
Thomson et al., Embryonic stem cell lines derived from human blastocysts. Science. Nov. 6, 1998;282(5391):1145-7. Erratum in: Science Dec. 4, 1998;282(5395):1827.
Valamehr et al, Platform for induction and maintenance of transgene-free hiPSCs resembling ground state pluripotent stem cells. Stem Cell Reports. Mar. 6, 2014;2(3):366-81. doi: 10.1016/j.stemcr.2014.01.014. eCollection Mar. 11, 2014.
Wang et al, Rapid and efficient reprogramming of somatic cells to induced pluripotent stem cells by retinoic acid receptor gamma and liver receptor homolog 1. Proc Natl Acad Sci U S A. Nov. 8, 2011;108(45):18283-8. doi:10.1073/pnas.1100893108. Epub Oct. 11, 2011.
Ware et al., Derivation of naïve human embryonic stem cells. Proc Natl Acad Sci U S A. Mar. 25, 2014;111(12):4484-9. doi: 10.1073/pnas.1319738111. Epub Mar. 12, 2014.
Wernig et al., In vitro reprogramming of fibroblasts into a pluripotent ES-cell-like state. Nature. Jul. 19, 2007;448(7151):318-24. Epub Jun. 6, 2007.
Wray et al, The ground state of pluripotency. Biochem Soc Trans. Aug. 2010;38(4):1027-32. doi: 10.1042/BST0381027.
Yan et al, Single-cell RNA-Seq profiling of human preimplantation embryos and embryonic stem cells. Nat Struct Mol Biol. Sep. 2013;20(9):1131-9. doi: 10.1038/nsmb.2660. Epub Aug. 11, 2013.
Ye et al, Embryonic stem cell self-renewal pathways converge on the transcription factor Tfcp2l1. EMBO J. Oct. 2, 2013;32(19):2548-60. doi: 10.1038/emboj.2013.175. Epub Aug. 13, 2013.
Yeom et al, Germline regulatory element of Oct-4 specific for the totipotent cycle of embryonal cells. Development. Mar. 1996;122(3):881-94.
Ying et al, BMP induction of Id proteins suppresses differentiation and sustains embryonic stem cell self-renewal in collaboration with STAT3. Cell. Oct. 31, 2003;115(3):281-92.
Ying et al, The ground state of embryonic stem cell self-renewal. Nature. May 22, 2008;453(7194):519-23. doi: 10.1038/nature06968.
Yu et al., Pluripotent stem cell lines. Genes Dev. Aug. 1, 2008;22(15):1987-97. doi: 10.1101/gad.1689808.
U.S. Appl. No. 15/318,533, filed Dec. 13, 2016, Theunissen et al.
PCT/US2015/036692, Nov. 27, 2015, International Search Report and Written Opinion.
PCT/US2015/036692, Dec. 29, 2016, International Preliminary Report on Patentability.

* cited by examiner

| Compound | Target(s) |
|----------|-----------|
| AMG706 | VEGFR1 |
| AMN-107 | ANL |
| AZ-628 | BRAF |
| BAY-439006 | BRAF |
| BAY 73-4506 | VEGFR2-TIE2 |
| GDC-0879 | BRAF |
| KIN001-260 | IKKβ |
| PD173074 | FGFR1 |
| SB590885 | BRAF |
| XMD11-50 | LRRK2/ERK5 |

2i/L/DOX

2i/L/SB59
(P8-DOX)

Transgene-free conversion

WIBR3 OCT4-ΔPE-GFP

|  | Gafni (2013) | Chan (2013) | Valamehr (2014) | Ware (2014) | 5i/L/A |
|---|---|---|---|---|---|
| Inhibitors | MEKi | MEKi | MEKi | MEKi | MEKi |
|  | GSK3i | GSK3i | GSK3i | GSK3i | GSK3i |
|  | JNKi | | | | |
|  | P38i | | | | |
|  | PKCi | | | | |
|  | ROCKi | | ROCKi | | ROCKi |
|  | | BMPi | | | |
|  | | | | | BRAFi |
|  | | | | | SRCi |
| Growth factors | bFGF | | bFGF | bFGF | |
|  | TGFβ | | | | Activin |
|  | hLIF | hLIF | hLIF | | hLIF |
| Base | Albumax+N2 or 20% KSR | mTesr1 (bFGF+TGFβ) | 20% KSR | 20% KSR | N2B27 |

Figure 5A

| Compound | Target(s) |
|---|---|
| WH-4-023 | SRC |
| KIN001-220 | Aurora kinase |
| PD0332991 | CDK4 |
| KU55933 | ATM |
| KIN001-244 | PDK |
| XMD 8-85 | ERK5 |
| XMD 8-92 | ERK5 |
| SU11274* | MET |
| PHA-665752* | MET |
| BIBF-1120* | VEGFR, PDGFR, FGFR |
| SU11248 | VEGFR1, PDGFR, KIT, FLT3 |

Figure 10B

| 5i/L/FA medium Human-Mouse injections | | | | | |
|---|---|---|---|---|---|
| Dev. Stage | 8-cell | 8-cell | Morula | Morula | Blastocyst | Blastocyst | Total |
| Cell line | WIBR3 AAVS1-tdTomato | WIBR3 AAVS1-GFP | WIBR3 AAVS1-tdTomato | WIBR3 AAVS1-GFP | WIBR3 AAVS1-tdTomato | WIBR3 AAVS1-GFP | - |
| Injected embryos | 245 | 363 | 92 | 60 | 50 | 50 | 860 |
| Embryos recovered at E10.5 | 92 | 164* | 47 | 28 | 11 | 26 | 368 |
| Positive embryos | 0 | 0 | 0 | 0 | 0 | 0 | 0 |

| Gafni et al. (2013) medium Human-Mouse injections | | | | | |
|---|---|---|---|---|---|
| Dev. Stage | 8-cell | 8-cell | Morula | Morula | Blastocyst | Blastocyst | Total |
| Cell line | C1 AAVS1-GFP on MEFs | C1 AAVS1-GFP on gel/vit | C1 AAVS1-GFP on matrigel | C1 AAVS1-GFP on MEFs | C1 AAVS1-GFP on gel/vit | C1 AAVS1-GFP on matrigel | - |
| Injected embryos | 140 | 100 | 40 | 40 | 40 | 76 | 436 |
| Embryos recovered at E10.5 | 96* | 28 | 12 | 24 | 7** | 28 | 195 |
| Positive embryos | 0 | 0 | 0 | 0 | 0 | 0 | 0 |

Figure 14C

USES OF KINASE INHIBITORS FOR INDUCING AND MAINTAINING PLURIPOTENCY

RELATED APPLICATIONS

This application is a continuation of U.S. application Ser. No. 15/318,533, filed Dec. 13, 2016, which is a national stage filing under 35 U.S.C. § 371 of international PCT application, PCT/US2015/036692, filed Jun. 19, 2015, which claims priority under 35 U.S.C. § 119(e) to U.S. provisional applications, U.S. Ser. No. 62/014,674, filed Jun. 19, 2014, and U.S. Ser. No. 62/045,337, filed Sep. 3, 2014, each of which is incorporated herein by reference.

GOVERNMENT SUPPORT

This invention was made with Government support under grant number RO1-CA084198 awarded by the National Institutes of Health. The Government has certain rights in the invention.

BACKGROUND OF THE INVENTION

Human pluripotent stem cells, including embryonic stem cells (ESCs) and induced pluripotent stem cells (iPSCs), hold great promise for regenerative medicine and disease modeling (Hanna et al., 2010b). Full realization of their potential is currently constrained by laborious culture requirements and inconsistencies in developmental potential between lines (Melichar et al., 2011; Osafune et al., 2008). Researchers have had a relatively easy time genetically manipulating and preventing differentiation in mouse ES and iPS cells. However, human ES cells can be more technically demanding to culture and exhibit properties such as slow growth and poor tolerance to passaging as single cells. Thus, there is a need for more effective techniques to isolate and culture human pluripotent stem cells.

SUMMARY OF THE INVENTION

One aspect of the disclosure provides methods for changing the pluripotency state of a vertebrate cell to a more naïve state, the methods comprising: culturing a pluripotent vertebrate cell in the presence of a serine/threonine-protein kinase B-Raf (BRAF) inhibitor, an epidermal growth factor receptor (EGFR) inhibitor, a vascular endothelial growth factor 1 (VEGFR1) inhibitor, or a fibroblast growth factor receptor 1 (FGFR1) inhibitor; and maintaining the cell in culture under conditions suitable and a time sufficient to convert the pluripotency state of the vertebrate cell to a more naïve state than the pluripotency state of the vertebrate cell of culturing step.

Another aspect of the disclosure provides methods for changing the pluripotency state of a vertebrate cell to a more naïve state, the method comprising: culturing a pluripotent vertebrate cell in the presence of a compound of any one of Formulae (A) to (L):

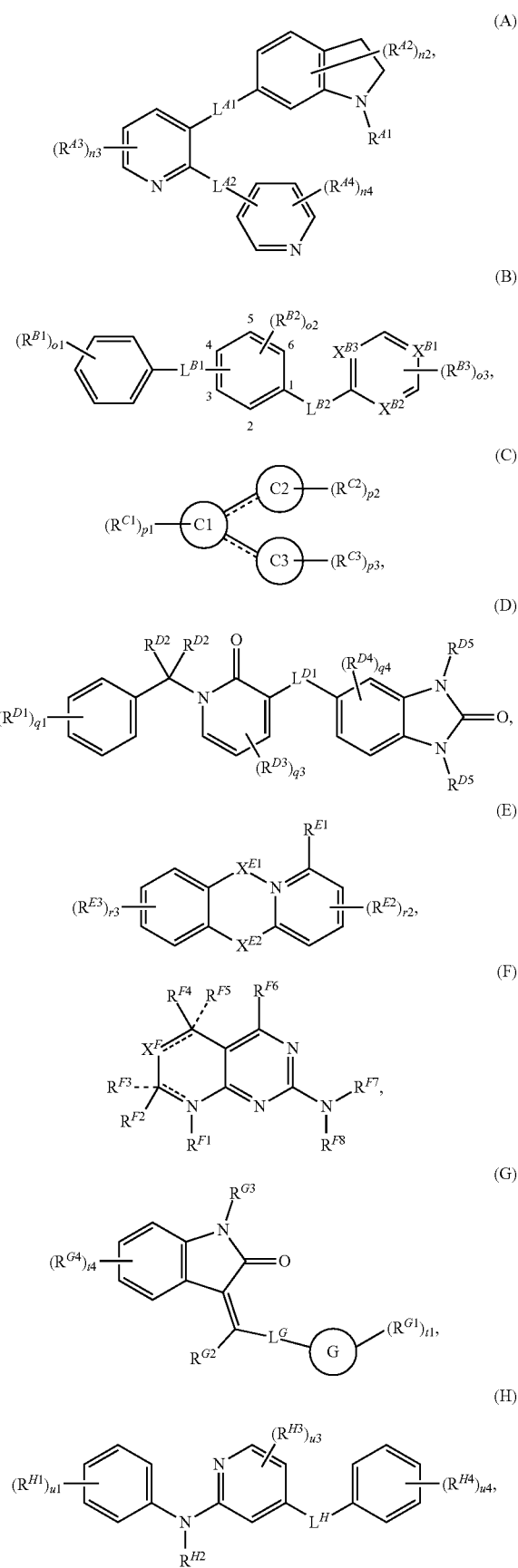

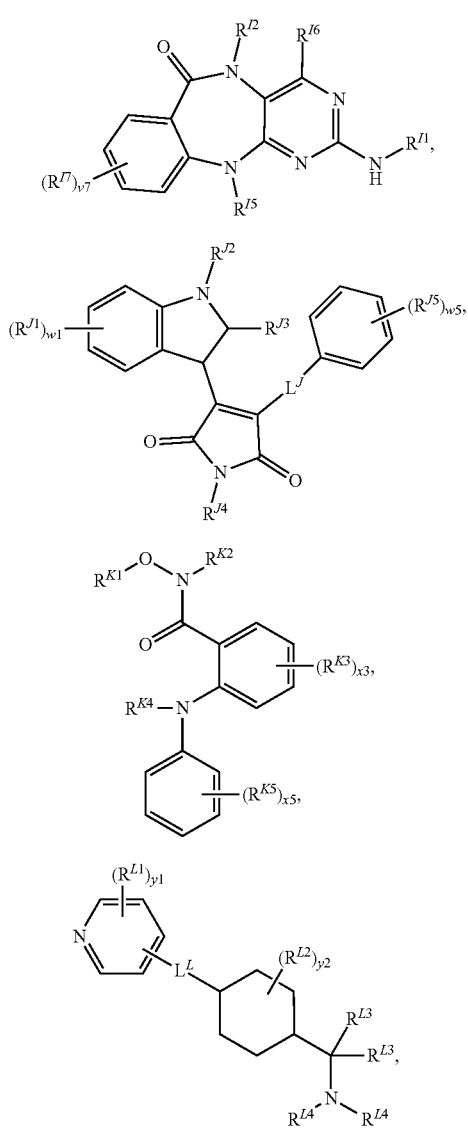

and pharmaceutically acceptable salts, solvates, hydrates, polymorphs, co-crystals, tautomers, stereoisomers, isotopically labeled derivatives, and prodrugs thereof; and maintaining the cell in culture under conditions suitable and a time sufficient to convert the pluripotency state of the vertebrate cell to a more naïve state than the pluripotency state of the vertebrate cell of culturing step. In some embodiments, the time sufficient to convert the pluripotency state of the vertebrate cell to a more naïve state is at least about 5 days (e.g., about 10 days).

Exemplary compounds useful in a system, composition, kit, or method described herein include, but are not limited to, AMG706, AMN-107, AZ-628, BAY 73-4506, BAY-439006, GDC-0879, KIN001-260, SB590885, CHIR99021, KIN001-244, KU55933, SP600125, PD0332991, PD173074, WZ-7043, BIBF-1120, PHA-665752, SU11248, SU11274, KIN001-220, WH-4-023, WH-4-025, XMD 8-92, XMD11-50, XMD 8-85, IM12, PD0325901, and Y-27632.

Another aspect of the disclosure provides compositions comprising naïve pluripotent vertebrate cells produced by a method described herein.

Another aspect of the disclosure provides naïve pluripotent vertebrate cells, wherein the cells have a global gene expression profile which clusters with naïve mouse ESCs as opposed to stem cell lines derived from mouse epiblast (EpiSCs) and/or less naïve human ESCs.

Yet another aspect of the disclosure relates to naïve pluripotent vertebrate cells, wherein the cells have a global gene expression profile which clusters with naïve mouse ESCs as opposed to stem cell lines derived from mouse epiblast (EpiSCs) and/or less naïve human ESCs.

Another aspect of the disclosure provides kits for changing the pluripotency state of a vertebrate cell to a more naïve state, the kits comprising a pluripotent vertebrate cell; and cell culture medium comprising a serine/threonine-protein kinase B-Raf (BRAF) inhibitor, an epidermal growth factor receptor (EGFR) inhibitor, a vascular endothelial growth factor 1 (VEGFR1) inhibitor, or a fibroblast growth factor receptor 1 (FGFR1) inhibitor.

In yet another aspect, the present disclosure provides compounds, compositions, and kits described herein for use in a method of the present disclosure.

The details of particular embodiments of the invention are set forth herein. Other features, objects, and advantages of the invention will be apparent from the Detailed Description, the Figures, the Examples, and the Claims.

Definitions

Definitions of specific functional groups and chemical terms are described in more detail below. The chemical elements are identified in accordance with the Periodic Table of the Elements, CAS version, Handbook of Chemistry and Physics, 75' Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, IN 1972). The disclosure additionally encompasses compounds as individual isomers substantially free of other isomers, and alternatively, as mixtures of various isomers.

In a formula, --- is absent or a single bond, and === or ≡≡≡ is a single or double bond.

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is unspecified (e.g., —CH=CHCH$_3$ or

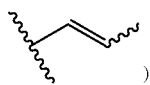

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_2$-8 alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_2$-s alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl. In some embodiments, carbocyclyl is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-}$cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR—, —ON(R$^{bb}$)$_2$, —N(R$^{bb}$)$_2$, —N(R$^{bb}$)$_3^+$X$^-$, —N(OR$^{cc}$)R$^{bb}$, —SH, —SR—, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{aa}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{aa}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^+$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{cc}$, —SO$_2$OR$^{ee}$, —OSO$_2$R$^{cc}$, —S(=O)R$^{ee}$, —Si(R$^{ee}$)$_3$, —OSi(R$^{ee}$)$_3$, —C(=S)N ($R^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two Ra groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(=O)(R$^{cc}$)$_2$, —OP(=O)(OR$^{cc}$)$_2$, and —OP(=O)(N(R$^{bb}$))$_2$, wherein X$^-$, R$^{aa}$, R$^{bb}$, and R$^{cc}$ are as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{aa}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a mono-substituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(N(R$^{bb}$)$_2$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein.

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$, —C(=NR$^{bb}$)N(R$^{bb}$)$_2$), wherein R$^{aa}$ and R$^{bb}$ are as defined herein.

The term "silyl" refers to the group —Si(R$^{aa}$)$_3$, wherein R$^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N—S-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)Ra, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{cc}$)$_2$, —P(=O)(OR$^{cc}$)$_2$, and —P(=O)(N(R$^{bb}$)$_2$)$_2$, wherein R$^{aa}$, R$^{bb}$, and R$^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^+$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

An "aliphatic chain" refers to a substituted or unsubstituted divalent alkyl, alkenyl, or alkynyl group. An aliphatic chain includes (1) one or more chains of carbon atoms immediately between the two radicals of the aliphatic chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of an aliphatic chain may include any atoms, including hydrogen atoms, carbon atoms, and heteroatoms. For example, aliphatic chain —$C^A$H ($C^BH_2C^CH_3$)— includes one chain atom $C^A$, one hydrogen atom on $C^A$, and non-chain substituent —($C^BH_2C^CH_3$). The term "$C_x$ aliphatic chain," wherein x is a positive integer, refers to an aliphatic chain that includes x number of chain atom(s) between the two radicals of the aliphatic chain. If there is more than one possible value of x, the smallest possible value of x is used for the definition of the aliphatic chain. For example, —$CH(C_2H_5)$— is a $C_1$ aliphatic chain, and

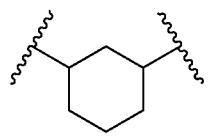 [SMILES: *C1CCCC(*)C1]

is a $C_3$ aliphatic chain. When a range of values is used, the meaning of the range is as described herein. For example, a $C_{3-10}$ aliphatic chain refers to an aliphatic chain where the number of chain atoms of the shortest chain of carbon atoms immediately between the two radicals of the aliphatic chain is 3, 4, 5, 6, 7, 8, 9, or 10. An aliphatic chain may be saturated (e.g., —$(CH_2)_4$—). An aliphatic chain may also be unsaturated and include one or more C=C and/or C≡C bonds anywhere in the aliphatic chain. For instance, —CH=CH—$(CH_2)_2$—, —$CH_2$—C≡C—$CH_2$—, and —C≡C—CH=CH— are all examples of a unsubstituted and unsaturated aliphatic chain. In certain embodiments, the aliphatic chain is unsubstituted (e.g., —C≡C— or —$(CH_2)_4$—). In certain embodiments, the aliphatic chain is substituted (e.g., —$CH(C_2H_5)$— and —$CF_2$—). Any two substituents on the aliphatic chain may be joined to form an optionally substituted carbocyclyl, optionally substituted heterocyclyl, optionally substituted aryl, or optionally substituted heteroaryl ring. For instance,

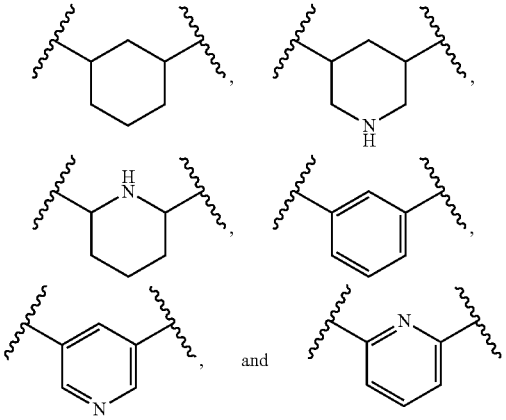

are all examples of an aliphatic chain. In contrast, in certain embodiments,

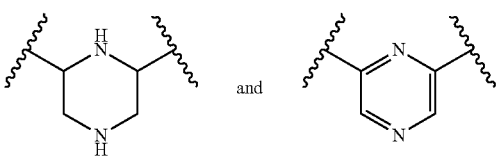 [SMILES: *C1CNCC(*)N1 ; *c1cncc(*)n1]

are not within the scope of the aliphatic chains described herein. A "heteroaliphatic chain" is an aliphatic chain where at least one chain atom of each chain of the aliphatic chain is independently replaced with a heteroatom. In certain embodiments, an aliphatic chain described herein is a $C_{1-4}$ aliphatic chain, a $C_{1-6}$ aliphatic chain, a $C_{3-7}$ aliphatic chain, a $C_2$ aliphatic chain, a $C_3$ aliphatic chain, or a $C_5$ aliphatic chain. In certain embodiments, one, two, or three chain atoms of an aliphatic chain described herein are independently replaced with —O—, —S—, —$NR^1$—, —N=, or =N—, wherein each instance of $R^1$ is independently hydrogen, substituted or unsubstituted $C_{1-6}$ alkyl, or a nitrogen protecting group. In certain embodiments, one, two, or three chain atoms of an aliphatic chain described herein are independently replaced with —O—, —S—, or —$NR^1$—. In certain embodiments, the molecular weight of an aliphatic or heteroaliphatic chain is not more than about 300 g/mol, not more than about 200 g/mol, not more than about 150 g/mol, not more than about 100 g/mol, not more than about 70 g/mol, not more than about 50 g/mol, or not more than 30 g/mol. In certain embodiments, an aliphatic or heteroaliphatic chain consists of not more than about 70 atoms, not more than about 50 atoms, not more than about 30 atoms, not more than about 20 atoms, not more than about 15 atoms, or not more than 10 atoms. In certain embodiments, an aliphatic or heteroaliphatic chain does not include unsaturated bonds in the shortest chain. In certain embodiments, an aliphatic or heteroaliphatic chain consists of one or two unsaturated bonds in the shortest chain. In certain embodiments, an aliphatic or heteroaliphatic chain includes at least one instance of =O as a non-chain substituent on a chain atom (e.g., carbon or sulfur atom).

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·$0.5H_2O$)), and polyhydrates (x is a number greater than 1, e.g., dihydrates (R·$2H_2O$) and hexahydrates (R·$6H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds which have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The "molecular weight" of a monovalent moiety —R is calculated by subtracting 1 from the molecular weight of the compound R—H. The "molecular weight" of a divalent moiety -L- is calculated by subtracting 2 from the molecular weight of the compound H-L-H.

The terms "composition" and "formulation" are used interchangeably.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs); and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is a non-human animal. In certain embodiments, the animal is a fish or reptile.

The term "administer," "administering," or "administration" refers to implanting, absorbing, ingesting, injecting, inhaling, or otherwise introducing a compound or cell described herein or generated as described herein, or a composition thereof, in or on a subject.

The terms "treatment," "treat," and "treating" refer to reversing, alleviating, delaying the onset of, or inhibiting the progress of a disease. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen and/or in light of detecting that the subject has a genotype associated with the disease). Treatment may also be continued after symptoms have resolved, for example, to delay or prevent recurrence.

The terms "condition," "disease," and "disorder" are used interchangeably.

A "kinase" is a type of enzyme that transfers phosphate groups from high energy donor molecules, such as ATP, to specific substrates, referred to as phosphorylation. Kinases are part of the larger family of phosphotransferases. One of the largest groups of kinases are protein kinases, which act on and modify the activity of specific proteins. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. These exemplary human protein kinases include, but are not limited to, AAK1, ABL, ACK, ACTR2, ACTR2B, AKT1, AKT2, AKT3, ALK, ALK1, ALK2, ALK4, ALK7, AMPKa1, AMPKa2, ANKRD3, ANPa, ANPb, ARAF, ARAFps, ARG, AurA, AurAps1, AurAps2, AurB, AurBps1, AurC, AXL, BARK1, BARK2, BIKE, BLK, BMPR1A, BMPR1Aps1, BMPR1Aps2, BMPR1B, BMPR2, BMX, BRAF, BRAFps, BRK, BRSK1, BRSK2, BTK, BUB1, BUBR1, CaMK1a, CaMK1b, CaMK1d, CaMK1g, CaMK2a, CaMK2b, CaMK2d, CaMK2g, CaMK4, CaMKK1, CaMKK2, caMLCK, CASK, CCK4, CCRK, CDC2, CDC7, CDK10, CDK11, CDK2, CDK3, CDK4, CDK4ps, CDK5, CDK5ps, CDK6, CDK7, CDK7ps, CDK8, CDK8ps, CDK9, CDKL1, CDKL2, CDKL3, CDKL4, CDKL5, CGDps, CHED, CHK1, CHK2, CHK2ps1, CHK2ps2, CK1a, CK1a2, CK1aps1, CK1aps2, CK1aps3, CK1d, CK1e, CK1g1, CK1g2, CK1g2ps, CK1g3, CK2a1, CK2a1-rs, CK2a2, CLIK1, CLIK1L, CLK1, CLK2, CLK2ps, CLK3, CLK3ps, CLK4, COT, CRIK, CRK7, CSK, CTK, CYGD, CYGF, DAPK1, DAPK2, DAPK3, DCAMKL1, DCAMKL2, DCAMKL3, DDR1, DDR2, DLK, DMPK1, DMPK2, DRAK1, DRAK2, DYRK1A, DYRK1B, DYRK2, DYRK3, DYRK4, EGFR, EphA1, EphA10, EphA2, EphA3, EphA4, EphA5, EphA6, EphA7, EphA8, EphB1, EphB2, EphB3, EphB4, EphB6, Erk1, Erk2, Erk3, Erk3ps1, Erk3ps2, Erk3ps3, Erk3ps4, Erk4, Erk5, Erk7, FAK, FER, FERps, FES, FGFR1, FGFR2, FGFR3, FGFR4, FGR, FLT1, FLT1ps, FLT3, FLT4, FMS, FRK, Fused, FYN, GAK, GCK, GCN2, GCN22, GPRK4, GPRK5, GPRK6, GPRK6ps, GPRK7, GSK3A, GSK3B, Haspin, HCK, HER2/ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAK1, IRAK2, IRAK3, IRAK4, IRE1, IRE2, IRR, ITK, JAK1, JAK2, JAK3, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB1, LMR1, LMR2, LMR3, LOK, LRRK1, LRRK2, LTK, LYN, LZK, MAK, MAP2K1, MAP2K1ps, MAP2K2, MAP2K2ps, MAP2K3, MAP2K4, MAP2K5, MAP2K6, MAP2K7, MAP3K1, MAP3K2, MAP3K3, MAP3K4, MAP3K5, MAP3K6, MAP3K7, MAP3K8, MAPKAPK2, MAPKAPK3, MAPKAPK5, MAPKAPKps1, MARK1, MARK2, MARK3, MARK4, MARKps01, MARKps02, MARKps03, MARKps04, MARKps05, MARKps07, MARKps08, MARKps09, MARKps10, MARKps11, MARKps12, MARKps13, MARKps15, MARKps16, MARKps17, MARKps18, MARKps19, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNK1ps, MNK2, MOK, MOS, MPSK1, MPSK1ps, MRCKa, MRCKb, MRCKps, MSK1, MSK12, MSK2, MSK22, MSSK1, MST1, MST2, MST3, MST3ps, MST4, MUSK, MYO3A, MYO3B, MYT1, NDR1, NDR2, NEK1, NEK10, NEK11, NEK2, NEK2ps1, NEK2ps2, NEK2ps3, NEK3, NEK4, NEK4ps, NEK5, NEK6, NEK7, NEK8, NEK9, NIK, NIM1, NLK, NRBP1, NRBP2, NuaK1, NuaK2, Obsen, Obscn2, OSR1, p38a, p38b, p38d, p38g, p70S6K, p70S6Kb, p70S6Kps1, p70S6Kps2, PAK1, PAK2, PAK2ps, PAK3, PAK4, PAK5, PAK6, PASK, PBK, PCTAIRE1, PCTAIRE2, PCTAIRE3, PDGFRa, PDGFRb, PDK1, PEK, PFTAIRE1, PFTAIRE2, PHKg1, PHKg1ps1, PHKg1ps2, PHKg1ps3, PHKg2, PIK3R4, PIM1, PIM2, PIM3, PINK1, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLK1ps1, PLK1ps2, PLK2, PLK3, PLK4, PRKX, PRKXps, PRKY, PRP4, PRP4ps, PRPK, PSKH1, PSKH1ps, PSKH2, PYK2, QIK, QSK, RAF1, RAF1ps, RET, RHOK, RIPK1, RIPK2, RIPK3, RNAseL, ROCK1, ROCK2, RON, ROR1, ROR2, ROS, RSK1, RSK12, RSK2, RSK22, RSK3, RSK32, RSK4, RSK42, RSKL1, RSKL2, RYK, RYKps, SAKps, SBK, SCYL1, SCYL2, SCYL2ps, SCYL3, SGK, SgK050ps, SgK069, SgK071, SgK085, SgK110, SgK196, SGK2, SgK223, SgK269, SgK288, SGK3, SgK307, SgK384ps, SgK396, SgK424, SgK493, SgK494, SgK495, SgK496, SIK (e.g., SIK1, SIK2), skMLCK, SLK, Slob, smMLCK, SNRK, SPEG, SPEG2, SRC, SRM, SRPK1, SRPK2, SRPK2ps, SSTK, STK33, STK33ps, STLK3, STLK5, STLK6, STLK6ps1, STLK6-rs, SuRTK106, SYK, TAK1, TAO1, TAO2, TAO3, TBCK, TBK1, TEC, TESK1, TESK2, TGFbR1, TGFbR2, TIE1, TIE2, TLK1, TLK1ps, TLK2, TLK2ps1, TLK2ps2, TNK1, Trad, Trb1, Trb2, Trb3, Trio, TRKA, TRKB, TRKC, TSSK1, TSSK2, TSSK3, TSSK4, TSSKpsl, TSSKps2, TTBK1, TTBK2, TTK, TTN, TXK, TYK2, TYK22, TYRO3, TYRO3ps, ULK1, ULK2, ULK3, ULK4, VACAMKL, VRK1, VRK2, VRK3, VRK3ps, Wee1, Wee1B, Wee1Bps, Wee1ps1, Wee1ps2, Wnk1, Wnk2, Wnk3, Wnk4, YANK1, YANK2, YANK3, YES, YESps, YSK1, ZAK, ZAP70, ZC1/HGK, ZC2/TNIK, ZC3/MINK, and ZC4/NRK.

The term "inhibition", "inhibiting", "inhibit," or "inhibitor" refer to the ability of a compound to reduce, slow, halt, or prevent activity of a particular biological process (e.g., kinase activity) in a cell relative to vehicle.

By "pluripotency" and pluripotent stem cells it is meant that such cells have the ability under appropriate conditions to differentiate into cells that are derivatives of all three embryonic germ layers (endoderm, mesoderm and ectoderm). A pluripotent cell line or cell culture is often characterized in that the cells can differentiate into a wide variety of cell types in vitro and in vivo. Cells that are able to form teratomas containing cells having characteristics of endoderm, mesoderm, and ectoderm when injected into SCID mice are considered pluripotent. In addition, cells that possess the ability to participate in the formation of chimeras (upon injection into a blastocyst of the same species that is transferred to a suitable foster mother of the same species) that survive to term are considered pluripotent. Pluripotent cell types as used in the present invention may be provided in the form of human embryonic stem cells, or human induced pluripotent cell (iPS cell), or may be derived from a human embryonic stem cell line.

The term "stem cell" refers to a vertebrate cell that has the ability both to self-renew, and to generate differentiated progeny. The ability to generate differentiated progeny may be described as pluripotent (see Morrison et al. (1997) Cell 88:287-298). "Embryonic stem cells" (ES cells) are pluripotent stem cells derived from the inner cell mass of a blastocyst, an early-stage preimplantation embryo. Pluripotency distinguishes embryonic stem cells from adult stem cells found in adults; while embryonic stem cells can generate all cell types in the body, adult stem cells are multipotent and can produce only a limited number of cell types.

"Induced pluripotent stem cells", abbreviated as iPS cells, are a type of pluripotent stem cell artificially derived from a non-pluripotent cell, typically an adult somatic cell, by inducing expression of certain genes (e.g., injection of an expression construct). Induced pluripotent stem cells are identical in many respects to natural pluripotent stem cells, such as embryonic stem (ES) cells (e.g., in their physical properties). They may be the same in their expressions of certain stem cell genes and proteins, chromatin methylation patterns, doubling time, embryoid body formation, teratoma formation, viable chimera formation, and potency and differentiability. The term "induced pluripotent stem cell" encompasses pluripotent cells, that, like embryonic stem (ES) cells, can be cultured over a long period of time while maintaining the ability to differentiate into all types of cells in an organism. However, unlike ES cells (which are typically derived from the inner cell mass of blastocysts), iPS cells are derived from differentiated somatic cells, that is, cells that have a narrower, more defined potential.

By "culturing" the cell means growing the cells in an artificial, in vitro environment. By "maintaining" means continuing to grow the cells in culture under suitable conditions until the pluripotency state of the cell is converted to a more naïve state.

A "cell culture medium" (also referred to herein as a "culture medium" or "medium") is a medium for culturing cells containing nutrients that maintain cell viability and support proliferation. The cell culture medium may contain any of the following nutrients in appropriate amounts and combinations: salt(s), buffer(s), amino acids, glucose or other sugar(s), antibiotics, serum or serum replacement, and other components such as, but not limited to, peptide growth factors, cofactors, and trace elements. Cell culture media ordinarily used for particular cell types are known to those skilled in the art. For example, cell culture media of use for culturing and maintaining pluripotent cells are known in the art.

In some embodiments, the cell culture medium is chemically defined medium. In some embodiments, cell culture medium is serum-free medium, e.g., mTeSR1™ medium (StemCell Technologies, Vancouver, BC). In some embodiments, the culture medium comprises one or more supplements, such as, but not limited to N2 and B27. In some embodiments, the cell culture medium comprises a serum replacement composition. In some embodiments, the cell culture medium comprises low amount, such as less than 1% or less than 0.5%, of knock-out serum replacement medium. In some embodiments, the cell culture medium does not comprise a serum replacement composition. In some embodiments, the cell culture medium comprises an activator of STAT3 pathways, for example but not limited to leukemia inhibitory factor (LIF). In some embodiments, the cell culture comprises serum free recombinant human LIF.

In some embodiments, the cell culture medium comprises a basal medium to which one or more supplements are added, such as: DMEM/F12, Neurobasal, N2 supplement, 10 mL B27 supplement, human LIF, glutamine, nonessential amino acids, β-mercaptoethanol, penicillin-streptomycin, and/or BSA (Sigma). In some embodiments, the supplemented basal cell culture medium further comprises fibroblast growth factor 2 (FGF2) and 1%, 0.8%, 0.6%, 0.4%, 0.2%, or 0.1% KSR.

In some embodiments, the cell culture medium is free or essentially free of components of non-human origin. In some embodiments, the cell culture medium is free or essentially free of components isolated from humans or non-human animals. In some embodiments, the cell culture medium uses recombinant human proteins (e.g., recombinant human albumin).

"Cell line" refers to a population of largely or substantially identical cells, wherein the cells have often been derived from a single ancestor cell or from a defined and/or substantially identical population of ancestor cells. For example, a cell line may consist of descendants of a single cell. A cell line may have been or may be capable of being maintained in culture for an extended period (e.g., months, years, for an unlimited period of time). It will be appreciated that cells may acquire mutations and possibly epigenetic changes over time such that some individual cells of a cell line may differ with respect to each other. In some embodiments, at least 80%, 85%, 86%, 87%, 88%, 89%, 90%, 91%, 92%, 93%, 94%, 95%, 96%, 97%, 98%, or 99% of the cells of a cell line or cell culture are at least 95%, 96%, 97%, 98%, or 99% genetically identical. In some embodiments, at least 80%, 85%, 86%, 87%, 88%, 89%, 90%, 91%, 92%, 93%, 94%, 95%, 96%, 97%, 98%, or 99% of the cells of a cell line or cell culture express the same set of cell surface markers. The set of markers could be markers indicative of ground state (naïve) pluripotency or cell-type specific markers.

A "clone" refers to a cell derived from a single cell without change. It will be understood that if cells of a clone are subjected to different culture conditions or if some of the cells are subjected to genetic modification, the resulting cells may be considered distinct clones.

BRIEF DESCRIPTION OF THE DRAWINGS

In FIG. 1A, the proximal enhancer (PE) targeting strategy in human ESCs containing a 2A-GFP sequence in frame with the 3' UTR of OCT4 is shown. FIG. 1B is a Southern blot analysis confirming disruption of the PE in OCT4-GFP ESCs. NdeI-digested genomic DNA was hybridized with 5' and 3' external probes. Expected fragment size: WT (wild type)=5.6 kb, T (targeted)=6.4 kb. FIG. 1C shows the images of OCT4-GFP human ESCs before (left) and after TALEN-mediated deletion of the PE (right). FIG. 1D shows the single molecule RNA FISH analysis for OCT4 and GFP transcripts in OCT4-GFP human ESCs before and after TALEN-mediated disruption of the PE. FIG. 1E shows the flow cytometric analysis of the proportion of OCT4-ΔPE-GFP+ cells obtained after DOX induction of lentiviral KLF2, NANOG or KLF2+NANOG. Following primary infection WIBR3 human ESCs containing the OCT4-ΔPE-GFP reporter allele were trypsinized and treated with hESM, 2i/L, or 2i/L/DOX for one week. FIG. 1F are phase and fluorescence images and flow cytometric analysis of the proportion of OCT4-ΔPE-GFP+ cells of a clonal line of 38 hESCs derived in 2i/L/DOX (left). Phase and fluorescence images and flow cytometric analysis after replating in the absence of DOX for one week (right). FIG. 1G shows the quantitative gene expression analysis for FUW-KLF2, FUW-NANOG, endogenous OCT4, and endogenous KLF4 in WIBR3 hESCs cultured in hESM and clonal OCT4-ΔPE-GFP+ derivatives generated in 2i/L/DOX. FIG. 1H are phase and fluorescence images of primitive neural stem cells (pNSCs) derived by treating WIBR3 hESCs containing the OCT4-ΔPE-GFP allele with 2i/L for three passages. FIG. 1I shows immunofluorescence staining for NANOG and NES-TIN in a clonal line of OCT4-ΔPE-GFP-positive cells derived in 2i/L/DOX, and a clonal line of OCT4-ΔPE-GFP-negative pNSCs derived in 2i/L. FIG. 1J is a model representing the distinct phenotypic responses of hESCs to treatment with 2i/L and 2i/L/DOX. OCT4-ΔPE-GFP+ cells generated in 2i/L/DOX do not maintain reporter activity upon transgene withdrawal. OCT4-ΔPE-GFP+ cells can revert back to the conventional 'primed' hESC state by re-exposure to serum and FGF.

FIG. 2A shows the strategy for screening a kinase inhibitor library to identify compounds that maintain OCT4-ΔPE-GFP reporter activity upon withdrawal of DOX-dependent KLF2 and NANOG expression. FIG. 2B is the raw data obtained from high-throughput flow cytometric analysis of the proportion of OCT4-ΔPE-GFP+ cells in 96 wells supplemented with a kinase inhibitor library (n=2). FIG. 2C shows the hit compounds from a maintenance screen using a clonal line of WIBR3 OCT4-ΔPE-GFP+ ESCs established in 2i/L/DOX. FIG. 2D are the phase images (top) and flow cytometric analysis of the proportion of OCT4-ΔPE-GFP+ cells (bottom) in a clonal line of OCT4-ΔPE-GFP+ cells derived in 2i/L/DOX and maintained for 10 passages without DOX in the presence of each candidate compound. FIG. 2E is the quantitative gene expression analysis for FUW-KLF2, FUW-NANOG, endogenous OCT4, and EGFP in a clonal line of OCT4-ΔPE-GFP+ cells maintained in 2i/L/DOX or for five passages without DOX in the presence of each candidate compound. FIG. 2F is the chemical structure of the BRAF inhibitor, SB590885. FIG. 2G shows phase images of a clonal line of WIBR3 human ESCs established in 2i/L/DOX and maintained for 8 passages without DOX in 2i/L/SB590885 (1 μM). FIG. 2H is the quantitative gene expression analysis for FUW-KLF2, FUW-NANOG, and endogenous OCT4 in two clonal lines of WIBR3 human ESCs maintained for 8 passages without DOX in 2i/L/SB590885 (1 μM).

FIG. 3A shows the flow cytometric analyses of the proportion of OCT4-ΔPE-GFP+ cells in a 96 well one week after culture in 2i/L/DOX, 2i/L alone or 2i/L/SB590885 (1 μM). Top panel shows quantification of OCT4-ΔPE-GFP+ cells without including live/dead discrimination. Bottom panel shows quantification of OCT4-ΔPE-GFP+ cells after gating out DAPI+ cells. FIG. 3B shows the strategy for screening a kinase inhibitor library to identify compounds that improve the fraction of viable (DAPI-) OCT4-ΔPE-GFP+ cells maintained without DOX for 2 passages in 2i/L/SB590995 (1 μM). FIG. 3C is the raw data obtained from high-throughput flow cytometric analysis of the proportion of DAPI-/OCT4-ΔPE-GFP+ cells in 96 wells supplemented with one plate of a kinase inhibitor library (n=2). Hit compound WH-4-023 is indicated with chemical structure. FIGS. 3D-3E show high-throughput flow cytometric quantification of the proportion of DAPI-/OCT4-ΔPE-GFP+ cells in 96 wells cultured for one passage (FIG. 3D) or two passages (FIG. 3E) in 64 different concentrations of PD0325901, CHIR99021, and SB590885. All the legends in FIG. 3E also apply in FIG. 3D. Asterisk denotes rank of the standard concentration of the three inhibitors used in the preceding experiments (1 μM PD0325901, 0.3 μM CHIR99021 and 0.5 μM SB590885). FIG. 3F are the phase and fluorescence images (top) and flow cytometric analysis of the proportion of OCT4-ΔPE-GFP+ cells (bottom) in a clonal line of OCT4-ΔPE-GFP+ cells derived in 2i/L/DOX and maintained for 2 passages without DOX in 2i/L/SB590885$^{opt}$/Y-27632 or 2i/L/SB590885$^{opt}$/Y-27632/WH-4-023. Opt=optimized concentrations of PD0325901, CHIR99021, and SB590885 (see FIG. 4E). FIG. 3G are the phase and fluorescence images of a clonal line of WIBR3 OCT4-ΔPE-GFP+ cells (left) and a clonal line of wild-type WIBR3 human ESCs generated in 2i/L/DOX (right) and maintained for 3 passages in PD0325901/IM12/SB590885/Y-27632/WH-4-023 (5i) and hLIF. FIG. 3H shows the teratoma generated from wild-type WIBR3 human ESCs maintained in PD0325901/IM12/SB590885/Y-27632/WH-4-023 (5i) and hLIF after transgene withdrawal. Representative tissues of the three germ layers are indicated.

FIG. 4A shows the strategy for assessing direct conversion of primed human ESCs into OCT4-ΔPE-GFP+ cells under optimized chemical conditions. FIG. 4B shows phase and fluorescence images of emerging naïve colony and expanded cells from WIBR3 OCT4-ΔPE-GFP human ESCs treated with 5i/L for 10 days. FIG. 4C are the phase and fluorescence images and flow cytometric analyses of the proportion of GFP+ cells during conversion experiments in 5i/L supplemented with FGF and/or Activin A (FA). FIG. 4D are the phase images of wild-type naïve WIBR2 human ES cells converted in 5i/L supplemented with FGF and/or Activin A (FA). FIG. 4E shows the phase image of a primary human ESC line derived in 5i/L/FA conditions from an explanted human blastocyst. Cell line is called Whitehead Institute Naïve Human ESC (WIN)-1. FIG. 4F is the flow cytometric analysis of the proportion of OCT4-ΔPE-GFP+ cells three passages after withdrawal of individual inhibitors and growth factors. FIG. 4G is the quantitative gene expression analysis for OCT4, NANOG, KLF4, KLF2, SOX2, and REX1 three passages after withdrawal of individual inhibitors and growth factors.

FIGS. 5A-5F show the evaluation of alternative culture conditions for naïve human pluripotency. FIG. 5A is a table comparing the components of four recent protocols for capturing naïve-like human ESCs with 5i/L/A medium. FIG. 5B show the phase and fluorescence images and flow cytometric analyses showing the response of OCT4-ΔPE-GFP-negative primed cells to recently reported protocols for naïve human pluripotency (see FIG. 5A) and 5i/L/A. FIG. 5C shows the quantification of the proportion of GFP-positive cells in WIBR3 OCT4-GFP and OCT4-ΔPE-GFP human ESCs upon removal of DOX-inducible KLF2 and NANOG expression in primed medium (PM) and four alternative conditions for naïve human pluripotency. FIG. 5D shows the flow cytometric analysis of the proportion of OCT4-ΔPE-GFP+ cells in 5i/L/A and the JNK inhibitor SP600125 (6i/L/A) in serum-free N2B27 basal medium vs. 20% KSR basal medium. FIG. 5E is the quantitative gene expression analysis for OCT4, SOX2, KLF2 and NANOG in human ESCs cultured in 6i/L/A and supplemented with 1-10% FBS or KSR. FIG. 5F are the phase and fluorescence images of induction of OCT4-ΔPE-GFP activity from the primed state in 6i/L/A, and 6i/L/A supplemented with 0.5-1% KSR.

FIG. 6A shows the cross-species hierarchical clustering of naïve and primed pluripotent cells from mice and humans, as performed previously by Gafni et al. (2013). Affymetrix expression data were normalized using RNA spike-in. Two groups of human ESC samples are included: WIBR2, WIBR3 and WIN1 human ESCs derived in the optimized naïve medium (5i/L/A or 6i/L/A, as indicated), and parental WIBR2 and WIBR3 human ESCs in primed human ESC medium. Correlation matrix of gene expression was clustered using Pearson correlation coefficients (PCCs). The average linkage hierarchical clustering of the Pearson correlation is shown in the heatmap. mEpiSCs, mouse EpiSCs; mESC, mouse ESC; miPSC, mouse iPSC.

FIG. 6B shows the gene ontology (GO) analysis showing up- and down-regulated gene categories with most significant p values between the naïve human conditions and primed human ESCs. FIG. 6C is a volcano plot showing fold change (x axis) between the naïve human ESC samples and primed human ESCs on all genes (left); volcano plot showing previously published fold change (x axis) between the naïve human ESC samples of Gafni et al. (2013) and primed human ESCs on all genes (right). The open circles are those that are log 2 fold change >1 and <−1 & meet a p<0.05. FIG. 6D shows the fold changes in expression of naïve pluripotency-associated transcripts in the naïve human ESC samples vs. primed hESCs (blue or black), and the naïve human samples published by Gafni et al. (2013) vs. primed human ESCs (red or grey). FIG. 6E shows, for comparison with (FIG. 6D), fold changes in expression of naïve pluripotency-associated transcripts in naïve mouse ESCs vs. primed mouse EpiSCs were curated from a previously published study (Najm et al., 2011). FIG. 6F shows the quantitative gene expression analysis for NANOG and STELLA in human ESCs cultured in parallel in primed medium, the medium of Gafni et al. (2013) and 5i/L/FA. FIG. 6G shows single molecule (sm) RNA FISH analysis using OCT4 and NANOG probes in WIBR2 human ESCs cultured in primed medium, the medium of Gafni et al. (2013) or 5i/L/A. FIG. 6H shows single molecule (sm) RNA FISH analysis using OCT4, NANOG, KLF4 and REX1 probes in human ESCs cultured in primed medium, the medium of Gafni et al. (2013) or 5i/L/A.

FIG. 7A-7E show the ChIP-Seq tracks for H3K4me3 and H3K27me3 at four classes of genes: (FIG. 7A) developmental genes that are bivalent in the primed state and exhibit loss of H3K27me3 in the naïve state; (FIG. 7B) naïve pluripotency genes that are bivalent in the primed state and exhibit loss of H3K27me3 in the naïve state; (FIG. 7C) naïve pluripotency genes that acquire H3K4me3 in the naïve state; (FIG. 7D) master transcription factors that have a signal for H3K4me3, but not H3K27me3, in both naïve and primed states; (FIG. 7E) ChIP-Seq tracks for H3K4me3 and H3K27me3 at the DUSP6 and SOX11 loci in WIBR2 human ESCs cultured under primed (red or grey) or naïve 6i/L/A (blue or black) conditions. FIG. 7F shows the ChIP-Seq analysis for H3K4me3 and H3K27me3 at Polycomb target genes in WIBR2 human ESCs cultured in primed medium (left) or naïve 6i/L/A medium (right). FIG. 7G shows average H3K4me3 and H3K27me3 signal at Polycomb target genes in WIBR2 human ESCs cultured in primed medium (red or grey) or naïve 6i/L/A medium (blue or black).

FIG. 8A: southern blot analysis confirming deletion of the PE in OCT4-GFP ESCs and the removal of floxed PGK-puro cassette. NdeI-digested genomic DNA was hybridized with 5' and 3' external probes. Expected fragment size: WT (wild type) =5.6 kb, T (targeted)=6.4 kb, PEKO (targeted allele after PGK-puro removal)=4.6 kb. FIG. 8B: phase and GFP images of OCT4-ΔPE-GFP+ cells obtained after DOX induction of lentiviral KLF2+NANOG. Following primary infection, WIBR3 human ESCs containing the OCT4-ΔPE-GFP reporter allele were trypsinized and treated with hESM, 2i/L or 2i/L/DOX for one week. FIG. 8C: immunofluorescence staining for OCT4 in a clonal line of OCT4-ΔPE-GFP-positive cells derived in 2i/L/DOX, and a clonal line of OCT4-ΔPE-GFP-negative pNSCs derived in 2i/L. FIG. 8D: quantitative gene expression analysis for EGFP, SOX2, PRMD14 and PAX6 in clonal OCT4-ΔPE-GFP+ human ESC lines generated in 2i/L/DOX, secondary primed cells generated by withdrawal of DOX and expansion in conventional hESM, and clonal lines of OCT4-ΔPE-GFP-negative pNSCs derived in 2i/L.

FIG. 9A: raw data obtained from high-throughput flow cytometric analysis of the proportion of OCT4-ΔPE-GFP+ cells in 96 wells supplemented with a kinase inhibitor library (n=2). FIG. 9B: quantitative gene expression analysis for STELLA, KLF4, PRDM14 and SOX2 in a clonal line of OCT4-ΔPE-GFP+ cells maintained in 2i/L/DOX or for five passages without DOX in the presence of each candidate compound. FIG. 9C: flow cytometric analyses of the proportion of viable (DAPI-negative)

and OCT4-ΔPE-GFP+ cells in 2i/L/DOX or two passages after DOX withdrawal in 2i/L/SB590885 (1 μM).

Figures 1, 10A:
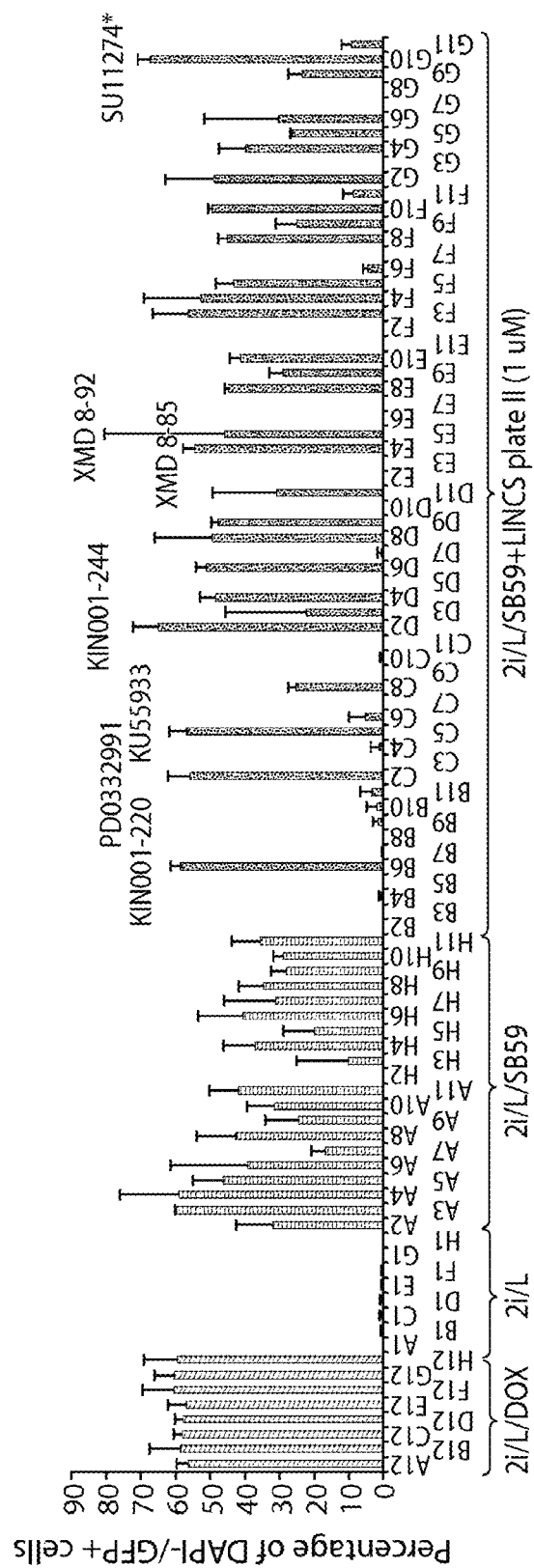
Figures 2, 10A:
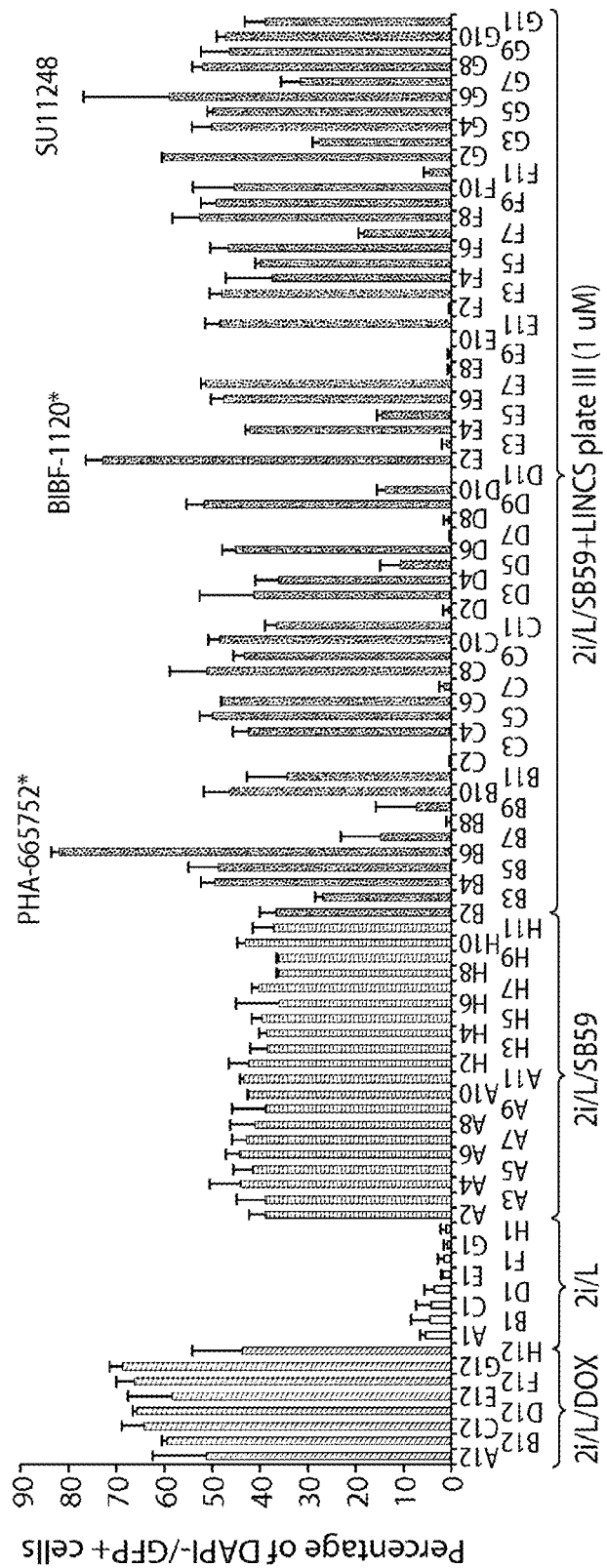
Figures 3, 10A:
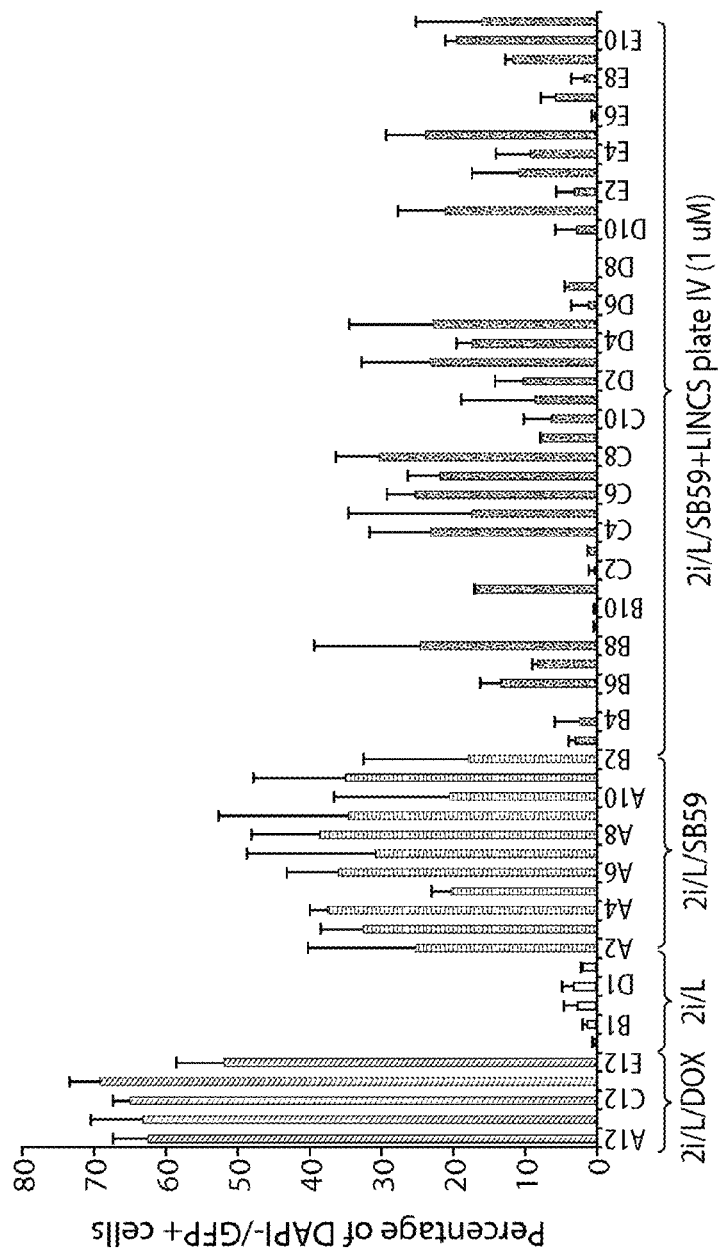
Figure 10C:
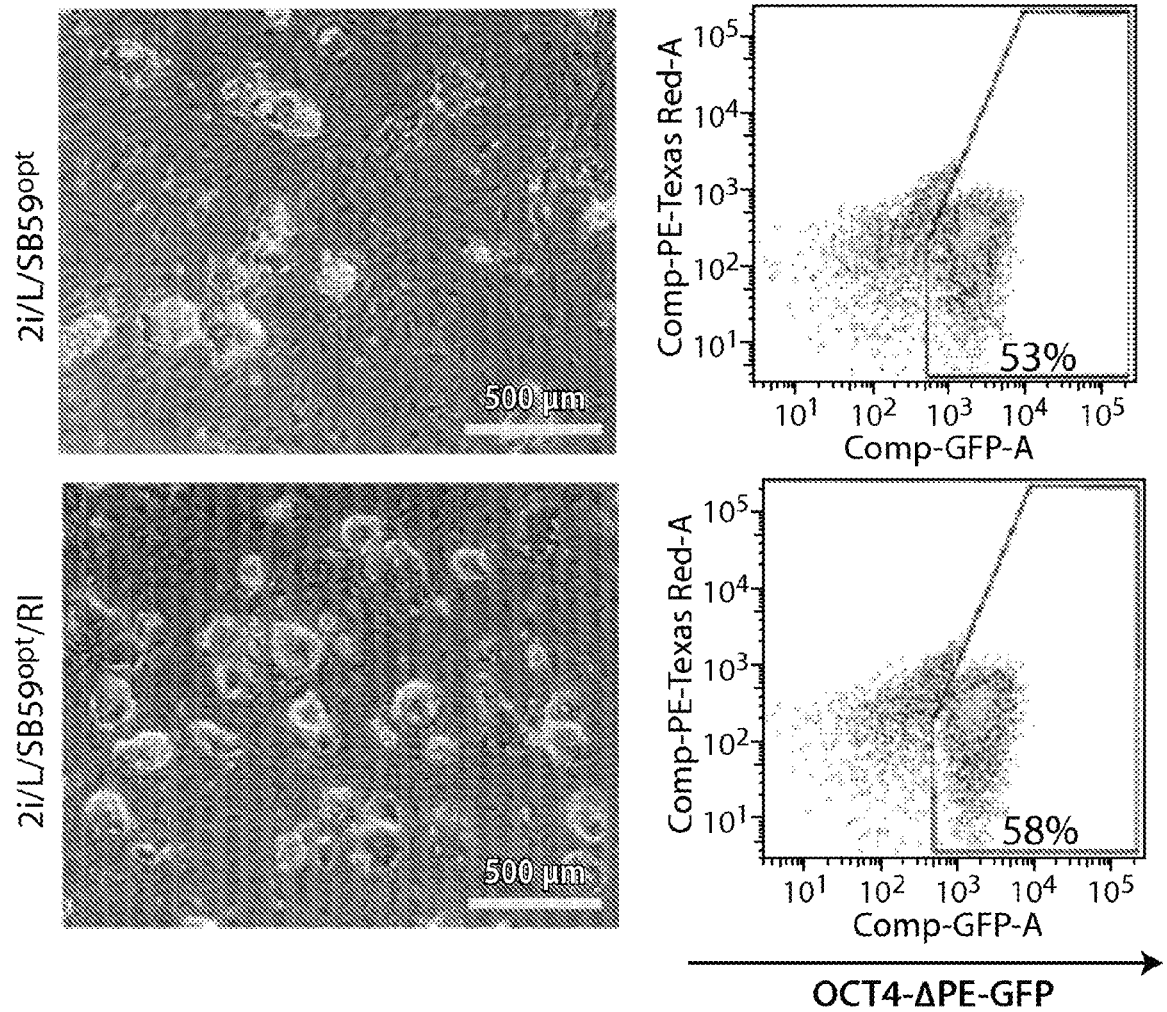
Figure 10D:
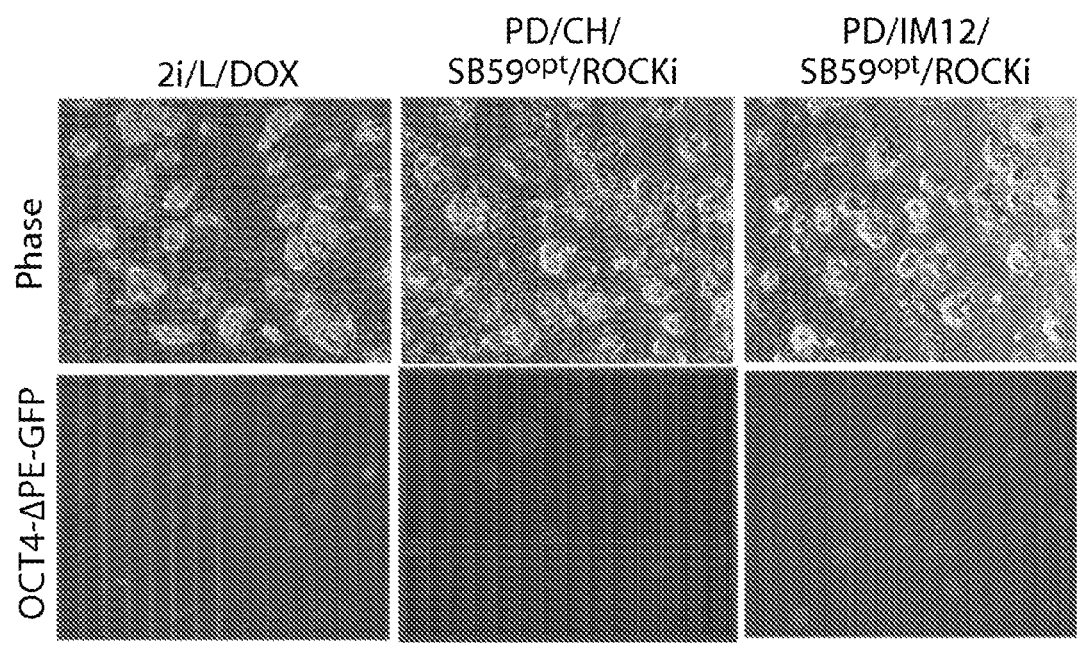

FIGS. 10A-1-10D show the optimization of medium for maintaining viable OCT4-ΔPE-GFP+ cells (associated with FIG. 3A-3H). FIG. 10A1-10A3: raw data obtained from high-throughput flow cytometric analysis of the proportion of DAPI-/OCT4-ΔPE-GFP+ cells in 96 wells supplemented with three plates of a kinase inhibitor library in the presence of the primary hit compound SB590885 (n=2). FIG. 10B: hit compounds from a viability screen using a clonal line of WIBR3 OCT4-ΔPE-GFP+ ESCs established in 2i/L/DOX. FIG. 10C: phase images and flow cytometric analyses of OCT4-ΔPE-GFP+ cells maintained in 2i/L/SB590885 (0.5 μM)±ROCK inhibitor Y-27632 (10 μM) for two passages. FIG. 10D: phase and GFP images of OCT4-ΔPE-GFP+ cells maintained for four passages in 2i/L/DOX, 2i/L/SB590885 (0.5 μM)+ROCK inhibitor Y-27632 (10 μM) or the same medium in which CHIR99021 was replaced with an alternative GSK3 inhibitor, IM-12 (1.0 μM).

Figure 11A:
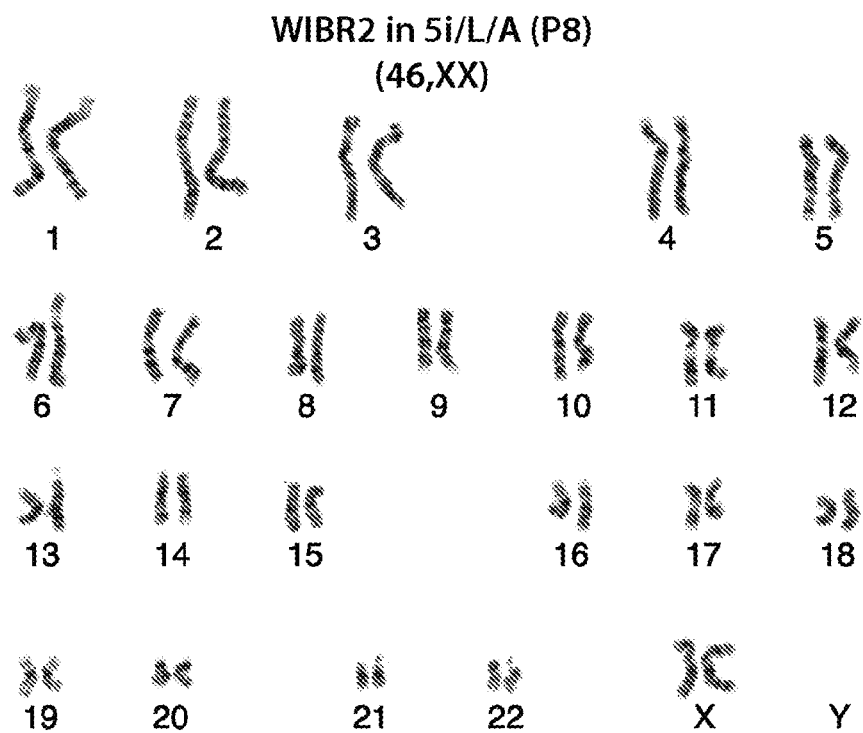
Figure 11B:
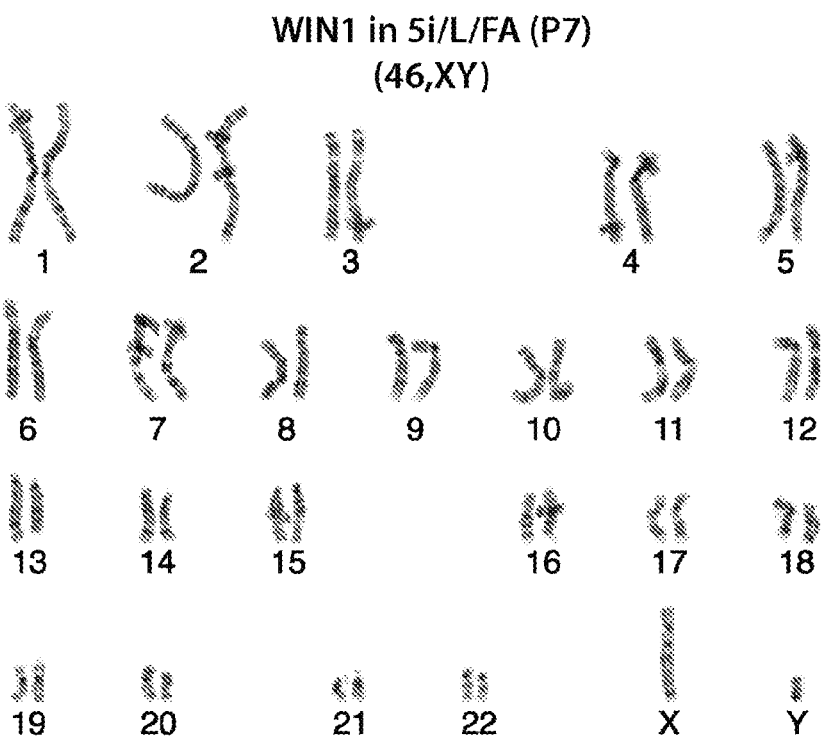
Figure 11C:
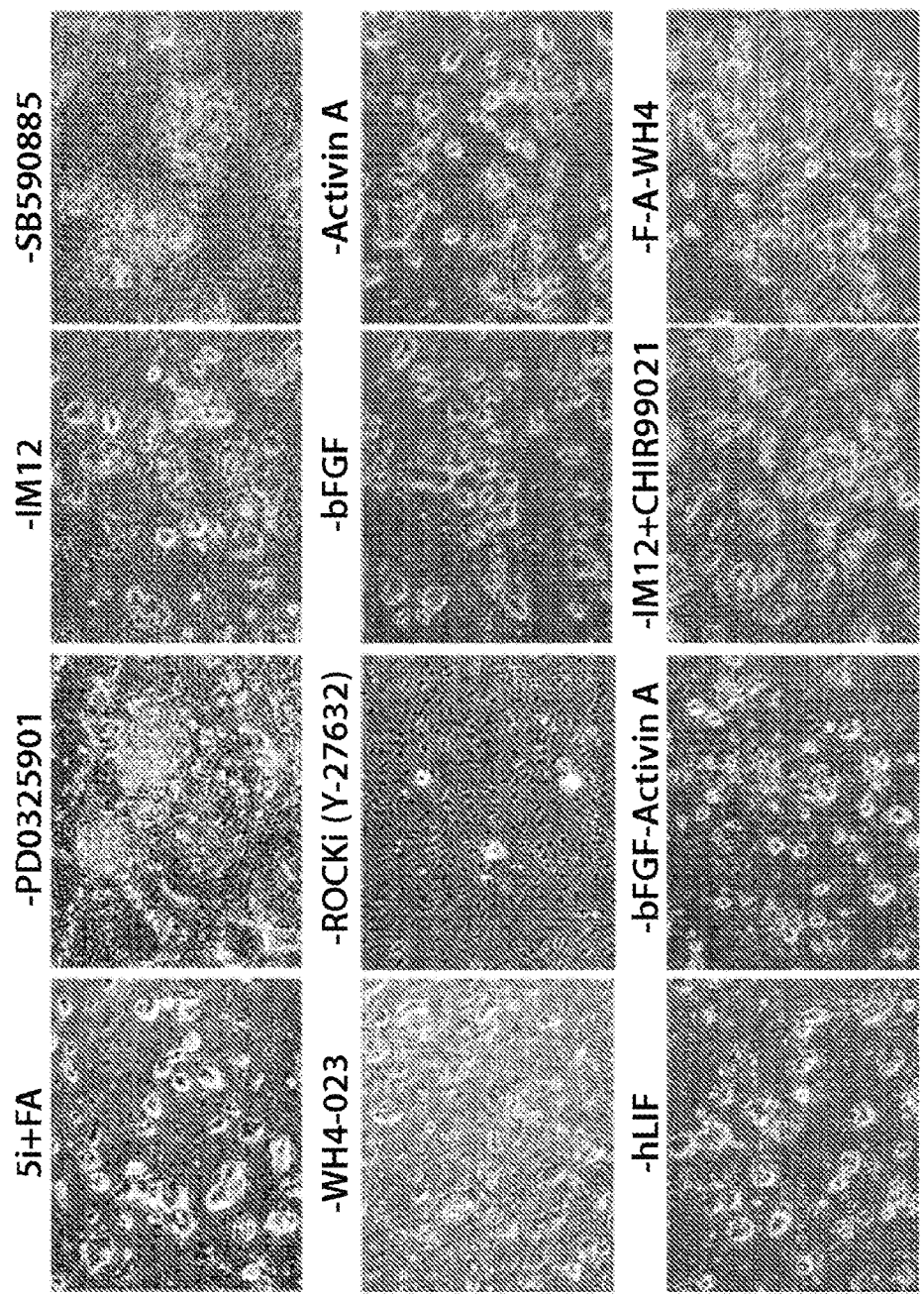

FIGS. 11A-11C show the direct conversion of conventional human ESCs to naïve pluripotency in 5i/L [associated with FIGS. 4A-4G]. FIG. 11A: karyotype analysis of naïve human ESCs WIBR2 (P8 in 5i/L/A). Cytogenetic analysis was performed on 20 metaphase cells. FIG. 11B: karyotype analysis of naïve human ESCs WIN1 (P7 in 5i/L/FA). Cytogenetic analysis was performed on 20 metaphase cells. FIG. 11C: phase images of OCT4-ΔPE-GFP+ cells three passages after withdrawal of individual inhibitors and growth factors.

Figure 12A:
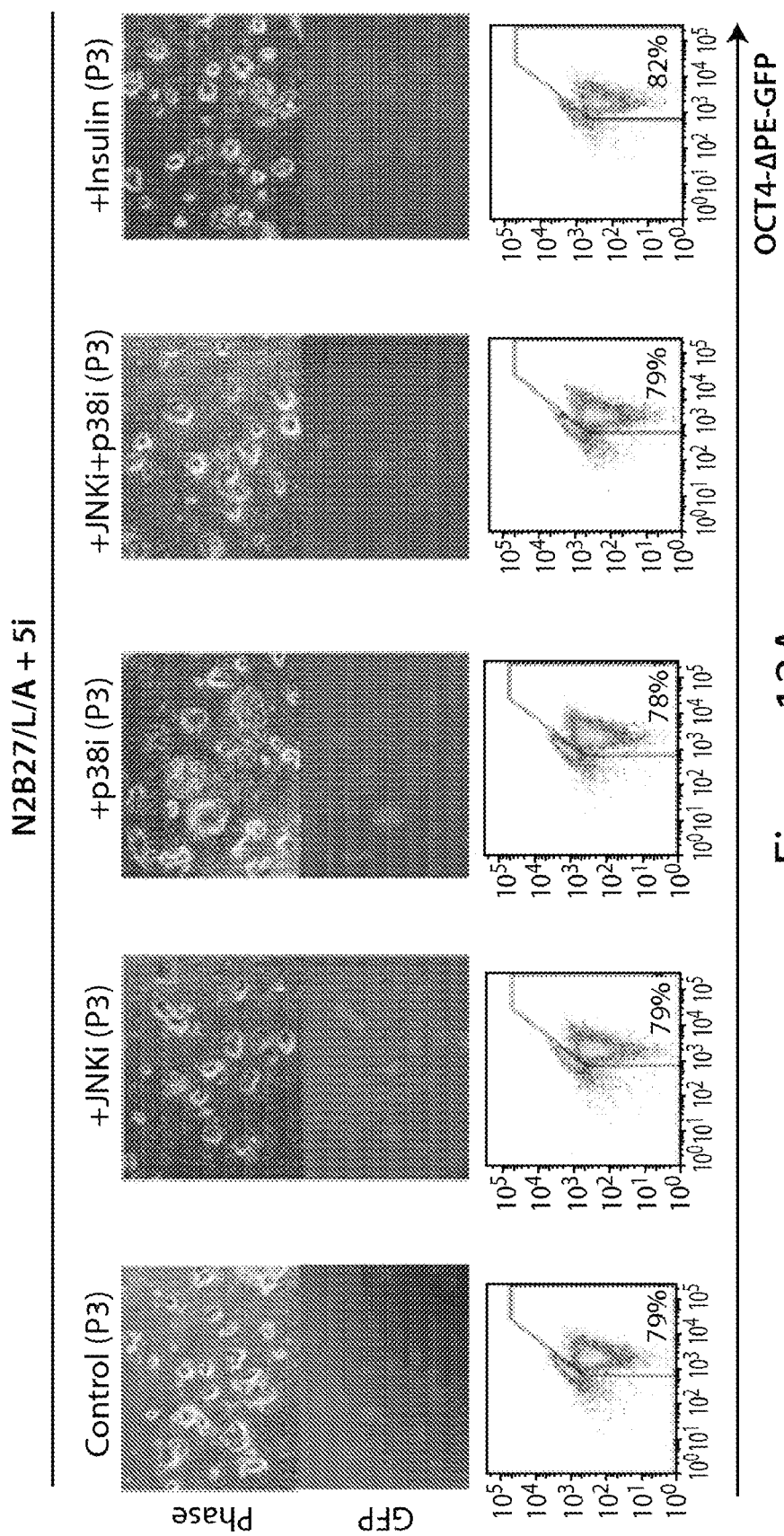
Figure 12B:
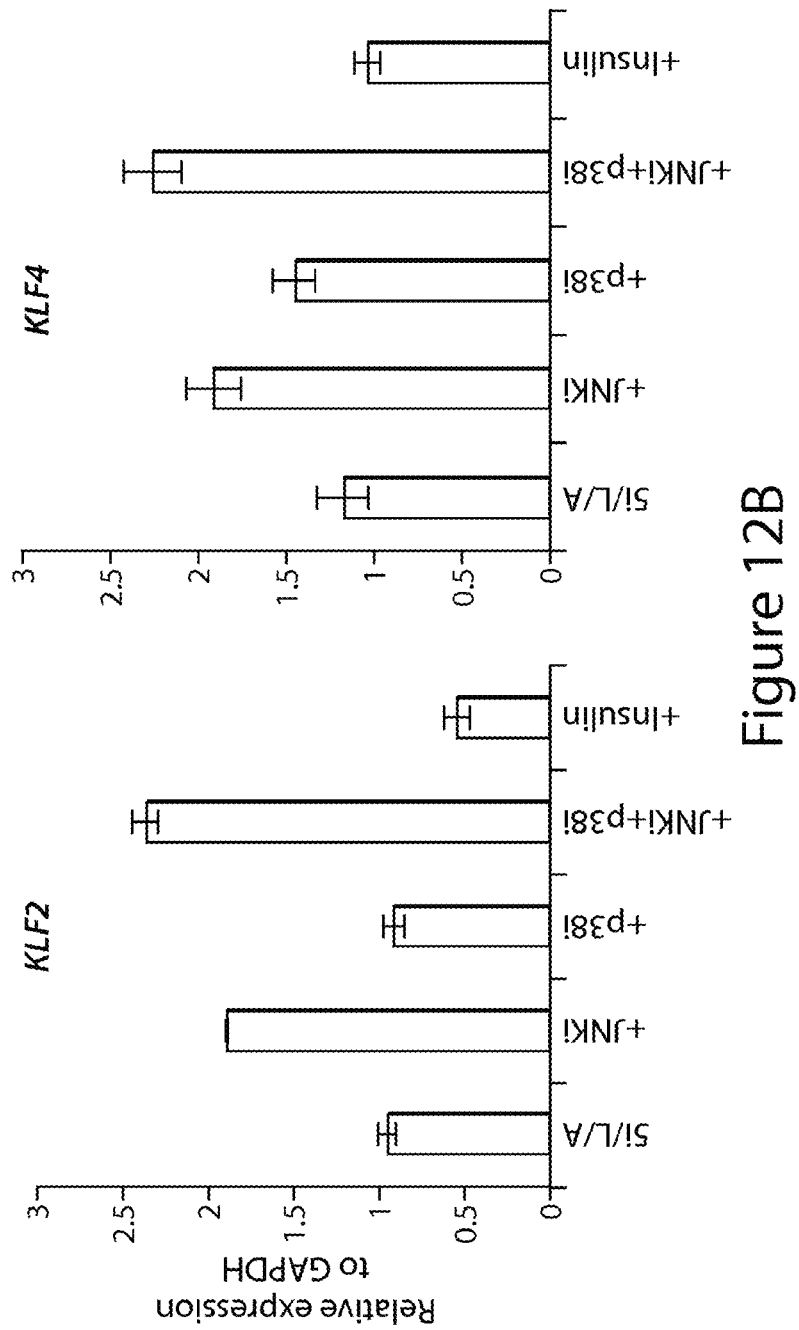
Figure 12C:
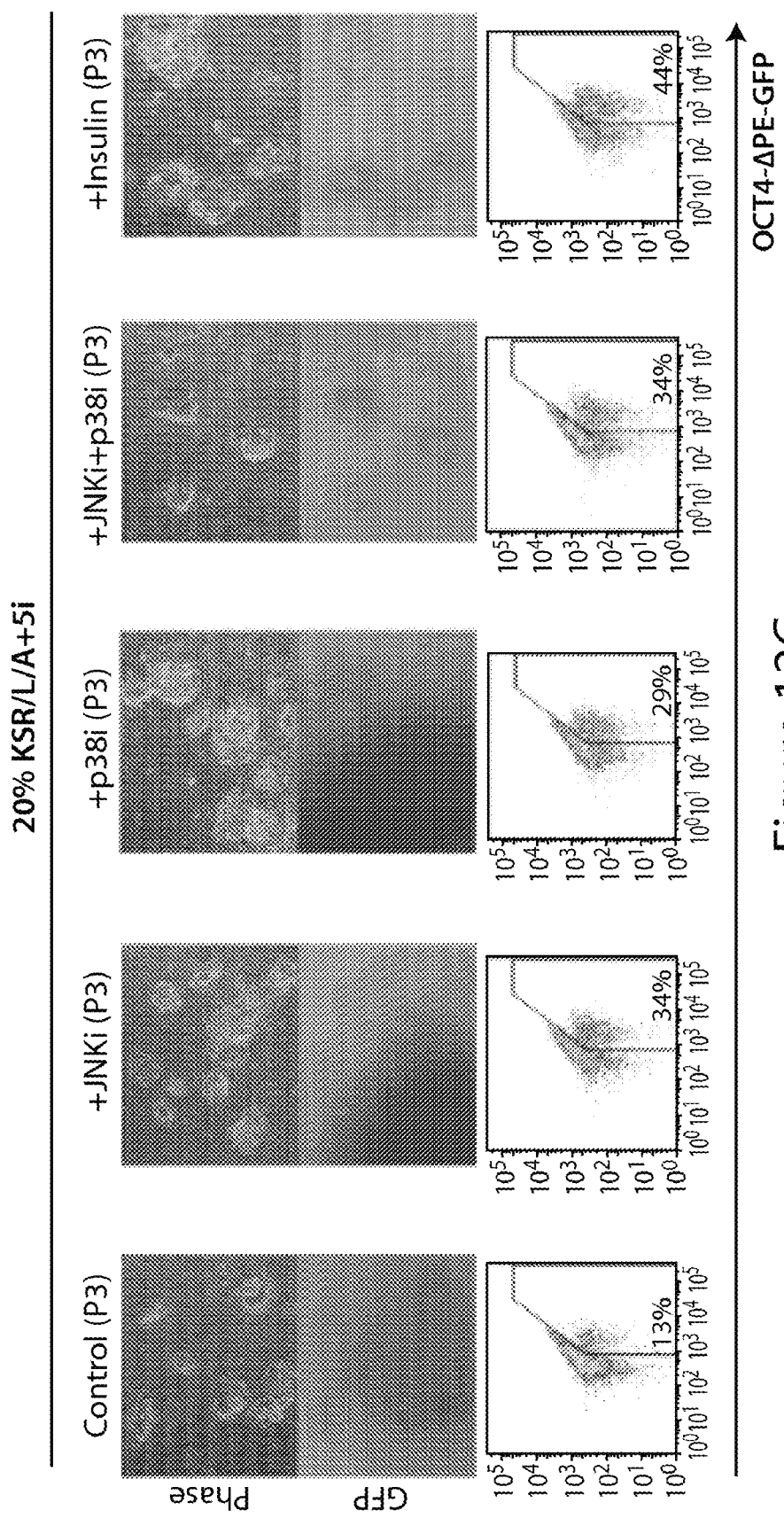

FIGS. 12A-12C show the evaluation of alternative culture conditions for naïve human pluripotency [associated with FIGS. 5A-5F]. FIG. 12A: phase and fluorescence images (Top) and flow cytometric analysis of the proportion of OCT4-ΔPE-GFP+ cells (Bottom) in OCT4-ΔPE-GFP+ cells derived in 5i/L/FA and maintained for three passages in the presence of additional media additives, as indicated. FIG. 12B: quantitative gene expression analysis for KLF2 and KLF4 in OCT4-ΔPE-GFP-positive naïve human ESCs cultured in 5i/L/A and supplemented with various components of the medium of Gafni et al. (2013). FIG. 12C: phase and fluorescence images (Top) and flow cytometric analysis of the proportion of OCT4-ΔPE-GFP+ cells (Bottom) in OCT4-ΔPE-GFP+ cells derived in 5i/L/FA and maintained for three passages in 20% KSR basal medium supplemented with the media additives described in (FIG. 12A).

Figure 13A:
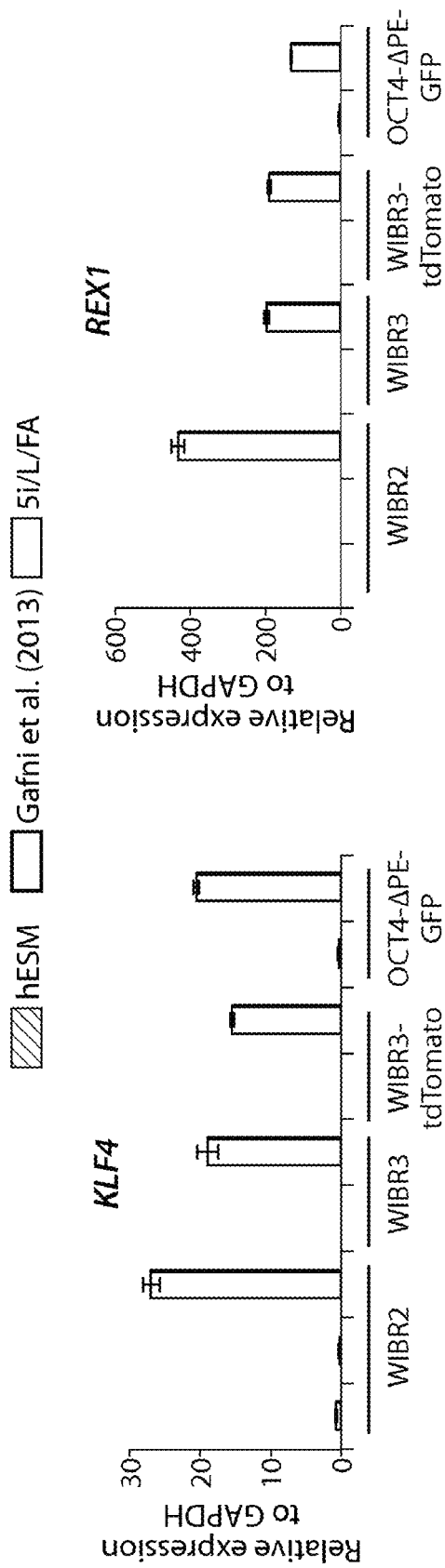
Figure 13B:
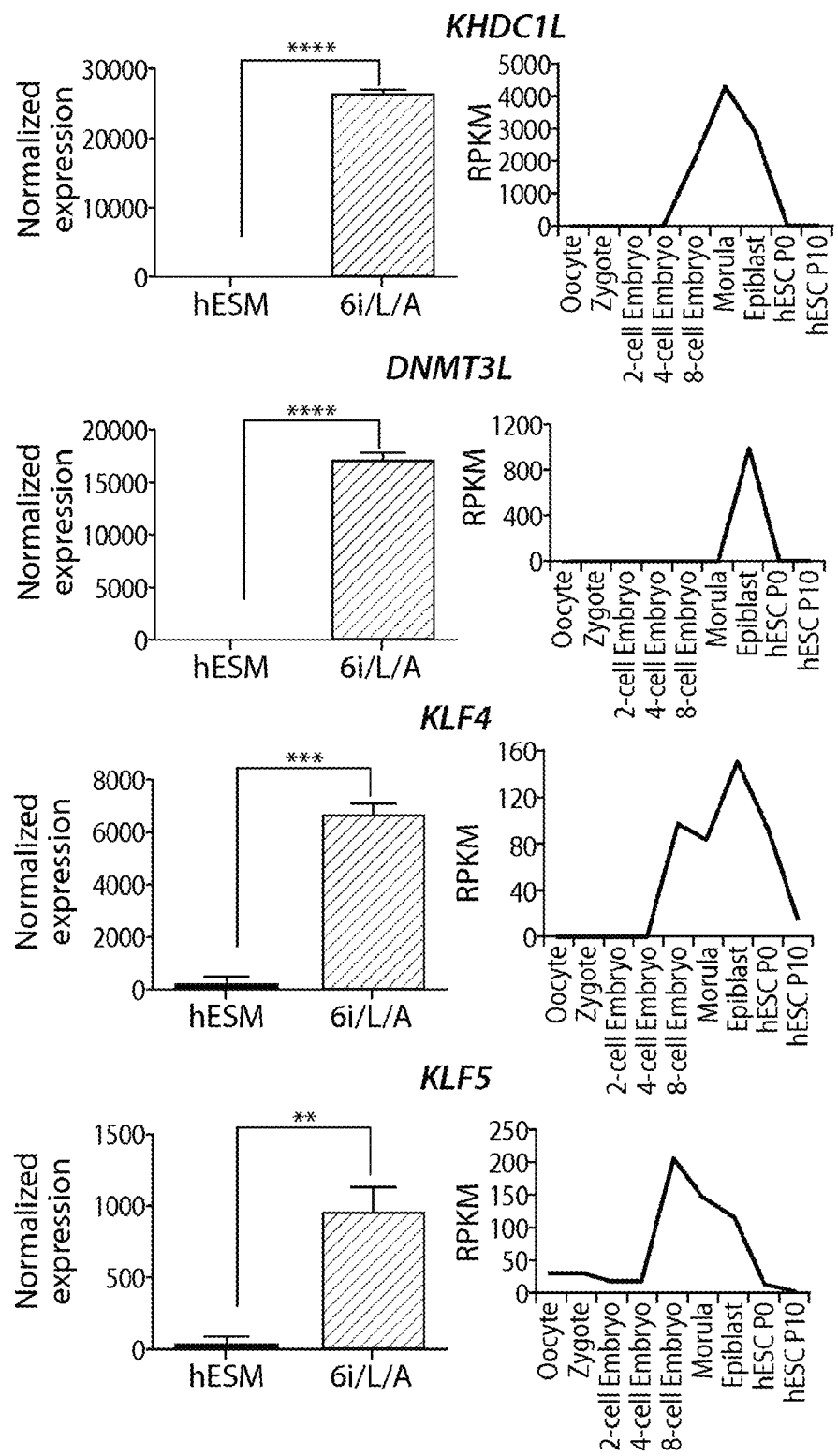
Figure 13B:
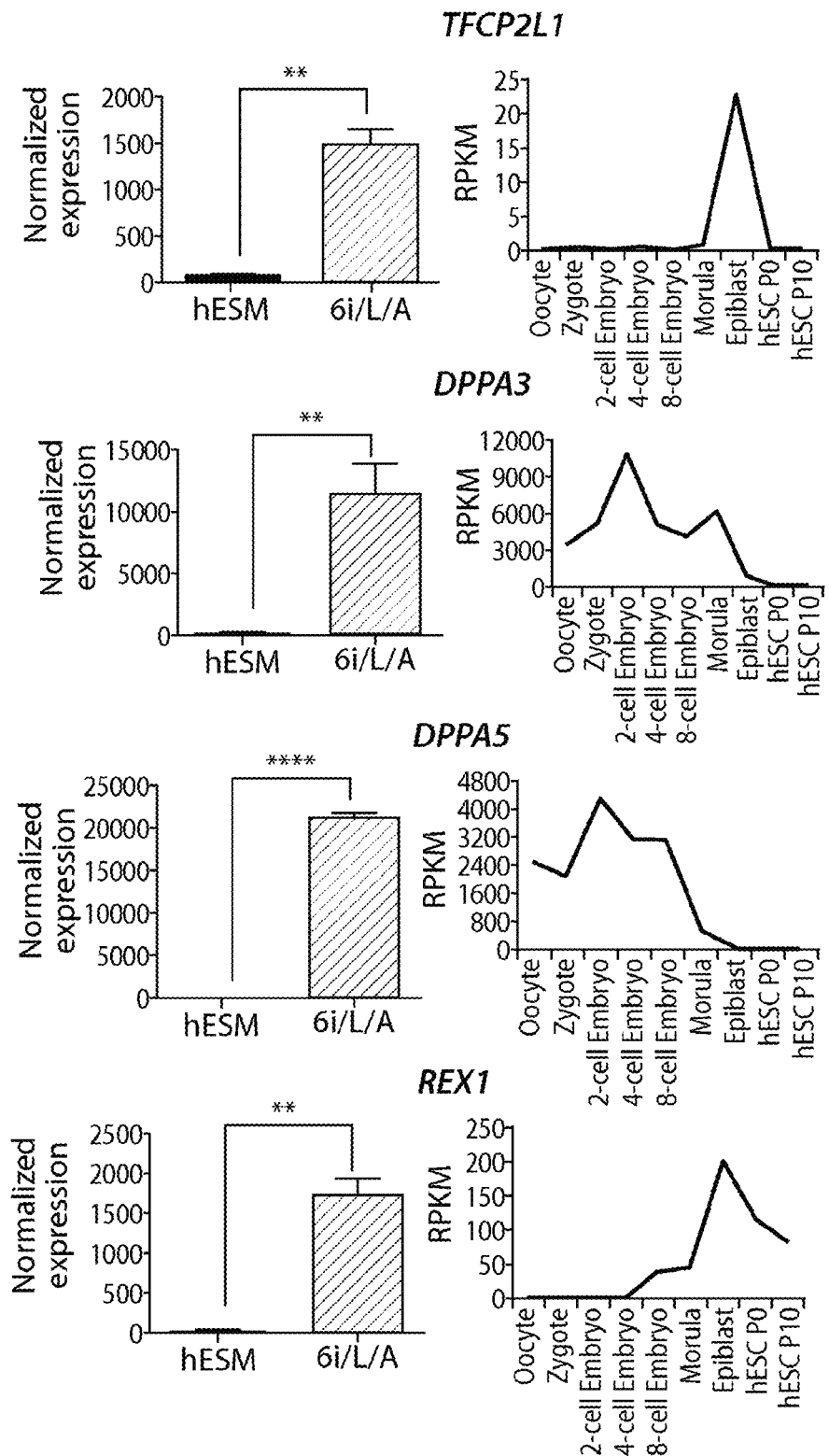
Figure 13B:
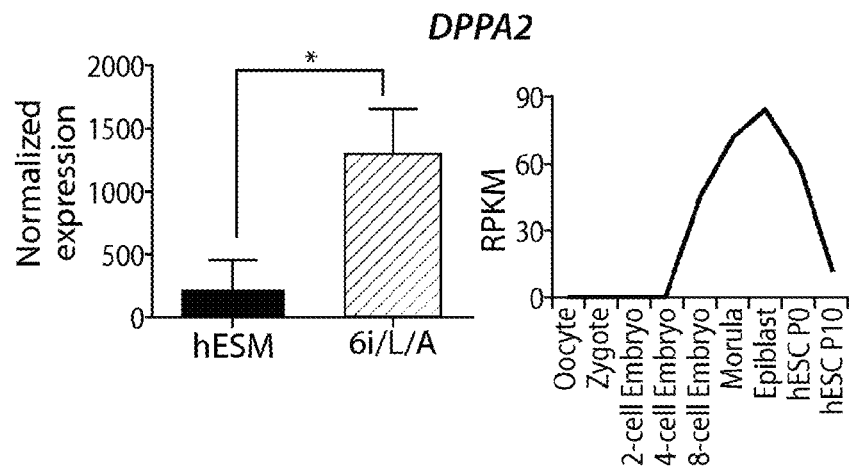
Figure 13C:
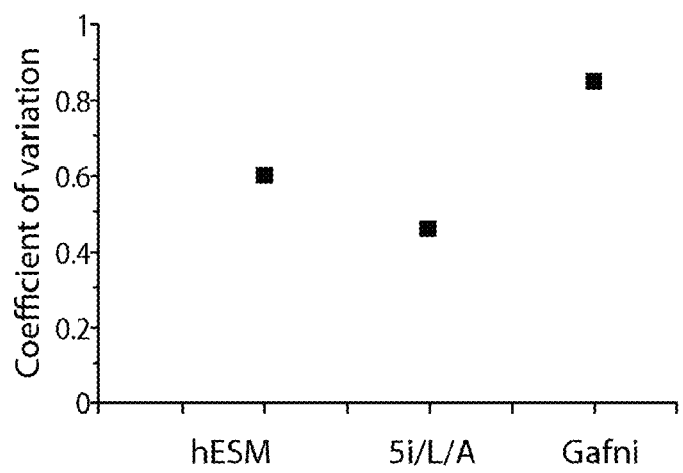

FIGS. 13A-13C show the transcriptional profiling of naïve human ESCs in 5i/L/A and 6i/L/A [associated with FIGS. 6A-6H]. FIG. 13A: quantitative gene expression analysis for KLF4 and REX1 in human ESCs cultured in parallel in primed medium, 5i/L/FA and the medium of Gafni et al. (2013). FIG. 13B: expression profile of transcripts upregulated in 6i/L/A during human embryonic development. For each gene, the normalized expression values in human ESCs cultured in 6i/L/A vs. primed human ESCs are indicated (Left). An unpaired two-tailed t test was performed to establish the degree of significance. Expression of the corresponding transcript is shown at nine stages of human pre-implantation development, as detected by single cell RNA-Seq profiling (Yan et al., 2013) (Right). This comparison indicates that naïve-associated transcripts upregulated in 6i/L/A are enriched at the morula/epiblast stage of human development when compared to human ESCs at passage 0 or passage 10. FIG. 13C: variability in NANOG expression compared between single human ESCs cultured in primed medium, 5i/L/A or the medium of Gafni et al. (2013).

Figure 14A:
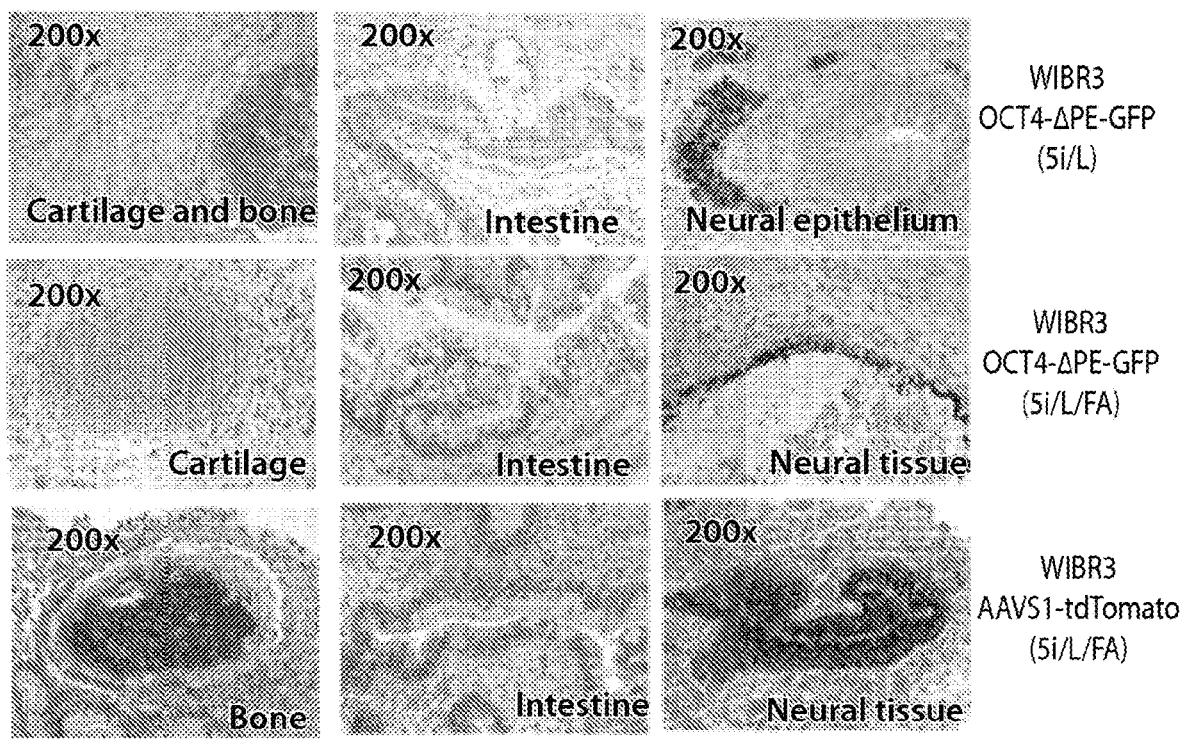
Figure 14B:
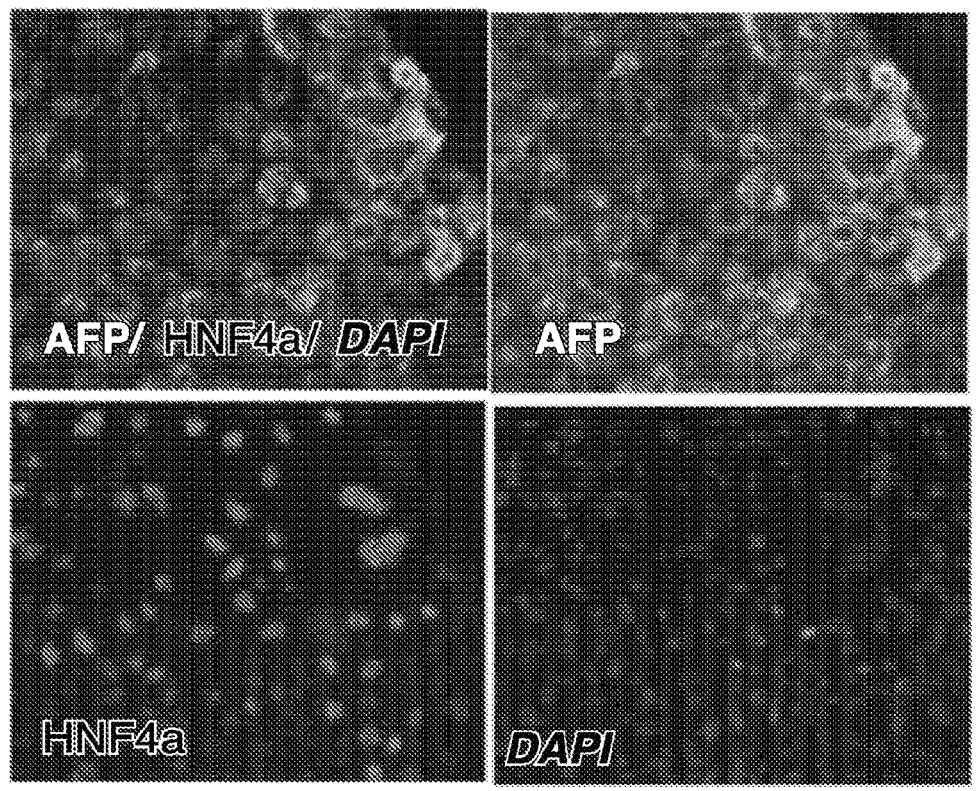

FIGS. 14A-14C show the developmental potential of naïve human ESCs in 5i/L/A. FIG. 14A: teratomas generated from WIBR3 OCT4-ΔPE-GFP-positive human ESCs derived and maintained in 5i/L±FA and WIBR3 AAVS1-tdTomato human ESCs in 5i/L/FA. Representative tissues of the three germ layers are indicated. FIG. 14B: immunofluorescence staining for AFP and HNF4a following 20d of hepatic differentiation in naïve WIBR2 human ESCs derived and maintained in 5i/L/A. FIG. 14C: table summarizing injections of human ESCs maintained in 5i/L/FA (top) or the medium of Gafni et al. (2013) (bottom) in mouse embryos. C1-AAVS1-GFP human ESCs in the medium of Gafni et al. (2013) were cultured on MEFs, gelatin/vitronectin or matrigel prior to injection. (*) E10.5 embryos injected with human ESCs cultured in 5i/L/FA and the medium of Gafni et al. (2013) were mixed during collection, but none were identified as positive. (**) 30 injected embryos were lost during transfer.

Figure 15A:
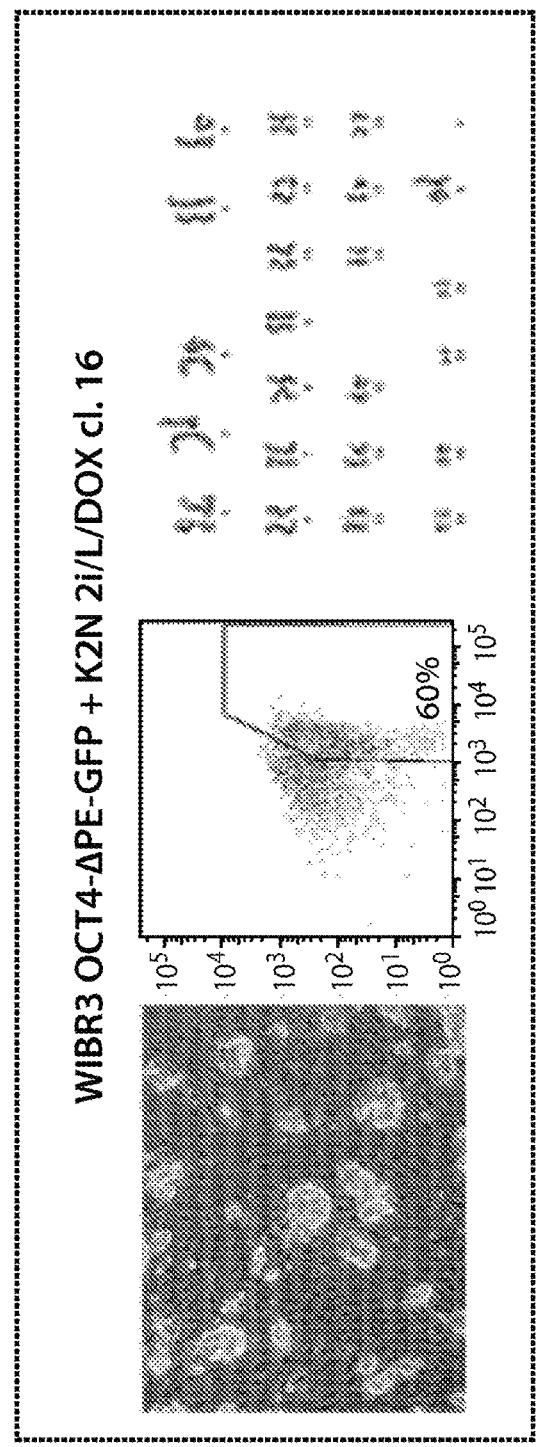
Figure 15B:
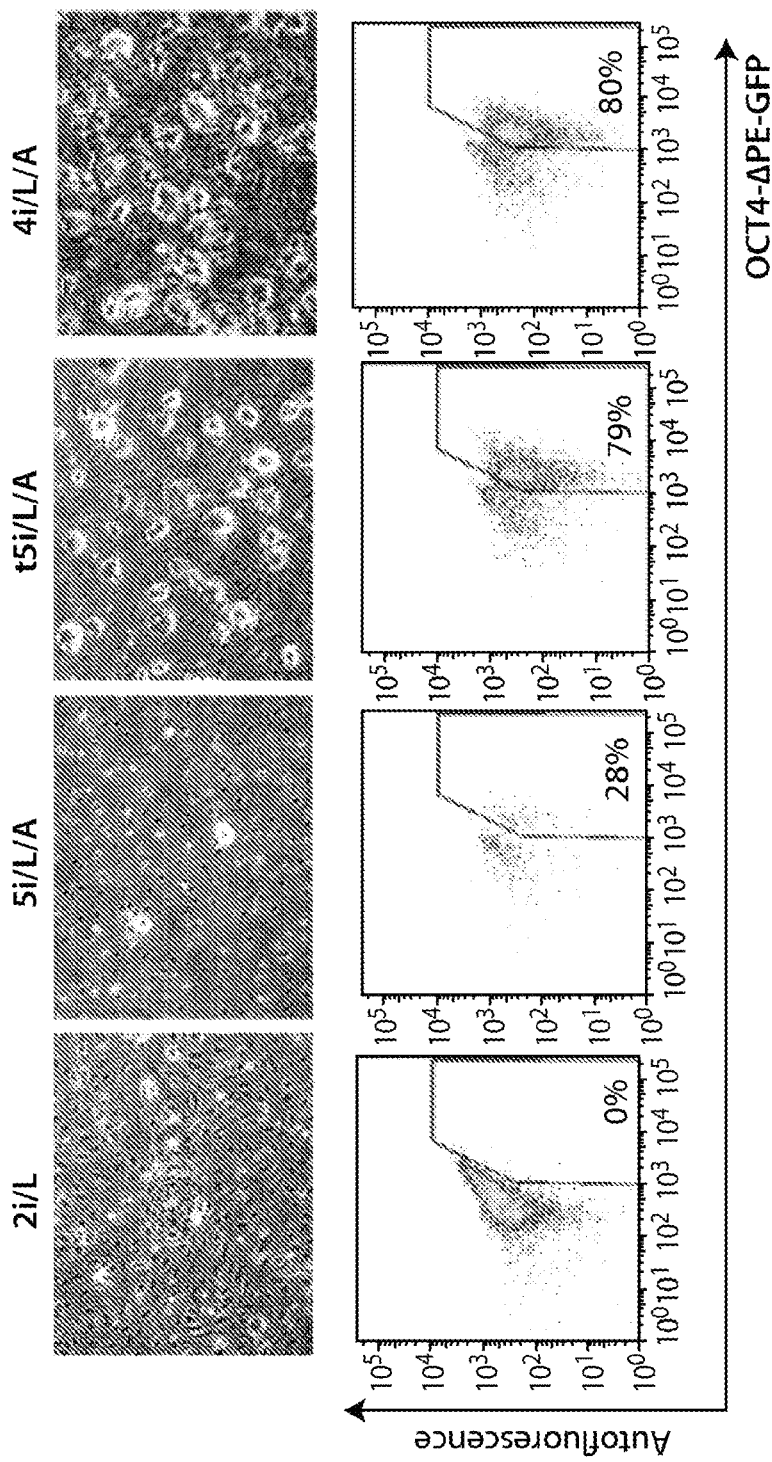
Figure 15C:
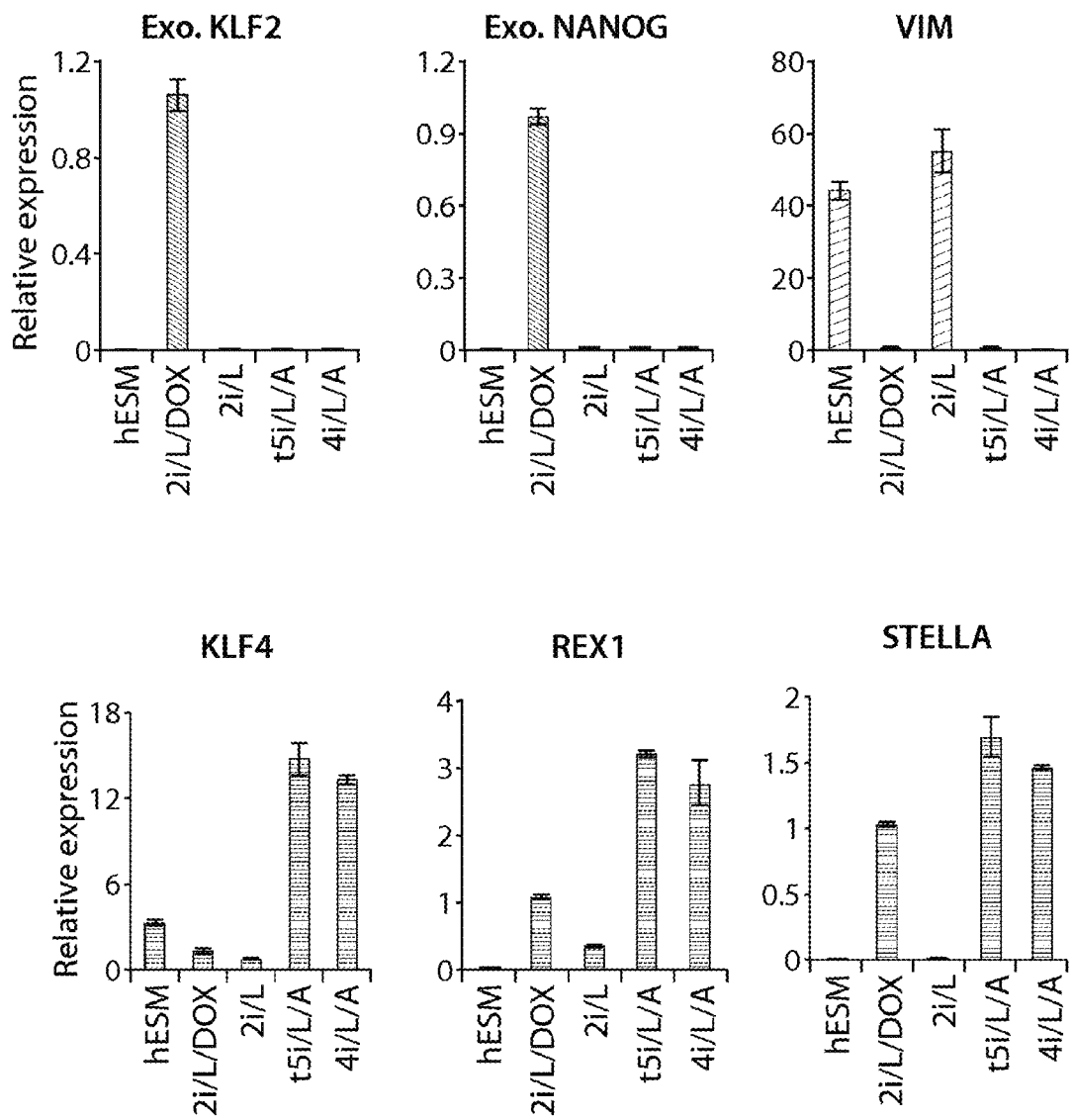

FIGS. 15A-15C show that the proliferation of naïve human embryonic stem cells is enhanced by reduction or removal of GSK3 inhibition. FIG. 15A: transgene-dependent naïve human embryonic stem (ES) cell line used to titrate the concentrations of inhibitors in 5i/L/A (see Theunissen et al., Cell Stem Cell, 2014). This subclone of WIBR3 is dependent on Doxycycline (DOX) to maintain expression of two lentiviral transgenes, KLF2 and NANOG. Left, phase image shows colony morphology in 2i/L/DOX. Middle, flow cytometric quantification shows the proportion of cells positive for the OCT4-ΔPE-GFP reporter in 2i/L/DOX. Right, this cell line has a normal (46,XX) karyotype. FIG. 15B: titration assay to attain optimal concentrations of small molecule inhibitors for maintenance of naïve human ES cells. Top, phase images showing colony morphology after sequential passaging by single cell dissociation at low density (1:10) in four different conditions: 2i/L, 5i/L/A, t5i/L/A (0.2 μM GSK3 inhibitor IM12) and 4i/L/A (removal of GSK3 inhibitor IM12). Bottom, flow cytometric quantification shows the proportion of cells positive for the OCT4-ΔPE-GFP reporter in each condition. FIG. 15C: quantitative RT-PCR (qRT-PCR) analysis confirming the downregulation of exogenous KLF2 and NANOG transgenes and primed marker VIMENTIN and upregulation of naïve markers KLF4, REX1 and STELLA in t5i/L/A and 4i/L/A. Error bars indicate one standard deviation.

Figure 16:
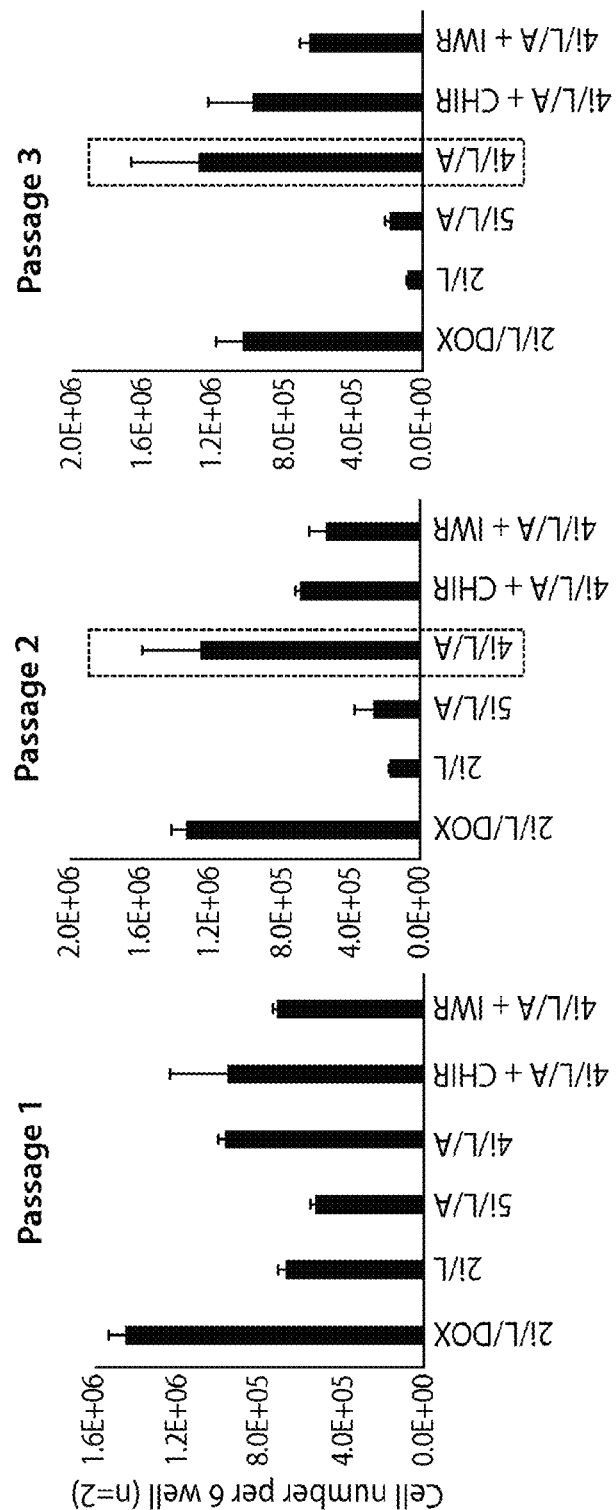

FIG. 16 shows the quantification of the proliferation of naïve human cells in presence of different Wnt signal modulators. Quantification of cell number in naïve culture conditions supplemented with distinct Wnt signal modulators after withdrawal of DOX from transgene-dependent naïve human ES cells (see FIG. 15A). 1×105 cells were seeded per individual well of a 6 well plate and cells were dissociated and re-seeded at 1:5 density for three successive passages. Cell numbers at successive passages were recorded in six conditions (n=2): 2i/L/DOX (control), 2i/L, 5i/L/A, 4i/L/A (removal of GSK3 inhibitor IM12), 4i/L/A+CHIR99021 (1 μM), and 4i/L/A+IWR1 (2.5 μM). At passages 2 and 3 the proliferation was significantly elevated in 4i/L/A compared to 5i/L/A. Replacing IM12 with alternative GSK3 inhibitor CHIR99021 or addition of the Wnt inhibitor IWR1 did not further stimulate the proliferation of naïve human cells.

Figure 17A:
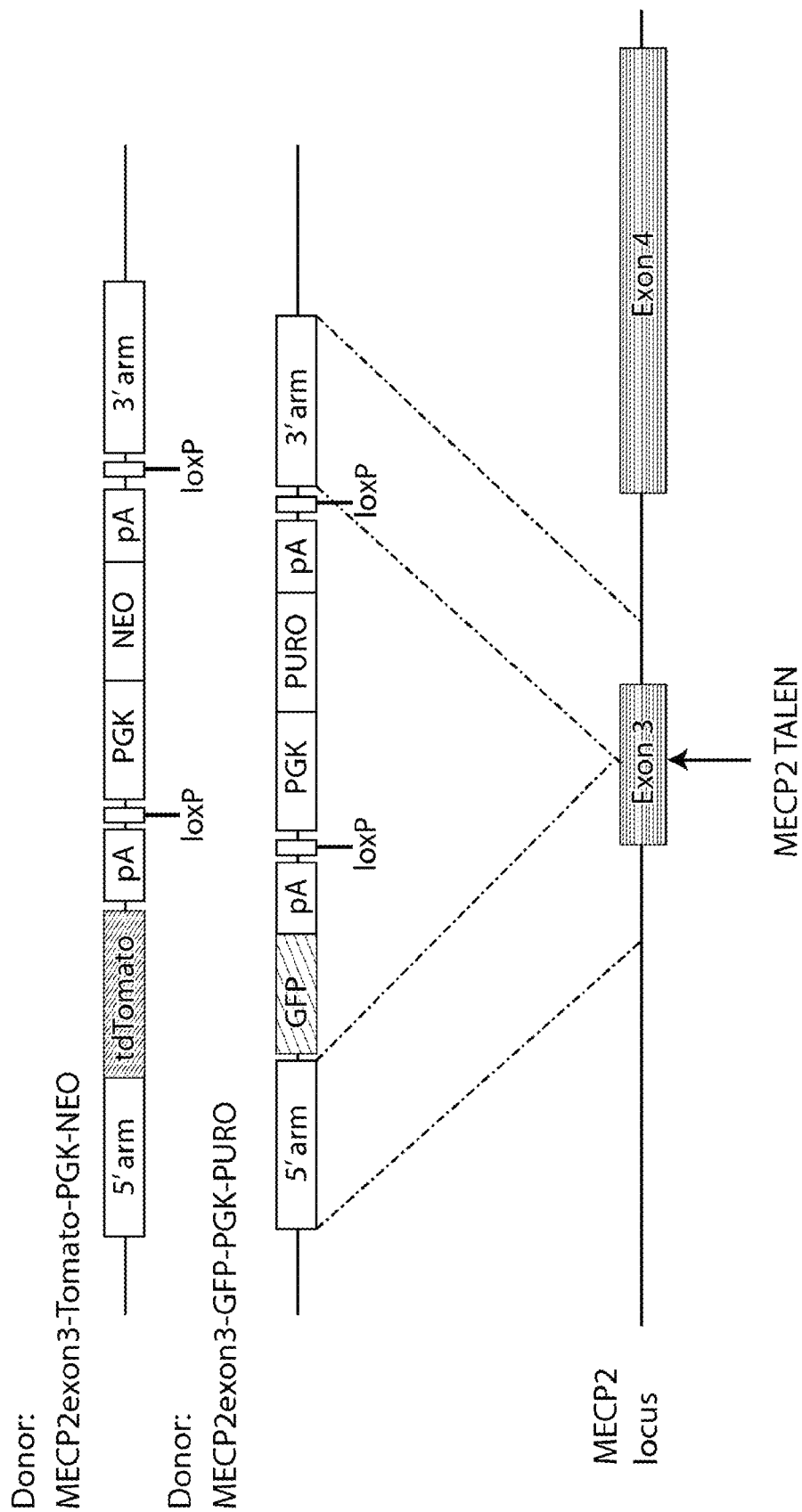
Figure 17B:
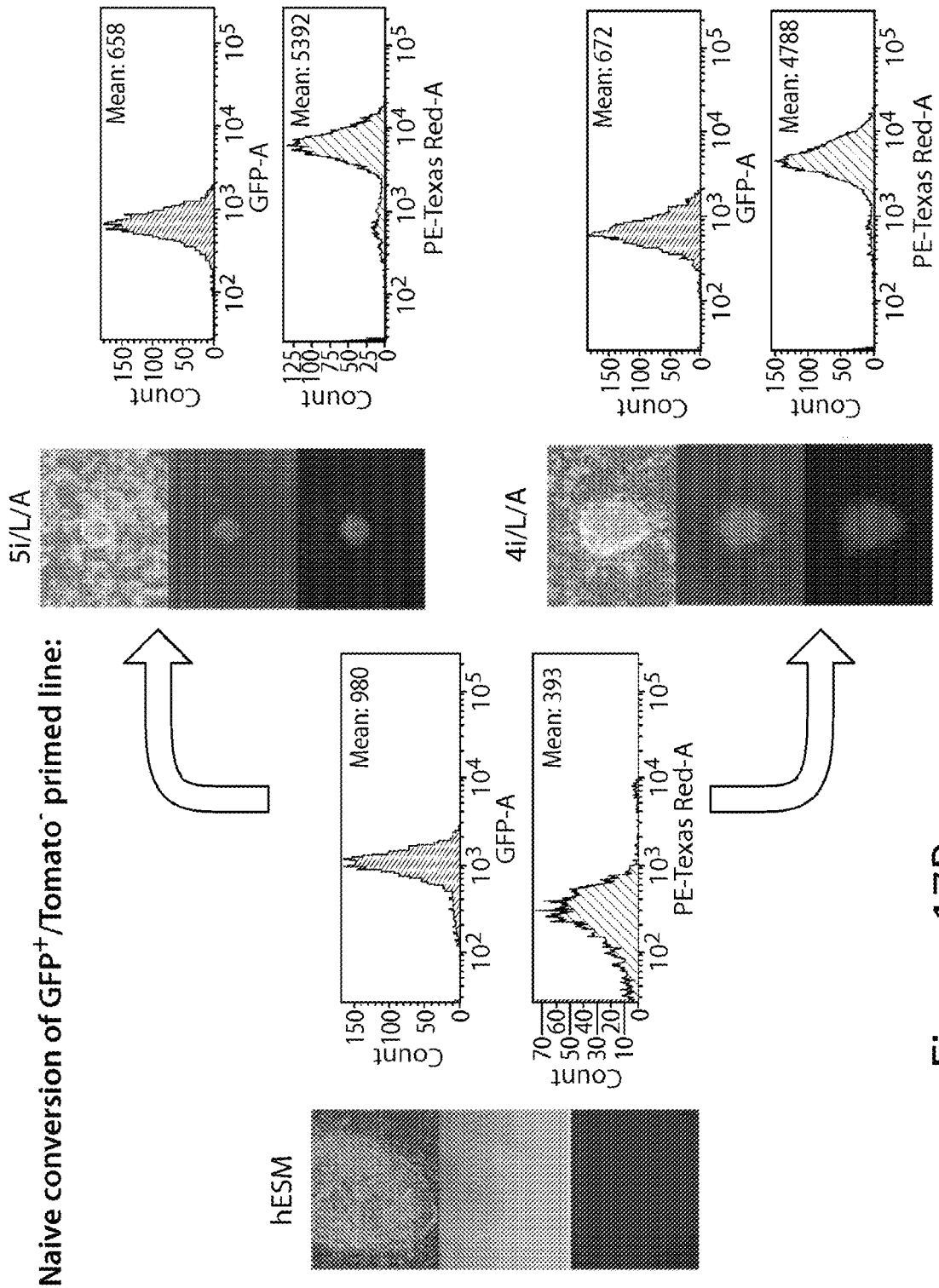
Figure 17C:
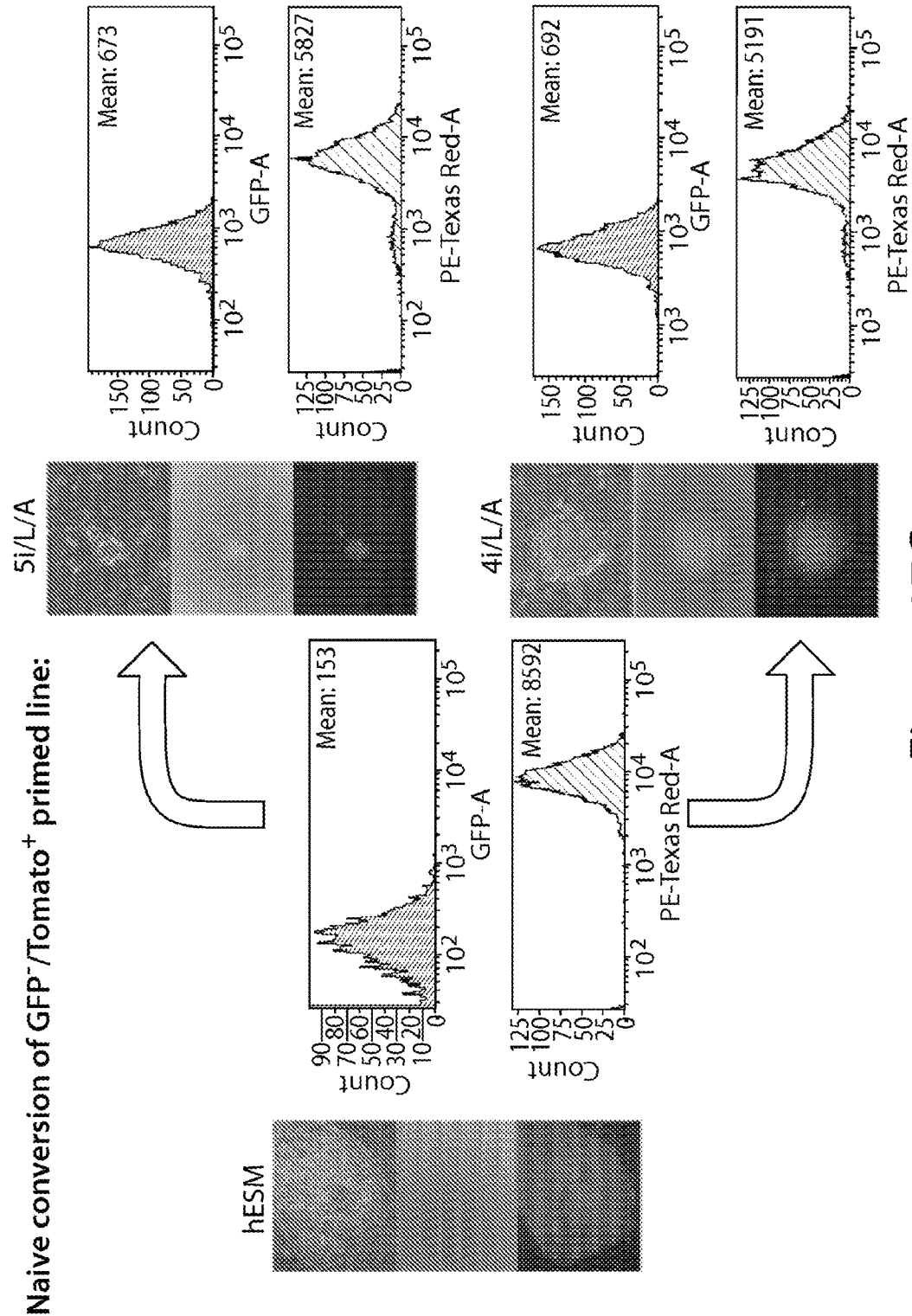

FIGS. 17A-17C show the induction of naïve human pluripotency in 5i/L/A or 4i/L/A is associated with X chromosome reactivation. FIG. 17A: a reporter system for X chromosome status of human ES cells was engineered by TALEN-mediated targeting of both alleles of the X-linked MECP2 gene with fluorescent reporters. FIG. 17B: starting from a single color (GFP-positive) primed line, conversion to the naïve state in 5i/L/A or 4i/L/A (-IM12) results in activation of the tdTomato-labelled allele while GFP activity is maintained. FIG. 17C: starting from a single color (tdTomato-positive) primed line, conversion to the naïve state in 5i/L/A or 4i/L/A (-IM12) results in activation of the GFP-labelled allele while tdTomato activity is maintained. These results indicate that induction of naïve human pluripotency is accompanied by a switch towards biallelic expression of X-linked genes, which is confirmed by RNA FISH data (not shown).

DETAILED DESCRIPTION OF THE INVENTION

The present disclosure, in one aspect, is based on the identification of compounds (e.g., compounds of any one of Formulae (A) to (L), and pharmaceutically acceptable salts, solvates, hydrates, polymorphs, co-crystals, tautomers, stereoisomers, isotopically labeled derivatives, and prodrugs thereof) that support self-renewal of naïve human ESCs. In particular, iterative chemical screening identified kinase inhibitors that induce and maintain OCT4 distal enhancer activity, a molecular signature of ground state pluripotency, when applied directly to conventional human ESCs. These inhibitors generate a homogeneous population of human pluripotent stem cells in which transcription factors associated with the ground state of pluripotency are highly upregulated. Comparison with previously reported naïve human ESCs indicates that the procedures defined herein capture a novel pluripotent state in humans that closely resembles mouse ESCs. Accordingly, aspects of the disclosure provide methods for converting the pluripotency state of a vertebrate (e.g., human) cell to a more naïve state. Also provided are naïve pluripotent vertebrate cells (e.g., human) and cell lines produced by the methods described herein. Some aspects of the invention also involve kits for converting the pluripotency state of a vertebrate (e.g., human) cell to a more naïve state.

Embryonic stem cells (ESCs) and induced pluripotent stem cells (iPSCs) have attracted much attention because of their potential to mature into virtually any cell type in the body. However, mouse ESCs and iPSCs have different growth factor requirements and provide a more reliable vehicle for directed differentiation as compared to human ESCs and iPSCs. It was thought for many years that these differences reflected variation between species. In 2007, however, two groups reported that novel stem cell lines derived from the post-implantation epiblast of mouse embryos, called EpiSCs, have properties similar to human ESCs (Brons et al., 2007; Tesar et al., 2007). These include a flat morphology, dependence on bFGF and activin signaling, and use of the OCT4 proximal enhancer element. The inner cell mass (ICM)-like state of mouse ESCs was described as "naïve," whereas EpiSCs and human ESCs were designated as "primed" (Nichols and Smith, 2009); the implication is that the primed state is prone to differentiate, whereas the naïve condition corresponds to the more immature "ground state" of pluripotency.

The present disclosure relates to the discovery that conventional human ESCs can be converted into a more immature/less restricted state (i.e., a more "naïve" pluripotent state) that extensively shares defining features with pluripotent mouse ESCs. Described herein are optimized conditions that enable the interconversion between conventional and naïve human ESCs in the absence of reprogramming factors, as well as the direct isolation of genetically unmodified naïve ESCs from human blastocysts. The methods described herein capture a distinct and novel state of human pluripotency that shares defining features with mouse ESCs.

Accordingly, some aspects of the disclosure provide a method for changing the pluripotency state of a vertebrate cell to a more naïve state. The method comprises (a) culturing a pluripotent vertebrate cell in the presence of a serine/threonine-protein kinase B-Raf (BRAF) inhibitor, an epidermal growth factor receptor (EGFR) inhibitor, a vascular endothelial growth factor 1 (VEGFR1) inhibitor, or a fibroblast growth factor receptor 1 (FGFR1) inhibitor; and (b) maintaining the cell in culture under conditions suitable and a time sufficient to changing the pluripotency state of the vertebrate cell to a more naïve state than the pluripotency state of the original vertebrate cell of step (a).

The kinase inhibitor(s) used herein may be a small molecule, antibodies/antibody fragments (at least for those kinases that have an extracellular domain), short interfering RNA, and/or aptamers. A "small molecule," (M) as used herein, refers to an alkyl, alkenyl, alkynyl, aryl, heteroaryl, carbocyclic, or heterocyclic moiety, as defined herein, comprising carbon and hydrogen, and optionally comprising one or more heteroatoms as a part of the molecule (in the case of heteroaryl and heterocyclic groups) and/or attached to the molecule selected from oxygen, nitrogen, sulfur, phosphorus, boron, silicon, and selenium. In certain embodiments, the specificity of the inhibitors is given by the IC50 value. The IC50 value is defined as the concentration of inhibitor required to inhibit 50% of the kinase activity. In certain embodiments, the compounds of Formula (I) or (II) may exhibit IC50 values <100 µM. In certain other embodiments, the compounds exhibit IC50 values <50 µM. In certain other embodiments, the compounds exhibit IC50 values <40 µM. In certain other embodiments, the compounds exhibit IC50 values <30 µM. In certain other embodiments, the compounds exhibit IC50 values <20 µM. In certain other embodiments, the compounds exhibit IC50 values <10 µM. In certain other embodiments, the compounds exhibit IC50 values <7.5 µM. In certain embodiments, the compounds exhibit IC50 values <5 µM. In certain other embodiments, the compounds exhibit IC50 values <2.5 µM. In certain embodiments, the compounds exhibit IC50 values <1 µM. In certain embodiments, the compounds exhibit IC50 values <0.75 µM. In certain embodiments, the compounds exhibit IC50 values <0.5 µM. In certain embodiments, the compounds exhibit IC50 values <0.25 µM. In certain embodiments, the compounds exhibit IC50 values <0.1 µM. In certain other embodiments, the compounds exhibit IC50 values <75 nM. In certain other embodiments, the compounds exhibit IC50 values <50 nM. In certain other embodiments, the compounds exhibit IC50 values <25 nM. In certain other embodiments, the compounds exhibit IC50 values <10 nM. In other embodiments, the compounds exhibit IC50 values <7.5 nM. In other embodiments, the compounds exhibit IC50 values <5 nM.

In certain embodiments, the BRAF inhibitor is a compound of Formula (B) (e.g., AZ-628 or BAY-439006) or Formula (C) (e.g., GDC-0879 or SB590885). In certain embodiments, the BRAF inhibitor is sorafenib; PLX4720; PLX-3603; GSK2118436; N-(3-(5-(4-chlorophenyl)-1H-pyrrolo[2;3-b]pyridine-3-carbonyl)-2;4-difluorophenyl)propane-1-sulfonamide; vemurafenib (also known as Zelobraf® and PLX-4032); GSK 2118436; RAF265 (Novartis); XL281; ARQ736; a compound described in international PCT application publication, WO 2007/002325, WO 2007/002433, WO 2009/111278, WO 2009/111279, WO 2009/111277, WO 2009/111280, or WO 2011/025927; or a compound described in U.S. Pat. No. 7,491,829 or 7,482,367. In certain embodiments, the VEGFR1 inhibitor is a compound of Formula (A) (e.g., AMG706), Formula (B) (e.g., BAY 73-4506), or Formula (G) (e.g., BIBF-1120 or SU11248). In certain embodiments, the VEGFR1 inhibitor is SU5416 or a compound described in U.S. patent application publication, US 2006/0030000. In certain embodiments, the FGFR1 inhibitor is a compound of Formula (F) (e.g., PD173074). In certain embodiments, the FGFR1 inhibitor is cediranib; brivanib; TSU-68; BIBF1120; dovitinib; Ki23057; MK-2461; E7080; SU5402; BGJ398; E-3810; AZD4547; PLX052; or a compound described in U.S. Pat. No. 8,709,718. In certain embodiments, the MEK inhibitor is a compound of Formula (K) (e.g., PD0325901). In certain embodiments, the MEK inhibitor is a compound described in international PCT application publication, WO 2010/138377, WO 2009/153554, WO 2009/093009, WO 2009/013462, WO 2009/093013, WO 2008/020206, WO 2008/078086, WO 2008/120004, WO 2008/125820, WO 2009/093008, WO 2009/074827, WO 2009/093009, WO 2010/108652, WO 2010/105110, WO 2010/105082, WO 2009/129246, WO 2009/018238, WO 2009/018233, WO 2008/089459, WO 2008/124085, WO 2008/076415, WO 2008/021389, WO 2010/051935, WO 2010/051933, WO 2009/129938, WO 2009/021887, WO 2008/101840, WO 2008/055236, WO 2010/003025, WO 2010/003022, WO 2007/096259, WO 2008/067481, WO 2008/024724, WO 2008/024725, or WO 2010/0145197; or a compound described in U.S. patent application publication, US 2008/0255133, US 2008/0058340, US 2009/0275606, or US 2009/0246198. In certain embodiments, the GSK3 inhibitor is a compound of Formula (C) (e.g., CHIR99021) or Formula (J) (e.g., IM12). In certain embodiments, the GSK3 inhibitor is CHIR98014; CHIR98023; BIO-acetoxime; BIO; LiCl; SB 216763; SB 415286; AR-A014418; 1-azakenpaullone; bis-7-indolylmaleimide; kenpaullone; CT 99021; CT 20026; SB216763; SB 415286; TDZD-8; TIBPO (2-thio(3-iodobenzyl)-5-(1-pyridyl)-[1,3,4]-oxadiazole); a compound described in U.S. patent application publication, US 2013/0059385, US 2001/0034051, US 2002/0156087, US 2004/0092535, US 2004/0209878, US 2004/0138273, US 2004/0077707, US 2005/0054663, US or 2006/0089369; a compound described in U.S. U.S. Pat. Nos. 6,057,117; 6,608,063; 6,417,185; 6,489,344; or U.S. Pat. No. 6,153,618; or a compound described in international PCT application publication, WO/2003/049739; WO/2002/085909; WO/2003/011287, WO/2005/039485, or WO/2006/091737. In certain embodiments, the ROCK inhibitor is a compound of Formula (L) (e.g., Y-27632). In certain embodiments, the ROCK inhibitor is fasudil (HA-1077); thiazovivin; AMA0076; AR-12286; AMA0076; AR-12286; AR-13324; ATS907; DE-104; INS-115644; INS-117548; K-115; PG324; Y-39983; RKI-983; SNJ-1656; a compound described in international PCT application publication, WO 2014/068035, WO 2013/030216, WO 2013/030367, WO 2013/030366, WO 2013/030365, WO 2011/107608, WO 2012/146724, WO 2006/137368, or WO 2005/035506; or a compound described in U.S. patent application publication, US 2013/196437. In certain embodiments, the Src inhibitor is a compound of Formula (H) (e.g., WH-4-023). In certain embodiments; the Src inhibitor is SKI606 (bosutinib); dasatinib (SPYRCEL); saracatenib (AZD-0530); PP1; PP2; PD173955; AGL1872; PD162531; radicicol R2146; geldanamycin; or a compound described in U.S. patent application publication, US 2006/258686, US 2009/0227608, US 2010/0249152, or US 2013/0040972.

ESCs are pluripotent cells. ESCs have been derived from vertebrate animals such as mice, primates (including humans), and some other species. ESCs are often derived from cells obtained from the inner cell mass (ICM) of a vertebrate blastocyst but can also be derived from single blastomeres (e.g., removed from a morula). Pluripotent cells can also be obtained using parthenogenesis, e.g., from germ cells, e.g., oocytes. Other pluripotent cells include embryonic carcinoma (EC) and embryonic germ (EG) cells. See, e.g., Yu J, Thomson J A, *Genes Dev*. Pluripotent stem cell lines. 22(15):1987-97, 2008.

Standard techniques for preparing deriving human ES cells typically involve the use of a MEF or human cell feeder layer and serum or, if cultured in serum-free medium, compounds such as bFGF. For example, the ICM of a human blastocyst is removed by immunosurgery, dissociated in $Ca^{2+}$—$Mg^{2+}$-free medium, and plated over mouse embryonic fibroblasts or human feeder cells (Thomson et al., Science 282, 1145 (1998). The mouse cells are irradiated to suppress their proliferation. See, e.g., B. E. Reubinoff et al., *Nature Biotechnol*. 18, 399, 2000; Mitalipova M & Palmarini G. Isolation and characterization of human embryonic stem cells. *Methods Mol. Biol*. 331:55-76, 2006; Ilic D, et al., Derivation of hESC from intact blastocysts. *Curr Protoc Stem Cell Biol*., Chapter 1:Unit 1A.2, 2007; Ludwig T, A Thomson J., Defined, feeder-independent medium for human embryonic stem cell culture. *Curr Protoc Stem Cell Biol*. Chapter 1:Unit 1C.2, 2007. It will be understood that culture conditions can be feeder layer free. It will also be understood that the culture conditions can include the use of matrices such as laminin, Matrigel™, and the like. In some embodiments, methods described in Chen A E, et al., Optimal timing of inner cell mass isolation increases the efficiency of human embryonic stem cell derivation and allows generation of sibling cell lines. *Cell Stem Cell*. 4(2): 103-6, 2009, are used. In some embodiments, mitomycin C-inactivated mouse embryonic fibroblast feeder cells are used for culturing human embryonic stem cells. It will be understood that in some embodiments other methods of inactivating feeder cells may be used such as other compounds or gamma irradiation.

A pluripotent vertebrate cell can be converted to a more naïve state by culturing the cell in the presence of a serine/threonine-protein kinase B-Raf (BRAF) inhibitor, an epidermal growth factor receptor (EGFR) inhibitor, a vascular endothelial growth factor 1 (VEGFR1) inhibitor, or a fibroblast growth factor receptor 1 (FGFR1) inhibitor; and maintaining the cell in culture under conditions suitable and a time sufficient to change the pluripotency state of the vertebrate cell to a more naïve state.

The cell is cultured and maintained in a culture medium under suitable conditions until the pluripotency state of the cell is converted to a more naïve state. Conditions suitable for conversion of the pluripotent state of the cell to a more naïve state include the presence of one or more kinase inhibitors in the culture medium. Thus, in some embodiments, the culture medium contains a serine/threonine-protein kinase B-Raf (BRAF) inhibitor, an epidermal growth factor receptor (EGFR) inhibitor, a vascular endothelial growth factor 1 (VEGFR1) inhibitor, or a fibroblast growth factor receptor 1 (FGFR1) inhibitor. In some embodiments, the culture medium further contains a mitogen-activated protein kinase kinase (MEK) inhibitor. In some embodiments, the culture medium further contains a ROCK inhibitor and/or an Src inhibitor. In some embodiments, the culture medium further contains a glycogen synthase kinase 3 (GSK3) inhibitor, a rho-associated protein kinase (ROCK)

inhibitor, and/or a proto-oncogene tyrosine-protein kinase (Src) inhibitor. In some embodiments, the culture medium contains a BRAF inhibitor, a MEK inhibitor, a GSK3 inhibitor, a ROCK inhibitor, and an Src inhibitor. In some embodiments, the culture medium further contains fibroblast growth factor and/or Activin A. In some embodiments, the culture medium contains one or more of the compounds described herein. In some embodiments, the culture medium contains a BRAF inhibitor, a MEK inhibitor, a ROCK inhibitor, and an Src inhibitor. In some embodiments, the culture medium does not contain a GSK3 inhibitor.

The concentration of the kinase inhibitors used in the culture medium will depend on the amount of culture medium being generated. In some embodiments, 0.1 µM, 0.2 µM, 0.3 µM, 0.4 µM, 0.5 µM, 1 µM, 1.5 µM, 2.0 µM, 2.5 µM, 3.0 µM, 3.5 µM, 4.0 µM, 4.5 µM, 5.0 µM, 5.5 µM, 6.0 µM, 6.5 µM, 7.0 µM, 8.0 µM, 8.5 µM, 9.0 µM, 9.5 µM, 10.5 µM, 11.0 µM, 12.0 µM 13.0 µM, 14.0 µM, or 15.0 µM of one or more kinase inhibitors are included in about 500 mL of culture medium. In some embodiments, 0.1-1.0 µM of BRAF inhibitor is used in about 500 ml of culture medium. In some embodiments, 0.5-1.5 µM of MEK inhibitor is used in about 500 ml of culture medium. In some embodiments, 0.5-1.5 µM of Src inhibitor is used in about 500 ml of culture medium. In some embodiments, 5.0-µM of ROCK inhibitor is used in about 500 ml of culture medium. In some embodiments, 1.0-5.0 µM of GSK3 inhibitor is used in about 500 ml of culture medium.

In some embodiments, the concentration of GSK3 inhibitor is 1 nM to 10 nM. In some embodiments, the concentration of GSK3 inhibitor is 10 nM to 0.1 µM. In some embodiments, the concentration of GSK3 inhibitor is 0.1 µM to 0.2 µM. In some embodiments, the concentration of GSK3 inhibitor is 0.2 µM to 0.5 µM. In some embodiments, the concentration of GSK3 inhibitor is 0.5 µM to 1 µM. In some embodiments, the culture medium contains a BRAF inhibitor, a MEK inhibitor, a ROCK inhibitor, and an Src inhibitor, and further contains a GSK3 inhibitor in concentration range listed above in this paragraph.

In some embodiments, if a different kinase inhibitor that targets the same kinase is used, such kinase inhibitor may be used at a concentration that provides an approximately equivalent effect.

In some embodiments, conditions suitable for conversion of the pluripotent state of the cell to a more naïve state include, in addition to the one or more kinase inhibitors described herein, the addition of one or more of the following components to the culture medium: N2 supplement, B27 supplement, human LIF, glutamine, nonessential amino acids, β-mercaptoethanol, penicillin-streptomycin, and/or albumin (e.g., BSA or human albumin). In some embodiments, the culture media comprise DMEM/F12 or Neurobasal. In some embodiments, the culture media comprise DMEM/F12 and Neurobasal in a suitable ratio (e.g., 10:90 to 90:10 (e.g., 25:75, 50:50, and 75:25) DMEM/F12: Neurobasal). In some embodiments, the culture media comprising DMEM/F12 and/or Neurobasal further comprise N2 supplement, B27 supplement, human LIF, glutamine, nonessential amino acids, β-mercaptoethanol, penicillin-streptomycin, and/or albumin (e.g., BSA or human albumin). In some embodiments, the culture medium further comprises fibroblast growth factor 2 (FGF2) and 1%, 0.8%, 0.6%, 0.4%, 0.2%, or 0.1% KSR. In some embodiment, the cells are maintained on mitomycin C-inactivated mouse embryonic fibroblast feeder cells. In some embodiments, conditions suitable for conversion of the pluripotent state of the cell to a more naïve state include growing the cells under physiological oxygen conditions, i.e., about 5% $O_2$. In some embodiments, the cells are grown under between about 1% $O_2$ and about 5% $O_2$. In some embodiments, the cells are grown under between about 2% $O_2$ and about 5% $O_2$. In some embodiments, the cells are grown under between about 5% $O_2$ and about 10% $O_2$. In some embodiments, the cells are grown under between about 10% $O_2$ and about 20% $O_2$. In some embodiments, the cells are grown under 1% $O_2$, 2% $O_2$, 3% $O_2$, 4% $O_2$, 5% $O_2$, 6% $O_2$, 7% $O_2$, 8% $O_2$, 9% $O_2$, 10% $O_2$, 11% $O_2$, 12% $O_2$, 13% $O_2$, 14% $O_2$, 15% $O_2$, 16% $O_2$, 17% $O_2$, 18% $O_2$, 19% $O_2$, 20% $O_2$, 21% $O_2$, 22% $O_2$, 23% $O_2$, 24% $O_2$, or 25% $O_2$.

Some aspects of the invention relate to a cell culture medium comprising: a basal medium; and a serine/threonine-protein kinase B-Raf (BRAF) inhibitor, an epidermal growth factor receptor (EGFR) inhibitor, a vascular endothelial growth factor 1 (VEGFR1) inhibitor, or a fibroblast growth factor receptor 1 (FGFR1) inhibitor. In some embodiments, the cell culture medium further comprises mitogen-activated protein kinase kinase (MEK) inhibitor. In some embodiments, the cell culture medium further comprises a glycogen synthase kinase 3 (GSK3) inhibitor, a rho-associated protein kinase (ROCK) inhibitor, and/or a proto-oncogene tyrosine-protein kinase (Src) inhibitor. In some embodiments, the culture medium further contains a ROCK inhibitor and/or an Src inhibitor. In some embodiments, the cell culture medium comprises a BRAF inhibitor, a MEK inhibitor, and a GSK3 inhibitor.

In some embodiments, the cell culture medium comprises a BRAF inhibitor, a MEK inhibitor, a GSK3 inhibitor, and a ROCK inhibitor. In some embodiments, the cell culture medium comprises a BRAF inhibitor, a MEK inhibitor, a GSK3 inhibitor, a ROCK inhibitor, and an Src inhibitor. In some embodiments, the culture medium contains an inhibitor of a receptor tyrosine kinase, a MEK inhibitor, and a GSK3 inhibitor. In some embodiments, the culture medium contains a BRAF inhibitor, a MEK inhibitor, a GSK3 inhibitor, and an Src inhibitor. In some embodiments, any of the culture media contains a VEGRF1 inhibitor, an EGFR inhibitor, a FGFR1 inhibitor, or a combination thereof, instead of, or in addition to, a BRAF inhibitor. In some embodiments, the culture medium contains a BRAF inhibitor and a MEK inhibitor. In some embodiments, the culture medium contains a BRAF inhibitor, a MEK inhibitor, and a ROCK inhibitor. In some embodiments, the culture medium contains a BRAF inhibitor, a MEK inhibitor, a ROCK inhibitor, and an Src inhibitor. In some embodiments, the culture medium contains an inhibitor of a receptor tyrosine kinase and a MEK inhibitor. In some embodiments, the culture medium contains a BRAF inhibitor, a MEK inhibitor, and an Src inhibitor. In some embodiments, the culture medium does not contain a GSK3 inhibitor.

In some embodiments, the concentration of GSK3 inhibitor is 1 nM to 10 nM. In some embodiments, the concentration of GSK3 inhibitor is 10 nM to 0.1 µM. In some embodiments, the concentration of GSK3 inhibitor is 0.1 µM to 0.2 µM. In some embodiments, the concentration of GSK3 inhibitor is 0.2 µM to 0.5 µM. In some embodiments, the concentration of GSK3 inhibitor is 0.5 µM to 1 µM. In some embodiments, the culture medium contains a BRAF inhibitor, a MEK inhibitor, a ROCK inhibitor, and an Src inhibitor, and further contains a GSK3 inhibitor in concentration range listed above in this paragraph. In some embodiments, the culture medium contains a BRAF inhibitor and a MEK inhibitor, and further contains a GSK3 inhibitor in concentration range listed above in this paragraph. In some embodiments, the culture medium contains a BRAF inhibitor, a MEK inhibitor, and a ROCK inhibitor and further contains a GSK3 inhibitor in concentration range listed above in this paragraph. In some embodiments, the culture medium contains a receptor tyrosine kinase and a MEK inhibitor, and further contains a GSK3 inhibitor in concentration range listed above in this paragraph. In some embodiments, the culture medium contains BRAF inhibitor, a MEK inhibitor, and an Src inhibitor, and further contains a GSK3 inhibitor in concentration range listed above in this paragraph.

As used herein, a "basal medium" is typically an unsupplemented medium (e.g., Eagle's minimal essential medium (EMEM); Dulbecco's modified Eagle's medium (DMEM)). As will be appreciated by those of skill in the art, a basal medium can comprises a variety of components such as one or more amino acids (e.g., non-essential amino acids, essential amino acids), salts (e.g., calcium chloride, potassium chloride, magnesium sulfate, sodium chloride, and monosodium phosphate), sugars (e.g., glucose), and vitamins (e.g., folic acid, nicotinamide, riboflavin, B12), iron and pH indicators (e.g., phenol red). The basal medium can further comprise proteins (e.g., albumin), hormones (e.g., insulin), glycoproteins (e.g., transferrin), minerals (e.g., selenium), serum (e.g., fetal bovine serum), antibiotics, antimycotics and glycosaminoglycans.

In some embodiments, the basal medium is serum-free medium. In some embodiments, the basal medium comprises one or more supplements, such as, but not limited to, supplements such as B27 and/or N2. In some embodiments, the basal medium is supplemented with one or more of the following: DMEM/F12, Neurobasal, N2 supplement, 10 mL B27 supplement, human LIF, glutamine, nonessential amino acids, β-mercaptoethanol, penicillin-streptomycin, and/or BSA (Sigma). In some embodiments, the supplemented basal cell culture medium further comprises fibroblast growth factor 2 (FGF2) and 1%, 0.8%, 0.6%, 0.4%, 0.2%, or 0.1% KSR.

The pluripotent vertebrate cell is maintained in culture for a time sufficient to change the pluripotency state of the cell to a more naïve state. In some embodiments, time sufficient to change the pluripotency state of the cell to a more naïve state is at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, or at least 20 days. In some embodiments, time sufficient to change the pluripotency state of the cell to a more naïve state is between 1-5 days, 1-10 days, 1-15 days, 1-20 days, 5-10 days, 5-15 days, 5-20 days, 10-15 days, 10-20 days, or 15-20 days. In some embodiments, time sufficient to change the pluripotency state of the cell to a more naïve state is at least about 5 days (e.g., about 10 days). In some embodiments, the culture medium is replenished as required during this time. In some embodiments, the cell is maintained in culture until the cell has at least one property which is similar to the corresponding property of mouse embryonic stem cells. In some embodiments, the at least one property which is similar to the corresponding property of mouse embryonic stem cells is the utilization of the distal OCT4 enhancer element. An important molecular signature of naïve pluripotency in the mouse system is the use of the distal enhancer (DE) of OCT4. Thus, in some embodiments, the cell is maintained in culture until the cell uses the distal Oct4 enhancer element for OCT4 expression. In some embodiments, the cell is maintained in culture until the cell uses the endogenous distal Oct4 enhancer element for OCT4 expression. In some embodiments, the cell is maintained in culture until the cell has enhanced utilization of the distal Oct4 enhancer element for OCT4 expression as compared to the cell prior to the culturing/maintenance period. In some embodiments, the cell is maintained in culture until the cell has enhanced utilization of the endogenous distal Oct4 enhancer element for OCT4 expression as compared to the cell prior to the culturing/maintenance period. The utilization of the distal OCT4 enhancer element can be tested using the OCT4-ΔPE-GFP reporter system described in the Examples below.

In some embodiments, the at least one property which is similar to the corresponding property of mouse embryonic stem cells is colony morphology. Naïve pluripotent cells that correspond to the more immature "ground state" of pluripotency, exhibit a dome-like colony morphology. Thus, in certain embodiments, the cell is maintained in culture until it exhibits a dome-like colony morphology.

In some embodiments, the at least one property which is similar to the corresponding property of mouse embryonic stem cells is gene expression profile. The cell is maintained in culture until it has a global gene expression profile which clusters with naïve mouse ESCs as opposed to mouse EpiSCs and/or less naïve human ESCs. In some embodiments, the gene expression profile includes markers of ground state pluripotency, such as, but not limited to, NANOG, OCT4, DPPA5, DPPA3 (also known as STELLA), KLF4, KLF5, TFCP2L1, and/or REX1. In some embodiments, the cell is maintained in culture until it exhibits a gene expression profile similar to that shown in FIG. 6.

Some aspects of the invention relate to a method for culturing vertebrate cells, the method comprising growing vertebrate cells in a cell culture medium comprising a serine/threonine-protein kinase B-Raf (BRAF) inhibitor, an epidermal growth factor receptor (EGFR) inhibitor, a vascular endothelial growth factor 1 (VEGFR1) inhibitor, or a fibroblast growth factor receptor 1 (FGFR1) inhibitor. The vertebrate cells can be naïve pluripotent cells, human pluripotent cells, or naïve human pluripotent cells. In some embodiments, the cell culture medium further comprises mitogen-activated protein kinase kinase (MEK) inhibitor. In some embodiments, the cell culture medium further comprises a glycogen synthase kinase 3 (GSK3) inhibitor, a rho-associated protein kinase (ROCK) inhibitor, and/or a proto-oncogene tyrosine-protein kinase (Src) inhibitor. In some embodiments, the culture medium further contains a ROCK inhibitor and/or an Src inhibitor. In some embodiments, the cell culture medium comprises a BRAF inhibitor, a MEK inhibitor, and a GSK3 inhibitor. In some embodiments, the cell culture medium comprises a BRAF inhibitor, a MEK inhibitor, a GSK3 inhibitor, and a ROCK inhibitor. In some embodiments, the cell culture medium comprises a BRAF inhibitor, a MEK inhibitor, a GSK3 inhibitor, a ROCK inhibitor, and an Src inhibitor. In some embodiments, the culture medium contains a BRAF inhibitor and a MEK inhibitor. In some embodiments, the culture medium contains a BRAF inhibitor, a MEK inhibitor, and a ROCK inhibitor. In some embodiments, the culture medium contains a BRAF inhibitor, a MEK inhibitor, a ROCK inhibitor, and an Src inhibitor. In some embodiments, the culture medium does not contain a GSK3 inhibitor.

In some embodiments, the concentration of GSK3 inhibitor is 1 nM to 10 nM. In some embodiments, the concentration of GSK3 inhibitor is 10 nM to 0.1 μM. In some embodiments, the concentration of GSK3 inhibitor is 0.1 μM to 0.2 μM. In some embodiments, the concentration of GSK3 inhibitor is 0.2 μM to 0.5 μM. In some embodiments, the concentration of GSK3 inhibitor is 0.5 µM to 1 µM. In some embodiments, the culture medium contains a BRAF inhibitor, a MEK inhibitor, a ROCK inhibitor, and an Src inhibitor, and further contains a GSK3 inhibitor in concentration range listed above in this paragraph. In some embodiments, the culture medium contains a BRAF inhibitor and a MEK inhibitor, and further contains a GSK3 inhibitor in concentration range listed above in this paragraph. In some embodiments, the culture medium contains a BRAF inhibitor, a MEK inhibitor, and a ROCK inhibitor and further contains a GSK3 inhibitor in concentration range listed above in this paragraph.

The cell culture medium may be a basal medium. As used herein, a "basal medium" is typically an unsupplemented medium (e.g., Eagle's minimal essential medium (EMEM); Dulbecco's modified Eagle's medium (DMEM)). As will be appreciated by those of skill in the art, a basal medium can comprises a variety of components such as one or more amino acids (e.g., non-essential amino acids, essential amino acids), salts (e.g., calcium chloride, potassium chloride, magnesium sulfate, sodium chloride, and monosodium phosphate), sugars (e.g., glucose), and vitamins (e.g., folic acid, nicotinamide, riboflavin, B12), iron and pH indicators (e.g., phenol red). The basal medium can further comprise proteins (e.g., albumin), hormones (e.g., insulin), glycoproteins (e.g., transferrin), minerals (e.g., selenium), serum (e.g., fetal bovine serum), antibiotics, antimycotics and glycosaminoglycans.

In some embodiments, the basal medium is serum-free medium. In some embodiments, the basal medium is supplemented with one or more of the following: DMEM/F12, Neurobasal, N2 supplement, 10 mL B27 supplement, human LIF, glutamine, nonessential amino acids, β-mercaptoethanol, penicillin-streptomycin, and/or BSA (Sigma). In some embodiments, the supplemented basal medium further comprises fibroblast growth factor 2 (FGF2) and 1%, 0.8%, 0.6%, 0.4%, 0.2%, or 0.1% KSR.

Some aspects of the disclosure relate to naïve pluripotent vertebrate cells produced by the methods described herein. Some aspects of the disclosure relate to compositions comprising the naïve pluripotent vertebrate cells produced by the methods described herein. The disclosure provides pluripotent cells, cell lines, and cell clones derived or cultured using the methods and/or compositions described herein. The invention further provides cell cultures, wherein at least some of the cells in the cell culture are derived or cultured using the methods and/or compositions described herein. Some aspects of the invention relate to a naïve pluripotent vertebrate cell line, e.g., a naïve pluripotent human cell line, produced by the methods described herein. In some aspects, a naïve pluripotent vertebrate cell is provided, wherein the cell uses the distal Oct4 enhancer element for OCT4 expression. In some embodiments, the cell primarily uses the endogenous distal OCT4 enhancer element, e.g., the ratio of the cell's use of endogenous distal OCT4 enhancer to the cell's use of endogenous proximal OCT4 enhancer is at least about 1:1 (e.g., about 2:1, about 3:1, about 5:1, or about 10:1). In some aspects, a naïve pluripotent vertebrate cell, e.g., a naïve pluripotent human cell, is provided, wherein the cell has a global gene expression profile which clusters with naïve mouse ESCs as opposed to stem cell lines derived from mouse epiblast (EpiSCs) and/or less naïve human ESCs. In some embodiments, these cells are produced by methods described herein. In some aspects, provided herein are conventional pluripotent vertebrate cells (e.g., conventional pluripotent human cells) with a deletion of the proximal OCT4 enhancer element (or other disabling mutation).

In some aspects, provided herein are methods of using the conventional pluripotent vertebrate cells (e.g., conventional pluripotent human cells) with a deletion of the proximal OCT4 enhancer element (or other disabling mutation), examples of such methods including methods of identifying compounds that induce a naïve pluripotent state.

In some embodiments, at least 80% or at least 90% of the pluripotent stem cells of a colony, cell line, or cell culture express one or more marker(s), e.g., a set of markers, indicative of pluripotency, e.g., a ground state of pluripotency. In some embodiments at least 91%, at least 92%, at least 93%, at least 94%, at least 95%, at least 96%, at least 97%, at least 98%, at least 99%, or more of the cells of a colony, cell line, or cell culture express the marker(s).

Some aspects of the invention provide a kit for culturing vertebrate cells. The kit comprises a serine/threonine-protein kinase B-Raf (BRAF) inhibitor, an epidermal growth factor receptor (EGFR) inhibitor, a vascular endothelial growth factor 1 (VEGFR1) inhibitor, or a fibroblast growth factor receptor 1 (FGFR1) inhibitor. In some embodiments, the kit also comprises instructions for culturing vertebrate cells.

In some embodiments, the kit further comprises mitogen-activated protein kinase kinase (MEK) inhibitor. In some embodiments, the kit further comprises a glycogen synthase kinase 3 (GSK3) inhibitor, a rho-associated protein kinase (ROCK) inhibitor, and/or a proto-oncogene tyrosine-protein kinase (Src) inhibitor. In some embodiments, the kit further comprises a ROCK inhibitor and/or an Src inhibitor. In some embodiments, the kit comprises a BRAF inhibitor, a MEK inhibitor, and a GSK3 inhibitor. In some embodiments, the kit comprises a BRAF inhibitor, a MEK inhibitor, a GSK3 inhibitor, and a ROCK inhibitor. In some embodiments, the kit comprises a BRAF inhibitor, a MEK inhibitor, a GSK3 inhibitor, a ROCK inhibitor, and an Src inhibitor. In some embodiments, the kit comprises a BRAF inhibitor and a MEK inhibitor. In some embodiments, the kit comprises a BRAF inhibitor, a MEK inhibitor, and a ROCK inhibitor. In some embodiments, the kit comprises a BRAF inhibitor, a MEK inhibitor, a ROCK inhibitor, and an Src inhibitor. In some embodiments, the kit does not comprise a GSK inhibitor. In some embodiments, the kit further comprises cell culture medium. The vertebrate cells can be naïve pluripotent cells, human pluripotent cells, or naïve human pluripotent cells. The compositions or contents of the kits can be provided in one or more containers (e.g., compounds that are compatible can be provided together in the same container). The components of the kit may be sterile.

Some aspects of the invention relate to a kit for preparing a cell culture medium. The kit comprises a serine/threonine-protein kinase B-Raf (BRAF) inhibitor, an epidermal growth factor receptor (EGFR) inhibitor, a vascular endothelial growth factor receptor 1 (VEGFR1) inhibitor, or a fibroblast growth factor receptor 1 (FGFR1) inhibitor; and instructions for preparing a cell culture medium. In some embodiments, the kit further comprises mitogen-activated protein kinase kinase (MEK) inhibitor. In some embodiments, the kit further comprises a glycogen synthase kinase 3 (GSK3) inhibitor, a rho-associated protein kinase (ROCK) inhibitor, and/or a proto-oncogene tyrosine-protein kinase (Src) inhibitor. In some embodiments, the kit further comprises a ROCK inhibitor and/or an Src inhibitor. In some embodiments, the kit comprises a BRAF inhibitor, a MEK inhibitor, and a GSK3 inhibitor. In some embodiments, the kit comprises a BRAF inhibitor, a MEK inhibitor, a GSK3 inhibitor, and a ROCK inhibitor. In some embodiments, the kit comprises a BRAF inhibitor, a MEK inhibitor, a GSK3 inhibitor, a ROCK inhibitor, and an Src inhibitor. In some embodiments, the kit comprises a BRAF inhibitor and a MEK inhibitor. In some embodiments, the kit comprises a BRAF inhibitor, a MEK inhibitor, and a ROCK inhibitor. In some embodiments, the kit comprises a BRAF inhibitor, a MEK inhibitor, a ROCK inhibitor, and an Src inhibitor. In some embodiments, the kit does not comprise a GSK3 inhibitor.

In some embodiments, the kit further comprises a basal medium. As used herein, a "basal medium" is typically an unsupplemented medium (e.g., Eagle's minimal essential medium (EMEM); Dulbecco's modified Eagle's medium (DMEM)). As will be appreciated by those of skill in the art, a basal medium can comprises a variety of components such as one or more amino acids (e.g., non-essential amino acids, essential amino acids), salts (e.g., calcium chloride, potassium chloride, magnesium sulfate, sodium chloride, and monosodium phosphate), sugars (e.g., glucose), and vitamins (e.g., folic acid, nicotinamide, riboflavin, B12), iron and pH indicators (e.g., phenol red). The basal medium can further comprise proteins (e.g., albumin), hormones (e.g., insulin), glycoproteins (e.g., transferrin), minerals (e.g., selenium), serum (e.g., fetal bovine serum), antibiotics, antimycotics and glycosaminoglycans.

In some embodiments, the basal medium is serum-free medium. In some embodiments, the basal medium comprises one or more supplements, such as, but not limited to, supplements such as B27 and/or N2. In some embodiments, the basal medium is supplemented with one or more of the following: DMEM/F12, Neurobasal, N2 supplement, 10 mL B27 supplement, human LIF, glutamine, nonessential amino acids, (3-mercaptoethanol, penicillin-streptomycin, and/or BSA (Sigma). In some embodiments, the supplemented basal cell culture medium further comprises fibroblast growth factor 2 (FGF2) and 1%, 0.8%, 0.6%, 0.4%, 0.2%, or 0.1% KSR.

Some aspects of the invention provide a kit for changing the pluripotency state of a vertebrate cell to a more naïve state. The kit comprises a pluripotent vertebrate cell; and cell culture medium comprising a serine/threonine-protein kinase B-Raf (BRAF) inhibitor, an epidermal growth factor receptor (EGFR) inhibitor, a vascular endothelial growth factor 1 (VEGFR1) inhibitor, or a fibroblast growth factor receptor 1 (FGFR1) inhibitor. In some embodiments, the cell culture medium further comprises mitogen-activated protein kinase kinase (MEK) inhibitor. In some embodiments, the cell culture medium further comprises a glycogen synthase kinase 3 (GSK3) inhibitor, a rho-associated protein kinase (ROCK) inhibitor, and/or a proto-oncogene tyrosine-protein kinase (Src) inhibitor. In some embodiments, the cell culture medium further comprises a ROCK inhibitor and/or an Src inhibitor. In some embodiments, the cell culture medium comprises a BRAF inhibitor, a MEK inhibitor, and a GSK3 inhibitor. In some embodiments, the cell culture medium comprises a BRAF inhibitor, a MEK inhibitor, a GSK3 inhibitor, and a ROCK inhibitor. In some embodiments, the cell culture medium comprises a BRAF inhibitor, a MEK inhibitor, a GSK3 inhibitor, a ROCK inhibitor, and an Src inhibitor. In some embodiments, the cell culture medium comprises a BRAF inhibitor and a MEK inhibitor. In some embodiments, the cell culture medium comprises a BRAF inhibitor, a MEK inhibitor, and a ROCK inhibitor. In some embodiments, the cell culture medium comprises a BRAF inhibitor, a MEK inhibitor, a ROCK inhibitor, and an Src inhibitor. In some embodiments, the cell culture medium does not comprise a GSK3 inhibitor.

Gene expression profiling may be used to assess the pluripotency state of a cell or population of cells. Primed or conventional pluripotent cells, such as embryonic stem cells, and multipotent cells (i.e., adult stem cells) exhibit a distinct pattern of global gene expression as compared to more naïve pluripotent cells (i.e., the more immature "ground state" of pluripotency). Thus, one may assess DNA methylation, gene expression, and/or epigenetic state of cellular DNA, and/or developmental potential of the cells, e.g., as described in Wernig et al., Nature, 448:318-24, 2007. Other methods of assessing pluripotency state include epigenetic analysis, e.g., analysis of DNA methylation state (Nazor et al. *Cell Stem Cell*. 2012 May 4; 10(5):620-34).

In some embodiments a pluripotent cell described herein is used to prepare a composition for cell therapy to be administered to a vertebrate subject, e.g., a non-human animal, or a human. In some embodiments, a pluripotent cell derived or cultured according to the systems and methods described herein is used to prepare a composition for cell therapy to be administered to a vertebrate subject, e.g., a non-human animal, or a human. In some embodiments, the composition comprises autologous cells. In other embodiments, the composition comprises non-autologous cells. In some embodiments, the cells are genetically matched to an individual.

The naïve pluripotent vertebrate stem cells may be used to treat a number of life-threatening diseases and disorders. Examples include, but are not limited to, cancers (such as, but not limited to, acute leukemia, chronic leukemia, high-risk solid tumors, Hodgkin & Non-Hodgkin Lymphoma, myelodysplastic syndromes), blood disorders (such as, but not limited to, aplastic anemia, beta thalassemia, Diamond-Blackfan Anemia, Fanconi Anemia, Sickle Cell Disease), immune disorders (such as, but not limited to, chronic granulomatous disease, hystiocytic disorders, leukocyte adhesion deficiency, severe combined immunodeficiency diseases, Wiskott-Aldrich Syndrome), and metabolic disorders (such as, but not limited to, Krabbe Disease, Hurler Syndrome, Metachromatic Leukodystrophy, and Sanfilippo Syndrome). The naïve pluripotent vertebrate stem cells produced by the methods described herein are administered to a subject having or suspected of having a disease or disorder that can be treated using stem cell therapy. Several approaches may be used for the introduction of the naïve pluripotent vertebrate stem cells stem cells into the subject, including but not limited to, catheter-mediated delivery I.V. (e.g., endovascular catheter), direct injection into a target site, intravenous injection, intraperitoneal injection, parenteral injection, subcutaneous injection, intramuscular injection, and/or intracardiac injection.

The compositions and methods of the disclosure may be applied to derive or culture naïve pluripotent cells from non-human animals including but not limited to, dogs, cats, horses, sheep, goats, cows, and/or rodents (such as rats, rabbits, hamsters, guinea pigs). The disclosure may be applied to derive or culture naïve pluripotent cells from primates, e.g., non-human primates, or humans. In many embodiments, the vertebrate is a mammal. In some embodiments the mammal is a bovine, ovine, caprine, equine, canine, or feline. It is also envisioned that compositions and methods of the invention may be used to derive naïve pluripotent cells, e.g., ES cells or iPS cells from non-mammalian vertebrates, e.g., zebrafish or other non-mammalian organisms of interest such as birds. In some embodiments, if the species is one from which ES or iPS cells have not heretofore been derived, techniques and culture conditions can be adapted from standard techniques used in other species, e.g., related species.

Systems, compositions, and methods of the invention can be applied in the derivation or culture of naïve pluripotent cells derived from cells obtained from any of a variety of sources. For example, cells obtained from the inner cell mass (ICM) or epiblast can be used to derive naïve ES cells. In some embodiments, the systems, compositions, and methods are applied to derive naïve pluripotent stem cells from blastomeres, e.g., blastomeres isolated from a morula or from a 4-8 cell stage embryo. In some embodiments, the compositions and methods are applied to derive naïve pluripotent stem cells from germ cells. In some embodiments the compositions and methods are used to derive naïve pluripotent cells using parthenogenesis or SCNT. In some embodiments the methods are applied to derive or culture naïve induced pluripotent stem (iPS) cells. Methods for generating iPS cells are well-known in the art (see, for example, WO2013159103, WO 2013177133, and U.S. Pat. No. 8,748,179). iPSCs are typically derived by introducing a specific set of pluripotency-associated genes, or "reprogramming factors", into a given cell type. The original set of reprogramming factors are the genes Oct4 (Pou5f1), Sox2, cMyc, and Klf4. While this combination is most conventional in producing iPSCs, each of the factors can be functionally replaced by related transcription factors, miRNAs, small molecules, or even non-related genes such as lineage specifiers. In some embodiments, somatic cells used to generate iPS cells include, but are not limited to, fibroblasts, keratinocytes, immune system cells, and epithelial cells. In some embodiments, iPS cells are generated without genomic modification. In some embodiments, iPS cells are free of exogenously introduced DNA. For example, they may be generated using synthetic modified mRNA, small molecules, or a combination thereof. For example, iPS cells may be generated using the methods described in Mandal, P K & Rossi, D J, Nature Protocols 8, 568-582 (2013). In some embodiments, iPS cells are generated using episomal expression of one or more of the reprogramming factors. After the iPS cells are generated, the episome(s) may be lost resulting in cells free of exogenously introduced DNA.

The invention contemplates a variety of uses for the pluripotent cells, cell lines derived, cultured, or generated as described herein. In general, pluripotent cells may be used for any purpose contemplated in the art for use of pluripotent cells, e.g., ES or iPS cells. See, e.g., international PCT applications, no. PCT/US2013/050077 (WO 2014/011881) and PCT/US2001/006912 (WO 2001/066697).

In some embodiments a pluripotent cell derived or cultured according to the invention is used to produce one or more differentiated cells. Such cells are considered to be an aspect of the disclosure. The cells could be, e.g., multipotent stem cells or fully differentiated cells. The cells may be, e.g., hematopoietic cells (e.g., of the myeloid or erythroid lineage), neural cells (e.g., neural precursors, neurons or glial cells), myoblasts, myocytes, cardiomyocytes, melanoblasts, keratinocytes, chondroblasts, chondrocytes, osteoblasts, osteoclasts, pancreatic beta cells, retinal cells, endothelial cells, etc. Protocols known in the art for differentiating cells into cells of a desired type may be used (see, for example, US 20130273651). In some embodiments a pluripotent cell may be differentiated to a cell type of interest ex vivo, e.g., before being administered to a subject. For example, a pluripotent cell may be differentiated to produce cells of a cell type that is affected by a disease or that may be useful in treating a disease for which the subject is in need of treatment. In some embodiments cells are used to generate a tissue or organ in vitro or to supplement a tissue or organ in vivo.

The disclosure also provides methods of producing non-human vertebrates, e.g., non-human mammals, which can be genetically modified or non-genetically modified, using the pluripotent cells of the disclosure. Such non-human vertebrates are aspects of the disclosure. In some embodiments the non-human vertebrates are mice. In some embodiments, non-human mammals are produced using methods known in the art for producing non-human mammals from ES or iPS cells (see, for example, WO 2010124290). For example, ES or iPS cells are introduced into a blastocyst of the same species which is transferred to a suitable foster mother (e.g., a pseudopregnant female of the same species) under conditions suitable for production of live offspring. If a diploid blastocyst is used, chimeric offspring may be produced, which are typically derived in part from the ES cell or iPS cell and in part from the blastocyst into which the cell was introduced. Chimeric offspring may be interbred to generate homozygous animals if the chimeric offspring contain ES-derived contribution to the germ line as known in the art. In some embodiments, the mice are produced using methods that do not require production of chimera or chimeric offspring. In some embodiments, pluripotent ES cells are introduced into tetraploid blastocysts of the same vertebrate species under conditions that result in production of an embryo (at least one/one or more embryos) and the resulting embryo(s) transferred into an appropriate foster mother, such as a pseudopregnant female of the same vertebrate species. The resulting female is maintained under conditions that result in development of live offspring, thereby producing a non-human mammal derived from the introduced ES cells. See, e.g., U.S. Pat. No. 6,784,336. In some embodiments, the mouse is produced by a method that involves laser-assisted injection or piezo-injection of ES cells of the invention into four- or eight-cell embryos. In some embodiments the mouse is produced without need to generate a chimera, e.g., using methods described in international PCT application, no. PCT/EP2003/002180 (WO 2003/073843). Another embodiment of the present invention is a method of producing a non-human mammalian strain, such as a mouse strain, e.g., a genetically engineered mouse strain, that is derived from a given (single) iPS or ES cell clone of the present disclosure without outcrossing with a wild type partner. See, e.g., U.S. Pat. No. 6,784,336. In some embodiments the mice are genetically modified, e.g., they are derived from an ES or iPS cell that is genetically modified. The invention contemplates interbreeding non-human vertebrates, e.g., mice, derived from the ES cells or iPS cells with mice of any strain of interest, the resulting strains being considered other aspects of the invention.

A naïve pluripotent cell can be derived from a cell, e.g., a somatic cell, obtained from an individual of interest. The individual can be, e.g., a human suffering from a disease or condition. In some embodiments the individual is immuno-compatible with an individual suffering from a disease or condition. In some embodiments the disease is a neurodegenerative disease, e.g., Parkinson's disease, Alzheimer's disease, or amyotrophic lateral sclerosis. In some embodiments the individual suffers from diabetes. In some embodiments the individual suffers from heart failure or a muscle disorder or an enzyme deficiency, sickle cell anemia, hemophilia, a glycogen storage disorder, or cystic fibrosis. In some embodiments the disease is a heritable disease. In some embodiments the disease is a monogenic disorder. In some embodiments the disease has an autosomal dominant inheritance pattern. In some embodiments the disease has an autosomal recessive inheritance pattern. In some embodiments the disease is sporadic, i.e., there is no evident pattern of inheritance. In some embodiments the individual has suffered an injury, e.g., traumatic brain injury, spinal cord injury. In some embodiments the individual is in need of cell therapy.

In some embodiments a naïve pluripotent cell, e.g., a naïve pluripotent human cell, is derived from a cell (e.g., a somatic cell) obtained from an individual who harbors a mutation or genetic variation that is known to cause or suspected of causing a disease (or an immunocompatible donor). The mutation or genetic variation is corrected ex vivo. Resulting cells or cells derived therefrom are administered to the subject.

In some embodiments, a naïve pluripotent cell, e.g., a naïve pluripotent human cell, may be used to generate a model of a disease, e.g., an animal model or a cellular model of a disease, e.g., any of the diseases mentioned herein or other diseases of interest. In some embodiments the naïve pluripotent cell is derived from a cell, e.g., a somatic cell, obtained from an individual who has the disease. In some embodiments the naïve pluripotent cell is genetically engineered to harbor a mutation or genetic variation that is known to cause or suspected of causing the disease. In some embodiments the naïve pluripotent cell may be differentiated to a cell of a cell type that is affected by the disease.

In some embodiments, a naïve pluripotent cell is not genetically modified. In some embodiments, the naïve pluripotent cell is devoid of DNA or genetic alterations (e.g., insertions, substitutions, deletions) introduced by the hand of man. In some embodiments, a naïve pluripotent cell may be genetically modified after it is derived. Any of a variety of different methods may be employed to genetically modify a naïve pluripotent cell or a cell derived therefrom, e.g., a differentiated cell. Examples of such methods include, but are not limited to, homologous recombination and transfection (see, for example, WO 2013042731, and U.S. Pat. No. 8,637,311). In some embodiments, genome editing technologies such as, but not limited to zinc fingers, TALENs, CRISPR/Cas systems are used to genetically modify the naïve pluripotent cell.

Compounds

Exemplary compounds that are useful in a composition, system, kit, or method described herein are provided below.

Compounds of Formula (A)

In one aspect, the present disclosure provides compounds of Formula (A):

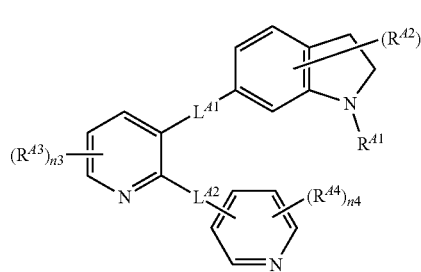

(A)

and pharmaceutically acceptable salts, solvates, hydrates, polymorphs, co-crystals, tautomers, stereoisomers, isotopically labeled derivatives, and prodrugs thereof, wherein:

$L^{A1}$ is a substituted or unsubstituted, saturated or unsaturated, $C_{1-4}$ aliphatic chain, optionally wherein one, two, or three chain atoms of the aliphatic chain are independently replaced with —O—, —S—, —NR$^{45}$—, —N=, or =N—, wherein each instance of R$^{45}$ is independently hydrogen, substituted or unsubstituted $C_{1-6}$ alkyl, or a nitrogen protecting group;

$L^{A2}$ is a substituted or unsubstituted, saturated or unsaturated, $C_{1-6}$ aliphatic chain, optionally wherein one, two, or three chain atoms of the aliphatic chain are independently replaced with —O—, —S—, —NR$^{46}$—, —N=, or =N—, wherein each instance of R$^{46}$ is independently hydrogen, substituted or unsubstituted $C_{1-6}$ alkyl, or a nitrogen protecting group;

$R^{A1}$ is hydrogen, substituted or unsubstituted $C_{1-6}$ alkyl, or a nitrogen protecting group;

each instance of $R^{A2}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ are joined to form a substituted or unsubstituted heterocyclic or substituted or unsubstituted heteroaryl ring;

n2 is 0, 1, 2, 3, 4, 5, 6, or 7;

each instance of $R^{A3}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

n3 is 0, 1, 2, or 3;

each instance of $R^{A4}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$; and n4 is 0, 1, 2, 3, or 4.

In certain embodiments, $L^{A1}$ is a substituted or unsubstituted, saturated or unsaturated, $C_2$ aliphatic chain, optionally wherein one chain atom of the aliphatic chain is replaced with —O—, —S—, —NR$^{45}$— (e.g., —NH—), —N=, or =N—. In certain embodiments, $L^{A1}$ is —C(=O)NR$^{A5}$— (e.g., —C(=O)NH—) or —NR$^{A5}$C(=O)— (e.g., —NHC(=O)—). In certain embodiments, $L^{A1}$ is a substituted or unsubstituted, saturated or unsaturated, $C_1$, $C_3$, or $C_4$ aliphatic chain, optionally wherein one or two chain atoms of the aliphatic chain are independently replaced with —O—, —S—, —NR$^{A5}$— (e.g., —NH—), —N=, or =N—.

In certain embodiments, all instances of $R^{A5}$ are the same. In certain embodiments, two instances of $R^{A5}$ are different from each other. In certain embodiments, at least one instance of $R^{A5}$ is hydrogen. In certain embodiments, all instances of $R^{A5}$ are hydrogen. In certain embodiments, at least one instance of $R^{A5}$ is substituted or unsubstituted $C_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, at least one instance of $R^{A5}$ is a nitrogen protecting group (e.g., Bn, Boc, Cbz, Fmoc, trifluoroacetyl, triphenylmethyl, acetyl, or Ts).

In certain embodiments, $L^{A2}$ is a substituted or unsubstituted, saturated or unsaturated, $C_2$ aliphatic chain, optionally wherein one chain atom of the aliphatic chain is replaced with —O—, —S—, —NR$^{A6}$— (e.g., —NH—), —N=, or =N—. In certain embodiments, $L^{A2}$ is —CH$_2$NR$^{A6}$— (e.g., —CH$_2$NH—) or —NR$^{A6}$CH$_2$— (e.g., —NHCH$_2$—). In certain embodiments, $L^{A2}$ is a substituted or unsubstituted, saturated or unsaturated, $C_1$, $C_3$, or $C_4$ aliphatic chain, optionally wherein one or two chain atoms of the aliphatic chain are independently replaced with —O—, —S—, —NR$^{A6}$— (e.g., —NH—), —N=, or =N—.

In certain embodiments, all instances of $R^{A6}$ are the same. In certain embodiments, two instances of $R^{A6}$ are different from each other. In certain embodiments, at least one instance of $R^{A6}$ is hydrogen. In certain embodiments, all instances of $R^{A6}$ are hydrogen. In certain embodiments, at least one instance of $R^{A6}$ is substituted or unsubstituted $C_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, at least one instance of $R^{A6}$ is a nitrogen protecting group (e.g., Bn, Boc, Cbz, Fmoc, trifluoroacetyl, triphenylmethyl, acetyl, or Ts).

In certain embodiments, $R^{A1}$ is hydrogen. In certain embodiments, $R^{A1}$ is substituted or unsubstituted $C_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, $R^{A1}$ is a nitrogen protecting group (e.g., Bn, Boc, Cbz, Fmoc, trifluoroacetyl, triphenylmethyl, acetyl, or Ts).

In certain embodiments, two instances of $R^{A2}$ are the same. In certain embodiments, two instances of $R^{A2}$ are different from each other. In certain embodiments, at least one instance of $R^{A2}$ is halogen (e.g., F, Cl, Br, or I). In certain embodiments, at least one instance of $R^{A2}$ is substituted or unsubstituted alkyl (e.g., substituted or unsubstituted $C_{1-6}$ alkyl). In certain embodiments, at least one instance of $R^{A2}$ is —CH$_3$. In certain embodiments, at least one instance of $R^{A2}$ is —CF$_3$, unsubstituted ethyl, perfluoroethyl, unsubstituted propyl, perfluoropropyl, unsubstituted butyl, or perfluorobutyl. In certain embodiments, at least one instance of $R^{A2}$ is substituted or unsubstituted alkenyl (e.g., substituted or unsubstituted $C_{1-6}$ alkenyl). In certain embodiments, at least one instance of $R^{A2}$ is substituted or unsubstituted alkynyl (e.g., substituted or unsubstituted $C_{1-6}$ alkynyl). In certain embodiments, at least one instance of $R^{A2}$ is substituted or unsubstituted carbocyclyl (e.g., substituted or unsubstituted, monocyclic, 3- to 7-membered carbocyclyl). In certain embodiments, at least one instance of $R^{A2}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{A2}$ is substituted or unsubstituted aryl (e.g., substituted or unsubstituted, 6- to 10-membered aryl). In certain embodiments, at least one instance of $R^{A2}$ is substituted or unsubstituted phenyl. In certain embodiments, at least one instance of $R^{A2}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{A2}$ is —OR$^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{A2}$ is —SR$^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{A2}$ is —N(R$^a$)$_2$ (e.g., —NH$_2$, —NH(substituted or unsubstituted $C_{1-6}$ alkyl) (e.g., —NHMe), or —N(substituted or unsubstituted $C_{1-6}$ alkyl)(substituted or unsubstituted $C_{1-6}$ alkyl) (e.g., —NMe$_2$)). In certain embodiments, at least one instance of $R^{A2}$ is —CN, —SCN, or —NO$_2$. In certain embodiments, at least one instance of $R^{A2}$ is —C(=NR$^a$)R$^a$, —C(=NR$^a$)OR$^a$, or —C(=NR$^a$)N(R$^a$)$_2$. In certain embodiments, at least one instance of $R^{A2}$ is —C(=O)R$^a$, —C(=O)OR$^a$, or —C(=O)N(R$^a$)$_2$ (e.g., —C(=O)NH$_2$, —C(=O)NHMe, or —C(=O)NMe$_2$). In certain embodiments, at least one instance of $R^{A2}$ is —NR$^a$C(=O)R$^a$, —NR$^a$C(=O)OR$^a$, or —NR$^a$C(=O)N(R$^a$)$_2$. In certain embodiments, at least one instance of $R^{A2}$ is —OC(=O)R$^a$, —OC(=O)OR$^a$, or —OC(=O)N(R$^a$)$_2$.

Each of Formulae (A) to (L) may independently include one or more substituents $R^a$. In certain embodiments, all instances of $R^a$ are the same. In certain embodiments, two instances of $R^a$ are different from each other. In certain embodiments, at least one instance of $R^a$ is H. In certain embodiments, at least one instance of $R^a$ is substituted or unsubstituted acyl (e.g., acetyl). In certain embodiments, at least one instance of $R^a$ is substituted or unsubstituted alkyl (e.g., substituted or unsubstituted $C_{1-6}$ alkyl). In certain embodiments, at least one instance of $R^a$ is —CH$_3$. In certain embodiments, at least one instance of $R^a$ is —CF$_3$, unsubstituted ethyl, perfluoroethyl, unsubstituted propyl, perfluoropropyl, unsubstituted butyl, or perfluorobutyl. In certain embodiments, at least one instance of $R^a$ is substituted or unsubstituted alkenyl (e.g., substituted or unsubstituted $C_{1-6}$ alkenyl). In certain embodiments, at least one instance of $R^a$ is substituted or unsubstituted alkynyl (e.g., substituted or unsubstituted $C_{1-6}$ alkynyl). In certain embodiments, at least one instance of $R^a$ is substituted or unsubstituted carbocyclyl (e.g., substituted or unsubstituted, monocyclic, 3- to 7-membered carbocyclyl). In certain embodiments, at least one instance of $R^a$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^a$ is substituted or unsubstituted aryl (e.g., substituted or unsubstituted, 6- to 10-membered aryl). In certain embodiments, at least one instance of $R^a$ is substituted or unsubstituted phenyl. In certain embodiments, at least one instance of $R^a$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^a$ is a nitrogen protecting group (e.g., Bn, Boc, Cbz, Fmoc, trifluoroacetyl, triphenylmethyl, acetyl, or Ts) when attached to a nitrogen atom. In certain embodiments, $R^a$ is an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom. In certain embodiments, $R^a$ is a sulfur protecting group (e.g., acetamidomethyl, t-Bu, 3-nitro-2-pyridine sulfenyl, 2-pyridinesulfenyl, or triphenylmethyl) when attached to a sulfur atom. In certain embodiments, two instances of $R^a$ are joined to form a substituted or unsubstituted heterocyclic ring (e.g., substituted or unsubstituted, monocyclic, 5- to 6-membed heterocyclic ring, wherein one, two, or three atoms in the heterocyclic ring system are independently nitrogen, oxygen, or sulfur). In certain embodiments, two instances of $R^a$ are joined to form a substituted or unsubstituted heteroaryl ring (e.g., substituted or unsubstituted, monocyclic, 5- to 6-membed heteroaryl ring, wherein one, two, three, or four atoms in the heteroaryl ring system are independently nitrogen, oxygen, or sulfur).

In certain embodiments, n2 is 0. In certain embodiments, n2 is 1. In certain embodiments, n2 is 2. In certain embodiments, n2 is 3. In certain embodiments, n2 is 4. In certain embodiments, n2 is 5. In certain embodiments, n2 is 6. In certain embodiments, n2 is 7.

In certain embodiments, all instances of $R^{43}$ are the same. In certain embodiments, two instances of $R^{43}$ are different from each other. In certain embodiments, at least one instance of $R^{43}$ is halogen (e.g., F, Cl, Br, or I). In certain embodiments, at least one instance of $R^{43}$ is substituted or unsubstituted alkyl (e.g., substituted or unsubstituted $C_{1-6}$ alkyl). In certain embodiments, at least one instance of $R^{43}$ is —CH$_3$. In certain embodiments, at least one instance of $R^{43}$ is —CF$_3$, unsubstituted ethyl, perfluoroethyl, unsubstituted propyl, perfluoropropyl, unsubstituted butyl, or perfluorobutyl. In certain embodiments, at least one instance of $R^{43}$ is substituted or unsubstituted alkenyl (e.g., substituted or unsubstituted $C_{1-6}$ alkenyl). In certain embodiments, at least one instance of $R^{43}$ is substituted or unsubstituted alkynyl (e.g., substituted or unsubstituted $C_{1-6}$ alkynyl). In certain embodiments, at least one instance of $R^{43}$ is substituted or unsubstituted carbocyclyl (e.g., substituted or unsubstituted, monocyclic, 3- to 7-membered carbocyclyl). In certain embodiments, at least one instance of $R^{43}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of RU is substituted or unsubstituted aryl (e.g., substituted or unsubstituted, 6- to 10-membered aryl). In certain embodiments, at least one instance of RU is substituted or unsubstituted phenyl. In certain embodiments, at least one instance of RU is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{43}$ is —OR$^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{43}$ is —SR$^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{43}$ is —N(R$^a$)$_2$ (e.g., —NH$_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —NMe$_2$)). In certain embodiments, at least one instance of $R^{43}$ is —CN, —SCN, or —NO$_2$. In certain embodiments, at least one instance of $R^{43}$ is —C(=NR$^a$)R$^a$, —C(=NR$^a$)OR$^a$, or —C(=NR$^a$)N(R$^a$)$_2$. In certain embodiments, at least one instance of $R^{43}$ is —C(=O)R$^a$, —C(=O)OR$^a$, or —C(=O)N(R$^a$)$_2$ (e.g., —C(=O)NH$_2$, —C(=O)NHMe, or —C(=O)NMe$_2$). In certain embodiments, at least one instance of $R^{43}$ is —NR$^a$C(=O)R$^a$, —NR$^a$C(=O)OR$^a$, or —NR$^a$C(=O)N(R$^a$)$_2$. In certain embodiments, at least one instance of $R^{43}$ is —OC(=O)R$^a$, —OC(=O)OR$^a$, or —OC(=O)N(R$^a$)$_2$.

In certain embodiments, n3 is 0. In certain embodiments, n3 is 1. In certain embodiments, n3 is 2. In certain embodiments, n3 is 3.

In certain embodiments, all instances of $R^{44}$ are the same. In certain embodiments, two instances of $R^{44}$ are different from each other. In certain embodiments, at least one instance of $R^{44}$ is halogen (e.g., F, Cl, Br, or I). In certain embodiments, at least one instance of $R^{44}$ is substituted or unsubstituted alkyl (e.g., substituted or unsubstituted $C_{1-6}$ alkyl). In certain embodiments, at least one instance of $R^{44}$ is —CH$_3$. In certain embodiments, at least one instance of $R^{44}$ is —CF$_3$, unsubstituted ethyl, perfluoroethyl, unsubstituted propyl, perfluoropropyl, unsubstituted butyl, or perfluorobutyl. In certain embodiments, at least one instance of $R^{44}$ is substituted or unsubstituted alkenyl (e.g., substituted or unsubstituted $C_{1-6}$ alkenyl). In certain embodiments, at least one instance of $R^{44}$ is substituted or unsubstituted alkynyl (e.g., substituted or unsubstituted $C_{1-6}$ alkynyl). In certain embodiments, at least one instance of $R^{44}$ is substituted or unsubstituted carbocyclyl (e.g., substituted or unsubstituted, monocyclic, 3- to 7-membered carbocyclyl). In certain embodiments, at least one instance of $R^{44}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{44}$ is substituted or unsubstituted aryl (e.g., substituted or unsubstituted, 6- to 10-membered aryl). In certain embodiments, at least one instance of $R^{44}$ is substituted or unsubstituted phenyl. In certain embodiments, at least one instance of $R^{44}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{44}$ is —OR$^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{44}$ is —SR$^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{44}$ is —N(R$^a$)$_2$ (e.g., —NH$_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —NMe$_2$)). In certain embodiments, at least one instance of $R^{44}$ is —CN, —SCN, or —NO$_2$. In certain embodiments, at least one instance of $R^{44}$ is —C(=NR$^a$)R$^a$, —C(=NR$^a$)OR$^a$, or —C(=NR$^a$)N(R$^a$)$_2$. In certain embodiments, at least one instance of $R^{A4}$ is —C(=O)$R^a$, —C(=O)O$R^a$, or —C(=O)N($R^a$)$_2$ (e.g., —C(=O)NH$_2$, —C(=O)NHMe, or —C(=O)NMe$_2$). In certain embodiments, at least one instance of $R^{A4}$ is —N$R^a$C(=O)$R^a$, —N$R^a$C(=O)O$R^a$, or —N$R^a$C(=O)N($R^a$)$_2$. In certain embodiments, at least one instance of $R^{A4}$ is —OC(=O)$R^a$, —OC(=O)O$R^a$, or —OC(=O)N($R^a$)$_2$.

In certain embodiments, n4 is 0. In certain embodiments, n4 is 1. In certain embodiments, n4 is 2. In certain embodiments, n4 is 3. In certain embodiments, n4 is 4.

In certain embodiments, the compound of Formula (A) is of the formula:

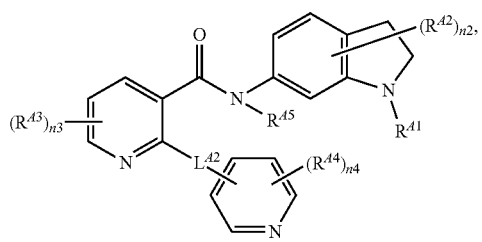

or a pharmaceutically acceptable salt, solvate, hydrate, polymorph, co-crystal, tautomer, stereoisomer, isotopically labeled derivative, or prodrug thereof.

In certain embodiments, the compound of Formula (A) is of the formula:

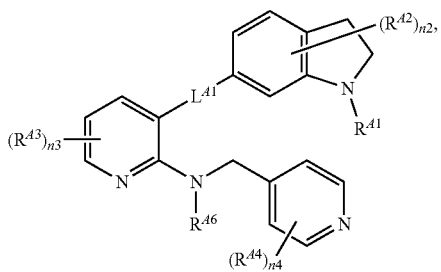

or a pharmaceutically acceptable salt, solvate, hydrate, polymorph, co-crystal, tautomer, stereoisomer, isotopically labeled derivative, or prodrug thereof.

In certain embodiments, the compound of Formula (A) is of the formula:

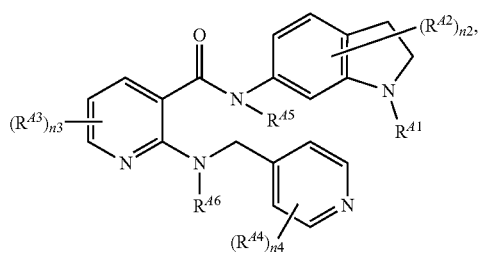

or a pharmaceutically acceptable salt, solvate, hydrate, polymorph, co-crystal, tautomer, stereoisomer, isotopically labeled derivative, or prodrug thereof.

In certain embodiments, the compound of Formula (A) is of the formula:

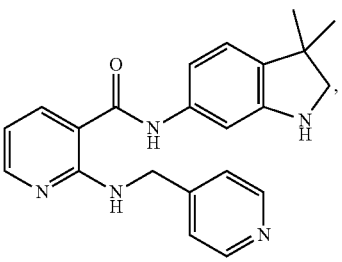

(AMG706)

or a pharmaceutically acceptable salt, solvate, hydrate, polymorph, co-crystal, tautomer, stereoisomer, isotopically labeled derivative, or prodrug thereof.

In certain embodiments, a compound of Formula (A) is not AMG706, or a pharmaceutically acceptable salt, solvate, hydrate, polymorph, co-crystal, tautomer, stereoisomer, or isotopically labeled derivative thereof.

It is believed that compounds of Formula (A), and pharmaceutically acceptable salts, solvates, hydrates, polymorphs, co-crystals, tautomers, stereoisomers, isotopically labeled derivatives, and prodrugs thereof, are VEGFR inhibitors (e.g., VEGFR1 inhibitors).

Compounds of Formula (B)

In another aspect, the present disclosure provides compounds of Formula (B):

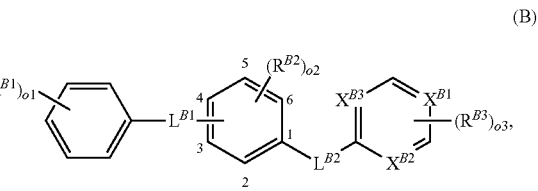

(B)

and pharmaceutically acceptable salts, solvates, hydrates, polymorphs, co-crystals, tautomers, stereoisomers, isotopically labeled derivatives, and prodrugs thereof, wherein:

$L^{B1}$ is —N($R^{B4}$)C(=O)—, —C(=O)N($R^{B4}$)—, or —N($R^{B4}$)C(=O)N($R^{B4}$)—, wherein each instance of $R^{B4}$ is independently hydrogen, substituted or unsubstituted $C_{1-6}$ alkyl, or a nitrogen protecting group;

when $L^{B1}$ is —N($R^{B4}$)C(=O)— or —C(=O)N($R^{B4}$)—, $L^{B1}$ is directly attached to the carbon atom labeled with 3 or 5;

when $L^{B1}$ is —N($R^{B4}$)C(=O)N($R^{B4}$)—, $L^{B1}$ is directly attached to the carbon atom labeled with 4;

$L^{B2}$ is —O—, —S—, —N$R^{B5}$—, or —C($R^{B6}$)$_2$—, wherein $R^{B5}$ is hydrogen, substituted or unsubstituted $C_{1-6}$ alkyl, or a nitrogen protecting group; and each instance of $R^{B6}$ is independently hydrogen, halogen, or substituted or unsubstituted alkyl;

each of $X^{B1}$, $X^{B2}$, and $X^{B3}$ is independently N or C$R^{B7}$, wherein each instance of $R^{B7}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^a$, —N($R^a$)$_2$, —S$R^a$, —CN, —SCN, —C(=N$R^a$)$R^a$, —C(=N$R^a$)O$R^a$, —C(=N$R^a$)N($R^a$)$_2$, —C(=O)$R^a$, —C(=O)O$R^a$, —C(=O)N($R^a$)$_2$, —NO$_2$, —N$R^a$C(=O)$R^a$, —N$R^a$C $-C(=O)OR^a$, $-NR^aC(=O)N(R^a)_2$, $-OC(=O)R^a$, $-OC(=O)OR^a$, or $-OC(=O)N(R^a)_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^a$ groups are joined to form a substituted or unsubstituted heterocyclic or substituted or unsubstituted heteroaryl ring;

each instance of $R^{B1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^a$, $-N(R^a)_2$, $-SR^a$, $-CN$, $-SCN$, $-C(=NR^a)R^a$, $-C(=NR^a)OR^a$, $-C(=NR^a)N(R^a)_2$, $-C(=O)R^a$, $-C(=O)OR^a$, $-C(=O)N(R^a)_2$, $-NO_2$, $-NR^aC(=O)R^a$, $-NR^aC(=O)OR^a$, $-NR^aC(=O)N(R^a)_2$, $-OC(=O)R^a$, $-OC(=O)OR^a$, or $-OC(=O)N(R^a)_2$;

o1 is 0, 1, 2, 3, 4, or 5;

each instance of $R^{B2}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^a$, $-N(R^a)_2$, $-SR^a$, $-CN$, $-SCN$, $-C(=NR^a)R^a$, $-C(=NR^a)OR^a$, $-C(=NR^a)N(R^a)_2$, $-C(=O)R^a$, $-C(=O)OR^a$, $-C(=O)N(R^a)_2$, $-NO_2$, $-NR^aC(=O)R^a$, $-NR^aC(=O)OR^a$, $-NR^aC(=O)N(R^a)_2$, $-OC(=O)R^a$, $-OC(=O)OR^a$, or $-OC(=O)N(R^a)_2$;

o2 is 0, 1, 2, 3, or 4;

each instance of $R^{B3}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^a$, $-N(R^a)_2$, $-SR^a$, $-CN$, $-SCN$, $-C(=O)N(R^a)_2$, $-NO_2$, $-NR^aC(=O)R^a$, $-NR^aC(=O)OR^a$, $-NR^aC(=O)N(R^a)_2$, $-OC(=O)R^a$, $-OC(=O)OR^a$, or $-OC(=O)N(R^a)_2$, or an instance of $R^{B3}$ and an instance of $R^{B7}$ are joined to form a substituted or unsubstituted heterocyclic ring; and o3 is 0, 1, or 2.

In certain embodiments, $L^{B1}$ is $-N(R^{B4})C(=O)-$ (e.g., $-NHC(=O)-$) or $-C(=O)N(R^{B4})-$ (e.g., $-C(=O)NH-$). In certain embodiments, $L^{B1}$ is $-N(R^{B4})C(=O)N(R^{B4})-$ (e.g., $-NHC(=O)NH-$).

In certain embodiments, all instances of $R^{B4}$ are the same. In certain embodiments, two instances of $R^{B4}$ are different from each other. In certain embodiments, at least one instance of $R^{B4}$ is hydrogen. In certain embodiments, at least one instance of $R^{B4}$ is substituted or unsubstituted $C_{1-6}$ alkyl (e.g., $-CH_3$, $-CF_3$, unsubstituted ethyl, perfluoroethyl, unsubstituted propyl, perfluoropropyl, unsubstituted butyl, or perfluorobutyl). In certain embodiments, at least one instance of $R^{B4}$ is a nitrogen protecting group (e.g., Bn, Boc, Cbz, Fmoc, trifluoroacetyl, triphenylmethyl, acetyl, or Ts).

In certain embodiments, $L^{B2}$ is $-O-$ or $-S-$. In certain embodiments, $L^{B2}$ is $-NR^{B5}-$ (e.g., $-NH-$). In certain embodiments, $L^{B2}$ is $-C(R^{B6})_2-$ (e.g., $-CH_2-$).

In certain embodiments, $R^{B5}$ is hydrogen. In certain embodiments, $R^{B5}$ is substituted or unsubstituted $C_{1-6}$ alkyl (e.g., $-CH_3$, $-CF_3$, unsubstituted ethyl, perfluoroethyl, unsubstituted propyl, perfluoropropyl, unsubstituted butyl, or perfluorobutyl). In certain embodiments, $R^{B5}$ is a nitrogen protecting group (e.g., Bn, Boc, Cbz, Fmoc, trifluoroacetyl, triphenylmethyl, acetyl, or Ts).

In certain embodiments, all instances of $R^{B6}$ are the same. In certain embodiments, two instances of $R^{B6}$ are different from each other. In certain embodiments, at least one instance of $R^{B6}$ is hydrogen. In certain embodiments, at least one instance of $R^{B6}$ is halogen (e.g., F, Cl, Br, or I). In certain embodiments, at least one instance of $R^{B6}$ is substituted or unsubstituted $C_{1-6}$ alkyl (e.g., $-CH_3$, $-CF_3$, unsubstituted ethyl, perfluoroethyl, unsubstituted propyl, perfluoropropyl, unsubstituted butyl, or perfluorobutyl).

In certain embodiments, $X^{B1}$, $X^{B2}$, and $X^{B3}$ are $CR^{B7}$ (e.g., CH), N, and N, respectively. In certain embodiments, each of $X^{B1}$, $X^{B2}$, and $X^{B3}$ is $CR^{B7}$ (e.g., CH). In certain embodiments, $X^{B1}$, $X^{B2}$, and $X^{B3}$ are N, $CR^{B7}$ (e.g., CH), and $CR^{B7}$ (e.g., CH), respectively.

In certain embodiments, all instances of $R^{B7}$ are the same. In certain embodiments, two instances of $R^{B7}$ are different from each other. In certain embodiments, at least one instance of $R^{B7}$ is hydrogen. In certain embodiments, at least one instance of $R^{B7}$ is halogen (e.g., F, Cl, Br, or I). In certain embodiments, at least one instance of $R^{B7}$ is substituted or unsubstituted alkyl (e.g., substituted or unsubstituted $C_{1-6}$ alkyl). In certain embodiments, at least one instance of $R^{B7}$ is $-CH_3$. In certain embodiments, at least one instance of $R^{B7}$ is $-CF_3$, unsubstituted ethyl, perfluoroethyl, unsubstituted propyl, perfluoropropyl, unsubstituted butyl, or perfluorobutyl. In certain embodiments, at least one instance of $R^{B7}$ is substituted or unsubstituted alkenyl (e.g., substituted or unsubstituted $C_{1-6}$ alkenyl). In certain embodiments, at least one instance of $R^{B7}$ is substituted or unsubstituted alkynyl (e.g., substituted or unsubstituted $C_{1-6}$ alkynyl). In certain embodiments, at least one instance of $R^{B7}$ is substituted or unsubstituted carbocyclyl (e.g., substituted or unsubstituted, monocyclic, 3- to 7-membered carbocyclyl). In certain embodiments, at least one instance of $R^{B7}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{B7}$ is substituted or unsubstituted aryl (e.g., substituted or unsubstituted, 6- to 10-membered aryl). In certain embodiments, at least one instance of $R^{B7}$ is substituted or unsubstituted phenyl. In certain embodiments, at least one instance of $R^{B7}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{B7}$ is $-OR^a$ (e.g., $-OH$, $-O$(substituted or unsubstituted $C_{1-6}$ alkyl) (e.g., $-OMe$, $-OEt$, $-OPr$, $-OBu$, or $-OBn$), or $-O$(substituted or unsubstituted phenyl) (e.g., $-OPh$)). In certain embodiments, at least one instance of $R^{B7}$ is $-SR^a$ (e.g., $-SH$, $-S$(substituted or unsubstituted $C_{1-6}$ alkyl) (e.g., $-SMe$, $-SEt$, $-SPr$, $-SBu$, or $-SBn$), or $-S$(substituted or unsubstituted phenyl) (e.g., $-SPh$)). In certain embodiments, at least one instance of $R^{B7}$ is —N(R$^a$)$_2$ (e.g., —NH$_2$, —NH(substituted or unsubstituted C$_{1-6}$ alkyl) (e.g., —NHMe), or —N(substituted or unsubstituted C$_{1-6}$ alkyl)-(substituted or unsubstituted C$_{1-6}$ alkyl) (e.g., —NMe$_2$)). In certain embodiments, at least one instance of $R^{B7}$ is —CN, —SCN, or —NO$_2$. In certain embodiments, at least one instance of $R^{B7}$ is —C(=NR$^a$)R$^a$, —C(=NR$^a$)OR$^a$, or —C(=NR$^a$)N(R$^a$)$_2$. In certain embodiments, at least one instance of $R^{B7}$ is —C(=O)R$^a$, —C(=O)OR$^a$, or —C(=O)N(R$^a$)$_2$ (e.g., —C(=O)NH$_2$, —C(=O)NHMe, or —C(=O)NMe$_2$). In certain embodiments, at least one instance of $R^{B7}$ is —NR$^a$C(=O)R$^a$, —NR$^a$C(=O)OR$^a$, or —NR$^a$C(=O)N(R$^a$)$_2$. In certain embodiments, at least one instance of $R^{B7}$ is —OC(=O)R$^a$, —OC(=O)OR$^a$, or —OC(=O)N(R$^a$)$_2$.

In certain embodiments, all instances of $R^{B1}$ are the same. In certain embodiments, two instances of $R^{B1}$ are different from each other. In certain embodiments, at least one instance of $R^{B1}$ is halogen (e.g., F, Cl, Br, or I). In certain embodiments, at least one instance of $R^{B1}$ is substituted or unsubstituted alkyl (e.g., substituted or unsubstituted C$_{1-6}$ alkyl). In certain embodiments, at least one instance of $R^{B1}$ is —CF$_3$ or —C(Me)$_2$CN. In certain embodiments, at least one instance of $R^{B1}$ is —CH$_3$, unsubstituted ethyl, perfluoroethyl, unsubstituted propyl, perfluoropropyl, unsubstituted butyl, or perfluorobutyl. In certain embodiments, at least one instance of $R^{B1}$ is substituted or unsubstituted alkenyl (e.g., substituted or unsubstituted C$_{1-6}$ alkenyl). In certain embodiments, at least one instance of $R^{B1}$ is substituted or unsubstituted alkynyl (e.g., substituted or unsubstituted C$_{1-6}$ alkynyl). In certain embodiments, at least one instance of $R^{B1}$ is substituted or unsubstituted carbocyclyl (e.g., substituted or unsubstituted, monocyclic, 3- to 7-membered carbocyclyl). In certain embodiments, at least one instance of $R^{B1}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{B1}$ is substituted or unsubstituted aryl (e.g., substituted or unsubstituted, 6- to 10-membered aryl). In certain embodiments, at least one instance of $R^{B1}$ is substituted or unsubstituted phenyl. In certain embodiments, at least one instance of $R^{B1}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{B1}$ is substituted or unsubstituted imidazolyl (e.g., substituted or unsubstituted 1-imidazolyl). In certain embodiments, at least one instance of $R^{B1}$ is —OR$^a$ (e.g., —OH, —O(substituted or unsubstituted C$_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{B1}$ is —SR$^a$ (e.g., —SH, —S(substituted or unsubstituted C$_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{B1}$ is —N(R$^a$)$_2$ (e.g., —NH$_2$, —NH(substituted or unsubstituted C$_{1-6}$ alkyl) (e.g., —NHMe), or —N(substituted or unsubstituted C$_{1-6}$ alkyl)-(substituted or unsubstituted C$_{1-6}$ alkyl) (e.g., —NMe$_2$)). In certain embodiments, at least one instance of $R^{B1}$ is —CN, —SCN, or —NO$_2$. In certain embodiments, at least one instance of $R^{B1}$ is —C(=NR$^a$)R$^a$, —C(=NR$^a$)OR$^a$, or —C(=NR$^a$)N(R$^a$)$_2$. In certain embodiments, at least one instance of $R^{B1}$ is —C(=O)R$^a$, —C(=O)OR$^a$, or —C(=O)N(R$^a$)$_2$ (e.g., —C(=O)NH$_2$, —C(=O)NHMe, or —C(=O)NMe$_2$). In certain embodiments, at least one instance of $R^{B1}$ is —NR$^a$C(=O)R$^a$, —NR$^a$C(=O)OR$^a$, or —NR$^a$C(=O)N(R$^a$)$_2$. In certain embodiments, at least one instance of $R^{B1}$ is —OC(=O)R$^a$, —OC(=O)OR$^a$, or —OC(=O)N(R$^a$)$_2$.

In certain embodiments, at least one instance of $R^{B1}$ is halogen, substituted or unsubstituted alkyl, or substituted or unsubstituted, monocyclic, 5- to 6-membed heteroaryl, wherein one, two, three, or four atoms in the heteroaryl ring system are independently nitrogen, oxygen, or sulfur.

In certain embodiments, o1 is 0. In certain embodiments, o1 is 1. In certain embodiments, o1 is 2. In certain embodiments, o1 is 3. In certain embodiments, o1 is 4. In certain embodiments, o1 is 5.

In certain embodiments, all instances of $R^{B2}$ are the same. In certain embodiments, two instances of $R^{B2}$ are different from each other. In certain embodiments, at least one instance of $R^{B2}$ is halogen (e.g., F, Cl, Br, or I). In certain embodiments, at least one instance of $R^{B2}$ is substituted or unsubstituted alkyl (e.g., substituted or unsubstituted C$_{1-6}$ alkyl). In certain embodiments, at least one instance of $R^{B2}$ is —CH$_3$. In certain embodiments, at least one instance of $R^{B2}$ is —CF$_3$, unsubstituted ethyl, perfluoroethyl, unsubstituted propyl, perfluoropropyl, unsubstituted butyl, or perfluorobutyl. In certain embodiments, at least one instance of $R^{B2}$ is substituted or unsubstituted alkenyl (e.g., substituted or unsubstituted C$_{1-6}$ alkenyl). In certain embodiments, at least one instance of $R^{B2}$ is substituted or unsubstituted alkynyl (e.g., substituted or unsubstituted C$_{1-6}$ alkynyl). In certain embodiments, at least one instance of $R^{B2}$ is substituted or unsubstituted carbocyclyl (e.g., substituted or unsubstituted, monocyclic, 3- to 7-membered carbocyclyl). In certain embodiments, at least one instance of $R^{B2}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{B2}$ is substituted or unsubstituted aryl (e.g., substituted or unsubstituted, 6- to 10-membered aryl). In certain embodiments, at least one instance of $R^{B2}$ is substituted or unsubstituted phenyl. In certain embodiments, at least one instance of $R^{B2}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{B2}$ is —OR$^a$ (e.g., —OH, —O(substituted or unsubstituted C$_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{B2}$ is —SR$^a$ (e.g., —SH, —S(substituted or unsubstituted C$_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{B2}$ is —N(R$^a$)$_2$ (e.g., —NH$_2$, —NH(substituted or unsubstituted C$_{1-6}$ alkyl) (e.g., —NHMe), or —N(substituted or unsubstituted C$_{1-6}$ alkyl)-(substituted or unsubstituted C$_{1-6}$ alkyl) (e.g., —NMe$_2$)). In certain embodiments, at least one instance of $R^{B2}$ is —CN, —SCN, or —NO$_2$. In certain embodiments, at least one instance of $R^{B2}$ is —C(=NR$^a$)R$^a$, —C(=NR$^a$)OR$^a$, or —C(=NR$^a$)N(R$^a$)$_2$. In certain embodiments, at least one instance of $R^{B2}$ is —C(=O)R$^a$, —C(=O)OR$^a$, or —C(=O)N(R$^a$)$_2$ (e.g., —C(=O)NH$_2$, —C(=O)NHMe, or —C(=O)NMe$_2$). In certain embodiments, at least one instance of $R^{B2}$ is —NR$^a$C(=O)R$^a$, —NR$^a$C(=O)OR$^a$, or —NR$^a$C(=O)N(R$^a$)$_2$. In certain embodiments, at least one instance of $R^{B2}$ is —OC(=O)R$^a$, —OC(=O)OR$^a$, or —OC(=O)N(R$^a$)$_2$.

In certain embodiments, o2 is 0. In certain embodiments, o2 is 1. In certain embodiments, o2 is 2. In certain embodiments, o2 is 3. In certain embodiments, o2 is 4.

In certain embodiments, all instances of $R^{B3}$ are the same. In certain embodiments, two instances of $R^{B3}$ are different from each other. In certain embodiments, at least one instance of $R^{B3}$ is halogen (e.g., F, Cl, Br, or I). In certain embodiments, at least one instance of $R^{B3}$ is substituted or unsubstituted alkyl (e.g., substituted or unsubstituted $C_{1-6}$ alkyl). In certain embodiments, at least one instance of $R^{B3}$ is —$CH_3$. In certain embodiments, at least one instance of $R^{B3}$ is —$CF_3$, unsubstituted ethyl, perfluoroethyl, unsubstituted propyl, perfluoropropyl, unsubstituted butyl, or perfluorobutyl. In certain embodiments, at least one instance of $R^{B3}$ is substituted or unsubstituted alkenyl (e.g., substituted or unsubstituted $C_{1-6}$ alkenyl). In certain embodiments, at least one instance of $R^{B3}$ is substituted or unsubstituted alkynyl (e.g., substituted or unsubstituted $C_{1-6}$ alkynyl). In certain embodiments, at least one instance of $R^{B3}$ is substituted or unsubstituted carbocyclyl (e.g., substituted or unsubstituted, monocyclic, 3- to 7-membered carbocyclyl). In certain embodiments, at least one instance of $R^{B3}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{B3}$ is substituted or unsubstituted aryl (e.g., substituted or unsubstituted, 6- to 10-membered aryl). In certain embodiments, at least one instance of $R^{B3}$ is substituted or unsubstituted phenyl. In certain embodiments, at least one instance of $R^{B3}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{B3}$ is substituted or unsubstituted pyridyl (e.g., 3-pyridyl). In certain embodiments, at least one instance of $R^{B3}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{B3}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{B3}$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^{B3}$ is —CN, —SCN, or —$NO_2$. In certain embodiments, at least one instance of $R^{B3}$ is —C(=O)N($R^a$)$_2$ (e.g., —C(=O)$NH_2$, —C(=O)NHMe, or —C(=O)$NMe_2$). In certain embodiments, at least one instance of $R^{B3}$ is —$NR^aC$(=O)$R^a$, —$NR^aC$(=O)$OR^a$, or —$NR^aC$(=O)N($R^a$)$_2$. In certain embodiments, at least one instance of $R^{B3}$ is —OC(=O)$R^a$, —OC(=O)$OR^a$, or —OC(=O)N($R^a$)$_2$. In certain embodiments, an instance of $R^{B3}$ and an instance of $R^{B7}$ are joined to form a substituted or unsubstituted heterocyclic ring (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, an instance of $R^{B3}$ and an instance of $R^{B7}$ are joined to form O or

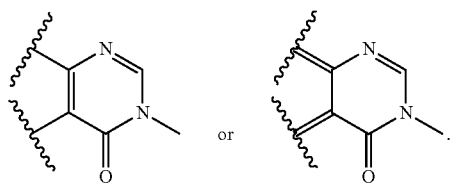

In certain embodiments, at least one instance of $R^{B3}$ is substituted or unsubstituted heteroaryl or —C(=O)N($R^a$)$_2$, or an instance of $R^{B3}$ and an instance of $R^{B7}$ are joined to form a substituted or unsubstituted, monocyclic, 5- to 6-membed heterocyclic ring, wherein one, two, or three atoms in the heterocyclic ring system are independently nitrogen, oxygen, or sulfur.

In certain embodiments, o3 is 0. In certain embodiments, o3 is 1. In certain embodiments, o3 is 2.

In certain embodiments, the compound of Formula (B) is of the formula:

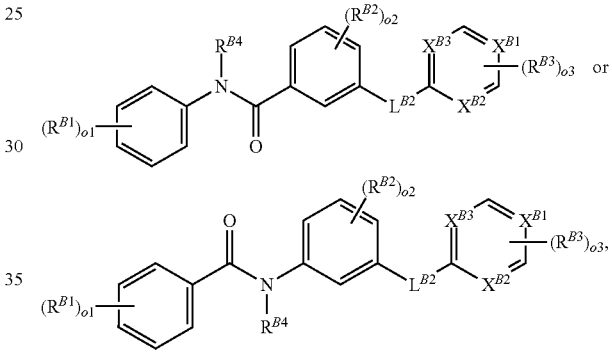

or a pharmaceutically acceptable salt, solvate, hydrate, polymorph, co-crystal, tautomer, stereoisomer, isotopically labeled derivative, or prodrug thereof.

In certain embodiments, the compound of Formula (B) is of the formula:

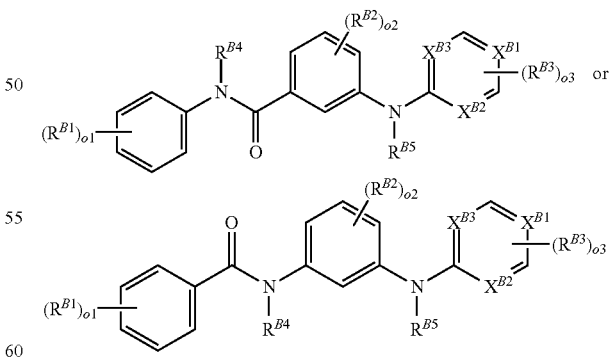

or a pharmaceutically acceptable salt, solvate, hydrate, polymorph, co-crystal, tautomer, stereoisomer, isotopically labeled derivative, or prodrug thereof.

In certain embodiments, the compound of Formula (B) is of the formula:

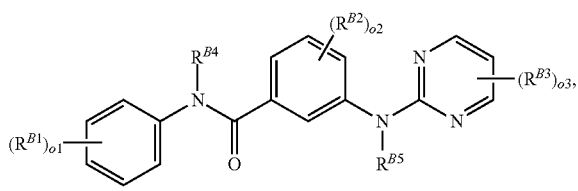

or a pharmaceutically acceptable salt, solvate, hydrate, polymorph, co-crystal, tautomer, stereoisomer, isotopically labeled derivative, or prodrug thereof.

In certain embodiments, the compound of Formula (B) is of the formula:

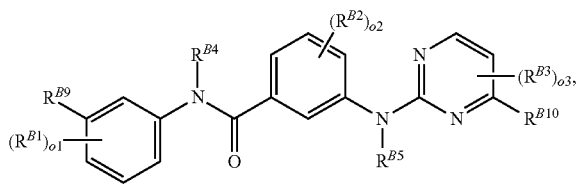

or a pharmaceutically acceptable salt, solvate, hydrate, polymorph, co-crystal, tautomer, stereoisomer, isotopically labeled derivative, or prodrug thereof, wherein each of $R^{B9}$ and $R^{B10}$ is independently substituted or unsubstituted, monocyclic, 5- to 6-membered heteroaryl, wherein one, two, three, or four atoms in the heteroaryl ring system are independently nitrogen, oxygen, or sulfur. In certain embodiments, $R^{B9}$ is substituted or unsubstituted imidazolyl (e.g., substituted or unsubstituted 1-imidazolyl). In certain embodiments, $R^{B10}$ is substituted or unsubstituted pyridyl (e.g., substituted or unsubstituted 3-pyridyl).

In certain embodiments, the compound of Formula (B) is of the formula:

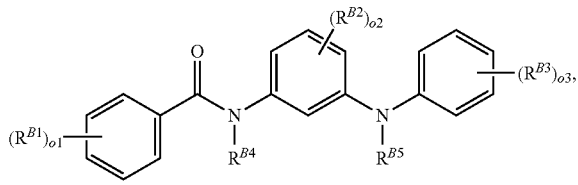

or a pharmaceutically acceptable salt, solvate, hydrate, polymorph, co-crystal, tautomer, stereoisomer, isotopically labeled derivative, or prodrug thereof.

In certain embodiments, the compound of Formula (B) is of the formula:

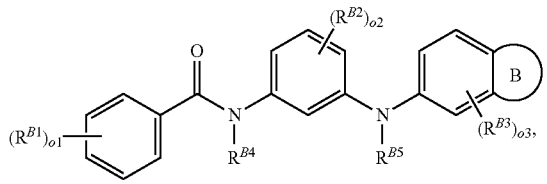

or a pharmaceutically acceptable salt, solvate, hydrate, polymorph, co-crystal, tautomer, stereoisomer, isotopically labeled derivative, or prodrug thereof, wherein Ring B is a substituted or unsubstituted, monocyclic, 5- to 6-membed heterocyclic ring, wherein one, two, or three atoms in the heterocyclic ring system are independently nitrogen, oxygen, or sulfur.

In certain embodiments, the compound of Formula (B) is of the formula:

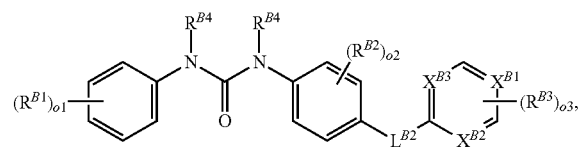

or a pharmaceutically acceptable salt, solvate, hydrate, polymorph, co-crystal, tautomer, stereoisomer, isotopically labeled derivative, or prodrug thereof.

In certain embodiments, the compound of Formula (B) is of the formula:

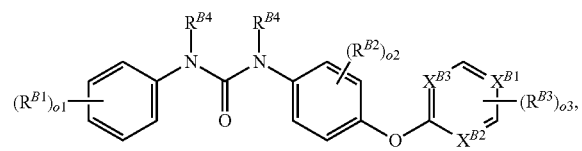

or a pharmaceutically acceptable salt, solvate, hydrate, polymorph, co-crystal, tautomer, stereoisomer, isotopically labeled derivative, or prodrug thereof.

In certain embodiments, the compound of Formula (B) is of the formula:

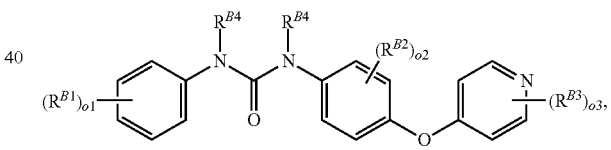

or a pharmaceutically acceptable salt, solvate, hydrate, polymorph, co-crystal, tautomer, stereoisomer, isotopically labeled derivative, or prodrug thereof.

In certain embodiments, the compound of Formula (B) is of the formula:

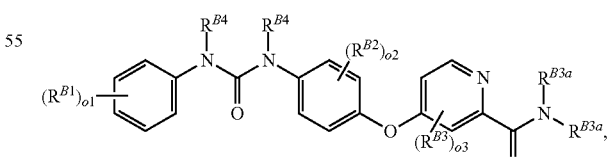

or a pharmaceutically acceptable salt, solvate, hydrate, polymorph, co-crystal, tautomer, stereoisomer, isotopically labeled derivative, or prodrug thereof.

In certain embodiments, the compound of Formula (B) is of the formula:

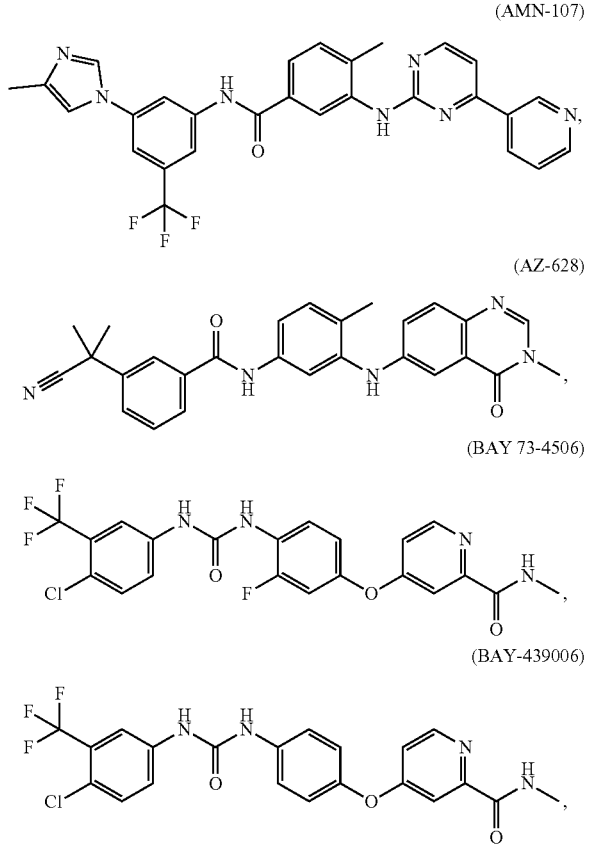

or a pharmaceutically acceptable salt, solvate, hydrate, polymorph, co-crystal, tautomer, stereoisomer, isotopically labeled derivative, or prodrug thereof.

In certain embodiments, a compound of Formula (B) is not AMN-107, AZ-628, BAY 73-4506, BAY-439006, or a pharmaceutically acceptable salt, solvate, hydrate, polymorph, co-crystal, tautomer, stereoisomer, or isotopically labeled derivative thereof.

It is believed that compounds of Formula (B), and pharmaceutically acceptable salts, solvates, hydrates, polymorphs, co-crystals, tautomers, stereoisomers, isotopically labeled derivatives, and prodrugs thereof, are ANL inhibitors (e.g., AMN-107), BRAF inhibitors (e.g., AZ-628 and BAY-439006), VEGFR inhibitors (e.g., VEGFR2 inhibitors, such as BAY 73-4506), and/or TIE2 inhibitors (e.g., BAY 73-4506).

Compounds of Formula (C)

In another aspect, the present disclosure provides compounds of Formula (C):

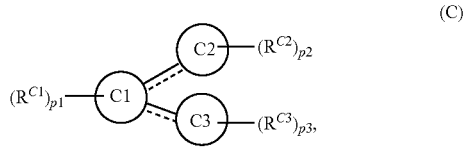

(C)

and pharmaceutically acceptable salts, solvates, hydrates, polymorphs, co-crystals, tautomers, stereoisomers, isotopically labeled derivatives, and prodrugs thereof, wherein:

Ring C1 is a substituted or unsubstituted, monocyclic, 5- to 6-membered heterocyclic ring or a substituted or unsubstituted, monocyclic, 5- to 6-membered heteroaryl ring, wherein one or two atoms in the heterocyclic or heteroaryl ring system are nitrogen;

Ring C2 is a substituted or unsubstituted, monocyclic, 6-membered carbocyclic ring or a substituted or unsubstituted phenyl ring;

Ring C3 is a substituted or unsubstituted, monocyclic, 5- to 6-membered heterocyclic ring or a substituted or unsubstituted, monocyclic, 5- to 6-membered heteroaryl ring, wherein one or two atoms in the heterocyclic or heteroaryl ring system are nitrogen;

each instance of $R^{C1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted heterocyclic or substituted or unsubstituted heteroaryl ring;

p1 is 0, 1, 2, 3, 4, 5, 6, 7, 8, or 9;

each instance of $R^{C2}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$, or two instances of $R^{C2}$ are joined to form a substituted or unsubstituted carbocyclic ring;

p2 is 0, 1, 2, 3, 4, 5, 6, 7, 8, 9, 10, or 11;

each instance of $R^{C3}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$; and p3 is 0, 1, 2, 3, 4, 5, 6, 7, 8, 9, or 10.

In certain embodiments, Ring C1 is a substituted or unsubstituted, monocyclic, 5- to 6-membered heterocyclic ring, wherein one or two atoms in the heterocyclic ring system are nitrogen. In certain embodiments, Ring C1 is a substituted or unsubstituted 1,2-dihydropyridinyl ring. In certain embodiments, Ring C1 is a substituted or unsubstituted, monocyclic, 5- to 6-membered heteroaryl ring, wherein one or two atoms in the heteroaryl ring system are nitrogen. In certain embodiments, Ring C1 is a substituted or unsubstituted pyrazolyl ring, substituted or unsubstituted imidazolyl ring, substituted or unsubstituted pyridyl ring, or substituted or unsubstituted pyrimidinyl ring.

In certain embodiments, Ring C2 is a substituted or unsubstituted, monocyclic, 6-membered carbocyclic ring. In certain embodiments, Ring C2 is a cyclohexa-2,4-dienone ring or cyclohexa-1,4-diene ring. In certain embodiments, Ring C2 is a substituted or unsubstituted phenyl ring.

In certain embodiments, Ring C3 is a substituted or unsubstituted, monocyclic, 5- to 6-membered heterocyclic ring, wherein one or two atoms in the heterocyclic ring system are nitrogen. In certain embodiments, Ring C3 is a substituted or unsubstituted piperidinyl ring (e.g., substituted or unsubstituted 4-piperidinyl ring) or substituted or unsubstituted 1,4-dihydropyridinyl ring (e.g., substituted or unsubstituted 1,4-dihydropyridin-4-yl ring). In certain embodiments, Ring C3 is a substituted or unsubstituted, monocyclic, 5- to 6-membered heteroaryl ring, wherein one or two atoms in the heteroaryl ring system are nitrogen. In certain embodiments, Ring C3 is a substituted or unsubstituted pyridinyl ring (e.g., substituted or unsubstituted 4-pyridinyl ring) or substituted or unsubstituted imidazolyl ring (e.g., substituted or unsubstituted 2-imidazolyl ring).

In certain embodiments, all instances of $R^{C1}$ are the same. In certain embodiments, two instances of $R^{C1}$ are different from each other. In certain embodiments, at least one instance of $R^{C1}$ is halogen (e.g., F, Cl, Br, or I). In certain embodiments, at least one instance of $R^{C1}$ is substituted or unsubstituted alkyl (e.g., substituted or unsubstituted $C_{1-6}$ alkyl). In certain embodiments, at least one instance of $R^{C1}$ is —CH$_2$CH$_2$OH. In certain embodiments, at least one instance of $R^{C1}$ is —CH$_3$, —CF$_3$, unsubstituted ethyl, perfluoroethyl, unsubstituted propyl, perfluoropropyl, unsubstituted butyl, or perfluorobutyl. In certain embodiments, at least one instance of $R^{C1}$ is substituted or unsubstituted alkenyl (e.g., substituted or unsubstituted $C_{1-6}$ alkenyl). In certain embodiments, at least one instance of $R^{C1}$ is substituted or unsubstituted alkynyl (e.g., substituted or unsubstituted $C_{1-6}$ alkynyl). In certain embodiments, at least one instance of $R^{C1}$ is substituted or unsubstituted carbocyclyl (e.g., substituted or unsubstituted, monocyclic, 3- to 7-membered carbocyclyl). In certain embodiments, at least one instance of $R^{C1}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{C1}$ is substituted or unsubstituted aryl (e.g., substituted or unsubstituted, 6- to 10-membered aryl). In certain embodiments, at least one instance of $R^{C1}$ is substituted or unsubstituted phenyl. In certain embodiments, at least one instance of $R^{C1}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{C1}$ is —OR$^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{C1}$ is —OCH$_2$CH$_2$N(Me)$_2$. In certain embodiments, at least one instance of $R^{C1}$ is —SR$^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{C1}$ is —N(R$^a$)$_2$ (e.g., —NH(substituted or unsubstituted $C_{1-6}$ alkyl) (e.g., —NHMe) or —N(substituted or unsubstituted $C_{1-6}$ alkyl)-(substituted or unsubstituted $C_{1-6}$ alkyl) (e.g., —NMe$_2$)). In certain embodiments, at least one instance of $R^{C1}$ is —NH$_2$. In certain embodiments, at least one instance of $R^{C1}$ is —CN, —SCN, or —NO$_2$. In certain embodiments, at least one instance of $R^{C1}$ is —C(=NR$^a$)R$^a$, —C(=NR$^a$)OR$^a$, or —C(=NR$^a$)N(R$^a$)$_2$. In certain embodiments, at least one instance of $R^{C1}$ is —C(=O)R$^a$, —C(=O)OR$^a$, or —C(=O)N(R$^a$)$_2$ (e.g., —C(=O)NH$_2$, —C(=O)NHMe, or —C(=O)NMe$_2$). In certain embodiments, at least one instance of $R^{C1}$ is —NR$^a$C(=O)R$^a$, —NR$^a$C(=O)OR$^a$, or —NR$^a$C(=O)N(R$^a$)$_2$. In certain embodiments, at least one instance of $R^{C1}$ is —OC(=O)R$^a$, —OC(=O)OR$^a$, or —OC(=O)N(R$^a$)$_2$.

In certain embodiments, at least one instance of $R^{C1}$ is substituted or unsubstituted alkyl, —OR$^a$, —N(R$^a$)$_2$, or —CN.

In certain embodiments, p1 is 0. In certain embodiments, p1 is 1. In certain embodiments, p1 is 2. In certain embodiments, p1 is 3. In certain embodiments, p1 is 4. In certain embodiments, p1 is 5. In certain embodiments, p1 is 6. In certain embodiments, p1 is 7. In certain embodiments, p1 is 8. In certain embodiments, p1 is 9.

In certain embodiments, all instances of $R^{C2}$ are the same. In certain embodiments, two instances of $R^{C2}$ are different from each other. In certain embodiments, at least one instance of $R^{C2}$ is halogen (e.g., F, Cl, Br, or I). In certain embodiments, at least one instance of $R^{C2}$ is substituted or unsubstituted alkyl (e.g., substituted or unsubstituted $C_{1-6}$ alkyl). In certain embodiments, at least one instance of $R^{C2}$ is —CH$_3$. In certain embodiments, at least one instance of $R^{C2}$ is —CF$_3$, unsubstituted ethyl, perfluoroethyl, unsubstituted propyl, perfluoropropyl, unsubstituted butyl, or perfluorobutyl. In certain embodiments, at least one instance of $R^{C2}$ is substituted or unsubstituted alkenyl (e.g., substituted or unsubstituted $C_{1-6}$ alkenyl). In certain embodiments, at least one instance of $R^{C2}$ is substituted or unsubstituted alkynyl (e.g., substituted or unsubstituted $C_{1-6}$ alkynyl). In certain embodiments, at least one instance of $R^{C2}$ is substituted or unsubstituted carbocyclyl (e.g., substituted or unsubstituted, monocyclic, 3- to 7-membered carbocyclyl). In certain embodiments, at least one instance of $R^{C2}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{C2}$ is substituted or unsubstituted aryl (e.g., substituted or unsubstituted, 6- to 10-membered aryl). In certain embodiments, at least one instance of $R^{C2}$ is substituted or unsubstituted phenyl. In certain embodiments, at least one instance of $R^{C2}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{C2}$ is —OR$^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{C2}$ is —OCH$_2$ (unsubstituted cyclopropyl). In certain embodiments, at least one instance of $R^{C2}$ is —SR$^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{C2}$ is —N(R$^a$)$_2$ (e.g., —NH$_2$, —NH(substituted or unsubstituted C$_{1-6}$ alkyl) (e.g., —NHMe), or —N(substituted or unsubstituted C$_{1-6}$ alkyl)-(substituted or unsubstituted C$_{1-6}$ alkyl) (e.g., —NMe$_2$)). In certain embodiments, at least one instance of $R^{C2}$ is —CN, —SCN, or —NO$_2$. In certain embodiments, at least one instance of $R^{C2}$ is —C(=NR$^a$)R$^a$, —C(=NR$^a$)OR$^a$, or —C(=NR$^a$)N(R$^a$)$_2$. In certain embodiments, at least one instance of $R^{C2}$ is —C(=O)R$^a$, —C(=O)OR$^a$, or —C(=O)N(R$^a$)$_2$ (e.g., —C(=O)NH$_2$, —C(=O)NHMe, or —C(=O)NMe$_2$). In certain embodiments, at least one instance of $R^{C2}$ is —NR$^a$C(=O)R$^a$, —NR$^a$C(=O)OR$^a$, or —NR$^a$C(=O)N(R$^a$)$_2$. In certain embodiments, at least one instance of $R^{C2}$ is —OC(=O)R$^a$, —OC(=O)OR$^a$, or —OC(=O)N(R$^a$)$_2$. In certain embodiments, two instances of $R^{C2}$ are joined to form a substituted or unsubstituted carbocyclic ring (e.g., substituted or unsubstituted, monocyclic, 5- to 6-membed carbocyclic ring). In certain embodiments, two instances of $R^{C2}$ are joined to form a substituted or unsubstituted cyclopentyl ring or substituted or unsubstituted cyclopentenyl ring.

In certain embodiments, at least one instance of $R^{C2}$ is halogen or —OR$^a$.

In certain embodiments, p2 is 0. In certain embodiments, p2 is 1. In certain embodiments, p2 is 2. In certain embodiments, p2 is 3. In certain embodiments, p2 is 4. In certain embodiments, p2 is 5. In certain embodiments, p2 is 6. In certain embodiments, p2 is 7. In certain embodiments, p2 is 8. In certain embodiments, p2 is 9. In certain embodiments, p2 is 10. In certain embodiments, p2 is 11.

In certain embodiments, all instances of $R^{C3}$ are the same. In certain embodiments, two instances of $R^{C3}$ are different from each other. In certain embodiments, at least one instance of $R^{C3}$ is halogen (e.g., F, Cl, Br, or I). In certain embodiments, at least one instance of $R^{C3}$ is substituted or unsubstituted alkyl (e.g., substituted or unsubstituted C$_{1-6}$ alkyl). In certain embodiments, at least one instance of $R^{C3}$ is —CH$_3$. In certain embodiments, at least one instance of $R^{C3}$ is —CF$_3$, unsubstituted ethyl, perfluoroethyl, unsubstituted propyl, perfluoropropyl, unsubstituted butyl, or perfluorobutyl. In certain embodiments, at least one instance of $R^{C3}$ is substituted or unsubstituted alkenyl (e.g., substituted or unsubstituted C$_{1-6}$ alkenyl). In certain embodiments, at least one instance of $R^{C3}$ is substituted or unsubstituted alkynyl (e.g., substituted or unsubstituted C$_{1-6}$ alkynyl). In certain embodiments, at least one instance of $R^{C3}$ is substituted or unsubstituted carbocyclyl (e.g., substituted or unsubstituted, monocyclic, 3- to 7-membered carbocyclyl). In certain embodiments, at least one instance of $R^{C3}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{C3}$ is substituted or unsubstituted aryl (e.g., substituted or unsubstituted, 6- to 10-membered aryl). In certain embodiments, at least one instance of $R^{C3}$ is substituted or unsubstituted phenyl. In certain embodiments, at least one instance of $R^{C3}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{C3}$ is —OR$^a$ (e.g., —OH, —O(substituted or unsubstituted C$_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{C3}$ is —SR$^a$ (e.g., —SH, —S(substituted or unsubstituted C$_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{C3}$ is —N(R$^a$)$_2$ (e.g., —NH$_2$, —NH(substituted or unsubstituted C$_{1-6}$ alkyl) (e.g., —NHMe), or —N(substituted or unsubstituted C$_{1-6}$ alkyl)-(substituted or unsubstituted C$_{1-6}$ alkyl) (e.g., —NMe$_2$)). In certain embodiments, at least one instance of $R^{C3}$ is —CN, —SCN, or —NO$_2$. In certain embodiments, at least one instance of $R^{C3}$ is —C(=NR$^a$)R$^a$, —C(=NR$^a$)OR$^a$, or —C(=NR$^a$)N(R$^a$)$_2$. In certain embodiments, at least one instance of $R^{C3}$ is —C(=O)R$^a$, —C(=O)OR$^a$, or —C(=O)N(R$^a$)$_2$ (e.g., —C(=O)NH$_2$, —C(=O)NHMe, or —C(=O)NMe$_2$). In certain embodiments, at least one instance of $R^{C3}$ is —NR$^a$C(=O)R$^a$, —NR$^a$C(=O)OR$^a$, or —NR$^a$C(=O)N(R$^a$)$_2$. In certain embodiments, at least one instance of $R^{C3}$ is —OC(=O)R$^a$, —OC(=O)OR$^a$, or —OC(=O)N(R$^a$)$_2$.

In certain embodiments, p3 is 0. In certain embodiments, p3 is 1. In certain embodiments, p3 is 2. In certain embodiments, p3 is 3. In certain embodiments, p3 is 4. In certain embodiments, p3 is 5. In certain embodiments, p3 is 6. In certain embodiments, p3 is 7. In certain embodiments, p3 is 8. In certain embodiments, p3 is 9. In certain embodiments, p3 is 10.

In certain embodiments, the compound of Formula (C) is of the formula:

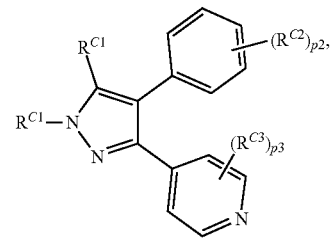

or a pharmaceutically acceptable salt, solvate, hydrate, polymorph, co-crystal, tautomer, stereoisomer, isotopically labeled derivative, or prodrug thereof.

In certain embodiments, the compound of Formula (C) is of the formula:

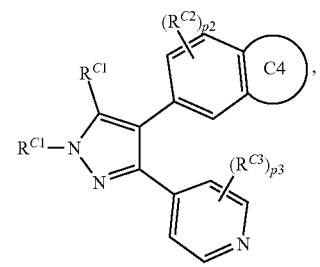

or a pharmaceutically acceptable salt, solvate, hydrate, polymorph, co-crystal, tautomer, stereoisomer, isotopically labeled derivative, or prodrug thereof, wherein Ring C4 is a substituted or unsubstituted, monocyclic, 5- to 6-membed carbocyclic ring (e.g., substituted or unsubstituted cyclopentyl ring or substituted or unsubstituted cyclopentenyl ring).

In certain embodiments, the compound of Formula (C) is of the formula:

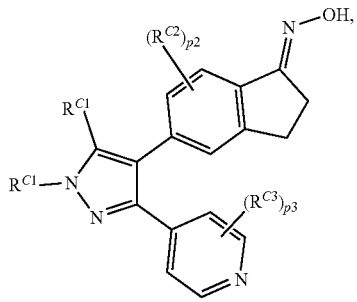

or a pharmaceutically acceptable salt, solvate, hydrate, polymorph, co-crystal, tautomer, stereoisomer, isotopically labeled derivative, or prodrug thereof.

In certain embodiments, the compound of Formula (C) is of the formula:

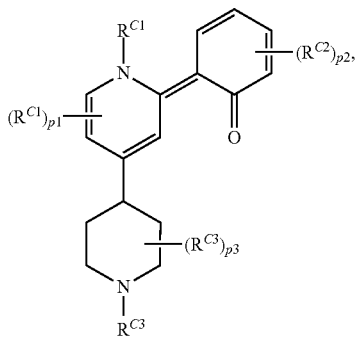

or a pharmaceutically acceptable salt, solvate, hydrate, polymorph, co-crystal, tautomer, stereoisomer, isotopically labeled derivative, or prodrug thereof.

In certain embodiments, the compound of Formula (C) is of the formula:

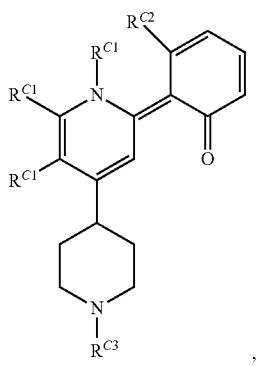

or a pharmaceutically acceptable salt, solvate, hydrate, polymorph, co-crystal, tautomer, stereoisomer, isotopically labeled derivative, or prodrug thereof.

In certain embodiments, the compound of Formula (C) is of the formula:

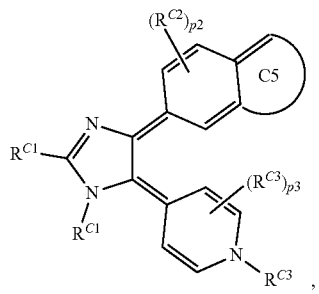

or a pharmaceutically acceptable salt, solvate, hydrate, polymorph, co-crystal, tautomer, stereoisomer, isotopically labeled derivative, or prodrug thereof, wherein Ring C5 is a substituted or unsubstituted, monocyclic, 5- to 6-membed carbocyclic ring (e.g., substituted or unsubstituted cyclopentenyl ring).

In certain embodiments, the compound of Formula (C) is of the formula:

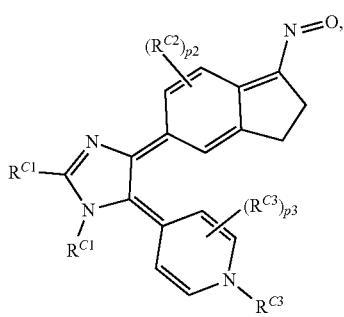

or a pharmaceutically acceptable salt, solvate, hydrate, polymorph, co-crystal, tautomer, stereoisomer, isotopically labeled derivative, or prodrug thereof.

In certain embodiments, the compound of Formula (C) is of the formula:

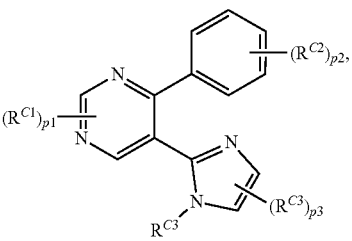

or a pharmaceutically acceptable salt, solvate, hydrate, polymorph, co-crystal, tautomer, stereoisomer, isotopically labeled derivative, or prodrug thereof.

In certain embodiments, the compound of Formula (C) is of the formula:

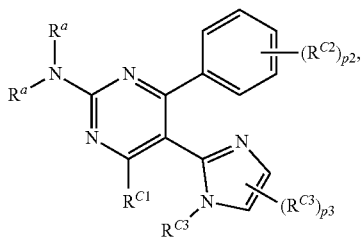

or a pharmaceutically acceptable salt, solvate, hydrate, polymorph, co-crystal, tautomer, stereoisomer, isotopically labeled derivative, or prodrug thereof.

In certain embodiments, the compound of Formula (C) is of the formula:

(GDC-0879 or GDC0879)

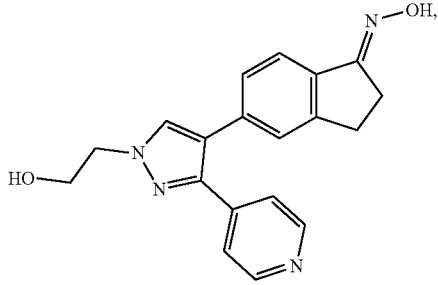

(KIN001-260)

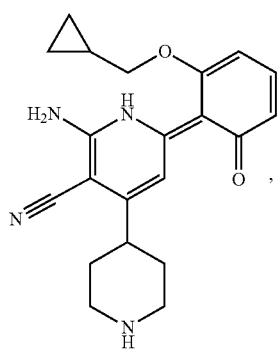

(SB590885, SB59, or SB)

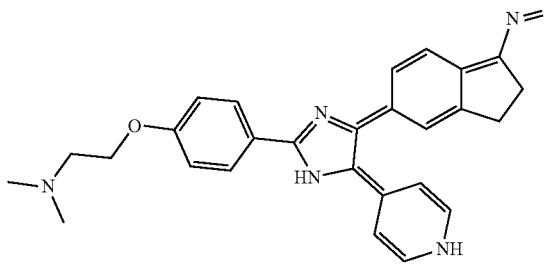

(CHIR99021 or CH)

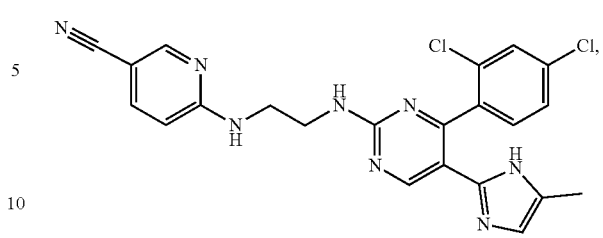

or a pharmaceutically acceptable salt, solvate, hydrate, polymorph, co-crystal, tautomer, stereoisomer, isotopically labeled derivative, or prodrug thereof.

In certain embodiments, a compound of Formula (C) is not GDC-0879, KIN001-260, SB590885, CHIR99021, or a pharmaceutically acceptable salt, solvate, hydrate, polymorph, co-crystal, tautomer, stereoisomer, or isotopically labeled derivative thereof.

It is believed that compounds of Formula (C), and pharmaceutically acceptable salts, solvates, hydrates, polymorphs, co-crystals, tautomers, stereoisomers, isotopically labeled derivatives, and prodrugs thereof, are BRAF inhibitors (e.g., GDC-0879 and SB590885), IKK inhibitors (e.g., IKKβ inhibitors, such as KIN001-260), and/or GSK3 inhibitors (e.g., GSK3B inhibitors, such as CHIR99021).

Compounds of Formula (D)

In another aspect, the present disclosure provides compounds of Formula (D):

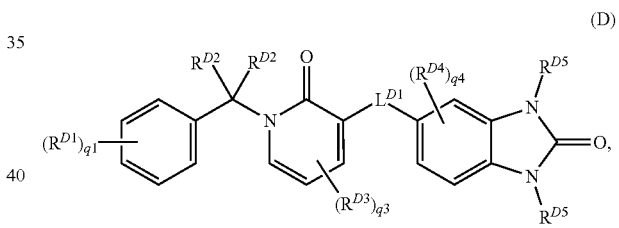

(D)

and pharmaceutically acceptable salts, solvates, hydrates, polymorphs, co-crystals, tautomers, stereoisomers, isotopically labeled derivatives, and prodrugs thereof, wherein:

$L^{D1}$ is a substituted or unsubstituted, saturated or unsaturated, $C_{3-7}$ aliphatic chain, optionally wherein one, two, or three chain atoms of the aliphatic chain are independently replaced with —O—, —S—, —NR$^{D6}$—, —N═, or ═N—, wherein each instance of $R^{D6}$ is independently hydrogen, substituted or unsubstituted $C_{1-6}$ alkyl, or a nitrogen protecting group;

each instance of $R^{D1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(═NR$^a$)R$^a$, —C(═NR$^a$)OR$^a$, —C(═NR$^a$)N(R$^a$)$_2$, —C(═O)R$^a$, —C(═O)OR$^a$, —C(═O)N(R$^a$)$_2$, —NO$_2$, —NR$^a$C(═O)R$^a$, —NR$^a$C(═O)OR$^a$, —NR$^a$C(═O)N(R$^a$)$_2$, —OC(═O)R$^a$, —OC(═O)OR$^a$, or —OC(═O)N(R$^a$)$_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted heterocyclic or substituted or unsubstituted heteroaryl ring;

q1 is 0, 1, 2, 3, 4, or 5;

each instance of $R^{D2}$ is independently hydrogen, halogen, or substituted or unsubstituted $C_{1-6}$ alkyl;

each instance of $R^{D3}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$;

q3 is 0, 1, 2, or 3;

each instance of $R^{D4}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$;

q4 is 0, 1, 2, or 3; and each instance of $R^{D5}$ is independently hydrogen, substituted or unsubstituted $C_{1-6}$ alkyl, or a nitrogen protecting group.

In certain embodiments, $L^{D1}$ is a substituted or unsubstituted, saturated or unsaturated, $C_5$ aliphatic chain, optionally wherein one, two, or three chain atoms of the aliphatic chain are independently replaced with —O—, —S—, —$NR^{D6}$— (e.g., —NH—), —N=, or =N—. In certain embodiments, $L^{D1}$ is of the formula:

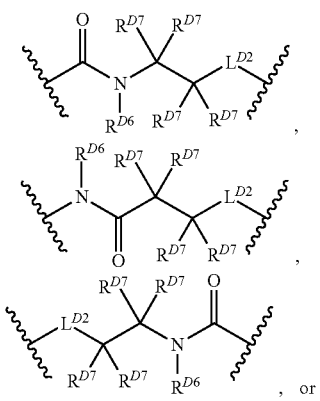

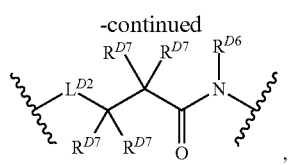

wherein each instance of $R^{D7}$ is independently hydrogen, halogen, substituted or unsubstituted $C_{1-6}$ alkyl, or substituted or unsubstituted phenyl; and $L^{D2}$ is —O—, —S—, —$N(R^{D8})$—, or —$C(R^{D9})_2$—, wherein $R^{D8}$ is hydrogen, substituted or unsubstituted $C_{1-6}$ alkyl, or a nitrogen protecting group, and each instance of $R^{D9}$ is independently hydrogen, halogen, or substituted or unsubstituted $C_{1-6}$ alkyl. In certain embodiments, $L^{D1}$ is of the formula:

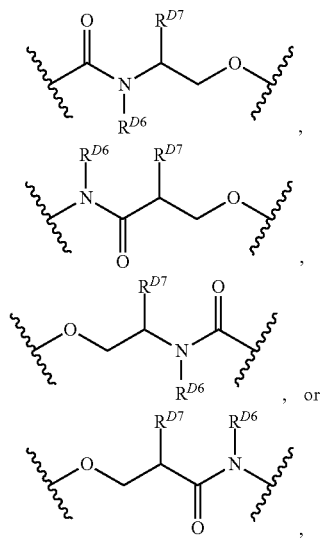

wherein $R^{D7}$ is substituted or unsubstituted phenyl. In certain embodiments, $L^{D1}$ is a substituted or unsubstituted, saturated or unsaturated, $C_3$, $C_4$, $C_6$, or $C_7$ aliphatic chain, optionally wherein one, two, or three chain atoms of the aliphatic chain are independently replaced with —O—, —S—, —$NR^{D6}$— (e.g., —NH—), —N=, or =N—.

In certain embodiments, all instances of $R^{D6}$ are the same. In certain embodiments, two instances of $R^{D6}$ are different from each other. In certain embodiments, at least one instance of $R^{D6}$ is hydrogen. In certain embodiments, at least one instance of $R^{D6}$ is substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, or perfluorobutyl). In certain embodiments, at least one instance of $R^{D6}$ is a nitrogen protecting group (e.g., Bn, Boc, Cbz, Fmoc, trifluoroacetyl, triphenylmethyl, acetyl, or Ts).

In certain embodiments, all instances of $R^{D1}$ are the same. In certain embodiments, two instances of $R^{D1}$ are different from each other. In certain embodiments, at least one instance of $R^{D1}$ is halogen (e.g., F, Cl, Br, or I). In certain embodiments, at least one instance of $R^{D1}$ is substituted or unsubstituted alkyl (e.g., substituted or unsubstituted $C_{1-6}$ alkyl). In certain embodiments, at least one instance of $R^{D1}$ is —$CH_3$. In certain embodiments, at least one instance of $R^{D1}$ is —$CF_3$, unsubstituted ethyl, perfluoroethyl, unsubstituted propyl, perfluoropropyl, unsubstituted butyl, or perfluorobutyl. In certain embodiments, at least one instance of $R^{D1}$ is substituted or unsubstituted alkenyl (e.g., substituted or unsubstituted $C_{1-6}$ alkenyl). In certain embodiments, at least one instance of $R^{D1}$ is substituted or unsubstituted alkynyl (e.g., substituted or unsubstituted $C_{1-6}$ alkynyl). In certain embodiments, at least one instance of $R^{D1}$ is substituted or unsubstituted carbocyclyl (e.g., substituted or unsubstituted, monocyclic, 3- to 7-membered carbocyclyl). In certain embodiments, at least one instance of $R^{D1}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{D1}$ is substituted or unsubstituted aryl (e.g., substituted or unsubstituted, 6- to 10-membered aryl). In certain embodiments, at least one instance of $R^{D1}$ is substituted or unsubstituted phenyl. In certain embodiments, at least one instance of $R^{D1}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{D1}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{D1}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{D1}$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^{D1}$ is —CN, —SCN, or —$NO_2$. In certain embodiments, at least one instance of $R^{D1}$ is —C(=$NR^a$)$R^a$, —C(=$NR^a$)$OR^a$, or —C(=$NR^a$)$N(R^a)_2$. In certain embodiments, at least one instance of $R^{D1}$ is —C(=O)$R^a$, —C(=O)$OR^a$, or —C(=O)$N(R^a)_2$ (e.g., —C(=O)$NH_2$, —C(=O)NHMe, or —C(=O)$NMe_2$). In certain embodiments, at least one instance of $R^{D1}$ is —$NR^a$C(=O)$R^a$, —$NR^a$C(=O)$OR^a$, or —$NR^a$C(=O)$N(R^a)_2$. In certain embodiments, at least one instance of $R^{D1}$ is —OC(=O)$R^a$, —OC(=O)$OR^a$, or —OC(=O)$N(R^a)_2$.

In certain embodiments, q1 is 0. In certain embodiments, q1 is 1. In certain embodiments, q1 is 2. In certain embodiments, q1 is 3. In certain embodiments, q1 is 4. In certain embodiments, q1 is 5.

In certain embodiments, both instances of $R^{D2}$ are the same. In certain embodiments, two instances of $R^{D2}$ are different from each other. In certain embodiments, at least one instance of $R^{D2}$ is hydrogen. In certain embodiments, each instance of $R^{D2}$ is hydrogen. In certain embodiments, at least one instance of $R^{D2}$ is halogen (e.g., F, Cl, Br, or I). In certain embodiments, at least one instance of $R^{D2}$ is substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, or perfluorobutyl).

In certain embodiments, all instances of $R^{D3}$ are the same. In certain embodiments, two instances of $R^{D3}$ are different from each other. In certain embodiments, at least one instance of $R^{D3}$ is halogen (e.g., F, Cl, Br, or I). In certain embodiments, at least one instance of $R^{D3}$ is substituted or unsubstituted $C_{1-6}$ alkyl (e.g., substituted or unsubstituted $C_{1-6}$ alkyl). In certain embodiments, at least one instance of $R^{D3}$ is —$CH_3$. In certain embodiments, at least one instance of $R^{D3}$ is —$CF_3$, unsubstituted ethyl, perfluoroethyl, unsubstituted propyl, perfluoropropyl, unsubstituted butyl, or perfluorobutyl. In certain embodiments, at least one instance of $R^{D3}$ is substituted or unsubstituted alkenyl (e.g., substituted or unsubstituted $C_{1-6}$ alkenyl). In certain embodiments, at least one instance of $R^{D3}$ is substituted or unsubstituted alkynyl (e.g., substituted or unsubstituted $C_{1-6}$ alkynyl). In certain embodiments, at least one instance of $R^{D3}$ is substituted or unsubstituted carbocyclyl (e.g., substituted or unsubstituted, monocyclic, 3- to 7-membered carbocyclyl). In certain embodiments, at least one instance of $R^{D3}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{D3}$ is substituted or unsubstituted aryl (e.g., substituted or unsubstituted, 6- to 10-membered aryl). In certain embodiments, at least one instance of $R^{D3}$ is substituted or unsubstituted phenyl. In certain embodiments, at least one instance of $R^{D3}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{D3}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{D3}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{D3}$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$Nme_2$)). In certain embodiments, at least one instance of $R^{D3}$ is —CN, —SCN, or —$NO_2$. In certain embodiments, at least one instance of $R^{D3}$ is —C(=$NR^a$)$R^a$, —C(=$NR^a$)$OR^a$, or —C(=$NR^a$)$N(R^a)_2$. In certain embodiments, at least one instance of $R^{D3}$ is —C(=O)$R^a$, —C(=O)$OR^a$, or —C(=O)$N(R^a)_2$ (e.g., —C(=O)$NH_2$, —C(=O)NHMe, or —C(=O)$Nme_2$). In certain embodiments, at least one instance of $R^{D3}$ is —$NR^a$C(=O)$R^a$, —$NR^a$C(=O)$OR^a$, or —$NR^a$C(=O)$N(R^a)_2$. In certain embodiments, at least one instance of $R^{D3}$ is —OC(=O)$R^a$, —OC(=O)$OR^a$, or —OC(=O)$N(R^a)_2$.

In certain embodiments, q3 is 0. In certain embodiments, q3 is 1. In certain embodiments, q3 is 2. In certain embodiments, q3 is 3.

In certain embodiments, all instances of RN are the same. In certain embodiments, two instances of $R^{D4}$ are different from each other. In certain embodiments, at least one instance of RN is halogen (e.g., F, Cl, Br, or I). In certain embodiments, at least one instance of $R^{D4}$ is substituted or unsubstituted alkyl (e.g., substituted or unsubstituted $C_{1-6}$ alkyl). In certain embodiments, at least one instance of RN is —$CH_3$. In certain embodiments, at least one instance of $R^{D4}$ is —$CF_3$, unsubstituted ethyl, perfluoroethyl, unsubstituted propyl, perfluoropropyl, unsubstituted butyl, or perfluorobutyl. In certain embodiments, at least one instance of $R^{D4}$ is substituted or unsubstituted alkenyl (e.g., substituted or unsubstituted $C_{1-6}$ alkenyl). In certain embodiments, at least one instance of RN is substituted or unsubstituted alkynyl (e.g., substituted or unsubstituted $C_{1-6}$ alkynyl). In certain embodiments, at least one instance of $R^{D4}$ is substituted or unsubstituted carbocyclyl (e.g., substituted or unsubstituted, monocyclic, 3- to 7-membered carbocyclyl).

In certain embodiments, at least one instance of $R^{D4}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{D4}$ is substituted or unsubstituted aryl (e.g., substituted or unsubstituted, 6- to 10-membered aryl). In certain embodiments, at least one instance of RN is substituted or unsubstituted phenyl. In certain embodiments, at least one instance of RN is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{D4}$ is —OR$^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{D4}$ is —SR$^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{D4}$ is —N(R$^a$)$_2$ (e.g., —NH$_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —Nme$_2$)). In certain embodiments, at least one instance of $R^{D4}$ is —CN, —SCN, or —NO$_2$. In certain embodiments, at least one instance of $R^{D4}$ is —C(=NR$^a$)R$^a$, —C(=NR$^a$)OR$^a$, or —C(=NR$^a$)N(R$^a$)$_2$. In certain embodiments, at least one instance of $R^{D4}$ is —C(=O)R$^a$, —C(=O)OR$^a$, or —C(=O)N(R$^a$)$_2$ (e.g., —C(=O)NH$_2$, —C(=O)NHMe, or —C(=O)Nme$_2$). In certain embodiments, at least one instance of $R^{D4}$ is —NR$^a$C(=O)R$^a$, —NR$^a$C(=O)OR$^a$, or —NR$^a$C(=O)N(R$^a$)$_2$. In certain embodiments, at least one instance of $R^{D4}$ is —OC(=O)R$^a$, —OC(=O)OR$^a$, or —OC(=O)N(R$^a$)$_2$.

In certain embodiments, q4 is 0. In certain embodiments, q4 is 1. In certain embodiments, q4 is 2. In certain embodiments, q4 is 3.

In certain embodiments, both instances of $R^{D5}$ are the same. In certain embodiments, two instances of $R^{D5}$ are different from each other. In certain embodiments, at least one instance of $R^{D5}$ is hydrogen. In certain embodiments, each instance of $R^{D5}$ is hydrogen. In certain embodiments, at least one instance of $R^{D5}$ is substituted or unsubstituted $C_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, at least one instance of $R^{D5}$ is a nitrogen protecting group (e.g., Bn, Boc, Cbz, Fmoc, trifluoroacetyl, triphenylmethyl, acetyl, or Ts).

In certain embodiments, the compound of Formula (D) is of the formula:

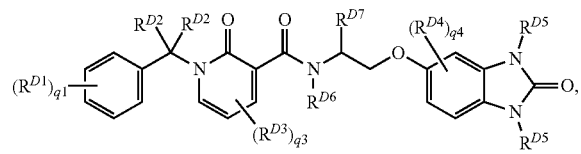

or a pharmaceutically acceptable salt, solvate, hydrate, polymorph, co-crystal, tautomer, stereoisomer, isotopically labeled derivative, or prodrug thereof, wherein $R^{D7}$ is substituted or unsubstituted phenyl.

In certain embodiments, the compound of Formula (D) is of the formula:

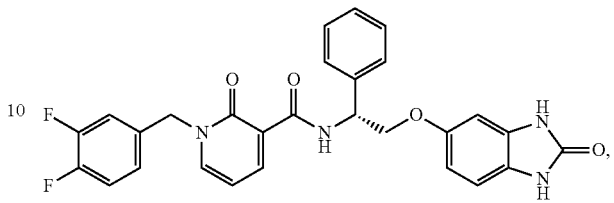

(KIN001-244)

or a solvate, hydrate, polymorph, co-crystal, tautomer, stereoisomer, isotopically labeled derivative, or prodrug thereof.

In certain embodiments, a compound of Formula (D) is not KIN001-244, or a pharmaceutically acceptable salt, solvate, hydrate, polymorph, co-crystal, tautomer, stereoisomer, or isotopically labeled derivative thereof.

It is believed that compounds of Formula (D), and pharmaceutically acceptable salts, solvates, hydrates, polymorphs, co-crystals, tautomers, stereoisomers, isotopically labeled derivatives, and prodrugs thereof, are PDK inhibitors.

Compounds of Formula (E)

In another aspect, the present disclosure provides compounds of Formula (E):

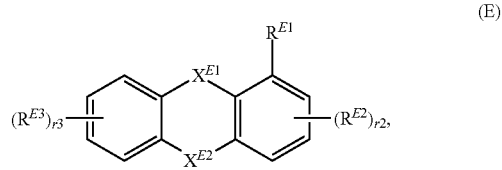

(E)

and pharmaceutically acceptable salts, solvates, hydrates, polymorphs, co-crystals, tautomers, stereoisomers, isotopically labeled derivatives, and prodrugs thereof, wherein:

$X^{E1}$ is —O—, —S—, —C(=O)—, —C(=S)—, or —C(=NR$^{E4}$)—, wherein $R^{E4}$ is hydrogen, substituted or unsubstituted $C_{1-6}$ alkyl, or a nitrogen protecting group;

$X^{E2}$ is —O—, —S—, —C(=O)—, or —C(=S)—;

$R^{E1}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$, or $R^{E1}$ and $R^{E4}$ are joined to form a substituted or unsubstituted heterocyclic ring or a substituted or unsubstituted heteroaryl ring;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted heterocyclic or substituted or unsubstituted heteroaryl ring;

each instance of $R^{E2}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$;

r2 is 0, 1, 2, or 3;

each instance of $R^{E3}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$; and r3 is 0, 1, 2, 3, or 4.

In certain embodiments, $X^{E1}$ is —S—. In certain embodiments, $X^{E1}$ is —$C(=NR^{E4})$—. In certain embodiments, $X^{E1}$ is —O—, —$C(=O)$—, or —$C(=S)$—.

In certain embodiments, $R^{E4}$ is hydrogen. In certain embodiments, $R^{E4}$ is substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, or perfluorobutyl). In certain embodiments, $R^{E4}$ is a nitrogen protecting group (e.g., Bn, Boc, Cbz, Fmoc, trifluoroacetyl, triphenylmethyl, acetyl, or Ts).

In certain embodiments, $X^{E2}$ is —S—. In certain embodiments, $X^{E2}$ is —$C(=O)$—. In certain embodiments, $X^{E2}$ is —O— or —$C(=S)$—.

In certain embodiments, $R^{E1}$ is hydrogen. In certain embodiments, $R^{E1}$ is halogen (e.g., F, Cl, Br, or I). In certain embodiments, $R^{E1}$ is substituted or unsubstituted alkyl (e.g., substituted or unsubstituted $C_{1-6}$ alkyl). In certain embodiments, $R^{E1}$ is —$CH_3$. In certain embodiments, $R^{E1}$ is —$CF_3$, unsubstituted ethyl, perfluoroethyl, unsubstituted propyl, perfluoropropyl, unsubstituted butyl, or perfluorobutyl. In certain embodiments, $R^{E1}$ is substituted or unsubstituted alkenyl (e.g., substituted or unsubstituted $C_{1-6}$ alkenyl). In certain embodiments, $R^{E1}$ is substituted or unsubstituted alkynyl (e.g., substituted or unsubstituted $C_{1-6}$ alkynyl). In certain embodiments, $R^{E1}$ is substituted or unsubstituted carbocyclyl (e.g., substituted or unsubstituted, monocyclic, 3- to 7-membered carbocyclyl). In certain embodiments, $R^{E1}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, $R^{E1}$ is a substituted or unsubstituted 4H-pyran-4-one moiety. In certain embodiments, $R^{E1}$ is substituted or unsubstituted aryl (e.g., substituted or unsubstituted, 6- to 10-membered aryl). In certain embodiments, $R^{E1}$ is substituted or unsubstituted phenyl. In certain embodiments, $R^{E1}$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, $R^{E1}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, $R^{E1}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{E1}$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^{E1}$ is —CN, —SCN, or —$NO_2$. In certain embodiments, $R^{E1}$ is —$C(=NR^a)R^a$, —$C(=NR^a)OR^a$, or —$C(=NR^a)N(R^a)_2$. In certain embodiments, $R^{E1}$ is —$C(=O)R^a$, —$C(=O)OR^a$, or —$C(=O)N(R^a)_2$ (e.g., —$C(=O)NH_2$, —$C(=O)NHMe$, or —$C(=O)NMe_2$). In certain embodiments, $R^{E1}$ is —$NR^aC(=O)R^a$, —$NR^aC(=O)OR^a$, or —$NR^aC(=O)N(R^a)_2$. In certain embodiments, $R^{E1}$ is —$OC(=O)R^a$, —$OC(=O)OR^a$, or —$OC(=O)N(R^a)_2$. In certain embodiments, $R^{E1}$ and $R^{E4}$ are joined to form a substituted or unsubstituted heterocyclic ring (e.g., substituted or unsubstituted, monocyclic, 5- to 6-membered heterocyclic ring, wherein one, two, or three atoms in the heterocyclic ring system are independently nitrogen, oxygen, or sulfur) or a substituted or unsubstituted heteroaryl ring (e.g., substituted or unsubstituted, monocyclic, 5- to 6-membed heteroaryl ring, wherein one, two, three, or four atoms in the heteroaryl ring system are independently nitrogen, oxygen, or sulfur).

In certain embodiments, all instances of $R^{E2}$ are the same. In certain embodiments, two instances of $R^{E2}$ are different from each other. In certain embodiments, at least one instance of $R^{E2}$ is halogen (e.g., F, Cl, Br, or I). In certain embodiments, at least one instance of $R^{E2}$ is substituted or unsubstituted alkyl (e.g., substituted or unsubstituted $C_{1-6}$ alkyl). In certain embodiments, at least one instance of $R^{E2}$ is —$CH_3$. In certain embodiments, at least one instance of $R^{E2}$ is —$CF_3$, unsubstituted ethyl, perfluoroethyl, unsubstituted propyl, perfluoropropyl, unsubstituted butyl, or perfluorobutyl. In certain embodiments, at least one instance of $R^{E2}$ is substituted or unsubstituted alkenyl (e.g., substituted or unsubstituted $C_{1-6}$ alkenyl). In certain embodiments, at least one instance of $R^{E2}$ is substituted or unsubstituted alkynyl (e.g., substituted or unsubstituted $C_{1-6}$ alkynyl). In certain embodiments, at least one instance of $R^{E2}$ is substituted or unsubstituted carbocyclyl (e.g., substituted or unsubstituted, monocyclic, 3- to 7-membered carbocyclyl). In certain embodiments, at least one instance of $R^{E2}$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, at least one instance of $R^{E2}$ is substituted or unsubstituted aryl (e.g., substituted or unsubstituted, 6- to 10-membered aryl). In certain embodiments, at least one instance of $R^{E2}$ is substituted or unsubstituted phenyl. In certain embodiments, at least one instance of $R^{E2}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{E2}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{E2}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{E2}$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^{E2}$ is —CN, —SCN, or —$NO_2$. In certain embodiments, at least one instance of $R^{E2}$ is —$C(=NR^a)R^a$, —$C(=NR^a)OR^a$, or —$C(=NR^a)N(R^a)_2$. In certain embodiments, at least one instance of $R^{E2}$ is —$C(=O)R^a$, —$C(=O)OR^a$, or —$C(=O)N(R^a)_2$ (e.g., —$C(=O)NH_2$, —$C(=O)NHMe$, or —$C(=O)NMe_2$). In certain embodiments, at least one instance of $R^{E2}$ is —$NR^aC(=O)R^a$, —$NR^aC(=O)OR^a$, or —$NR^aC(=O)N(R^a)_2$. In certain embodiments, at least one instance of $R^{E2}$ is —$OC(=O)R^a$, —$OC(=O)OR^a$, or —$OC(=O)N(R^a)_2$.

In certain embodiments, r2 is 0. In certain embodiments, r2 is 1. In certain embodiments, r2 is 2. In certain embodiments, r2 is 3.

In certain embodiments, all instances of $R^{E3}$ are the same. In certain embodiments, two instances of $R^{E3}$ are different from each other. In certain embodiments, at least one instance of $R^{E3}$ is halogen (e.g., F, Cl, Br, or I). In certain embodiments, at least one instance of $R^{E3}$ is substituted or unsubstituted alkyl (e.g., substituted or unsubstituted $C_{1-6}$ alkyl). In certain embodiments, at least one instance of $R^{E3}$ is —$CH_3$. In certain embodiments, at least one instance of $R^{E3}$ is —$CF_3$, unsubstituted ethyl, perfluoroethyl, unsubstituted propyl, perfluoropropyl, unsubstituted butyl, or perfluorobutyl. In certain embodiments, at least one instance of $R^{E3}$ is substituted or unsubstituted alkenyl (e.g., substituted or unsubstituted $C_{1-6}$ alkenyl). In certain embodiments, at least one instance of $R^{E3}$ is substituted or unsubstituted alkynyl (e.g., substituted or unsubstituted $C_{1-6}$ alkynyl). In certain embodiments, at least one instance of $R^{E3}$ is substituted or unsubstituted carbocyclyl (e.g., substituted or unsubstituted, monocyclic, 3- to 7-membered carbocyclyl). In certain embodiments, at least one instance of $R^{E3}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{E3}$ is substituted or unsubstituted aryl (e.g., substituted or unsubstituted, 6- to 10-membered aryl). In certain embodiments, at least one instance of $R^{E3}$ is substituted or unsubstituted phenyl. In certain embodiments, at least one instance of $R^{E3}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{E3}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{E3}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{E3}$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^{E3}$ is —CN, —SCN, or —$NO_2$. In certain embodiments, at least one instance of $R^{E3}$ is —$C(=NR^a)R^a$, —$C(=NR^a)OR^a$, or —$C(=NR^a)N(R^a)_2$. In certain embodiments, at least one instance of $R^{E3}$ is —$C(=O)R^a$, —$C(=O)OR^a$, or —$C(=O)N(R^a)_2$ (e.g., —$C(=O)NH_2$, —$C(=O)NHMe$, or —$C(=O)NMe_2$). In certain embodiments, at least one instance of $R^{E3}$ is —$NR^aC(=O)R^a$, —$NR^aC(=O)OR^a$, or —$NR^aC(=O)N(R^a)_2$. In certain embodiments, at least one instance of $R^{E3}$ is —$OC(=O)R^a$, —$OC(=O)OR^a$, or —$OC(=O)N(R^a)_2$.

In certain embodiments, r3 is 0. In certain embodiments, r3 is 1. In certain embodiments, r3 is 2. In certain embodiments, r3 is 3. In certain embodiments, r3 is 4.

In certain embodiments, the compound of Formula (E) is of the formula:

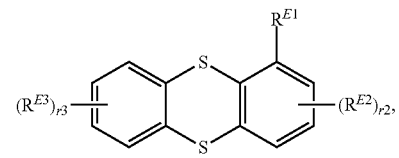

or a pharmaceutically acceptable salt, solvate, hydrate, polymorph, co-crystal, tautomer, stereoisomer, isotopically labeled derivative, or prodrug thereof.

In certain embodiments, the compound of Formula (E) is of the formula:

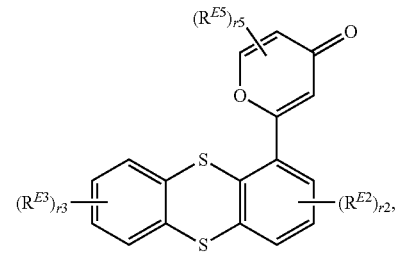

or a pharmaceutically acceptable salt, solvate, hydrate, polymorph, co-crystal, tautomer, stereoisomer, isotopically labeled derivative, or prodrug thereof, wherein:

each instance of $R^{E5}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$; and r5 is 0, 1, 2, or 3.

In certain embodiments, all instances of $R^{E5}$ are the same. In certain embodiments, two instances of $R^{E5}$ are different from each other. In certain embodiments, at least one instance of $R^{E5}$ is halogen (e.g., F, Cl, Br, or I). In certain embodiments, at least one instance of $R^{E5}$ is substituted or unsubstituted alkyl (e.g., substituted or unsubstituted $C_{1-6}$ alkyl). In certain embodiments, at least one instance of R$^{E5}$ is —CH$_3$. In certain embodiments, at least one instance of R$^{E5}$ is —CF$_3$, unsubstituted ethyl, perfluoroethyl, unsubstituted propyl, perfluoropropyl, unsubstituted butyl, or perfluorobutyl. In certain embodiments, at least one instance of R$^{E5}$ is substituted or unsubstituted alkenyl (e.g., substituted or unsubstituted C$_{1-6}$ alkenyl). In certain embodiments, at least one instance of R$^{E5}$ is substituted or unsubstituted alkynyl (e.g., substituted or unsubstituted C$_{1-6}$ alkynyl). In certain embodiments, at least one instance of R$^{E5}$ is substituted or unsubstituted carbocyclyl (e.g., substituted or unsubstituted, monocyclic, 3- to 7-membered carbocyclyl). In certain embodiments, at least one instance of R$^{E5}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of R$^{E5}$ is substituted or unsubstituted morpholinyl (e.g., substituted or unsubstituted N-morpholinyl). In certain embodiments, at least one instance of R$^{E5}$ is substituted or unsubstituted aryl (e.g., substituted or unsubstituted, 6- to 10-membered aryl). In certain embodiments, at least one instance of R$^{E5}$ is substituted or unsubstituted phenyl. In certain embodiments, at least one instance of R$^{E5}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of R$^{E5}$ is —OR$^a$ (e.g., —OH, —O(substituted or unsubstituted C$_{1-6}$ alkyl) (e.g., —OMe, —OEt, —OPr, —OBu, or —OBn), or —O(substituted or unsubstituted phenyl) (e.g., —OPh)). In certain embodiments, at least one instance of R$^{E5}$ is —SR$^a$ (e.g., —SH, —S(substituted or unsubstituted C$_{1-6}$ alkyl) (e.g., —SMe, —SEt, —SPr, —SBu, or —SBn), or —S(substituted or unsubstituted phenyl) (e.g., —SPh)). In certain embodiments, at least one instance of R$^{E5}$ is —N(R$^a$)$_2$ (e.g., —NH$_2$, —NH(substituted or unsubstituted C$_{1-6}$ alkyl) (e.g., —NHMe), or —N(substituted or unsubstituted C$_{1-6}$ alkyl)-(substituted or unsubstituted C$_{1-6}$ alkyl) (e.g., —NMe$_2$)). In certain embodiments, at least one instance of R$^{E5}$ is —CN, —SCN, or —NO$_2$. In certain embodiments, at least one instance of R$^{E5}$ is —C(=NR$^a$)R$^a$, —C(=NR$^a$)OR$^a$, or —C(=NR$^a$)N(R$^a$)$_2$. In certain embodiments, at least one instance of R$^{E5}$ is —C(=O)R$^a$, —C(=O)OR$^a$, or —C(=O)N(R$^a$)$_2$ (e.g., —C(=O)NH$_2$, —C(=O)NHMe, or —C(=O)NMe$_2$). In certain embodiments, at least one instance of R$^{E5}$ is —NR$^a$C(=O)R$^a$, —NR$^a$C(=O)OR$^a$, or —NR$^a$C(=O)N(R$^a$)$_2$. In certain embodiments, at least one instance of R$^{E5}$ is —OC(=O)R$^a$, —OC(=O)OR$^a$, or —OC(=O)N(R$^a$)$_2$.

In certain embodiments, r5 is 0. In certain embodiments, r5 is 1. In certain embodiments, r5 is 2. In certain embodiments, r5 is 3.

In certain embodiments, the compound of Formula (E) is of the formula:

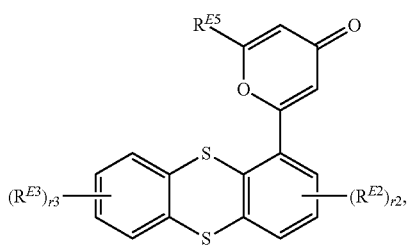

or a pharmaceutically acceptable salt, solvate, hydrate, polymorph, co-crystal, tautomer, stereoisomer, isotopically labeled derivative, or prodrug thereof.

In certain embodiments, the compound of Formula (E) is of the formula:

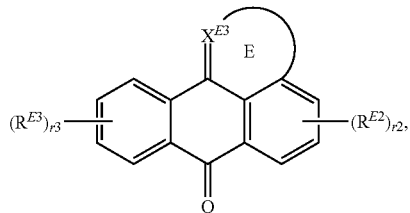

or a pharmaceutically acceptable salt, solvate, hydrate, polymorph, co-crystal, tautomer, stereoisomer, isotopically labeled derivative, or prodrug thereof, wherein X$^{E3}$ is C or N, and Ring E is a substituted or unsubstituted, monocyclic, 5- to 6-membered heterocyclic ring or a substituted or unsubstituted, monocyclic, 5- to 6-membered heteroaryl ring, wherein one, two, or three atoms in the heterocyclic or heteroaryl ring system are independently nitrogen, oxygen, or sulfur.

In certain embodiments, the compound of Formula (E) is of the formula:

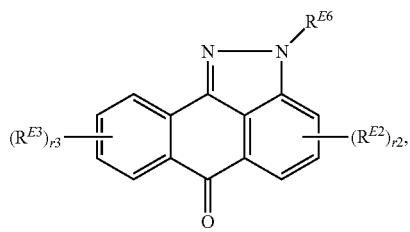

or a pharmaceutically acceptable salt, solvate, hydrate, polymorph, co-crystal, tautomer, stereoisomer, isotopically labeled derivative, or prodrug thereof, wherein R$^{E6}$ is hydrogen, substituted or unsubstituted C$_{1-6}$ alkyl (e.g., CH$_3$, —CF$_3$, unsubstituted ethyl, perfluoroethyl, unsubstituted propyl, perfluoropropyl, unsubstituted butyl, or perfluorobutyl), or a nitrogen protecting group (e.g., Bn, Boc, Cbz, Fmoc, trifluoroacetyl, triphenylmethyl, acetyl, or Ts).

In certain embodiments, the compound of Formula (E) is of the formula:

(KU55933)

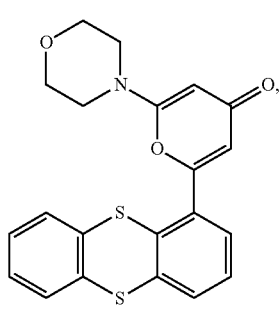

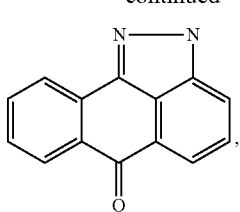

(SP600125)

or a pharmaceutically acceptable salt, solvate, hydrate, polymorph, co-crystal, tautomer, stereoisomer, isotopically labeled derivative, or prodrug thereof.

In certain embodiments, a compound of Formula (E) is not KU55933, SP600125, or a pharmaceutically acceptable salt, solvate, hydrate, polymorph, co-crystal, tautomer, stereoisomer, or isotopically labeled derivative thereof.

It is believed that compounds of Formula (E), and pharmaceutically acceptable salts, solvates, hydrates, polymorphs, co-crystals, tautomers, stereoisomers, isotopically labeled derivatives, and prodrugs thereof, are ATM inhibitors (e.g., KU55933) and/or JNK inhibitors (e.g., SP600125).

Compounds of Formula (F)

In another aspect, the present disclosure provides compounds of Formula (F):

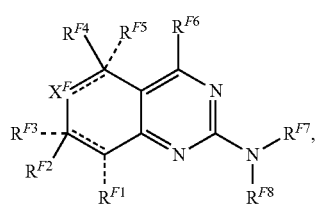

(F)

and pharmaceutically acceptable salts, solvates, hydrates, polymorphs, co-crystals, tautomers, stereoisomers, isotopically labeled derivatives, and prodrugs thereof, wherein:

$X^F$ is —N($R^{F9}$)—, =N—, —C($R^{F10}$)$_2$—, or =C($R^{F10}$)—, wherein:

$R^{F9}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; and each instance of $R^F10$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ are joined to form a substituted or unsubstituted heterocyclic or substituted or unsubstituted heteroaryl ring;

$R^{F1}$ is absent, hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{F2}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

$R^{F3}$ is absent, hydrogen, halogen, or substituted or unsubstituted $C_{1-6}$ alkyl, or $R^{F3}$ and $R^{F2}$ are joined to form =O;

$R^{F4}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

$R^{F5}$ is absent, hydrogen, halogen, or substituted or unsubstituted $C_{1-6}$ alkyl;

$R^{F6}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

$R^{F7}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; and $R^{F8}$ is hydrogen, substituted or unsubstituted $C_{1-6}$ alkyl, or a nitrogen protecting group.

In certain embodiments, $X^F$ is —N($R^{F9}$)— or =N—. In certain embodiments, $X^F$ is —C($R^{F10}$)$_2$— or =C($R^{F10}$)—.

In certain embodiments, $R^{F9}$ is hydrogen. In certain embodiments, $R^{F9}$ is substituted or unsubstituted alkyl, such as substituted or unsubstituted $C_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, $R^{F9}$ is substituted or unsubstituted alkenyl (e.g., substituted or unsubstituted $C_{1-6}$ alkenyl). In certain embodiments, $R^{F9}$ is substituted or unsubstituted alkynyl (e.g., substituted or unsubstituted $C_{1-6}$ alkynyl). In certain embodiments, $R^{F9}$ is substituted or unsubstituted carbocyclyl (e.g., substituted or unsubstituted, monocyclic, 3- to 7-membered carbocyclyl). In certain embodiments, $R^{F9}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, $R^{F9}$ is substituted or unsubstituted aryl (e.g., substituted or unsubstituted, 6- to 10-membered aryl). In certain embodiments, $R^{F9}$ is substituted or unsubstituted phenyl (e.g.,

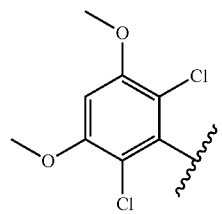 [SMILES: *c1c(Cl)c(OC)cc(OC)c1Cl]

In certain embodiments, $R^{F9}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, $R^{F9}$ is a nitrogen protecting group (e.g., Bn, Boc, Cbz, Fmoc, trifluoroacetyl, triphenylmethyl, acetyl, or Ts).

In certain embodiments, two instances of $R^{F10}$ are the same. In certain embodiments, two instances of $R^{F10}$ are different from each other. In certain embodiments, at least one instance of $R^{F10}$ is halogen (e.g., F, Cl, Br, or I). In certain embodiments, at least one instance of $R^{F10}$ is substituted or unsubstituted alkyl (e.g., substituted or unsubstituted $C_{1-6}$ alkyl). In certain embodiments, at least one instance of $R^{F10}$ is —$CH_3$. In certain embodiments, at least one instance of $R^{F10}$ is —$CF_3$, unsubstituted ethyl, perfluoroethyl, unsubstituted propyl, perfluoropropyl, unsubstituted butyl, or perfluorobutyl. In certain embodiments, at least one instance of $R^{F10}$ is substituted or unsubstituted alkenyl (e.g., substituted or unsubstituted $C_{1-6}$ alkenyl). In certain embodiments, at least one instance of $R^{F10}$ is substituted or unsubstituted alkynyl (e.g., substituted or unsubstituted $C_{1-6}$ alkynyl). In certain embodiments, at least one instance of $R^{F10}$ is substituted or unsubstituted carbocyclyl (e.g., substituted or unsubstituted, monocyclic, 3- to 7-membered carbocyclyl). In certain embodiments, at least one instance of $R^{F10}$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, at least one instance of $R^{F10}$ is substituted or unsubstituted aryl (e.g., substituted or unsubstituted, 6- to 10-membered aryl). In certain embodiments, at least one instance of $R^{F10}$ is substituted or unsubstituted phenyl (e.g.

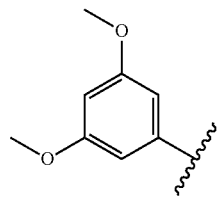 [SMILES: *c1cc(OC)cc(OC)c1]

In certain embodiments, at least one instance of $R^{F10}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{F10}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{F10}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{F10}$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^{F10}$ is —CN, —SCN, or —$NO_2$. In certain embodiments, at least one instance of $R^{F10}$ is —$C(=NR^a)R^a$, —$C(=NR^a)OR^a$, or —$C(=NR^a)N(R^a)_2$. In certain embodiments, at least one instance of $R^{F10}$ is —$C(=O)R^a$ (e.g., —C(=O)Me), —$C(=O)OR^a$, or —$C(=O)N(R^a)_2$ (e.g., —$C(=O)NH_2$, —C(=O)NHMe, or —$C(=O)NMe_2$). In certain embodiments, at least one instance of $R^{F10}$ is —$NR^aC(=O)R^a$, —$NR^aC(=O)OR^a$, or —$NR^aC(=O)N(R^a)_2$. In certain embodiments, at least one instance of $R^{F10}$ is —$OC(=O)R^a$, —$OC(=O)OR^a$, or —$OC(=O)N(R^a)_2$.

In certain embodiments, at least one instance of $R^{F10}$ is substituted or unsubstituted phenyl, or —$C(=O)R^a$.

In certain embodiments, $R^{F1}$ is absent. In certain embodiments, $R^{F1}$ is hydrogen. In certain embodiments, $R^{F1}$ is substituted or unsubstituted alkyl, such as substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, or perfluorobutyl). In certain embodiments, $R^{F1}$ is substituted or unsubstituted alkenyl (e.g., substituted or unsubstituted $C_1$-6 alkenyl). In certain embodiments, $R^{F1}$ is substituted or unsubstituted alkynyl (e.g., substituted or unsubstituted $C_{1-6}$ alkynyl). In certain embodiments, $R^{F1}$ is substituted or unsubstituted carbocyclyl (e.g., substituted or unsubstituted, monocyclic, 3- to 7-membered carbocyclyl). In certain embodiments, $R^{F1}$ is substituted or unsubstituted cyclopentyl. In certain embodiments, $R^{F1}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, $R^{F1}$ is substituted or unsubstituted aryl (e.g., substituted or unsubstituted, 6- to 10-membered aryl). In certain embodiments, $R^{F1}$ is substituted or unsubstituted phenyl. In certain embodiments, $R^{F1}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, $R^{F1}$ is a nitrogen protecting group (e.g., Bn, Boc, Cbz, Fmoc, trifluoroacetyl, triphenylmethyl, acetyl, or Ts). In certain embodiments, $R^{F1}$ is absent, substituted or unsubstituted alky, or substituted or unsubstituted, monocyclic, 5- to 6-membed carbocyclyl.

In certain embodiments, $R^{F2}$ is hydrogen. In certain embodiments, $R^{F2}$ is halogen (e.g., F, Cl, Br, or I). In certain embodiments, $R^{F2}$ is substituted or unsubstituted alkyl (e.g., substituted or unsubstituted $C_{1-6}$ alkyl). In certain embodiments, $R^{F2}$ is —$CH_3$. In certain embodiments, $R^{F2}$ is —$CF_3$, unsubstituted ethyl, perfluoroethyl, unsubstituted propyl, perfluoropropyl, unsubstituted butyl, or perfluorobutyl. In certain embodiments, $R^{F2}$ is substituted or unsubstituted alkenyl (e.g., substituted or unsubstituted $C_{1-6}$ alkenyl). In certain embodiments, $R^{F2}$ is substituted or unsubstituted alkynyl (e.g., substituted or unsubstituted $C_{1-6}$ alkynyl). In certain embodiments, $R^{F2}$ is substituted or unsubstituted carbocyclyl (e.g., substituted or unsubstituted, monocyclic, 3- to 7-membered carbocyclyl). In certain embodiments, $R^{F2}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, $R^{F2}$ is substituted or unsubstituted aryl (e.g., substituted or unsubstituted, 6- to 10-membered aryl). In certain embodiments, $R^{F2}$ is substituted or unsubstituted phenyl. In certain embodiments, $R^{F2}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, $R^{F2}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, $R^{F2}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{F2}$ is —$N(R^a)_2$ (e.g., —$NH_2$, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^F$ is —CN, —SCN, or —$NO_2$. In certain embodiments, $R^{F2}$ is —C(=$NR^a$)$R^a$, —C(=$NR^a$)$OR^a$, or —C(=$NR^a$)$N(R^a)_2$. In certain embodiments, $R^{F2}$ is —C(=O)$R^a$, —C(=O)$OR^a$, or —C(=O)$N(R^a)_2$ (e.g., —C(=O)$NH_2$, —C(=O)NHMe, or —C(=O)$NMe_2$). In certain embodiments, $R^F$ is —$NR^aC$(=O)$R^a$ or —$NR^aC$(=O)$OR^a$. In certain embodiments, $R^{F2}$ is —$NR^aC$(=O)N($R^a)_2$ (e.g., —NHC(=O)NH(substituted or unsubstituted $C_{1-6}$ alkyl), such as —NHC(=O)NH(t-Bu)). In certain embodiments, $R^{F2}$ is —OC(=O)$R^a$, —OC(=O)$OR^a$, or —OC(=O)$N(R^a)_2$.

In certain embodiments, $R^{F3}$ is absent. In certain embodiments, $R^{F3}$ is hydrogen. In certain embodiments, $R^{F3}$ is halogen (e.g., F, Cl, Br, or I). In certain embodiments, $R^{F3}$ is substituted or unsubstituted alkyl (e.g., substituted or unsubstituted $C_{1-6}$ alkyl). In certain embodiments, $R^{F3}$ is —$CH_3$. In certain embodiments, $R^{F3}$ is —$CF_3$, unsubstituted ethyl, perfluoroethyl, unsubstituted propyl, perfluoropropyl, unsubstituted butyl, or perfluorobutyl. In certain embodiments, $R^{F3}$ and $R^F$ are joined to form =O.

In certain embodiments, $R^{F4}$ is hydrogen. In certain embodiments, $R^{F4}$ is halogen (e.g., F, Cl, Br, or I). In certain embodiments, $R^{F4}$ is substituted or unsubstituted alkyl (e.g., substituted or unsubstituted $C_{1-6}$ alkyl). In certain embodiments, $R^{F4}$ is —$CH_3$. In certain embodiments, $R^{F4}$ is —$CF_3$, unsubstituted ethyl, perfluoroethyl, unsubstituted propyl, perfluoropropyl, unsubstituted butyl, or perfluorobutyl. In certain embodiments, $R^{F4}$ is substituted or unsubstituted alkenyl (e.g., substituted or unsubstituted $C_{1-6}$ alkenyl). In certain embodiments, $R^{F4}$ is substituted or unsubstituted alkynyl (e.g., substituted or unsubstituted $C_{1-6}$ alkynyl). In certain embodiments, $R^{F4}$ is substituted or unsubstituted carbocyclyl (e.g., substituted or unsubstituted, monocyclic, 3- to 7-membered carbocyclyl). In certain embodiments, $R^{F4}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, $R^{F4}$ is substituted or unsubstituted aryl (e.g., substituted or unsubstituted, 6- to 10-membered aryl). In certain embodiments, $R^{F4}$ is substituted or unsubstituted phenyl. In certain embodiments, $R^{F4}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, $R^{F4}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, $R^{F4}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{F4}$ is —$N(R^a)_2$ (e.g., —$NH_2$, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^{F4}$ is —CN, —SCN, or —$NO_2$. In certain embodiments, $R^{F4}$ is —C(=$NR^a$)$R^a$, —C(=$NR^a$)$OR^a$, or —C(=$NR^a$)$N(R^a)_2$. In certain embodiments, $R^{F4}$ is —C(=O)$R^a$, —C(=O)$OR^a$, or —C(=O)$N(R^a)_2$ (e.g., —C(=O)$NH_2$, —C(=O)NHMe, or —C(=O)$NMe_2$). In certain embodiments, $R^{F4}$ is —$NR^aC$(=O)$R^a$, —$NR^aC$(=O)$OR^a$, or —$NR^aC$(=O)N($R^a)_2$. In certain embodiments, $R^{F4}$ is —OC(=O)$R^a$, —OC(=O)$OR^a$, or —OC(=O)$N(R^a)_2$. In certain embodiments, $R^{F4}$ is hydrogen or substituted or unsubstituted alkyl.

In certain embodiments, $R^{F5}$ is absent. In certain embodiments, $R^{F5}$ is hydrogen. In certain embodiments, $R^{F5}$ is halogen (e.g., F, Cl, Br, or I). In certain embodiments, $R^{F5}$ is substituted or unsubstituted alkyl (e.g., substituted or unsubstituted $C_{1-6}$ alkyl). In certain embodiments, $R^{F5}$ is —$CH_3$. In certain embodiments, $R^{F5}$ is —CF5, unsubstituted ethyl, perfluoroethyl, unsubstituted propyl, perfluoropropyl, unsubstituted butyl, or perfluorobutyl.

In certain embodiments, $R^{F6}$ is hydrogen. In certain embodiments, $R^{F6}$ is halogen (e.g., F, Cl, Br, or I). In certain embodiments, $R^{F6}$ is substituted or unsubstituted alkyl (e.g., substituted or unsubstituted $C_{1-6}$ alkyl). In certain embodiments, $R^{F6}$ is —$CH_3$. In certain embodiments, $R^{F6}$ is —$CF_3$, unsubstituted ethyl, perfluoroethyl, unsubstituted propyl, perfluoropropyl, unsubstituted butyl, or perfluorobutyl. In certain embodiments, $R^{F6}$ is substituted or unsubstituted alkenyl (e.g., substituted or unsubstituted $C_{1-6}$ alkenyl). In certain embodiments, $R^{F6}$ is substituted or unsubstituted alkynyl (e.g., substituted or unsubstituted $C_{1-6}$ alkynyl). In certain embodiments, $R^{F6}$ is substituted or unsubstituted carbocyclyl (e.g., substituted or unsubstituted, monocyclic, 3- to 7-membered carbocyclyl). In certain embodiments, $R^{F6}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, $R^{F6}$ is substituted or unsubstituted aryl (e.g., substituted or unsubstituted, 6- to 10-membered aryl). In certain embodiments, $R^{F6}$ is substituted or unsubstituted phenyl. In certain embodiments, $R^{F6}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, $R^{F6}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, $R^{F6}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{F6}$ is —$N(R^a)_2$ (e.g., —$NH_2$, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^{F6}$ is —CN, —SCN, or —$NO_2$. In certain embodiments, $R^{F6}$ is —C(=$NR^a$)$R^a$, —C(=$NR^a$)$OR^a$, or —C(=$NR^a$)$N(R^a)_2$. In certain embodiments, $R^{F6}$ is —C(=O)$R^a$, —C(=O)$OR^a$, or —C(=O)$N(R^a)_2$ (e.g., —C(=O)$NH_2$, —C(=O)NHMe, or —C(=O)$NMe_2$). In certain embodiments, $R^{F6}$ is —$NR^aC$(=O)$R^a$, —$NR^aC$(=O)$OR^a$, or —$NR^aC$(=O)$N(R^a)_2$. In certain embodiments, $R^{F6}$ is —OC(=O)$R^a$, —OC(=O)$OR^a$, or —OC(=O)$N(R^a)_2$.

In certain embodiments, $R^{F7}$ is hydrogen. In certain embodiments, $R^{F7}$ is substituted or unsubstituted alkyl, such as substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, or perfluorobutyl). In certain embodiments, $R^{F7}$ is of the formula:

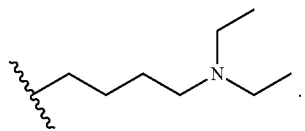 [SMILES: *CCCCN(CC)CC]

In certain embodiments, $R^{F7}$ is substituted or unsubstituted alkenyl (e.g., substituted or unsubstituted $C_{1-6}$ alkenyl). In certain embodiments, $R^{F7}$ is substituted or unsubstituted alkynyl (e.g., substituted or unsubstituted $C_{1-6}$ alkynyl). In certain embodiments, $R^{F7}$ is substituted or unsubstituted carbocyclyl (e.g., substituted or unsubstituted, monocyclic, 3- to 7-membered carbocyclyl). In certain embodiments, $R^{F7}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, $R^{F7}$ is substituted or unsubstituted aryl (e.g., substituted or unsubstituted, 6- to 10-membered aryl). In certain embodiments, $R^{F7}$ is substituted or unsubstituted phenyl. In certain embodiments, $R^{F7}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, $R^{F7}$ is substituted or unsubstituted pyridyl (e.g., substituted or unsubstituted 2-pyridyl). In certain embodiments, $R^{F7}$ is a nitrogen protecting group (e.g., Bn, Boc, Cbz, Fmoc, trifluoroacetyl, triphenylmethyl, acetyl, or Ts). In certain embodiments, $R^{F7}$ is substituted or unsubstituted alkyl or substituted or unsubstituted, monocyclic, 5- to 6-membed heteroaryl, wherein one, two, three, or four atoms in the heteroaryl ring system are independently nitrogen, oxygen, or sulfur.

In certain embodiments, $R^{F8}$ is hydrogen. In certain embodiments, $R^{F8}$ is substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, or perfluorobutyl). In certain embodiments, $R^{F8}$ is a nitrogen protecting group (e.g., Bn, Boc, Cbz, Fmoc, trifluoroacetyl, triphenylmethyl, acetyl, or Ts).

In certain embodiments, the compound of Formula (F) is of the formula:

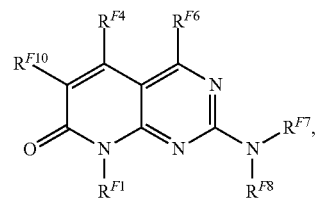

or a pharmaceutically acceptable salt, solvate, hydrate, polymorph, co-crystal, tautomer, stereoisomer, isotopically labeled derivative, or prodrug thereof.

In certain embodiments, the compound of Formula (F) is of the formula:

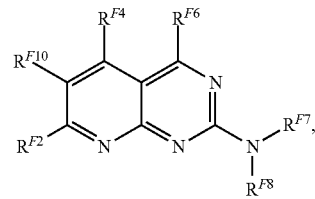

or a pharmaceutically acceptable salt, solvate, hydrate, polymorph, co-crystal, tautomer, stereoisomer, isotopically labeled derivative, or prodrug thereof.

In certain embodiments, the compound of Formula (F) is of the formula:

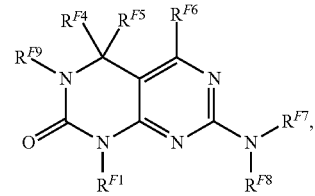

or a pharmaceutically acceptable salt, solvate, hydrate, polymorph, co-crystal, tautomer, stereoisomer, isotopically labeled derivative, or prodrug thereof.

In certain embodiments, the compound of Formula (F) is of the formula:

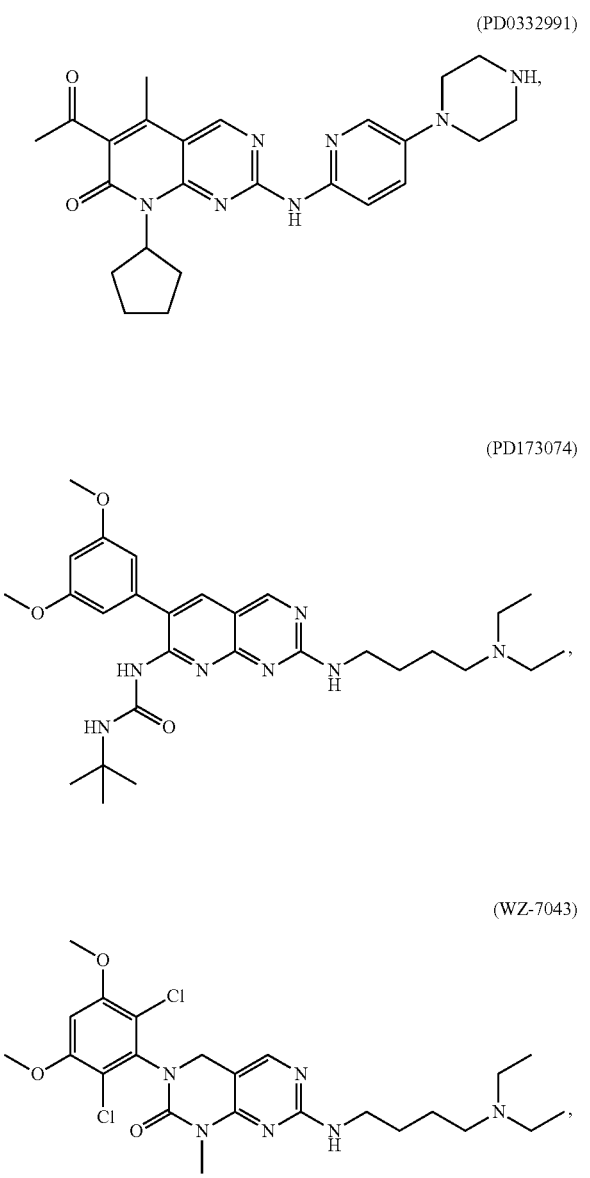

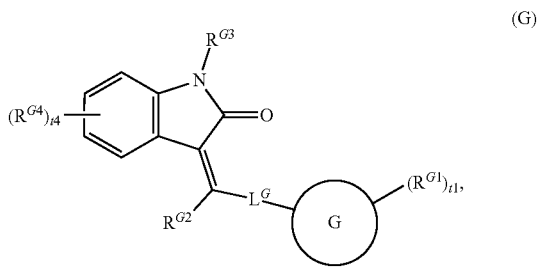

or a pharmaceutically acceptable salt, solvate, hydrate, polymorph, co-crystal, tautomer, stereoisomer, isotopically labeled derivative, or prodrug thereof.

In certain embodiments, a compound of Formula (F) is not PD0332991, PD173074, WZ-7043, or a pharmaceutically acceptable salt, solvate, hydrate, polymorph, co-crystal, tautomer, stereoisomer, or isotopically labeled derivative thereof.

It is believed that compounds of Formula (F), and pharmaceutically acceptable salts, solvates, hydrates, polymorphs, co-crystals, tautomers, stereoisomers, isotopically labeled derivatives, and prodrugs thereof, are CDK inhibitors (e.g., CDK4 inhibitors, such as PD0332991), FGFR inhibitors (e.g., FGFR1 inhibitors, such as PD173074), and/or CSF1R inhibitors (e.g., WZ-7043).

Compounds of Formula (G)

In another aspect, the present disclosure provides compounds of Formula (G):

and pharmaceutically acceptable salts, solvates, hydrates, polymorphs, co-crystals, tautomers, stereoisomers, isotopically labeled derivatives, and prodrugs thereof, wherein:

Ring G is a substituted or unsubstituted phenyl ring or a substituted or unsubstituted, monocyclic, 5- to 6-membered heteroaryl ring, wherein one or two atoms in the heteroaryl ring system are independently nitrogen, oxygen, or sulfur;

each instance of $R^{G1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted heterocyclic or substituted or unsubstituted heteroaryl ring;

t1 is 0, 1, 2, 3, 4, or 5;

$L^G$ is a bond, —O—, —S—, —$N(R^{G5})$—, or —$C(R^{G6})_2$—, wherein $R^{G5}$ is hydrogen, substituted or unsubstituted $C_{1-6}$ alkyl, or a nitrogen protecting group; and each instance of $R^{G6}$ is independently hydrogen, halogen, or substituted or unsubstituted $C_{1-6}$ alkyl;

$R^{G2}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^{G3}$ is hydrogen, substituted or unsubstituted $C_{1-6}$ alkyl, or a nitrogen protecting group;

each instance of $R^{G4}$ is independently halogen, substituted or unsubstituted alkyl, substituted or unsubstituted alkenyl, substituted or unsubstituted alkynyl, substituted or unsubstituted carbocyclyl, or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, —OC(=O)N(R$^a$)$_2$, —S(=O)$_2$R$^a$, —S(=O)$_2$OR$^a$, or —S(=O)$_2$N(R$^a$)$_2$; and t4 is 0, 1, 2, 3, or 4.

In certain embodiments, Ring G is a substituted or unsubstituted phenyl ring. In certain embodiments, Ring G is a substituted or unsubstituted, monocyclic, 5- to 6-membered heteroaryl ring, wherein one or two atoms in the heteroaryl ring system are independently nitrogen, oxygen, or sulfur. In certain embodiments, Ring G is substituted or unsubstituted pyrrolyl ring.

In certain embodiments, all instances of R$^{G1}$ are the same. In certain embodiments, two instances of R$^{G1}$ are different from each other. In certain embodiments, at least one instance of R$^{G1}$ is halogen (e.g., F, Cl, Br, or I). In certain embodiments, at least one instance of R$^{G1}$ is substituted or unsubstituted alkyl (e.g., substituted or unsubstituted C$_{1-6}$ alkyl). In certain embodiments, at least one instance of R$^{G1}$ is —CH$_3$. In certain embodiments, at least one instance of R$^{G1}$ is —CF$_3$, unsubstituted ethyl, perfluoroethyl, unsubstituted propyl, perfluoropropyl, unsubstituted butyl, or perfluorobutyl. In certain embodiments, at least one instance of R$^{G1}$ is substituted or unsubstituted alkenyl (e.g., substituted or unsubstituted C$_{1-6}$ alkenyl). In certain embodiments, at least one instance of R$^{G1}$ is substituted or unsubstituted alkynyl (e.g., substituted or unsubstituted C$_{1-6}$ alkynyl). In certain embodiments, at least one instance of R$^{G1}$ is substituted or unsubstituted carbocyclyl (e.g., substituted or unsubstituted, monocyclic, 3- to 7-membered carbocyclyl). In certain embodiments, at least one instance of R$^{G1}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of R$^{G1}$ is substituted or unsubstituted aryl (e.g., substituted or unsubstituted, 6- to 10-membered aryl). In certain embodiments, at least one instance of R$^{G1}$ is substituted or unsubstituted phenyl. In certain embodiments, at least one instance of R$^{G1}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of R$^{G1}$ is —OR$^a$ (e.g., —OH, —O(substituted or unsubstituted C$_{1-6}$ alkyl) (e.g., —OMe, —OEt, —OPr, —OBu, or —OBn), or —O(substituted or unsubstituted phenyl) (e.g., —OPh)). In certain embodiments, at least one instance of R$^{G1}$ is —SR$^a$ (e.g., —SH, —S(substituted or unsubstituted C$_{1-6}$ alkyl) (e.g., —SMe, —SEt, —SPr, —SBu, or —SBn), or —S(substituted or unsubstituted phenyl) (e.g., —SPh)). In certain embodiments, at least one instance of R$^{G1}$ is —N(R$^a$)$_2$ (e.g., —NH$_2$, —NH(substituted or unsubstituted C$_{1-6}$ alkyl) (e.g., —NHMe), or —N(substituted or unsubstituted C$_{1-6}$ alkyl)-(substituted or unsubstituted C$_{1-6}$ alkyl) (e.g., —NMe$_2$)). In certain embodiments, at least one instance of R$^{G1}$ is —CN, —SCN, or —NO$_2$. In certain embodiments, at least one instance of R$^{G1}$ is —C(=NR$^a$)R$^a$, —C(=NR$^a$)OR$^a$, or —C(=NR$^a$)N(R$^a$)$_2$. In certain embodiments, at least one instance of R$^{G1}$ is —C(=O)R$^a$ or —C(=O)OR$^a$. In certain embodiments, at least one instance of R$^{G1}$ is —C(=O)N(R$^a$)$_2$ (e.g., —C(=O)NH$_2$, —C(=O)NHMe, —C(=O)NMe$_2$, —C(=O)NHCH$_2$CH$_2$N(Et)$_2$, —C(=O)-(substituted or unsubstituted N-pyrrolidinyl), or —C(=O)-(substituted or unsubstituted N-piperazinyl)). In certain embodiments, at least one instance of R$^{G1}$ is —NR$^a$C(=O)R$^a$ (e.g., —N(substituted or unsubstituted C$_{1-6}$ alkyl)-C(=O)(substituted or unsubstituted C$_{1-6}$ alkyl), such as

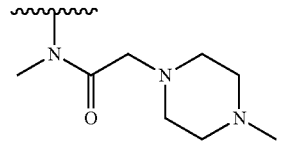

In certain embodiments, at least one instance of R$^{G1}$ is —NR$^a$C(=O)OR$^a$ or —NR$^a$C(=O)N(R$^a$)$_2$. In certain embodiments, at least one instance of R$^{G1}$ is —OC(=O)R$^a$, —OC(=O)OR$^a$, or —OC(=O)N(R$^a$)$_2$.

In certain embodiments, at least one instance of R$^{G1}$ is substituted or unsubstituted alkyl, —C(=O)N(R$^a$)$_2$, or —N(R$^a$)C(=O)R$^a$.

In certain embodiments, t1 is 0. In certain embodiments, t1 is 1. In certain embodiments, t1 is 2. In certain embodiments, t1 is 3. In certain embodiments, t1 is 4. In certain embodiments, t1 is 5.

In certain embodiments, L$^G$ is a bond. In certain embodiments, L$^G$ is —O—, —S—, or —C(R$^{G6}$)$_2$— (e.g., —CH$_2$—). In certain embodiments, L$^G$ is —N(R$^{G5}$)— (e.g., —NH—).

In certain embodiments, R$^{G5}$ is hydrogen. In certain embodiments, R$^{G5}$ is substituted or unsubstituted C$_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, R$^{G5}$ is a nitrogen protecting group (e.g., Bn, Boc, Cbz, Fmoc, trifluoroacetyl, triphenylmethyl, acetyl, or Ts).

In certain embodiments, both instances of R$^{G6}$ are the same. In certain embodiments, two instances of R$^{G6}$ are different from each other. In certain embodiments, at least one instance of R$^{G6}$ is hydrogen. In certain embodiments, each instance of R$^{G6}$ is hydrogen. In certain embodiments, at least one instance of R$^{G6}$ is halogen (e.g., F, Cl, Br, or I). In certain embodiments, at least one instance of R$^{G6}$ is substituted or unsubstituted C$_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl).

In certain embodiments, R$^{G2}$ is hydrogen. In certain embodiments, R$^{G2}$ is halogen (e.g., F, Cl, Br, or I). In certain embodiments, R$^{G2}$ is substituted or unsubstituted alkyl, such as substituted or unsubstituted C$_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, R$^{G2}$ is substituted or unsubstituted alkenyl (e.g., substituted or unsubstituted C$_{1-6}$ alkenyl). In certain embodiments, R$^{G2}$ is substituted or unsubstituted alkynyl (e.g., substituted or unsubstituted C$_{1-6}$ alkynyl). In certain embodiments, R$^{G2}$ is substituted or unsubstituted carbocyclyl (e.g., substituted or unsubstituted, monocyclic, 3- to 7-membered carbocyclyl). In certain embodiments, R$^{G2}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, R$^{G2}$ is substituted or unsubstituted aryl (e.g., substituted or unsubstituted, 6- to 10-membered aryl). In certain embodiments, R$^{G2}$ is substituted or unsubstituted phenyl. In certain embodiments, R$^{G2}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur).

In certain embodiments, $R^{G3}$ is hydrogen. In certain embodiments, $R^{G3}$ is substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, or perfluorobutyl). In certain embodiments, $R^{G3}$ is a nitrogen protecting group (e.g., Bn, Boc, Cbz, Fmoc, trifluoroacetyl, triphenylmethyl, acetyl, or Ts).

In certain embodiments, all instances of $R^{G4}$ are the same. In certain embodiments, two instances of $R^{G4}$ are different from each other. In certain embodiments, at least one instance of $R^{G4}$ is halogen (e.g., F, Cl, Br, or I). In certain embodiments, at least one instance of $R^{G4}$ is substituted or unsubstituted alkyl (e.g., substituted or unsubstituted $C_{1-6}$ alkyl). In certain embodiments, at least one instance of $R^{G4}$ is —$CH_3$. In certain embodiments, at least one instance of $R^{G4}$ is —$CF_3$, unsubstituted ethyl, perfluoroethyl, unsubstituted propyl, perfluoropropyl, unsubstituted butyl, or perfluorobutyl. In certain embodiments, at least one instance of $R^{G4}$ is substituted or unsubstituted alkenyl (e.g., substituted or unsubstituted $C_{1-6}$ alkenyl). In certain embodiments, at least one instance of $R^{G4}$ is substituted or unsubstituted alkynyl (e.g., substituted or unsubstituted $C_{1-6}$ alkynyl). In certain embodiments, at least one instance of $R^{G4}$ is substituted or unsubstituted carbocyclyl (e.g., substituted or unsubstituted, monocyclic, 3- to 7-membered carbocyclyl). In certain embodiments, at least one instance of $R^{G4}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{G4}$ is substituted or unsubstituted aryl (e.g., substituted or unsubstituted, 6- to 10-membered aryl). In certain embodiments, at least one instance of $R^{G4}$ is substituted or unsubstituted phenyl. In certain embodiments, at least one instance of $R^{G4}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{G4}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{G4}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{G4}$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^{G4}$ is —CN, —SCN, or —$NO_2$. In certain embodiments, at least one instance of $R^{G4}$ is —$C(=NR^a)R^a$, —$C(=NR^a)OR^a$, or —$C(=NR^a)N(R^a)_2$. In certain embodiments, at least one instance of $R^{G4}$ is —$C(=O)R^a$, —$C(=O)OR^a$ (e.g., —C(=O)O(substituted or unsubstituted $C_{1-6}$ alkyl), such as —C(=O)OMe), or —$C(=O)N(R^a)_2$ (e.g., —$C(=O)NH_2$, —C(=O)NHMe, or —$C(=O)NMe_2$). In certain embodiments, at least one instance of $R^{G4}$ is —$NR^aC(=O)R^a$, —$NR^aC(=O)OR^a$, or —$NR^aC(=O)N(R^a)_2$. In certain embodiments, at least one instance of $R^{G4}$ is —$OC(=O)R^a$, —$OC(=O)OR^a$, or —$OC(=O)N(R^a)_2$. In certain embodiments, at least one instance of $R^{G4}$ is —$S(=O)_2R^a$ (e.g., —$S(=O)_2$(substituted or unsubstituted $C_{1-6}$ alkyl), such as

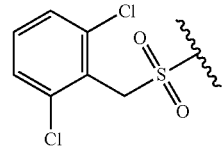 [SMILES: *S(=O)(=O)Cc1c(Cl)cccc1Cl]

—$S(=O)_2OR^a$, or —$S(=O)_2N(R^a)_2$ (e.g., —$S(=O)_2$N(substituted or unsubstituted $C_{1-6}$ alkyl)-(substituted or unsubstituted phenyl), such as

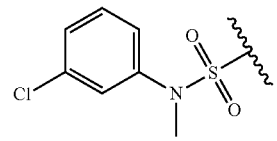 [SMILES: *S(=O)(=O)N(C)c1cccc(Cl)c1]

In certain embodiments, at least one instance of $R^{G4}$ is halogen, —$C(=O)OR^a$, —$S(=O)_2R^a$, or —$S(=O)_2N(R^a)_2$.

In certain embodiments, t4 is 0. In certain embodiments, t4 is 1. In certain embodiments, t4 is 2. In certain embodiments, t4 is 3. In certain embodiments, t4 is 4.

In certain embodiments, the compound of Formula (G) is of the formula:

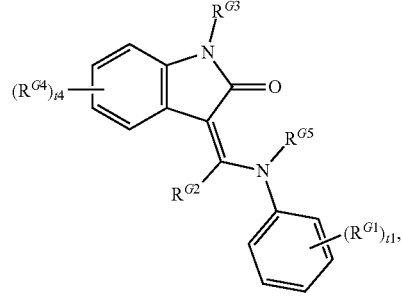

or a pharmaceutically acceptable salt, solvate, hydrate, polymorph, co-crystal, tautomer, stereoisomer, isotopically labeled derivative, or prodrug thereof.

In certain embodiments, the compound of Formula (G) is of the formula:

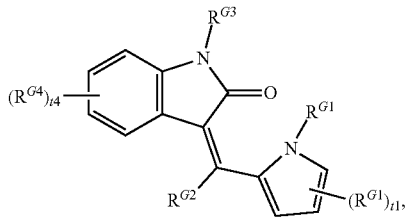

or a pharmaceutically acceptable salt, solvate, hydrate, polymorph, co-crystal, tautomer, stereoisomer, isotopically labeled derivative, or prodrug thereof.

In certain embodiments, the compound of Formula (G) is of the formula:

101

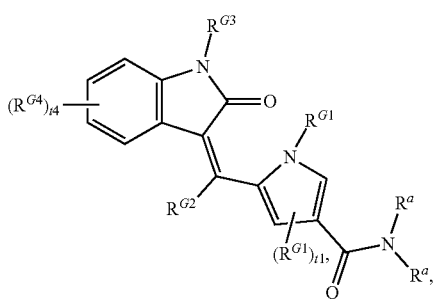

or a pharmaceutically acceptable salt, solvate, hydrate, polymorph, co-crystal, tautomer, stereoisomer, isotopically labeled derivative, or prodrug thereof.

In certain embodiments, the compound of Formula (G) is of the formula:

(BIBF-1120)

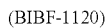

(PHA-665752)

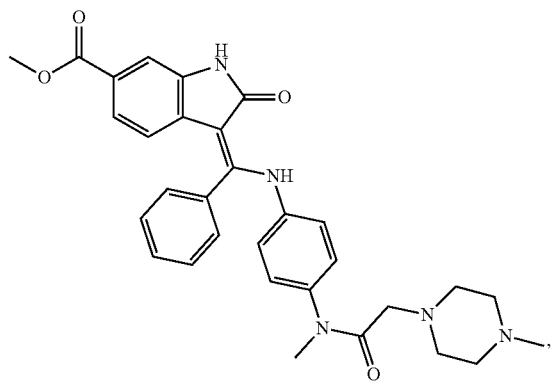

(SU11248)

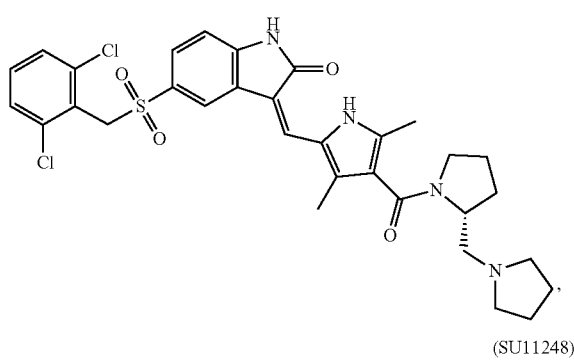

(SU11274)

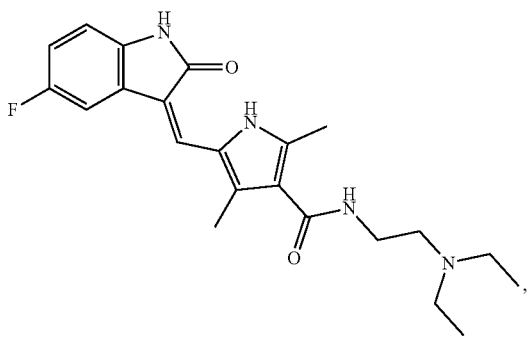

or a pharmaceutically acceptable salt, solvate, hydrate, polymorph, co-crystal, tautomer, stereoisomer, isotopically labeled derivative, or prodrug thereof.

In certain embodiments, a compound of Formula (G) is not BIBF-1120, PHA-665752, SU11248, SU11274, or a pharmaceutically acceptable salt, solvate, hydrate, polymorph, co-crystal, tautomer, stereoisomer, or isotopically labeled derivative thereof.

It is believed that compounds of Formula (G), and pharmaceutically acceptable salts, solvates, hydrates, polymorphs, co-crystals, tautomers, stereoisomers, isotopically labeled derivatives, and prodrugs thereof, are VEGFR inhibitors (e.g., SU11248 (a VEGFR1 inhibitor) and BIBF-1120), PDGFR inhibitors (e.g., BIBF-1120 and SU11248), FGFR inhibitors (e.g., BIBF-1120), MET inhibitors (e.g., PHA-665752 and SU11274), KIT inhibitors (e.g., SU11248), and/or FLT inhibitors (e.g., FLT3 inhibitors, such as SU11248).

Compounds of Formula (H)

In another aspect, the present disclosure provides compounds of Formula (H):

(H)

$(R^{H1})_{u1}$—⬡—$NR^{H2}$—pyrimidine($(R^{H3})_{u3}$)—$L^H$—⬡—$(R^{H4})_{u4}$, and pharmaceutically acceptable salts, solvates, hydrates, polymorphs, co-crystals, tautomers, stereoisomers, isotopically labeled derivatives, and prodrugs thereof, wherein:

$L^H$ is a substituted or unsubstituted, saturated or unsaturated, $C_{1-4}$ aliphatic chain, optionally wherein one or two chain atoms of the aliphatic chain are independently replaced with —O—, —S—, —$NR^{H5}$—, —N═, or ═N—, wherein each instance of $R^{H5}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

each instance of $R^{H1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(═$NR^a$)$R^a$, —C(═$NR^a$)$OR^a$, —C(═$NR^a$)N($R^a$)$_2$, —C(═O)$R^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ are joined to form a substituted or unsubstituted heterocyclic or substituted or unsubstituted heteroaryl ring;

u1 is 0, 1, 2, 3, 4, or 5;

R$^{H2}$ is hydrogen, substituted or unsubstituted C$_{1-6}$ alkyl, or a nitrogen protecting group;

each instance of R$^{H3}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

u3 is 0, 1, or 2;

each instance of R$^{H4}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$; and u4 is 0, 1, 2, 3, 4, or 5.

In certain embodiments, L$^H$ is a substituted or unsubstituted C$_1$ aliphatic chain. In certain embodiments, L$^H$ is —O— or —S—. In certain embodiments, L$^H$ is —NR$^{H5}$— (e.g., —NH—). In certain embodiments, L$^H$ is a substituted or unsubstituted, saturated or unsaturated, C$_3$ aliphatic chain, optionally wherein one or two chain atoms of the aliphatic chain are independently replaced with —O—, —S—, —NR$^{H5}$— (e.g., —NH—), =N—, or =N—. In certain embodiments, L$^{H5}$ is —NR$^{H5}$C(=O)O— (e.g., —NHC(=O)O)— or —N(substituted or unsubstituted phenyl)C(=O)O)—) or —OC(=O)NR$^{H5}$— (e.g., —OC(=O)NH— or —OC(=O)N(substituted or unsubstituted phenyl)-). In certain embodiments, L$^H$ is —NR$^{H5}$C(=O)NR$^{H5}$— (e.g., —NHC(=O)NH)—. In certain embodiments, L$^H$ is a substituted or unsubstituted, saturated or unsaturated, C$_2$ or C$_4$ aliphatic chain, optionally wherein one or two chain atoms of the aliphatic chain are independently replaced with —O—, —S—, —NR$^{H5}$— (e.g., —NH—), =N—, or =N—.

In certain embodiments, all instances of R$^{H5}$ are the same. In certain embodiments, two instances of R$^{H5}$ are different from each other. In certain embodiments, at least one instance of R$^{H5}$ is hydrogen. In certain embodiments, at least one instance of R$^{H5}$ is substituted or unsubstituted alkyl, such as substituted or unsubstituted C$_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, at least one instance of R$^{H5}$ is substituted or unsubstituted alkenyl (e.g., substituted or unsubstituted C$_{1-6}$ alkenyl). In certain embodiments, at least one instance of R$^{H5}$ is substituted or unsubstituted alkynyl (e.g., substituted or unsubstituted C$_{1-6}$ alkynyl). In certain embodiments, at least one instance of R$^{H5}$ is substituted or unsubstituted carbocyclyl (e.g., substituted or unsubstituted, monocyclic, 3- to 7-membered carbocyclyl). In certain embodiments, at least one instance of R$^{H5}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of R$^{H5}$ is substituted or unsubstituted aryl (e.g., substituted or unsubstituted, 6- to 10-membered aryl). In certain embodiments, at least one instance of R$^{H5}$ is substituted or unsubstituted phenyl. In certain embodiments, at least one instance of R$^{H5}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of R$^{H5}$ is a nitrogen protecting group (e.g., Bn, Boc, Cbz, Fmoc, trifluoroacetyl, triphenylmethyl, acetyl, or Ts). In certain embodiments, at least one instance of R$^{H5}$ is hydrogen or substituted or unsubstituted phenyl.

In certain embodiments, all instances of R$^{H1}$ are the same. In certain embodiments, two instances of R$^{H1}$ are different from each other. In certain embodiments, at least one instance of R$^{H1}$ is halogen (e.g., F, Cl, Br, or I). In certain embodiments, at least one instance of R$^{H1}$ is substituted or unsubstituted alkyl (e.g., substituted or unsubstituted C$_{1-6}$ alkyl). In certain embodiments, at least one instance of R$^{H1}$ is —CH$_3$. In certain embodiments, at least one instance of R$^{H1}$ is —CF$_3$, unsubstituted ethyl, perfluoroethyl, unsubstituted propyl, perfluoropropyl, unsubstituted butyl, or perfluorobutyl. In certain embodiments, at least one instance of R$^{H1}$ is of the formula:

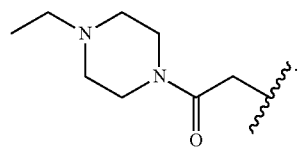 [SMILES: *CC(=O)N1CCN(CC)CC1]

In certain embodiments, at least one instance of R$^{H1}$ is substituted or unsubstituted alkenyl (e.g., substituted or unsubstituted C$_{1-6}$ alkenyl). In certain embodiments, at least one instance of R$^{H1}$ is substituted or unsubstituted alkynyl (e.g., substituted or unsubstituted C$_{1-6}$ alkynyl). In certain embodiments, at least one instance of R$^{H1}$ is substituted or unsubstituted carbocyclyl (e.g., substituted or unsubstituted, monocyclic, 3- to 7-membered carbocyclyl). In certain embodiments, at least one instance of R$^{H1}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{H1}$ is substituted or unsubstituted piperazinyl (e.g., substituted or unsubstituted N-piperazinyl, such as

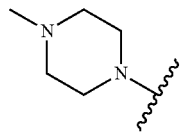 [SMILES: *N1CCN(C)CC1]

In certain embodiments, at least one instance of $R^{H1}$ is substituted or unsubstituted aryl (e.g., substituted or unsubstituted, 6- to 10-membered aryl). In certain embodiments, at least one instance of $R^{H1}$ is substituted or unsubstituted phenyl. In certain embodiments, at least one instance of $R^{H1}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{H1}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{H1}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{H1}$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^{H1}$ is —CN, —SCN, or —$NO_2$. In certain embodiments, at least one instance of $R^{H1}$ is —C(=$NR^a$)$R^a$, —C(=$NR^a$)$OR^a$, or —C(=$NR^a$)$N(R^a)_2$. In certain embodiments, at least one instance of $R^{H1}$ is —C(=O)$R^a$, —C(=O)$OR^a$, or —C(=O)$N(R^a)_2$ (e.g., —C(=O)$NH_2$, —C(=O)NHMe, or —C(=O)$NMe_2$). In certain embodiments, at least one instance of $R^{H1}$ is —$NR^a$C(=O)$R^a$, —$NR^a$C(=O)$OR^a$, or —$NR^a$C(=O)$N(R^a)_2$. In certain embodiments, at least one instance of $R^{H1}$ is —OC(=O)$R^a$, —OC(=O)$OR^a$, or —OC(=O)$N(R^a)_2$.

In certain embodiments, at least one instance of $R^{H1}$ is substituted or unsubstituted alkyl or substituted or unsubstituted, monocyclic, 5- to 6-membed heterocyclyl, wherein one, two, or three atoms in the heterocyclic ring system are independently nitrogen, oxygen, or sulfur.

In certain embodiments, u1 is 0. In certain embodiments, u1 is 1. In certain embodiments, u1 is 2. In certain embodiments, u1 is 3. In certain embodiments, u1 is 4. In certain embodiments, u1 is 5.

In certain embodiments, $R^{H2}$ is hydrogen. In certain embodiments, $R^{H2}$ is substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, or perfluorobutyl). In certain embodiments, $R^{H2}$ is a nitrogen protecting group (e.g., Bn, Boc, Cbz, Fmoc, trifluoroacetyl, triphenylmethyl, acetyl, or Ts).

In certain embodiments, all instances of $R^{H3}$ are the same. In certain embodiments, two instances of $R^{H3}$ are different from each other. In certain embodiments, at least one instance of $R^{H3}$ is halogen (e.g., F, Cl, Br, or I). In certain embodiments, at least one instance of $R^{H3}$ is substituted or unsubstituted alkyl (e.g., substituted or unsubstituted $C_{1-6}$ alkyl). In certain embodiments, at least one instance of $R^{H3}$ is —$CH_3$. In certain embodiments, at least one instance of $R^{H3}$ is —$CF_3$, unsubstituted ethyl, perfluoroethyl, unsubstituted propyl, perfluoropropyl, unsubstituted butyl, or perfluorobutyl. In certain embodiments, at least one instance of $R^{H3}$ is substituted or unsubstituted alkenyl (e.g., substituted or unsubstituted $C_{1-6}$ alkenyl). In certain embodiments, at least one instance of $R^{H3}$ is substituted or unsubstituted alkynyl (e.g., substituted or unsubstituted $C_{1-6}$ alkynyl). In certain embodiments, at least one instance of $R^{H3}$ is substituted or unsubstituted carbocyclyl (e.g., substituted or unsubstituted, monocyclic, 3- to 7-membered carbocyclyl). In certain embodiments, at least one instance of $R^{H3}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{H3}$ is substituted or unsubstituted aryl (e.g., substituted or unsubstituted, 6- to 10-membered aryl). In certain embodiments, at least one instance of $R^{H3}$ is substituted or unsubstituted phenyl. In certain embodiments, at least one instance of $R^{H3}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{H3}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{H3}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{H3}$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^{H3}$ is —CN, —SCN, or —$NO_2$. In certain embodiments, at least one instance of $R^{H3}$ is —C(=$NR^a$)$R^a$, —C(=$NR^a$)$OR^a$, or —C(=$NR^a$)$N(R^a)_2$. In certain embodiments, at least one instance of $R^{H3}$ is —C(=O)$R^a$, —C(=O)$OR^a$, or —C(=O)$N(R^a)_2$ (e.g., —C(=O)$NH_2$, —C(=O)NHMe, or —C(=O)$NMe_2$). In certain embodiments, at least one instance of $R^{H3}$ is —$NR^a$C(=O)$R^a$, —$NR^a$C(=O)$OR^a$, or —$NR^a$C(=O)$N(R^a)_2$. In certain embodiments, at least one instance of $R^{H3}$ is —OC(=O)$R^a$, —OC(=O)$OR^a$, or —OC(=O)$N(R^a)_2$.

In certain embodiments, u3 is 0. In certain embodiments, u3 is 1. In certain embodiments, u3 is 2. In certain embodiments, u3 is 3.

In certain embodiments, all instances of $R^{H4}$ are the same. In certain embodiments, two instances of $R^{H4}$ are different from each other. In certain embodiments, at least one instance of $R^{H4}$ is halogen (e.g., F, Cl, Br, or I). In certain embodiments, at least one instance of $R^{H4}$ is substituted or unsubstituted alkyl (e.g., substituted or unsubstituted $C_{1-6}$ alkyl). In certain embodiments, at least one instance of $R^{H4}$ is —$CH_3$. In certain embodiments, at least one instance of $R^{H4}$ is —$CF_3$, unsubstituted ethyl, perfluoroethyl, unsubstituted propyl, perfluoropropyl, unsubstituted butyl, or perfluorobutyl. In certain embodiments, at least one instance of $R^{H4}$ is substituted or unsubstituted alkenyl (e.g., substituted or unsubstituted $C_{1-6}$ alkenyl). In certain embodiments, at least one instance of $R^{H4}$ is substituted or unsubstituted alkynyl (e.g., substituted or unsubstituted $C_{1-6}$ alkynyl). In certain embodiments, at least one instance of $R^{H4}$ is substituted or unsubstituted carbocyclyl (e.g., substituted or unsubstituted, monocyclic, 3- to 7-membered carbocyclyl). In certain embodiments, at least one instance of $R^{H4}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{H4}$ is substituted or unsubstituted aryl (e.g., substituted or unsubstituted, 6- to 10-membered aryl). In certain embodiments, at least one instance of $R^{H4}$ is substituted or unsubstituted phenyl. In certain embodiments, at least one instance of $R^{H4}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{H4}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{H4}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{H4}$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^{H4}$ is —CN, —SCN, or —$NO_2$. In certain embodiments, at least one instance of $R^{H4}$ is —C(=$NR^a$)$R^a$, —C(=$NR^a$)$OR^a$, or —C(=$NR^a$)N($R^a$)$_2$. In certain embodiments, at least one instance of $R^{H4}$ is —C(=O)$R^a$, —C(=O)$OR^a$, or —C(=O)N($R^a$)$_2$ (e.g., —C(=O)$NH_2$, —C(=O)NHMe, —C(=O)NH(substituted or unsubstituted phenyl) (e.g., —C(=O)NH-(2-chlorophenyl)), or —C(=O)$NMe_2$). In certain embodiments, at least one instance of $R^{H4}$ is —$NR^aC$(=O)$R^a$, —$NR^aC$(=O)$OR^a$, or —$NR^aC$(=O)N($R^a$)$_2$. In certain embodiments, at least one instance of $R^{H4}$ is —OC(=O)$R^a$, —OC(=O)$OR^a$, or —OC(=O)N($R^a$)$_2$.

In certain embodiments, at least one instance of $R^{H4}$ is substituted or unsubstituted alkyl, or —C(=O)N($R^a$)$_2$.

In certain embodiments, u4 is 0. In certain embodiments, u4 is 1. In certain embodiments, u4 is 2. In certain embodiments, u4 is 3. In certain embodiments, u4 is 4. In certain embodiments, u4 is 5.

In certain embodiments, the compound of Formula (H) is of the formula:

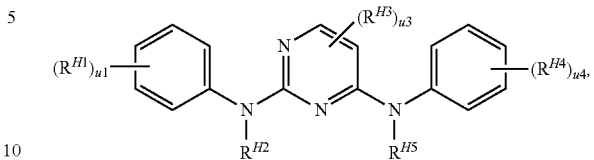

or a pharmaceutically acceptable salt, solvate, hydrate, polymorph, co-crystal, tautomer, stereoisomer, isotopically labeled derivative, or prodrug thereof.

In certain embodiments, the compound of Formula (H) is of the formula:

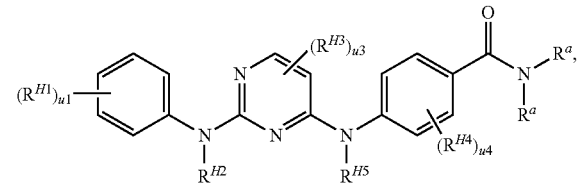

or a pharmaceutically acceptable salt, solvate, hydrate, polymorph, co-crystal, tautomer, stereoisomer, isotopically labeled derivative, or prodrug thereof.

In certain embodiments, the compound of Formula (H) is of the formula:

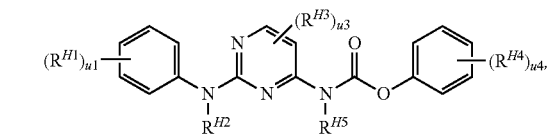

or a pharmaceutically acceptable salt, solvate, hydrate, polymorph, co-crystal, tautomer, stereoisomer, isotopically labeled derivative, or prodrug thereof.

In certain embodiments, the compound of Formula (H) is of the formula:

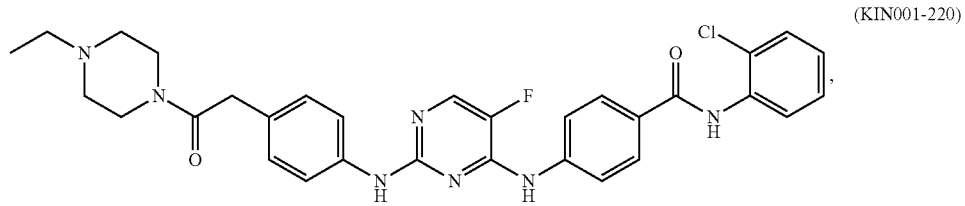

(KIN001-220)

-continued

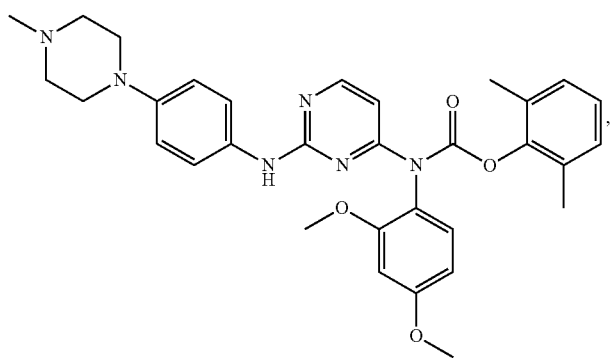

or a pharmaceutically acceptable salt, solvate, hydrate, polymorph, co-crystal, tautomer, stereoisomer, isotopically labeled derivative, or prodrug thereof.

In certain embodiments, the compound of Formula (H) is of the formula:

(WH-4-025)

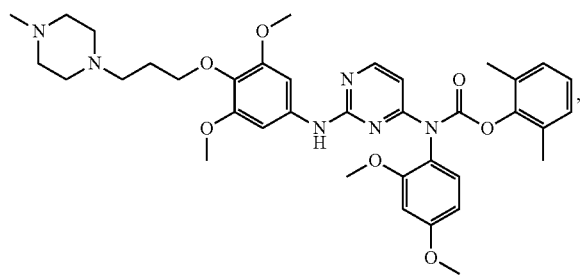

or a pharmaceutically acceptable salt, solvate, hydrate, polymorph, co-crystal, tautomer, stereoisomer, isotopically labeled derivative, or prodrug thereof.

Compounds WH-4-023 and WH-4-025 are disclosed in U.S. Patent Application Publication, US 2005/0026914, published Feb. 3, 2005, which is incorporated herein by reference. In certain embodiments, a compound of Formula (H) is not KIN001-220, WH-4-023, or a pharmaceutically acceptable salt, solvate, hydrate, polymorph, co-crystal, tautomer, stereoisomer, or isotopically labeled derivative thereof. In certain embodiments, a compound of Formula (H) is not WH-4-025, or a pharmaceutically acceptable salt, solvate, hydrate, polymorph, co-crystal, tautomer, stereoisomer, or isotopically labeled derivative thereof.

It is believed that compounds of Formula (H), and pharmaceutically acceptable salts, solvates, hydrates, polymorphs, co-crystals, tautomers, stereoisomers, isotopically labeled derivatives, and prodrugs thereof, are aurora kinase inhibitors (e.g., KIN001-220) and/or SRC inhibitors (e.g., WH-4-023).

Compounds of Formula (I)

In another aspect, the present disclosure provides compounds of Formula (I):

(WH-4-023, MH4-023, WH4, or WH)

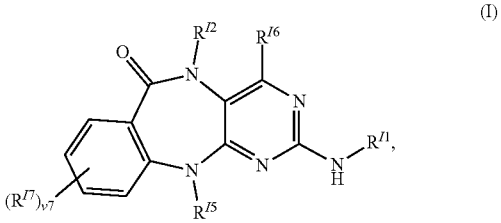

(I)

and pharmaceutically acceptable salts, solvates, hydrates, polymorphs, co-crystals, tautomers, stereoisomers, isotopically labeled derivatives, and prodrugs thereof, wherein:

$R^{I1}$ is substituted or unsubstituted alkyl, substituted or unsubstituted carbocyclyl, substituted or unsubstituted heterocyclyl, substituted or unsubstituted aryl, or substituted or unsubstituted heteroaryl;

$R^{I2}$ is hydrogen or substituted or unsubstituted alkyl;

$R^{I5}$ is hydrogen, substituted or unsubstituted alkyl, substituted or unsubstituted aralkyl, or substituted or unsubstituted carbocyclyl;

$R^{I6}$ is hydrogen or substituted or unsubstituted alkyl;

each instance of $R^{I7}$ is independently halogen, substituted or unsubstituted alkyl, substituted or unsubstituted aralkyl, substituted or unsubstituted alkenyl, substituted or unsubstituted carbocyclyl, substituted or unsubstituted heterocyclyl, substituted or unsubstituted aryl, substituted or unsubstituted heteroaryl, —O-(substituted or unsubstituted alkyl), —NH-(substituted or unsubstituted alkyl), —NH-(substituted or unsubstituted aryl), —N(substituted or unsubstituted alkyl)-(substituted or unsubstituted alkyl), —N(substituted or unsubstituted alkyl)-(substituted or unsubstituted aryl), —NO$_2$, or —CN; and v7 is 0, 1, 2, 3, or 4.

In certain embodiments, $R^{I1}$ is substituted or unsubstituted alkyl, such as substituted or unsubstituted $C_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, $R^{I1}$ is substituted or unsubstituted carbocyclyl (e.g., substituted or unsubstituted, monocyclic, 3- to 7-membered carbocyclyl). In certain embodiments, $R^{I1}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, $R^{I1}$ is substituted or unsubstituted aryl (e.g., substituted or unsubstituted, 6- to 10-membered aryl). In certain embodiments, $R^{J1}$ is substituted or unsubstituted phenyl. In certain embodiments, $R^{J1}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur).

In certain embodiments, $R^{J2}$ is hydrogen. In certain embodiments, $R^{J2}$ is substituted or unsubstituted alkyl, such as substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, or perfluorobutyl).

In certain embodiments, $R^{J5}$ is hydrogen. In certain embodiments, $R^{J5}$ is substituted or unsubstituted alkyl (e.g., substituted or unsubstituted $C_{1-6}$ alkyl). In certain embodiments, $R^{J5}$ is —$CH_3$. In certain embodiments, $R^{J5}$ is —$CF_3$, unsubstituted ethyl, perfluoroethyl, unsubstituted propyl, perfluoropropyl, unsubstituted butyl, or perfluorobutyl. In certain embodiments, $R^{J5}$ is substituted or unsubstituted aralkyl (e.g., Bn). In certain embodiments, $R^{J5}$ is substituted or unsubstituted carbocyclyl (e.g., substituted or unsubstituted, monocyclic, 5- to 6-membered carbocyclyl).

In certain embodiments, $R^{J6}$ is hydrogen. In certain embodiments, $R^{J6}$ is substituted or unsubstituted alkyl, such as substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, or perfluorobutyl).

In certain embodiments, all instances of $R^{J7}$ are the same. In certain embodiments, two instances of $R^{J7}$ are different from each other. In certain embodiments, at least one instance of $R^{J7}$ is halogen (e.g., F, Cl, Br, or I). In certain embodiments, at least one instance of $R^{J7}$ is substituted or unsubstituted alkyl (e.g., substituted or unsubstituted $C_{1-6}$ alkyl). In certain embodiments, at least one instance of $R^{J7}$ is —$CH_3$. In certain embodiments, at least one instance of $R^{J7}$ is —$CF_3$, unsubstituted ethyl, perfluoroethyl, unsubstituted propyl, perfluoropropyl, unsubstituted butyl, or perfluorobutyl. In certain embodiments, at least one instance of $R^{J7}$ is substituted or unsubstituted aralkyl (e.g., Bn). In certain embodiments, at least one instance of $R^{J7}$ is substituted or unsubstituted alkenyl (e.g., substituted or unsubstituted $C_{1-6}$ alkenyl). In certain embodiments, at least one instance of $R^{J7}$ is substituted or unsubstituted carbocyclyl (e.g., substituted or unsubstituted, monocyclic, 3- to 7-membered carbocyclyl). In certain embodiments, at least one instance of $R^{J7}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{J7}$ is substituted or unsubstituted aryl (e.g., substituted or unsubstituted, 6- to 10-membered aryl). In certain embodiments, at least one instance of $R^{J7}$ is substituted or unsubstituted phenyl. In certain embodiments, at least one instance of $R^{J7}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{J7}$ is —O-(substituted or unsubstituted alkyl) (e.g., —OMe, —OEt, —OPr, or —OBu). In certain embodiments, at least one instance of $R^{J7}$ is —NH-(substituted or unsubstituted alkyl) (e.g., —NHMe), —NH-(substituted or unsubstituted aryl) (e.g., —NHPh), —N(substituted or unsubstituted alkyl)-(substituted or unsubstituted alkyl) (e.g., —$NMe_2$), or —N(substituted or unsubstituted alkyl)-(substituted or unsubstituted aryl). In certain embodiments, at least one instance of $R^{J7}$ is —$NO_2$ or —CN.

In certain embodiments, v7 is 0. In certain embodiments, v7 is 1. In certain embodiments, v7 is 2. In certain embodiments, v7 is 3. In certain embodiments, v7 is 4.

In certain embodiments, the compound of Formula (I) is of the formula:

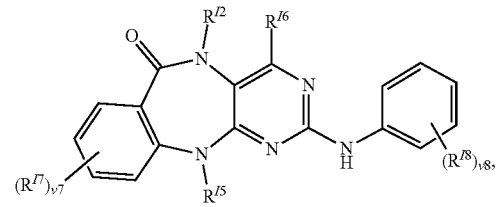

or a pharmaceutically acceptable salt, solvate, hydrate, polymorph, co-crystal, tautomer, stereoisomer, isotopically labeled derivative, or prodrug thereof, wherein:
each instance of $R^{J8}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^aC(=O)R^a$, —$NR^aC(=O)OR^a$, —$NR^aC(=O)N(R^a)_2$, —OC(=O)$R^a$, —OC(=O)$OR^a$, or —OC(=O)N($R^a$)$_2$; and
v8 is 0, 1, 2, 3, 4, or 5.

In certain embodiments, all instances of $R^{J8}$ are the same. In certain embodiments, two instances of $R^{J8}$ are different from each other. In certain embodiments, at least one instance of $R^{J8}$ is halogen (e.g., F, Cl, Br, or I). In certain embodiments, at least one instance of $R^{J8}$ is substituted or unsubstituted alkyl (e.g., substituted or unsubstituted $C_{1-6}$ alkyl). In certain embodiments, at least one instance of $R^{J8}$ is —$CH_3$. In certain embodiments, at least one instance of $R^{J8}$ is —$CF_3$, unsubstituted ethyl, perfluoroethyl, unsubstituted propyl, perfluoropropyl, unsubstituted butyl, or perfluorobutyl. In certain embodiments, at least one instance of $R^{J8}$ is substituted or unsubstituted alkenyl (e.g., substituted or unsubstituted $C_{1-6}$ alkenyl). In certain embodiments, at least one instance of $R^{J8}$ is substituted or unsubstituted alkynyl (e.g., substituted or unsubstituted $C_{1-6}$ alkynyl). In certain embodiments, at least one instance of $R^{J8}$ is substituted or unsubstituted carbocyclyl (e.g., substituted or unsubstituted, monocyclic, 3- to 7-membered carbocyclyl). In certain embodiments, at least one instance of $R^{J8}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur).

In certain embodiments, at least one instance of $R^{J8}$ is substituted or unsubstituted piperidinyl (e.g., substituted or unsubstituted N-piperidinyl, such as

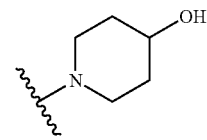 [SMILES: *N1CCC(O)CC1]

or substituted or unsubstituted piperazinyl (e.g., substituted or unsubstituted N-piperazinyl, such as

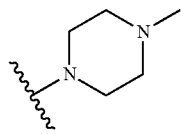 [SMILES: *N1CCN(C)CC1]

In certain embodiments, at least one instance of $R^{J8}$ is substituted or unsubstituted aryl (e.g., substituted or unsubstituted, 6- to 10-membered aryl). In certain embodiments, at least one instance of $R^{J8}$ is substituted or unsubstituted phenyl. In certain embodiments, at least one instance of $R^{J8}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{J8}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{J8}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{J8}$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^{J8}$ is —CN, —SCN, or —$NO_2$. In certain embodiments, at least one instance of $R^{J8}$ is —$C(=NR^a)R^a$, —$C(=NR^a)OR^a$, or —$C(=NR^a)N(R^a)_2$. In certain embodiments, at least one instance of $R^{J8}$ is —$C(=O)R^a$, —$C(=O)OR^a$, or —$C(=O)N(R^a)_2$ (e.g., —$C(=O)NH_2$, —$C(=O)NHMe$, —$C(=O)NMe_2$, or —C(=O)-(substituted or unsubstituted N-piperidinyl) (e.g.,

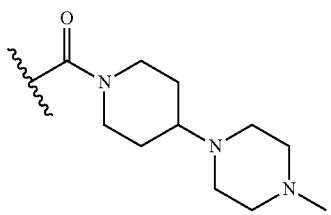 [SMILES: *C(=O)N1CCC(N2CCN(C)CC2)CC1]

certain embodiments, at least one instance of $R^{J8}$ is —$NR^aC(=O)R^a$, —$NR^aC(=O)OR^a$, or —$NR^aC(=O)N(R^a)_2$. In certain embodiments, at least one instance of $R^{J8}$ is —$OC(=O)R^a$, —$OC(=O)OR^a$, or —$OC(=O)N(R^a)_2$.

In certain embodiments, v8 is 0. In certain embodiments, v8 is 1. In certain embodiments, v8 is 2. In certain embodiments, v8 is 3. In certain embodiments, v8 is 4. In certain embodiments, v8 is 5.

In certain embodiments, the compound of Formula (I) is of the formula:

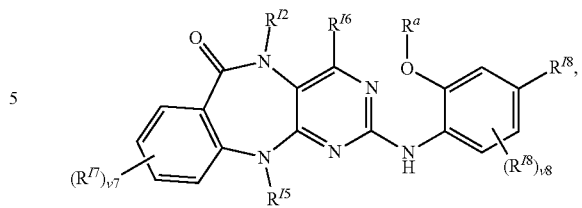

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

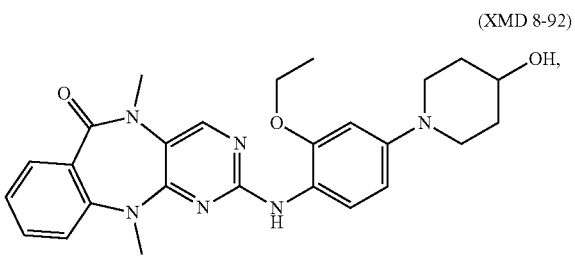

(XMD 8-92)

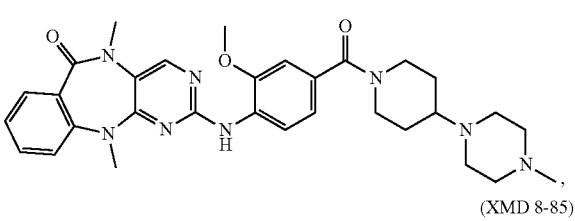

(XMD11-50)

(XMD 8-85)

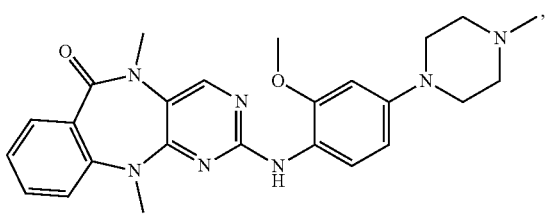

or a pharmaceutically acceptable salt, solvate, hydrate, polymorph, co-crystal, tautomer, stereoisomer, isotopically labeled derivative, or prodrug thereof.

In certain embodiments, a compound of Formula (I) is not XMD 8-92, XMD11-50, XMD 8-85, or a pharmaceutically acceptable salt, solvate, hydrate, polymorph, co-crystal, tautomer, stereoisomer, or isotopically labeled derivative thereof.

It is believed that compounds of Formula (I), and pharmaceutically acceptable salts, solvates, hydrates, polymorphs, co-crystals, tautomers, stereoisomers, isotopically labeled derivatives, and prodrugs thereof, are ERK inhibitors (e.g., ERK5 inhibitors, such as XMD 8-92, XMD11-50, and XMD 8-85) and/or LRRK inhibitors (e.g., LRRK2 inhibitors, such as XMD11-50).

Compounds of Formula (J)

In another aspect, the present disclosure provides compounds of Formula (J):

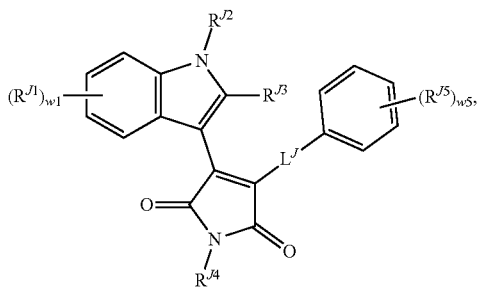

(J)

and pharmaceutically acceptable salts, solvates, hydrates, polymorphs, co-crystals, tautomers, stereoisomers, isotopically labeled derivatives, and prodrugs thereof, wherein:

$L^J$ is a substituted or unsubstituted, saturated or unsaturated, $C_{1-6}$ aliphatic chain, optionally wherein one or two chain atoms of the aliphatic chain are independently replaced with —O—, —S—, —NR$^{J6}$—, —N═, or ═N—, wherein each instance of R$^{J6}$ is independently hydrogen, substituted or unsubstituted $C_{1-6}$ alkyl, or a nitrogen protecting group;

each instance of R$^{J1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(═NR$^a$)R$^a$, —C(═NR$^a$)OR$^a$, —C(═NR$^a$)N(R$^a$)$_2$, —C(═O)R$^a$, —C(═O)OR$^a$, —C(═O)N(R$^a$)$_2$, —NO$_2$, —NR$^a$C(═O)R$^a$, —NR$^a$C(═O)OR$^a$, —NR$^a$C(═O)N(R$^a$)$_2$, —OC(═O)R$^a$, —OC(═O)OR$^a$, or —OC(═O)N(R$^a$)$_2$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ are joined to form a substituted or unsubstituted heterocyclic or substituted or unsubstituted heteroaryl ring;

w1 is 0, 1, 2, 3, or 4;

R$^{J2}$ is hydrogen, substituted or unsubstituted $C_{1-6}$ alkyl, or a nitrogen protecting group;

R$^{J3}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(═NR$^a$)R$^a$, —C(═NR$^a$)OR$^a$, —C(═NR$^a$)N(R$^a$)$_2$, —C(═O)R$^a$, —C(═O)OR$^a$, —C(═O)N(R$^a$)$_2$, —NO$_2$, —NR$^a$C(═O)R$^a$, —NR$^a$C(═O)OR$^a$, —NR$^a$C(═O)N(R$^a$)$_2$, —OC(═O)R$^a$, —OC(═O)OR$^a$, or —OC(═O)N(R$^a$)$_2$;

R$^{J4}$ is hydrogen, substituted or unsubstituted $C_{1-6}$ alkyl, or a nitrogen protecting group; each instance of R$^5$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(═NR$^a$)R$^a$, —C(═NR$^a$)OR$^a$, —C(═NR$^a$)N(R$^a$)$_2$, —C(═O)R$^a$, —C(═O)OR$^a$, —C(═O)N(R$^a$)$_2$, —NO$_2$, —NR$^a$C(═O)R$^a$, —NR$^a$C(═O)OR$^a$, —NR$^a$C(═O)N(R$^a$)$_2$, —OC(═O)R$^a$, —OC(═O)OR$^a$, or —OC(═O)N(R$^a$)$_2$; and w5 is 0, 1, 2, 3, 4, or 5.

In certain embodiments, L$^J$ is a substituted or unsubstituted, saturated or unsaturated, $C_3$ aliphatic chain, optionally wherein one or two chain atoms of the aliphatic chain are independently replaced with —O—, —S—, —NR$^{J6}$— (e.g., —NH—), —N═, or ═N—. In certain embodiments, L$^J$ is of the formula:

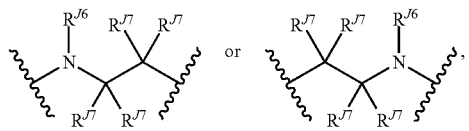

wherein each instance of R$^{J7}$ is independently hydrogen, halogen (e.g., F, Cl, Br, or I), or substituted or unsubstituted $C_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, all instances of R$^{J7}$ are the same. In certain embodiments, two instances of R$^{J7}$ are different from each other. In certain embodiments, each instance of R$^{J7}$ is hydrogen.

In certain embodiments, all instances of R$^{J6}$ are the same. In certain embodiments, two instances of R$^{J6}$ are different from each other. In certain embodiments, at least one instance of R$^{J6}$ is hydrogen. In certain embodiments, at least one instance of R$^{J6}$ is substituted or unsubstituted $C_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, at least one instance of R$^{J6}$ is a nitrogen protecting group (e.g., Bn, Boc, Cbz, Fmoc, trifluoroacetyl, triphenylmethyl, acetyl, or Ts).

In certain embodiments, all instances of R$^{J1}$ are the same. In certain embodiments, two instances of R$^{J1}$ are different from each other. In certain embodiments, at least one instance of R$^{J1}$ is halogen (e.g., F, Cl, Br, or I). In certain embodiments, at least one instance of R$^{J1}$ is substituted or unsubstituted alkyl (e.g., substituted or unsubstituted $C_{1-6}$ alkyl). In certain embodiments, at least one instance of R$^{J1}$ is —CH$_3$. In certain embodiments, at least one instance of R$^{J1}$ is —CF$_3$, unsubstituted ethyl, perfluoroethyl, unsubstituted propyl, perfluoropropyl, unsubstituted butyl, or perfluorobutyl. In certain embodiments, at least one instance of R$^{J1}$ is substituted or unsubstituted alkenyl (e.g., substituted or unsubstituted $C_{1-6}$ alkenyl). In certain embodiments, at least one instance of R$^{J1}$ is substituted or unsubstituted alkynyl (e.g., substituted or unsubstituted $C_{1-6}$ alkynyl). In certain embodiments, at least one instance of R$^J$ is substituted or unsubstituted carbocyclyl (e.g., substituted or unsubstituted, monocyclic, 3- to 7-membered carbocyclyl). In certain embodiments, at least one instance of R$^{J1}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of R$^J$ is substituted or unsubstituted aryl (e.g., substituted or unsubstituted, 6- to 10-membered aryl). In certain embodiments, at least one instance of $R^J$ is substituted or unsubstituted phenyl. In certain embodiments, at least one instance of $R^J$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{J1}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^J$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^J$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^{J1}$ is —CN, —SCN, or —$NO_2$. In certain embodiments, at least one instance of $R^{J1}$ is —$C(=NR^a)R^a$, —$C(=NR^a)OR^a$, or —$C(=NR^a)N(R^a)_2$. In certain embodiments, at least one instance of $R^{J1}$ is —$C(=O)R^a$, —$C(=O)OR^a$, or —$C(=O)N(R^a)_2$ (e.g., —$C(=O)NH_2$, —$C(=O)NHMe$, or —$C(=O)NMe_2$). In certain embodiments, at least one instance of $R^{J1}$ is —$NR^aC(=O)R^a$, —$NR^aC(=O)OR^a$, or —$NR^aC(=O)N(R^a)_2$. In certain embodiments, at least one instance of $R^{J1}$ is —$OC(=O)R^a$, —$OC(=O)OR^a$, or —$OC(=O)N(R^a)_2$.

In certain embodiments, w1 is 0. In certain embodiments, w1 is 1. In certain embodiments, w1 is 2. In certain embodiments, w1 is 3. In certain embodiments, w1 is 4.

In certain embodiments, $R^{J2}$ is hydrogen. In certain embodiments, $R^{J2}$ is substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, or perfluorobutyl). In certain embodiments, $R^{J2}$ is a nitrogen protecting group (e.g., Bn, Boc, Cbz, Fmoc, trifluoroacetyl, triphenylmethyl, acetyl, or Ts).

In certain embodiments, $R^{J3}$ is hydrogen. In certain embodiments, $R^{J3}$ is halogen (e.g., F, Cl, Br, or I). In certain embodiments, $R^{J3}$ is substituted or unsubstituted alkyl (e.g., substituted or unsubstituted $C_{1-6}$ alkyl). In certain embodiments, $R^{J3}$ is —$CH_3$. In certain embodiments, $R^{J3}$ is —$CF_3$, unsubstituted ethyl, perfluoroethyl, unsubstituted propyl, perfluoropropyl, unsubstituted butyl, or perfluorobutyl. In certain embodiments, $R^{J3}$ is substituted or unsubstituted alkenyl (e.g., substituted or unsubstituted $C_{1-6}$ alkenyl). In certain embodiments, $R^{J3}$ is substituted or unsubstituted alkynyl (e.g., substituted or unsubstituted $C_{1-6}$ alkynyl). In certain embodiments, $R^{J3}$ is substituted or unsubstituted carbocyclyl (e.g., substituted or unsubstituted, monocyclic, 3- to 7-membered carbocyclyl). In certain embodiments, $R^{J3}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, $R^{J3}$ is substituted or unsubstituted aryl (e.g., substituted or unsubstituted, 6- to 10-membered aryl). In certain embodiments, $R^{J3}$ is substituted or unsubstituted phenyl. In certain embodiments, $R^{J3}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, $R^{J3}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, $R^{J3}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{J3}$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^{J3}$ is —CN, —SCN, or —$NO_2$. In certain embodiments, $R^{J3}$ is —$C(=NR^a)R^a$, —$C(=NR^a)OR^a$, or —$C(=NR^a)N(R^a)_2$. In certain embodiments, $R^{J3}$ is —$C(=O)R^a$, —$C(=O)OR^a$, or —$C(=O)N(R^a)_2$ (e.g., —$C(=O)NH_2$, —$C(=O)NHMe$, or —$C(=O)NMe_2$). In certain embodiments, $R^{J3}$ is —$NR^aC(=O)R^a$, —$NR^aC(=O)OR^a$, or —$NR^aC(=O)N(R^a)_2$. In certain embodiments, $R^{J3}$ is —$OC(=O)R^a$, —$OC(=O)OR^a$, or —$OC(=O)N(R^a)_2$.

In certain embodiments, $R^{J4}$ is hydrogen. In certain embodiments, $R^{J4}$ is substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, or perfluorobutyl). In certain embodiments, $R^{J4}$ is a nitrogen protecting group (e.g., Bn, Boc, Cbz, Fmoc, trifluoroacetyl, triphenylmethyl, acetyl, or Ts).

In certain embodiments, all instances of $R^{J5}$ are the same. In certain embodiments, two instances of $R^{J5}$ are different from each other. In certain embodiments, at least one instance of $R^{J5}$ is halogen (e.g., F, Cl, Br, or I). In certain embodiments, at least one instance of $R^{J5}$ is substituted or unsubstituted alkyl (e.g., substituted or unsubstituted $C_{1-6}$ alkyl). In certain embodiments, at least one instance of $R^{J5}$ is —$CH_3$. In certain embodiments, at least one instance of $R^{J5}$ is —$CF_3$, unsubstituted ethyl, perfluoroethyl, unsubstituted propyl, perfluoropropyl, unsubstituted butyl, or perfluorobutyl. In certain embodiments, at least one instance of $R^{J5}$ is substituted or unsubstituted alkenyl (e.g., substituted or unsubstituted $C_{1-6}$ alkenyl). In certain embodiments, at least one instance of $R^{J5}$ is substituted or unsubstituted alkynyl (e.g., substituted or unsubstituted $C_{1-6}$ alkynyl). In certain embodiments, at least one instance of $R^{J5}$ is substituted or unsubstituted carbocyclyl (e.g., substituted or unsubstituted, monocyclic, 3- to 7-membered carbocyclyl). In certain embodiments, at least one instance of $R^{J5}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{J5}$ is substituted or unsubstituted aryl (e.g., substituted or unsubstituted, 6- to 10-membered aryl). In certain embodiments, at least one instance of $R^{J5}$ is substituted or unsubstituted phenyl. In certain embodiments, at least one instance of $R^{J5}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{J5}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{J5}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^5$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —NMe$_2$)). In certain embodiments, at least one instance of $R^{J5}$ is —CN, —SCN, or —NO$_2$. In certain embodiments, at least one instance of $R^5$ is —C(=NR$^a$)R$^a$, —C(=NR$^a$)OR$^a$, or —C(=NR$^a$)N(R$^a$)$_2$. In certain embodiments, at least one instance of $R^{J5}$ is —C(=O)R$^a$, —C(=O)OR$^a$, or —C(=O)N(R$^a$)$_2$ (e.g., —C(=O)NH$_2$, —C(=O)NHMe, or —C(=O)NMe$_2$). In certain embodiments, at least one instance of $R^{J5}$ is —NR$^a$C(=O)R$^a$, —NR$^a$C(=O)OR$^a$, or —NR$^a$C(=O)N(R$^a$)$_2$. In certain embodiments, at least one instance of $R^{J5}$ is —OC(=O)R$^a$, —OC(=O)OR$^a$, or —OC(=O)N(R$^a$)$_2$.

In certain embodiments, w5 is 0. In certain embodiments, w5 is 1. In certain embodiments, w5 is 2. In certain embodiments, w5 is 3. In certain embodiments, w5 is 4. In certain embodiments, w5 is 5.

In certain embodiments, the compound of Formula (J) is of the formula:

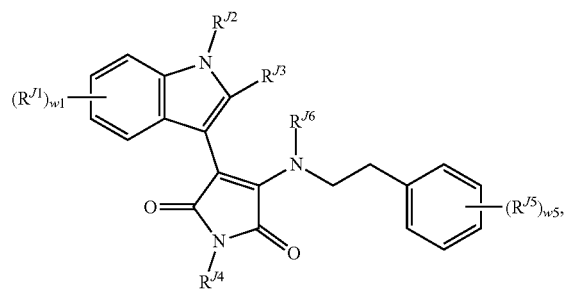

or a pharmaceutically acceptable salt, solvate, hydrate, polymorph, co-crystal, tautomer, stereoisomer, isotopically labeled derivative, or prodrug thereof.

In certain embodiments, the compound of Formula (J) is of the formula:

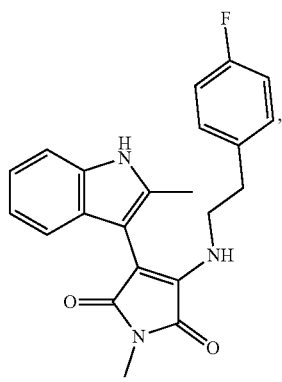

(IM12 OR IM)

or a pharmaceutically acceptable salt, solvate, hydrate, polymorph, co-crystal, tautomer, stereoisomer, isotopically labeled derivative, or prodrug thereof.

In certain embodiments, a compound of Formula (J) is not IM12, or a pharmaceutically acceptable salt, solvate, hydrate, polymorph, co-crystal, tautomer, stereoisomer, or isotopically labeled derivative thereof.

It is believed that compounds of Formula (J), and pharmaceutically acceptable salts, solvates, hydrates, polymorphs, co-crystals, tautomers, stereoisomers, isotopically labeled derivatives, and prodrugs thereof, are GSK inhibitors (e.g., GSK3 inhibitors).

Compounds of Formula (K)

In another aspect, the present disclosure provides compounds of Formula (K):

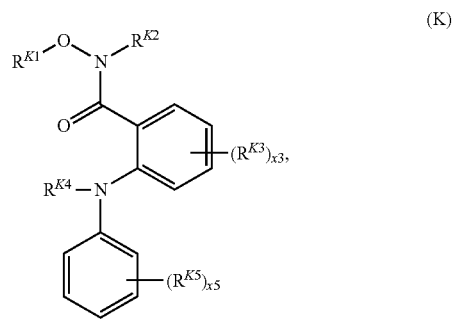

(K)

and pharmaceutically acceptable salts, solvates, hydrates, polymorphs, co-crystals, tautomers, stereoisomers, isotopically labeled derivatives, and prodrugs thereof, wherein:

$R^{K1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^{K2}$ is hydrogen, substituted or unsubstituted $C_{1-6}$ alkyl, or a nitrogen protecting group;

each instance of $R^{K3}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ are joined to form a substituted or unsubstituted heterocyclic or substituted or unsubstituted heteroaryl ring;

x3 is 0, 1, 2, 3, or 4;

$R^{K4}$ is hydrogen, substituted or unsubstituted $C_{1-6}$ alkyl, or a nitrogen protecting group;

each instance of $R^{K5}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C (=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$; and x5 is 0, 1, 2, 3, 4, or 5.

In certain embodiments, R$^{K1}$ is hydrogen. In certain embodiments, R$^{K1}$ is substituted or unsubstituted alkyl, such as substituted or unsubstituted C$_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, R$^{K1}$ is C$_{1-6}$ alkyl substituted with at least one —OH. In certain embodiments, R$^{K1}$ is of the formula:

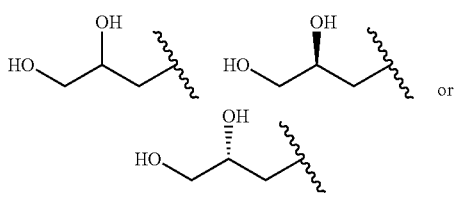

In certain embodiments, R$^{K1}$ is substituted or unsubstituted alkenyl (e.g., substituted or unsubstituted C$_{1-6}$ alkenyl). In certain embodiments, R$^{K1}$ is substituted or unsubstituted alkynyl (e.g., substituted or unsubstituted C$_{1-6}$ alkynyl). In certain embodiments, R$^{K1}$ is substituted or unsubstituted carbocyclyl (e.g., substituted or unsubstituted, monocyclic, 3- to 7-membered carbocyclyl). In certain embodiments, R$^{K1}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, R$^{K1}$ is substituted or unsubstituted aryl (e.g., substituted or unsubstituted, 6- to 10-membered aryl). In certain embodiments, R$^{K1}$ is substituted or unsubstituted phenyl. In certain embodiments, R$^{K1}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur).

In certain embodiments, R$^{K2}$ is hydrogen. In certain embodiments, R$^{K2}$ is substituted or unsubstituted C$_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, R$^{K2}$ is a nitrogen protecting group (e.g., Bn, Boc, Cbz, Fmoc, trifluoroacetyl, triphenylmethyl, acetyl, or Ts).

In certain embodiments, all instances of R$^{K3}$ are the same. In certain embodiments, two instances of R$^{K3}$ are different from each other. In certain embodiments, at least one instance of R$^{K3}$ is halogen (e.g., F, Cl, Br, or I). In certain embodiments, at least one instance of R$^{K3}$ is substituted or unsubstituted alkyl (e.g., substituted or unsubstituted C$_{1-6}$ alkyl). In certain embodiments, at least one instance of R$^{K3}$ is —CH$_3$. In certain embodiments, at least one instance of R$^{K3}$ is —CF$_3$, unsubstituted ethyl, perfluoroethyl, unsubstituted propyl, perfluoropropyl, unsubstituted butyl, or perfluorobutyl. In certain embodiments, at least one instance of R$^{K3}$ is substituted or unsubstituted alkenyl (e.g., substituted or unsubstituted C$_{1-6}$ alkenyl). In certain embodiments, at least one instance of R$^{K3}$ is substituted or unsubstituted alkynyl (e.g., substituted or unsubstituted C$_{1-6}$ alkynyl). In certain embodiments, at least one instance of R$^{K3}$ is substituted or unsubstituted carbocyclyl (e.g., substituted or unsubstituted, monocyclic, 3- to 7-membered carbocyclyl).

In certain embodiments, at least one instance of R$^{K3}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of R$^{K3}$ is substituted or unsubstituted aryl (e.g., substituted or unsubstituted, 6- to 10-membered aryl). In certain embodiments, at least one instance of R$^{K3}$ is substituted or unsubstituted phenyl. In certain embodiments, at least one instance of R$^{K3}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of R$^{K3}$ is —OR$^a$ (e.g., —OH, —O(substituted or unsubstituted C$_{1-6}$ alkyl) (e.g., —OMe, —OEt, —OPr, —OBu, or —OBn), or —O(substituted or unsubstituted phenyl) (e.g., —OPh)). In certain embodiments, at least one instance of R$^{K3}$ is —SR$^a$ (e.g., —SH, —S(substituted or unsubstituted C$_{1-6}$ alkyl) (e.g., —SMe, —SEt, —SPr, —SBu, or —SBn), or —S(substituted or unsubstituted phenyl) (e.g., —SPh)). In certain embodiments, at least one instance of R$^{K3}$ is —N(R$^a$)$_2$ (e.g., —NH$_2$, —NH(substituted or unsubstituted C$_{1-6}$ alkyl) (e.g., —NHMe), or —N(substituted or unsubstituted C$_{1-6}$ alkyl)-(substituted or unsubstituted C$_{1-6}$ alkyl) (e.g., —NMe$_2$)). In certain embodiments, at least one instance of R$^3$ is —CN, —SCN, or —NO$_2$. In certain embodiments, at least one instance of R$^K$ is —C(=NR$^a$)R$^a$, —C(=NR$^a$)OR$^a$, or —C(=NR$^a$)N(R$^a$)$_2$. In certain embodiments, at least one instance of R$^K$ is —C(=O)R$^a$, —C(=O)OR$^a$, or —C(=O)N(R$^a$)$_2$ (e.g., —C(=O)NH$_2$, —C(=O)NHMe, or —C(=O)NMe$_2$). In certain embodiments, at least one instance of R$^{K3}$ is —NR$^a$C(=O)R$^a$, —NR$^a$C(=O)OR$^a$, or —NR$^a$C(=O)N(R$^a$)$_2$. In certain embodiments, at least one instance of R$^K$3 is —OC(=O)R$^a$, —OC(=O)OR$^a$, or —OC(=O)N(R$^a$)$_2$.

In certain embodiments, x3 is 0. In certain embodiments, x3 is 1. In certain embodiments, x3 is 2. In certain embodiments, x3 is 3. In certain embodiments, x3 is 4.

In certain embodiments, R$^{K4}$ is hydrogen. In certain embodiments, R$^{K4}$ is substituted or unsubstituted C$_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, R$^{K4}$ is a nitrogen protecting group (e.g., Bn, Boc, Cbz, Fmoc, trifluoroacetyl, triphenylmethyl, acetyl, or Ts).

In certain embodiments, all instances of R$^{K5}$ are the same. In certain embodiments, two instances of R$^{K5}$ are different from each other. In certain embodiments, at least one instance of R$^{K5}$ is halogen (e.g., F, Cl, Br, or I). In certain embodiments, at least one instance of R$^{K5}$ is substituted or unsubstituted alkyl (e.g., substituted or unsubstituted C$_{1-6}$ alkyl). In certain embodiments, at least one instance of R$^{K5}$ is —CH$_3$. In certain embodiments, at least one instance of R$^{K5}$ is —CF$_3$, unsubstituted ethyl, perfluoroethyl, unsubstituted propyl, perfluoropropyl, unsubstituted butyl, or perfluorobutyl. In certain embodiments, at least one instance of R$^{K5}$ is substituted or unsubstituted alkenyl (e.g., substituted or unsubstituted C$_{1-6}$ alkenyl). In certain embodiments, at least one instance of R$^{K55}$ is substituted or unsubstituted alkynyl (e.g., substituted or unsubstituted C$_{1-6}$ alkynyl). In certain embodiments, at least one instance of R$^{K5}$ is substituted or unsubstituted carbocyclyl (e.g., substituted or unsubstituted, monocyclic, 3- to 7-membered carbocyclyl). In certain embodiments, at least one instance of R$^{K5}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of $R^{K5}$ is substituted or unsubstituted aryl (e.g., substituted or unsubstituted, 6- to 10-membered aryl). In certain embodiments, at least one instance of $R^{K5}$ is substituted or unsubstituted phenyl. In certain embodiments, at least one instance of $R^{K5}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of $R^{K5}$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^{K5}$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^{K5}$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^{K5}$ is —CN, —SCN, or —$NO_2$. In certain embodiments, at least one instance of $R^{K5}$ is —C(=$NR^a$)$R^a$, —C(=$NR^a$)$OR^a$, or —C(=$NR^a$)$N(R^a)_2$. In certain embodiments, at least one instance of $R^{K5}$ is —C(=O)$R^a$, —C(=O)$OR^a$, or —C(=O)$N(R^a)_2$ (e.g., —C(=O)$NH_2$, —C(=O)NHMe, or —C(=O)$NMe_2$). In certain embodiments, at least one instance of $R^{K5}$ is —$NR^a$C(=O)$R^a$, —$NR^a$C(=O)$OR^a$, or —$NR^a$C(=O)$N(R^a)_2$. In certain embodiments, at least one instance of $R^{K5}$ is —OC(=O)$R^a$, —OC(=O)$OR^a$, or —OC(=O)$N(R^a)_2$.

In certain embodiments, x5 is 0. In certain embodiments, x5 is 1. In certain embodiments, x5 is 2. In certain embodiments, x5 is 3. In certain embodiments, x5 is 4. In certain embodiments, x5 is 5.

In certain embodiments, the compound of Formula (K) is of the formula:

(PD0325901, PD03, or PD)

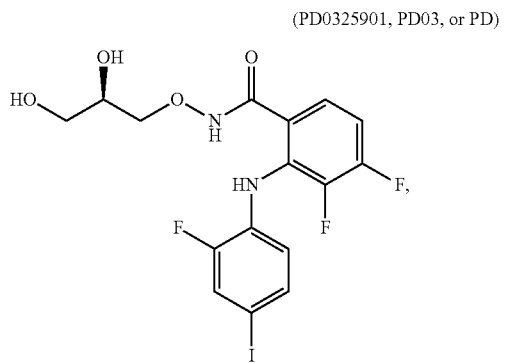 [SMILES: O=C(NOC[C@H](O)CO)c1ccc(F)c(F)c1Nc1ccc(I)cc1F]

or a pharmaceutically acceptable salt, solvate, hydrate, polymorph, co-crystal, tautomer, stereoisomer, isotopically labeled derivative, or prodrug thereof.

In certain embodiments, a compound of Formula (K) is not PD0325901, or a pharmaceutically acceptable salt, solvate, hydrate, polymorph, co-crystal, tautomer, stereoisomer, or isotopically labeled derivative thereof.

It is believed that compounds of Formula (K), and pharmaceutically acceptable salts, solvates, hydrates, polymorphs, co-crystals, tautomers, stereoisomers, isotopically labeled derivatives, and prodrugs thereof, are MEK inhibitors.

Compounds of Formula (L)

In another aspect, the present disclosure provides compounds of Formula (L):

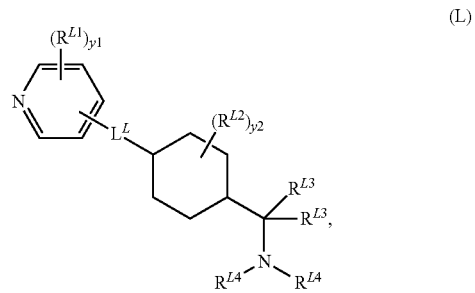

and pharmaceutically acceptable salts, solvates, hydrates, polymorphs, co-crystals, tautomers, stereoisomers, isotopically labeled derivatives, and prodrugs thereof, wherein:

$L^L$ is a substituted or unsubstituted, saturated or unsaturated, $C_{1-4}$ aliphatic chain, optionally wherein one or two chain atoms of the aliphatic chain are independently replaced with —O—, —S—, —$NR^{L5}$—, —N=, or =N—, wherein each instance of $R^L$ is independently hydrogen, substituted or unsubstituted $C_{1-6}$ alkyl, or a nitrogen protecting group;

each instance of $R^{L1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^a$C(=O)$R^a$, —$NR^a$C(=O)$OR^a$, —$NR^a$C(=O)$N(R^a)_2$, —OC(=O)$R^a$, —OC(=O)$OR^a$, or —OC(=O)$N(R^a)_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted heterocyclic or substituted or unsubstituted heteroaryl ring;

y1 is 0, 1, 2, 3, or 4;

each instance of $R^{L2}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^a$C —C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

y2 is 0, 1, 2, 3, 4, 5, 6, 7, 8, 9, or 10;

each instance of R$^{L3}$ is independently hydrogen, halogen, or substituted or unsubstituted C$_{1-6}$ alkyl; and each instance of R$^{L4}$ is independently hydrogen, substituted or unsubstituted C$_{1-6}$ alkyl, or a nitrogen protecting group.

In certain embodiments, L$^L$ is a substituted or unsubstituted, saturated or unsaturated, C$_2$ aliphatic chain, optionally wherein one chain atom of the aliphatic chain is replaced with —O—, —S—, —NR$^{L5}$— (e.g., —NH—), —N=, or =N—. In certain embodiments, L$^L$ is —C(=O)NR$^{L5}$— (e.g., —C(=O)NH—) or —NR$^{L5}$C(=O)— (e.g., —NHC(=O)—). In certain embodiments, L$^L$ is a substituted or unsubstituted, saturated or unsaturated, C$_1$, C$_3$, or C$_4$ aliphatic chain, optionally wherein one or two chain atoms of the aliphatic chain are independently replaced with —O—, —S—, —NR$^{L5}$— (e.g., —NH—), —N=, or =N—.

In certain embodiments, all instances of R$^{L5}$ are the same. In certain embodiments, two instances of R$^{L5}$ are different from each other. In certain embodiments, at least one instance of R$^{L5}$ is hydrogen. In certain embodiments, at least one instance of R$^L$ is substituted or unsubstituted C$_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, at least one instance of R$^{L5}$ is a nitrogen protecting group (e.g., Bn, Boc, Cbz, Fmoc, trifluoroacetyl, triphenylmethyl, acetyl, or Ts).

In certain embodiments, all instances of R$^{L1}$ are the same. In certain embodiments, two instances of R$^{L1}$ are different from each other. In certain embodiments, at least one instance of R$^{L1}$ is halogen (e.g., F, Cl, Br, or I). In certain embodiments, at least one instance of R$^{L1}$ is substituted or unsubstituted alkyl (e.g., substituted or unsubstituted C$_{1-6}$ alkyl). In certain embodiments, at least one instance of R$^{L1}$ is —CH$_3$. In certain embodiments, at least one instance of R$^{L1}$ is —CF$_3$, unsubstituted ethyl, perfluoroethyl, unsubstituted propyl, perfluoropropyl, unsubstituted butyl, or perfluorobutyl. In certain embodiments, at least one instance of R$^{L1}$ is substituted or unsubstituted alkenyl (e.g., substituted or unsubstituted C$_{1-6}$ alkenyl). In certain embodiments, at least one instance of R$^{L1}$ is substituted or unsubstituted alkynyl (e.g., substituted or unsubstituted C$_{1-6}$ alkynyl). In certain embodiments, at least one instance of R$^{L1}$ is substituted or unsubstituted carbocyclyl (e.g., substituted or unsubstituted, monocyclic, 3- to 7-membered carbocyclyl). In certain embodiments, at least one instance of R$^{L1}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of R$^{L1}$ is substituted or unsubstituted aryl (e.g., substituted or unsubstituted, 6- to 10-membered aryl). In certain embodiments, at least one instance of R$^{L1}$ is substituted or unsubstituted phenyl. In certain embodiments, at least one instance of R$^{L1}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of R$^{L1}$ is —OR$^a$ (e.g., —OH, —O(substituted or unsubstituted C$_{1-6}$ alkyl) (e.g., —OMe, —OEt, —OPr, —OBu, or —OBn), or —O(substituted or unsubstituted phenyl) (e.g., —OPh)). In certain embodiments, at least one instance of R$^{L1}$ is —SR$^a$ (e.g., —SH, —S(substituted or unsubstituted C$_{1-6}$ alkyl) (e.g., —SMe, —SEt, —SPr, —SBu, or —SBn), or —S(substituted or unsubstituted phenyl) (e.g., —SPh)). In certain embodiments, at least one instance of R$^{L1}$ is —N(R$^a$)$_2$ (e.g., —NH$_2$, —NH(substituted or unsubstituted C$_{1-6}$ alkyl) (e.g., —NHMe), or —N(substituted or unsubstituted C$_{1-6}$ alkyl)-(substituted or unsubstituted C$_{1-6}$ alkyl) (e.g., —NMe$_2$)). In certain embodiments, at least one instance of R$^{L1}$ is —CN, —SCN, or —NO$_2$. In certain embodiments, at least one instance of R$^{L1}$ is —C(=NR$^a$)R$^a$, —C(=NR$^a$)OR$^a$, or —C(=NR$^a$)N(R$^a$)$_2$. In certain embodiments, at least one instance of R$^L$ is —C(=O)R$^a$, —C(=O)OR$^a$, or —C(=O)N(R$^a$)$_2$ (e.g., —C(=O)NH$_2$, —C(=O)NHMe, or —C(=O)NMe$_2$). In certain embodiments, at least one instance of R$^{L1}$ is —NR$^a$C(=O)R$^a$, —NR$^a$C(=O)OR$^a$, or —NR$^a$C(=O)N(R$^a$)$_2$. In certain embodiments, at least one instance of R$^{L1}$ is —OC(=O)R$^a$, —OC(=O)OR$^a$, or —OC(=O)N(R$^a$)$_2$.

In certain embodiments, y1 is 0. In certain embodiments, y1 is 1. In certain embodiments, y1 is 2. In certain embodiments, y1 is 3. In certain embodiments, y1 is 4.

In certain embodiments, all instances of R$^{L2}$ are the same. In certain embodiments, two instances of R$^{L2}$ are different from each other. In certain embodiments, at least one instance of R$^{L2}$ is halogen (e.g., F, Cl, Br, or I). In certain embodiments, at least one instance of R$^{L2}$ is substituted or unsubstituted alkyl (e.g., substituted or unsubstituted C$_{1-6}$ alkyl). In certain embodiments, at least one instance of R$^{L2}$ is —CH$_3$. In certain embodiments, at least one instance of R$^{L2}$ is —CF$_3$, unsubstituted ethyl, perfluoroethyl, unsubstituted propyl, perfluoropropyl, unsubstituted butyl, or perfluorobutyl. In certain embodiments, at least one instance of R$^{L2}$ is substituted or unsubstituted alkenyl (e.g., substituted or unsubstituted C$_{1-6}$ alkenyl). In certain embodiments, at least one instance of R$^{L2}$ is substituted or unsubstituted alkynyl (e.g., substituted or unsubstituted C$_{1-6}$ alkynyl). In certain embodiments, at least one instance of R$^{L2}$ is substituted or unsubstituted carbocyclyl (e.g., substituted or unsubstituted, monocyclic, 3- to 7-membered carbocyclyl). In certain embodiments, at least one instance of R$^{L2}$ is substituted or unsubstituted heterocyclyl (e.g., substituted or unsubstituted, monocyclic, 5- to 6-membed heterocyclyl, wherein one, two, or three atoms in the heterocyclic ring system are independently nitrogen, oxygen, or sulfur). In certain embodiments, at least one instance of R$^{L2}$ is substituted or unsubstituted aryl (e.g., substituted or unsubstituted, 6- to 10-membered aryl). In certain embodiments, at least one instance of R$^{L2}$ is substituted or unsubstituted phenyl. In certain embodiments, at least one instance of R$^{L2}$ is substituted or unsubstituted heteroaryl (e.g., substituted or unsubstituted, monocyclic, 5- to 6-membed heteroaryl, wherein one, two, three, or four atoms in the heteroaryl ring system are independently nitrogen, oxygen, or sulfur). In certain embodiments, at least one instance of R$^{L2}$ is —OR$^a$ (e.g., —OH, —O(substituted or unsubstituted C$_{1-6}$ alkyl) (e.g., —OMe, —OEt, —OPr, —OBu, or —OBn), or —O(substituted or unsubstituted phenyl) (e.g., —OPh)). In certain embodiments, at least one instance of R$^{L2}$ is —SR$^a$ (e.g., —SH, —S(substituted or unsubstituted C$_{1-6}$ alkyl) (e.g., —SMe, —SEt, —SPr, —SBu, or —SBn), or —S(substituted or unsubstituted phenyl) (e.g., —SPh)). In certain embodiments, at least one instance of R$^{L2}$ is —N(R$^a$)$_2$ (e.g., —NH$_2$, —NH(substituted or unsubstituted C$_{1-6}$ alkyl) (e.g., —NHMe), or —N(substituted or unsubstituted C$_{1-6}$ alkyl)-(substituted or unsubstituted C$_{1-6}$ alkyl) (e.g., —NMe$_2$)). In certain embodiments, at least one instance of R$^{L2}$ is —CN, —SCN, or —NO$_2$. In certain embodiments, at least one instance of R$^{L2}$ is —C(=NR$^a$)R$^a$, —C(=NR$^a$)OR$^a$, or —C(=NR$^a$)N(R$^a$)$_2$. In certain embodiments, at least one instance of R$^{L2}$ is —C(=O)R$^a$, —C(=O)OR$^a$, or —C(=O)N(R$^a$)$_2$ (e.g., —C(=O)NH$_2$, —C(=O)NHMe, or —C(=O)NMe$_2$). In certain embodiments, at least one instance of R$^{L2}$ is —NR$^a$C(=O)R$^a$, —NR$^a$C(=O)OR$^a$, or —NR$^a$C(=O)N(R$^a$)$_2$. In certain embodiments, at least one instance of R$^{L2}$ is —OC(=O)R$^a$, —OC(=O)OR$^a$, or —OC(=O)N(R$^a$)$_2$.

In certain embodiments, y2 is 0. In certain embodiments, y2 is 1. In certain embodiments, y2 is 2. In certain embodiments, y2 is 3. In certain embodiments, y2 is 4. In certain embodiments, y2 is 5. In certain embodiments, y2 is 6. In certain embodiments, y2 is 7. In certain embodiments, y2 is 8. In certain embodiments, y2 is 9. In certain embodiments, y2 is 10.

In certain embodiments, both instances of R$^{L3}$ are the same. In certain embodiments, two instances of R$^{L3}$ are different from each other. In certain embodiments, at least one instance of R$^{L3}$ is hydrogen. In certain embodiments, each instance of R$^{L3}$ is hydrogen. In certain embodiments, at least one instance of R$^{L3}$ is halogen (e.g., F, Cl, Br, or I). In certain embodiments, at least one instance of R$^{L3}$ is substituted or unsubstituted C$_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, each instance of R$^{L3}$ is independently hydrogen or substituted or unsubstituted alkyl.

In certain embodiments, both instances of R$^L$ are the same. In certain embodiments, two instances of R$^L$ are different from each other. In certain embodiments, at least one instance of RN is hydrogen. In certain embodiments, each instance of R$^L$ is hydrogen. In certain embodiments, at least one instance of R$^L$ is substituted or unsubstituted C$_{1-6}$ alkyl (e.g., —CH$_3$, —CF$_3$, unsubstituted ethyl, perfluoroethyl, unsubstituted propyl, perfluoropropyl, unsubstituted butyl, or perfluorobutyl). In certain embodiments, at least one instance of R$^L$ is a nitrogen protecting group (e.g., Bn, Boc, Cbz, Fmoc, trifluoroacetyl, triphenylmethyl, acetyl, or Ts).

In certain embodiments, the compound of Formula (L) is of the formula:

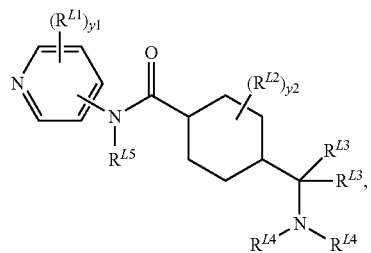

or a pharmaceutically acceptable salt, solvate, hydrate, polymorph, co-crystal, tautomer, stereoisomer, isotopically labeled derivative, or prodrug thereof.

In certain embodiments, the compound of Formula (L) is of the formula:

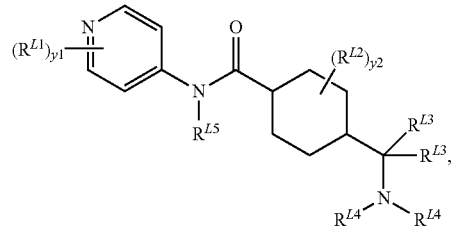

or a pharmaceutically acceptable salt, solvate, hydrate, polymorph, co-crystal, tautomer, stereoisomer, isotopically labeled derivative, or prodrug thereof.

In certain embodiments, the compound of Formula (L) is of the formula:

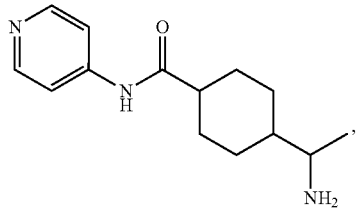

(Y-27632 or Y27632)

or a pharmaceutically acceptable salt, solvate, hydrate, polymorph, co-crystal, tautomer, stereoisomer, isotopically labeled derivative, or prodrug thereof.

In certain embodiments, a compound of Formula (L) is not Y-27632, or a pharmaceutically acceptable salt, solvate, hydrate, polymorph, co-crystal, tautomer, stereoisomer, or isotopically labeled derivative thereof.

It is believed that compounds of Formula (L), and pharmaceutically acceptable salts, solvates, hydrates, polymorphs, co-crystals, tautomers, stereoisomers, isotopically labeled derivatives, and prodrugs thereof, are ROCK inhibitors.

In another aspect, the present disclosure provides a mixture of compounds described herein. In certain embodiments, the mixture of compounds include two or more compounds of any one of Formula (A) to (L), and pharmaceutically acceptable salts, solvates, hydrates, polymorphs, co-crystals, tautomers, stereoisomers, isotopically labeled derivatives, and prodrugs thereof, wherein any two compounds of the mixture of compounds are of the same or different Formula (e.g., any one of Formula (A) to (L)).

EXAMPLES

Materials and Methods

Culture Conditions

Conventional (primed) human iPSC line C1 (Whitehead Institute Center for Human Stem Cell Research, Cambridge, MA) (Hockemeyer et al., 2008) and human ESC lines WIBR2 and WIBR3 (Whitehead Institute Center for Human Stem Cell Research, Cambridge, MA) (Lengner et al., 2010) (Lengner et al., 2010) were maintained on mitomycin C inactivated mouse embryonic fibroblast (MEF) feeder layers and passaged using Collagenase (1 mg/mL) or manual methods. Primed human ESCs and human iPSCs were cultured in human ESC medium [DMEM/F12 (Invitrogen) supplemented with 15% fetal bovine serum (FBS) (Hyclone), 5% KnockOut Serum Replacement (Invitrogen), 1 mM glutamine (Invitrogen), 1% nonessential amino acids (Invitrogen), 0.1 mM b-mercaptoethanol (Sigma) and 4 ng/ml FGF2 (R&D systems)]. Naïve human ESCs/hiPSCs were kept on mitomycin C-inactivated mouse embryonic fibroblast feeder cells, and were passaged by brief single-cell dissociation using Accutase (Gibco) every 5-10 days. Naïve human pluripotent cells were derived and maintained in serum-free N2B27-based media. 500 mL of medium was generated by including: 240 mL DMEM/F12 (Invitrogen; 11320), 240 mL Neurobasal (Invitrogen; 21103), 5 mL N2 supplement (Invitrogen; 17502048), 10 mL B27 supplement (Invitrogen; 17504044), 10 µg recombinant human LIF (made in-house), 1 mM glutamine (Invitrogen), 1% nonessential amino acids (Invitrogen), 0.1 mM 0-mercaptoethanol (Sigma), penicillin-streptomycin (Invitrogen), 5 mg/mL BSA (Sigma), and the following small molecules and cytokines: PD0325901 (Stemgent, 1 µM), IM-12 (Enzo, 1 µM), SB590885 (R&D systems, 0.5 µM), WH4-023 (A Chemtek, 1 µM), Y-27632 (Stemgent, 10 µM) and Activin A (Pepro-tech, 20 ng/mL). To accelerate the kinetics of naïve cell induction FGF2 (R&D systems, 8 ng/mL) and 0.5% KSR (Gibco) were also included. Additional inhibitors described in this work include: CHIR99021 (Stemgent, 3 µM), SP600125 (R&D systems, 1 µM), PD173074 (Stemgent, 0.1 µM), SB431542 (Tocris, 5 µM) and BIRB796 (Axon Medchem, 2 µM). Tissue culture media were filtered using a low protein-binding binding 0.22 µM filter (Corning). Alternative formulations for naïve human ESC culture were followed as described previously (Chan et al., 2013; Gafni et al., 2013; Valamehr et al., 2014; Ware et al., 2014).

Gene Targeting

Human ESCs and iPSCs were cultured in ROCK-inhibitor Y-27632 24 hours prior to electroporation. Cell were harvested using 0.25% trypsin/EDTA solution (Invitrogen) and $1 \times 10^7$ cells resuspended in phosphate buffered saline (PBS) were electroporated if not otherwise indicated with 40 µg of donor plasmids and 5 µg of each Talen encoding plasmid (Gene Pulser Xcell System, Bio-Rad: 250 V, 500p F, 0.4 cm cuvettes (Costa et al., 2007)). Cells were subsequently plated on MEF feeder layers (DR4 MEFs for puromycin selection) in human ESC medium supplemented with ROCK-inhibitor for the first 24 hours. Individual colonies were picked and expanded after puromycin selection (0.5 µg/ml) 10 to 14 days after electroporation. Correctly targeted clones were confirmed by southern blot (NdeI digested) and used for the removal of floxed PGK-puro cassette. Cells were harvested using 0.25% trypsin/EDTA solution (Invitrogen) and $1 \times 10^7$ cells resuspended in PBS were electroporated with pTurbo-Cre (40 µg; GenBank accession number AF334827) (Gene Pulser Xcell System, Bio-Rad; 250 V, 500 µF, 0.4-cm cuvettes). Cells were subsequently plated on MEF feeder layers at a low density in human ESC medium supplemented with ROCK inhibitor. Individual colonies were picked 10-14 d after electroporation. The excision of PGK-puro was confirmed by Southern blot analysis.

Lentiviral Infection

VSVG coated lentiviruses were generated in HEK-293 cells as described previously (Brambrink et al., 2008; Soldner et al., 2009; Soldner et al., 2011). Briefly, culture medium was changed 12 hr post-transfection and virus-containing supernatant was collected 48 to 72 hr post transfection. Viral supernatant was filtered through a 0.45 mm filter. Virus-containing supernatants of the 2 reprogramming viruses (FUW-tetO-lox-hKLF2 and FUW-tetO-lox-hNANOG) were pooled and supplemented with the FUW-lox-M2rtTA virus and an equal volume of fresh culture medium. $1 \times 10^6$ human ESCs were seeded 24 hr before transduction in T75 flasks on matrigel in mTesr1 medium (STEMCELL Technologies). Two consecutive infections in the presence of 2 mg/ml of polybrene were performed over a period of 24 hr. Culture medium was changed 12 hr after the last infection. Five days after transduction, human ESCs were passaged using 0.25% trypsin/EDTA solution (Invitrogen) and re-plated on mitomycin C inactivated mouse embryonic fibroblast (MEF) feeder layers in conventional human ESC medium. To induce conversion to the naïve state, human ESCs were trypsinized and seeded at a density of $1 \times 10^5$ cells per 6 individual well on a MEF feeder layer in presence of ROCK inhibitor Y-27632. Medium was replaced 24 hr later with N2B27 basal medium supplemented with PD0325901 (Stemgent, 1 µM), CHIR99021 (Stemgent, 3 µM), 20 ng/mL hLIF (2i/L) and doxycycline (DOX) (Sigma-Aldrich; 2 mg/ml). OCT4-ΔPE-GFP+ human ESC colonies were picked manually within 10 days after DOX induction and passaged using Accutase (Gibco) on a MEF feeder layer. Upon the addition of 2i/L/DOX, latent OCT4-ΔPE-GFP-negative cells could be removed almost entirely by additional treatment with 0.1 µM PD173074 and 5 µM SB431542, which effectively inhibit the signaling pathways on which primed human ESCs are reliant. These additional inhibitors also facilitated the isolation of transgene-dependent naïve human ESCs from wild-type WIBR3 human ESCs.

Chemical Screening

To screen for small molecules that support naïve human pluripotency, doxycycline was withdrawn from a clonal line of WIBR3 OCT4-ΔPE-GFP+ human ESCs derived in 2i/L/DOX. 24 h after Dox withdrawal, cells were dissociated in 0.25% trypsin/EDTA solution (Invitrogen) and seeded at a density of 5000 cells per individual well in 96 well plates on a MEF feeder layer in 2i/L supplemented with the ROCK-inhibitor Y-27632. After an additional 24 h, 2i/L medium in each individual 96 well was supplemented with a kinase inhibitor from the LINCS inhibitor library (Gray Laboratory, Dana Farber Cancer Institute, Boston, MA) at a final concentration of 1 µM. To improve experimental consistency the small molecule library was applied using the Caliper RapidPlate 96 well Liquid Handling System (Zymark, Westborough, MA). Briefly, a master plate containing 10 mM stock solution of the library in DMSO was first diluted to 100 µM in HEPES aqueous solution (daughter plate), and subsequently to 10 µM in N2B27 basal medium supplemented with 2i/L (granddaughter plate). This granddaughter plate was then diluted a further 10× in 2i/L medium, the final medium was pre-mixed and applied slowly to the 96 well assay plate. Following two medium changes during a seven day period the proportion of OCT4-ΔPE-GFP+ human ESCs in each well was assessed using the High-Throughput System on the LSRFortessa (Beckton-Dickinson, San Jose, CA). To screen for small molecules that improve the proportion of viable OCT4-ΔPE-GFP+ cells, this assay was modified by the addition of 1.0 µM SB590885 to each well and inclusion of a 10 minute DAPI (Life Technologies) staining prior to high-throughput FACS analysis. Viable cells were gated from the DAPI-negative fraction and subsequently assessed for GFP status.

Immunostaining

Immunostaining was performed according to standard protocols using the following primary antibodies: Oct-3/4 (mouse monoclonal, Santa Cruz Biotechnology); hNANOG (Cat. No. AF1997, goat polyclonal, R&D Systems); AFP (Cat. No. A8452, mouse monoclonal, Sigma); HNF4a (goat polyclonal, Santa Cruz); Nestin (Cat. No. AB5922, mouse monoclonal, Milipore); Pax6 (Cat. No. PRB-278P, rabbit polyclonal, Covance); appropriate Alexa Fluor dye conjugated secondary antibodies (Invitrogen) were used. Nuclei were stained with DAPI (Life Technologies) and analyzed (LSM710, Zeiss; Eclipse Ti—Nikon). Images were taken using LSM710 confocal microscope (Zeiss) or Inverted microscope (Eclipse Ti—Nikon).

RNA FISH and Imaging

RNA FISH was performed as outlined in (Faddah et al., 2013; Raj et al., 2010; Raj et al., 2008). All hybridizations were performed in solution using probes coupled to either tetramethylrhodamine (TMR) (Invitrogen), Alexa 594 (Invitrogen) or Cy5 (GE Amersham). TMR was used for the probes against human Klf4 mRNA, Alexa 594 for the probes against human Oct4, Rex1, and Nanog mRNA, and Cy5 for the probes against human Oct4 mRNA. Optimal probe concentrations during hybridization were determined empirically. Imaging involved taking stacks of images spaced 0.4 m apart using filters appropriate for DAPI, TMR, Alexa 594 and Cy5. All images were taken with a Nikon Ti-E inverted fluorescence microscope equipped with a 100× oil-immersion objective and a Photometrics Pixis 1024 CCD camera using MetaMorph software (Molecular Devices, Downington, PA). During imaging, photobleaching was minimized through the use of an oxygen-scavenging solution using glucose oxidase. The cells were segmented manually and counted the number of fluorescent spots, each of which corresponds to an individual mRNA, using a combination of a semi-automated method described in (Itzkovitz et al., 2011; Raj et al., 2008) and custom software written in MATLAB (Mathworks).

RNA Extraction and Synthetic RNA Spike-In

Total RNA and sample preparation was performed as previously described (Loven et al., 2012). Briefly, 1 million naïve or primed human ESCs were trypsinized and separated from GFP-labeled MEFs using the FACSAria (Beckton-Dickinson) prior to lysis and RNA extraction. Biological duplicates were subsequently collected and homogenized in 1 ml of TRIzol Reagent (Life Technologies, 15596-026), purified using the mirVANA miRNA isolation kit (Ambion, AM1560) following the manufacturer's instructions and resuspended in 100 ml nuclease-free water (Ambion, AM9938). Total RNA was spiked-in with ERCC RNA Spike-In Mix (Ambion, 4456740), treated with DNA-free™ DNase I (Ambion, AM1906) and analyzed on Agilent 2100 Bioanalyzer for integrity. RNA with the RNA Integrity Number (RIN) above 9.8 was hybridized to GeneChip PrimeView Human Gene Expression Arrays (Affymetrix).

Microarray Sample Preparation and Analysis

For microarray analysis, total RNA samples were used for microarray expression analysis. 100 ng of total RNA was used to prepare biotinylated cRNA (cRNA) according to the manufacturer's protocol (30 IVT Express Kit, Affymetrix 901228). GeneChip arrays (Primeview, Affymetrix 901837) were hybridized and scanned according to standard Affymetrix protocols. The raw data was obtained by using Affymetrix Gene Chip Operating Software using default settings. A Primeview CDF provided by Affymetrix was used to generate .CEL files. The CEL files were processed with the expresso command to convert the raw probe intensities to probeset expression values with MAS5 normalization using the standard tools available within the affy package in R. The probesets of the same gene were next collapsed into a single value to represent the gene by taking the mean value. Differential gene expression was determined using moderated t-statistic in the "limma" package (http://bioinf.we- hi.edu.au/limma/) from Bioconductor (www.bioconductor.org) (Smyth, 2004). A gene was considered differentially expressed if it met the following criteria: 1) absolute log 2 fold-change ≥1 between the mean expression of the two condition, 2) adjusted p-value less than 0.1 by a moderated t-test within the limma package with BH multiple hypothesis testing correction.

The previously published expression profiles from the naïve human ES cells were also processed (GSM1139484 and GSM1139494) and primed ES cells (GSM1139488 and GSM1139495) from Gafni et al., 2013. The Affymetric CDF file (version V1.r3) was used to generate .CEL files. The CEL files were processed with RMA normalization using the standard tools variable within the affy package in R. The p-values for differential gene expression analysis were determined using moderated t-statistic in the "limma" package (http://bioinf.wehi.edu.au/limma/) from Bioconductor (www.bioconductor.org) (Smyth, 2004).

Cross-Species Gene Expression Analysis

Cross-species gene expression analysis was performed as previously described (Gafni et al., 2013) with some modifications. Previously published mouse ES cell and EpiSC cell gene expression datasets on an Agilent 4 X 44 k array platform (GSE15603). Probeset mapping between the Agilent 4 X 44 k array platform and Affymetric Primeview platform of human-mouse homologous genes was downloaded from Enesembl biomart (www.ensembl.org/biomart). The probesets of the same gene in human or mouse were next collapsed into a single value to represent the gene independently in each species by taking the mean value. The relative expression values from mouse and human were next calculated independently by divining the expression values of the samples by the mean of expression values within the same genes across samples in the same species. Pair-wise comparisons were performed on the relative expression values from the human and mouse expression profiles using Pearson correlation coefficients (PCCs). The average linkage hierarchical clustering of the Pearson correlation was shown in the heatmap.

Chromatin Immunoprecipitation (ChIP)

Cells were crosslinked for 10 minutes at room temperature by the addition of one-tenth of the volume of 11% formaldehyde solution (11% formaldehyde, 50 mM HEPES pH 7.3, 100 mM NaCl, 1 mM EDTA pH 8.0, 0.5 mM EGTA pH 8.0) to the growth media followed by quenching with 100 mM glycine. Cells were washed twice with PBS, then the supernatant was aspirated and the cell pellet was flash frozen in liquid nitrogen. Frozen crosslinked cells were stored at −80 C. 20 ul of Dynal magnetic beads (Sigma) were blocked with 0.5% BSA (w/v) in PBS. Magnetic beads were bound with 2 ug of the indicated antibody. The antibodies used were as follows: H3K4me3 (Abcam ab8580) and H3K27me3 (Millipore 07-449). Crosslinked cells were lysed with lysis buffer 1 (50 mM HEPES pH 7.3, 140 mM NaCl, 1 mM EDTA, 10% glycerol, 0.5% NP-40, and 0.25% Triton X-100) and resuspended and sonicated in sonication buffer (50 mM Tris-HCl [pH 7.5], 140 mM NaCl, 1 mM EDTA, 1% Triton X-100, 0.1% Na-deoxycholate, 0.1% SDS). Cells were sonicated at 4 C with a Bioruptor (Diagenode) at high power for 25 cycles for 30 s with 30 s between cycles. Sonicated lysates were cleared and incubated overnight at 4_C with magnetic beads bound with antibody to enrich for DNA fragments bound by the indicated factor. Beads were washed two times with sonication buffer, one time with sonication buffer with 500 mM NaCl, one time with LiCl wash buffer (20 mM Tris pH 8.0, 1 mM EDTA, 250 mM LiCl, 0.5% NP-40, 0.5% Na-deoxycholate)

and one time with TE with 50 mM NaCl. DNA was eluted in elution buffer (50 mM Tris-HCL pH 8.0, 10 mM EDTA, 1% SDS). Cross-links were reversed overnight. RNA and protein were digested using RNase A and Proteinase K, respectively and DNA was purified with phenol chloroform extraction and ethanol precipitation.

Illumina Sequencing and Library Generation

Purified ChIP DNA was used to prepare Illumina multiplexed sequencing libraries. Libraries for Illumina sequencing were prepared following the Illumina TruSeq DNA Sample Preparation v2 kit protocol with the following exceptions. After end-repair and A-tailing, Immunoprecipitated DNA (10-50 ng) or Whole Cell Extract DNA (50 ng) was ligated to a 1:50 dilution of Illumina Adaptor Oligo Mix assigning one of 24 unique indexes in the kit to each sample. Following ligation, libraries were amplified by 18 cycles of PCR using the HiFi NGS Library Amplification kit from KAPA Biosystems. Amplified libraries were then size-selected using a 2% gel cassette in the Pippin Prep system from Sage Science set to capture fragments between 200 and 400 bp. Libraries were quantified by qPCR using the KAPA Biosystems Illumina Library Quantification kit according to kit protocols. Libraries with distinct TruSeq indexes were multiplexed by mixing at equimolar ratios and running together in a lane on the Illumina HiSeq 2000 for 40 bases in single read mode.

Gene Sets and Annotations

All analysis was performed using RefSeq (NCBI37/HG19) (Pruitt et al., 2007) human gene annotations.

ChIP-Seq Data Processing

All ChIP-Seq datasets were aligned using Bowtie (version 0.12.9) (Langmead et al., 2009) to build version NCBI37/HG19 of the human genome using -n2, -e70, -m2, -k2, --best. The MACS version 1.4.1 (Model based analysis of ChIP-Seq) was used (Zhang et al., 2008) peak finding algorithm to identify regions of ChIP-Seq enrichment over background. A p-value threshold of enrichment of 1e-9 was used for all datasets.

Heatmap Representation of Read Density Profiles.

A gene was defined as Polycomb-associated if an enriched region for H3K27me3 (representing polycomb complexes) was located within +/−1 kb of the TSS. H3K27me3 is a histone modification associated with Polycomb complexes (Boyer et al., 2006). The annotated TSS of Polycomb-associated genes were aligned at the center in the composite view of signal density profile. The average ChIP-seq read density (r.p.m./bp) around 5 kb centered on the centers in 50 bp bin was calculated.

Meta Representations of ChIP-Seq Occupancy

Genome-wide average "meta" representations of ChIP-seq occupancy of different factors were created by mapping ChIP-seq read density to Polycomb-associated genes. Three sets of regions were created: upstream, gene body and downstream. 80 equally-sized bins divided the −2000 to 0 promoter region, 200 equally-sized bins divided the length of the gene body, and 80 equally-sized bins divided the 0 to +2 kb downstream region. The average ChIP-Seq factor density in each bin was calculated to create a meta genome-wide average in units of rpm/bp.

Differentiation Assays

Teratoma Formation

Single cell dissociations of naïve human ESCs were resuspended in 250 μl of medium and co-injected subcutaneously with 250 ul of matrigel in the flank of NOD/SCID mice. Tumors generally developed within 8 to 12 weeks and animals were sacrificed before tumor size exceeded 3 cm in diameter. Teratomas were isolated after sacrificing the mice and fixed in formalin. After sectioning, teratomas were diagnosed based on hematoxylin and eosin staining.

Directed Differentiation into Hepatocytes

Differentiation of naïve human ESCs into hepatocytes was obtained as described previously in conventional human ESCs (Si-Tayeb et al., 2010). Single cells were cultivated on Matrigel coated plates (2 mg/ml) under low oxygen conditions. Differentiation was initiated by cultivating cells for 5 days in Activin A (100 ng/ml) containing RPMI/B27 medium under ambient oxygen, followed by 5 days in BMP4 (20 ng/ml)/FGF-2 (10 ng/ml) containing RPMI/B27 and 5 days in HGF (20 ng/ml) containing RPMI/B27 under 5% oxygen. Finally cells were cultured for 5 days in Hepatocyte Culture Medium supplemented with Oncostatin-M (20 ng/ml) under ambient oxygen conditions. Generated hepatocytes were identified by expression of AFP, HNF4a and human Albumin.

Morula and Blastocyst Injection

Six to eight weeks old B6D2F1 females were superovulated with 7.5 I.U. of Pregnant Mare Serum (PMS) each given by intraperitoneal (IP) injections followed by an IP injection of 7.5 I.U. of Human Chorionic Gonadotropin (HCG) 46 to 48 hours later. They were then mated with B6D2F1 stud males and checked for copulatory plugs the following day. One-cell fertilized embryos were harvested and incubated at 37° C., 5% $O_2$ for 2-3 days in KSOM medium (Zenith Biotech). At the 8-cell, morula, and blastocyst stage, embryos were injected with 10-15 naïve human ESCs using a 16 μm piezo needle (Humagen). During injection, the human cells were kept continuously in drops of their own culture medium, whereas the embryos were kept in M2+ROCKi drops. After injection, the injected embryos were cultured in KSOM+ROCKi for 3-4 hours, then washed in 5 individual drops of KSOM and cultured overnight to the blastocyst stage. When the injected embryos reached the blastocyst stage, 20 embryos were transferred into each E2.5 p.c pseudopregnant female by uterine transfer. Seven to eight days later, the post-op females were sacrificed by $CO_2$ asphyxiation and embryos were harvested at E9.5-E10.5 p.c for analysis.

qRT-PCR

Total RNA was isolated using the Rneasy Kit (QIAGEN) and reversed transcribed using the Superscript III First Strand Synthesis kit (Invitrogen). Quantitative RT-PCR analysis was performed in triplicate using the ABI 7900 HT system with FAST SYBR Green Master Mix (Applied Biosystems). Gene expression was normalized to GAPDH. Error bars represent the standard deviation (SD) of the mean of triplicate reactions. Primer sequences are included in Table 1.

TABLE 1

Primers used in this study

| Gene | Primer sequence (5'-3') | Application | SEQ ID NO: |
|---|---|---|---|
| NANOG-F | GCAGAAGGCCTCAGCACCTA | RT-PCR | 1 |
| NANOG-R | AGGTTCCCAGTCGGGTTCA | | 2 |
| OCT4-F | GCTCGAGAAGGATGTGGTCC | RT-PCR | 3 |
| OCT4-R | CGTTGTGCATAGTCGCTGCT | | 4 |
| SOX2-F | CACTGCCCCTCTCACACATG | RT-PCR | 5 |
| SOX2-R | TCCCATTTCCCTCGTTTTTCT | | 6 |
| STELLA-F | GTTACTGGGCGGAGTTCGTA | RT-PCR | 7 |
| STELLA-R | TGAAGTGGCTTGGTGTCTTG | | 8 |
| KLF4-F | GATGGGGTCTGTGACTGGAT | RT-PCR | 9 |
| KLF4-R | CCCCCAACTCACGGATATAA | | 10 |
| GAPDH-F | CGAGATCCCTCCAAAATCAA | RT-PCR | 11 |
| GAPDH-R | ATCCACAGTCTTCTGGGTGG | | 12 |
| REX1-F | GGAATGTGGGAAAGCGTTCGT | RT-PCR | 13 |
| REX1-R | CCGTGTGGATGCGCACGT | | 14 |
| PRDM14-F | TGAGCCTTCAGGTCACAGAG | RT-PCR | 15 |
| PRDM14-R | ATTTCCTATCGCCCTTGTCC | | 16 |
| EGFP-F | AGAACGGCATCAAGGTGAAC | RT-PCR | 17 |
| EGFP-R | TGCTCAGGTAGTGGTTGTCG | | 18 |
| FUW-KLF2-F | GATTTTGCTGGGTTGGTTTTT | RT-PCR | 19 |
| FUW-KLF2-R | CCACATAGCGTAAAAGGAGCA | | 20 |
| FUW-NANOG-F | GCTGGGGAAGGCCTTAATGT | RT-PCR | 21 |
| FUW-NANOG-R | CCACATAGCGTAAAAGGAGCA | | 22 |
| PAX6-F | CTTTGCTTGGGAAATCCGAG | RT-PCR | 23 |
| PAX6-R | AGCCAGGTTGCGAAGAACTC | | 24 |

Results

Figure 1A:
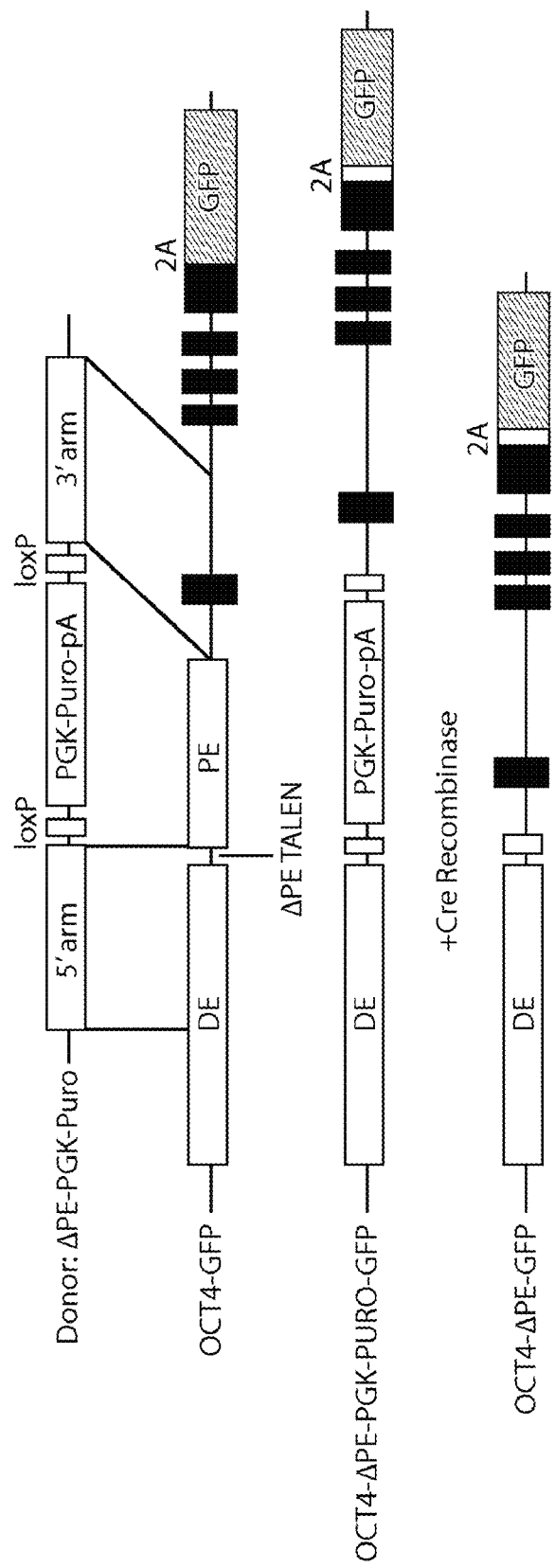
FIGS. 1A-1J show a reporter system for naïve human pluripotency based on endogenous OCT4 distal enhancer activity.
Figure 1C:
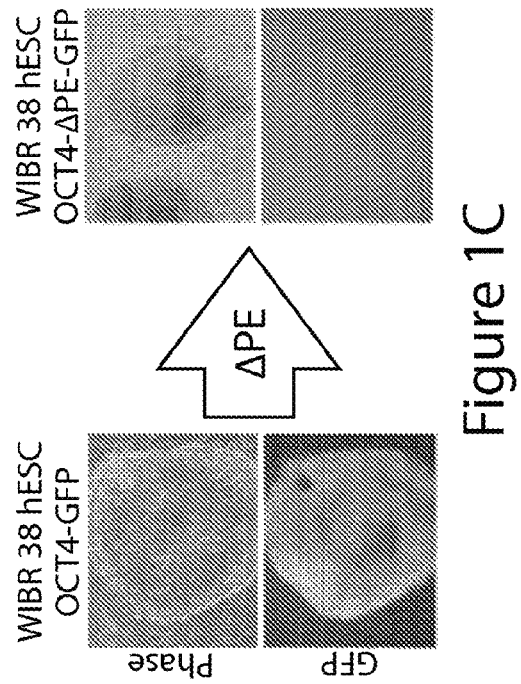
Figure 1B:
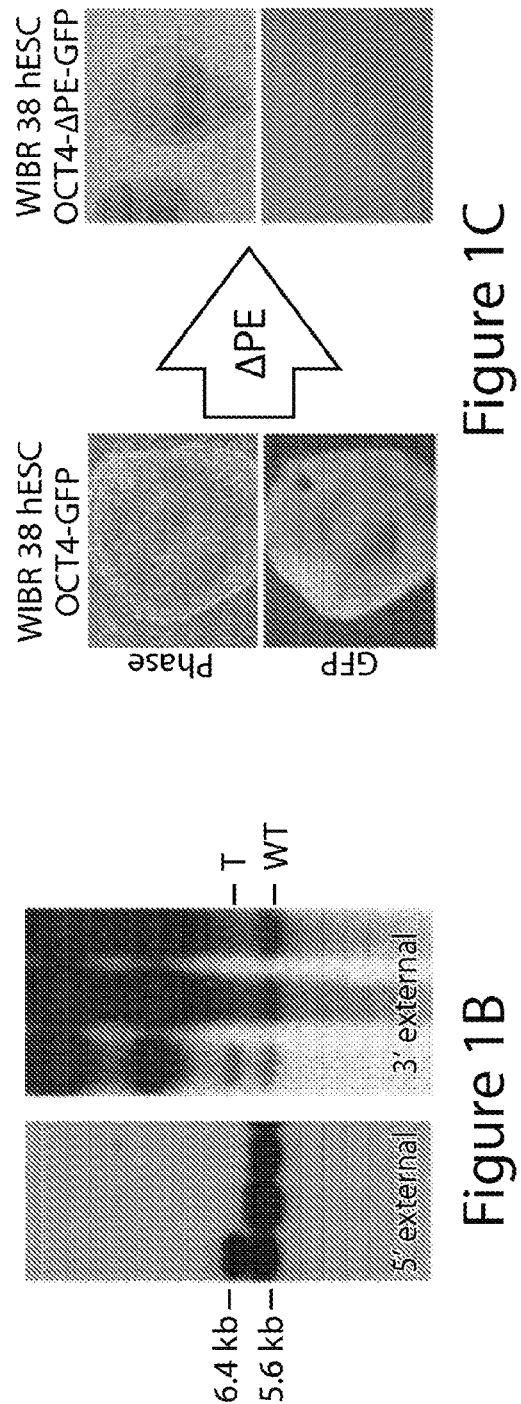
Figure 1D:
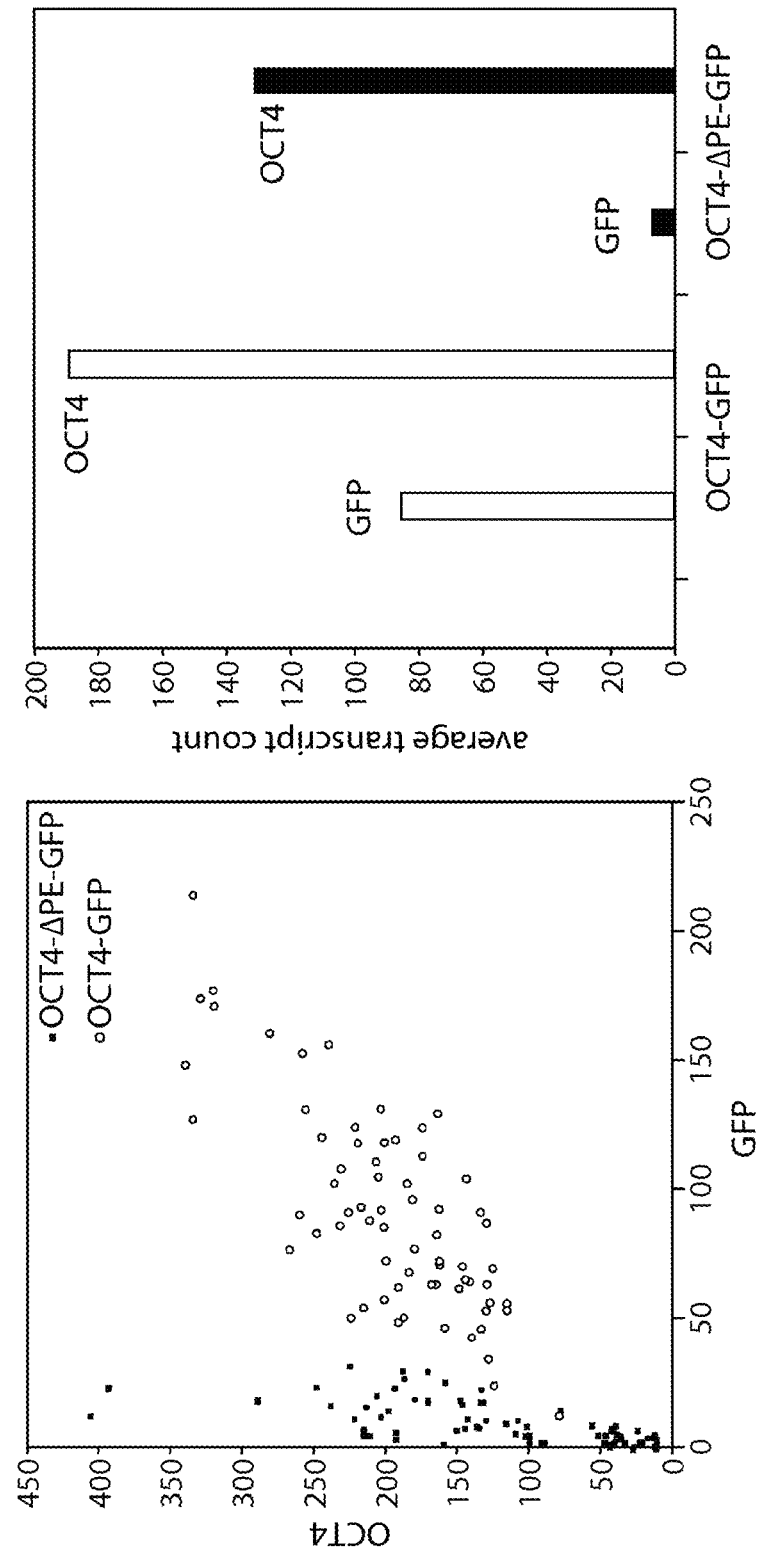
Figure 8A:
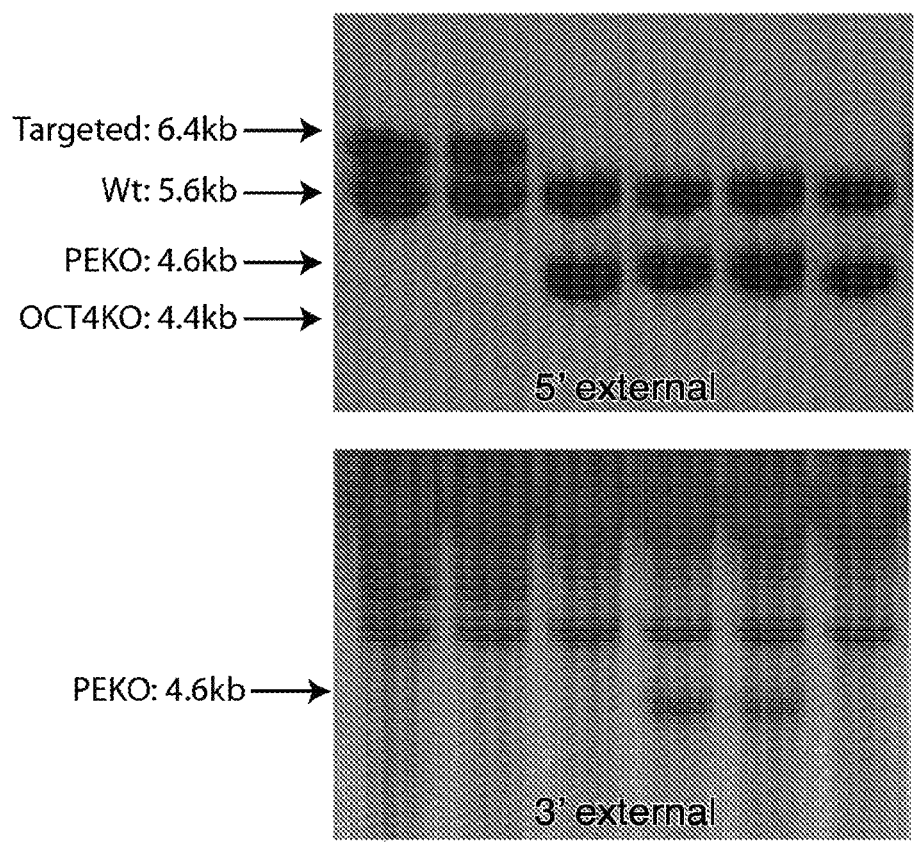
FIGS. 8A-8D show a reporter system for naïve human pluripotency based on endogenous OCT4 distal enhancer activity (associated with FIGS. 1A-1J).

A Reporter System for naïve Human Pluripotency Based on OCT4 Distal Enhancer Activity An important molecular signature of naïve pluripotency in the mouse system is the use of the distal enhancer (DE) of OCT4. This element controls Oct4 expression in naïve mouse ESCs, pre-implantation mouse embryos and germ cells (Yeom et al., 1996). In contrast, expression of Oct4 in primed EpiSCs and the mouse post-implantation embryo is under control of the proximal enhancer (PE) element (Tesar et al., 2007). To detect rare naïve human ESCs in a large population of primed cells, a reporter system for OCT4 DE activity was engineered using TALENs. The PE element was deleted in an OCT4-GFP allele that was previously established in WIBR3 primed human ESCs (Hockemeyer et al., 2011) (FIG. 1A and FIG. 8A). TALENs were designed to cleave in the 5' end of the PE, together with a donor vector containing LoxP sites bordering a selectable marker and gene sequences homologous to those flanking the PE. After targeting the allele harbors an approximately 1Kb deletion of the PE sequence. Successful integration of this PE targeting vector (FIG. 1B), and subsequent removal of the selection cassette (FIG. 8A) were confirmed. As expected, deletion of the PE resulted in substantial attenuation of the OCT4-GFP signal (FIG. 1C). Single molecule RNA FISH analysis in individual cells showed that GFP expression was diminished, while OCT4 expression was reduced approximately by 50%, following PE removal (FIG. 1D). These changes in OCT4 and GFP expression demonstrate that OCT4 expression in primed human ESCs is primarily dependent on the PE, rather than the DE, as observed in mouse EpiSCs.

Figure 1E:
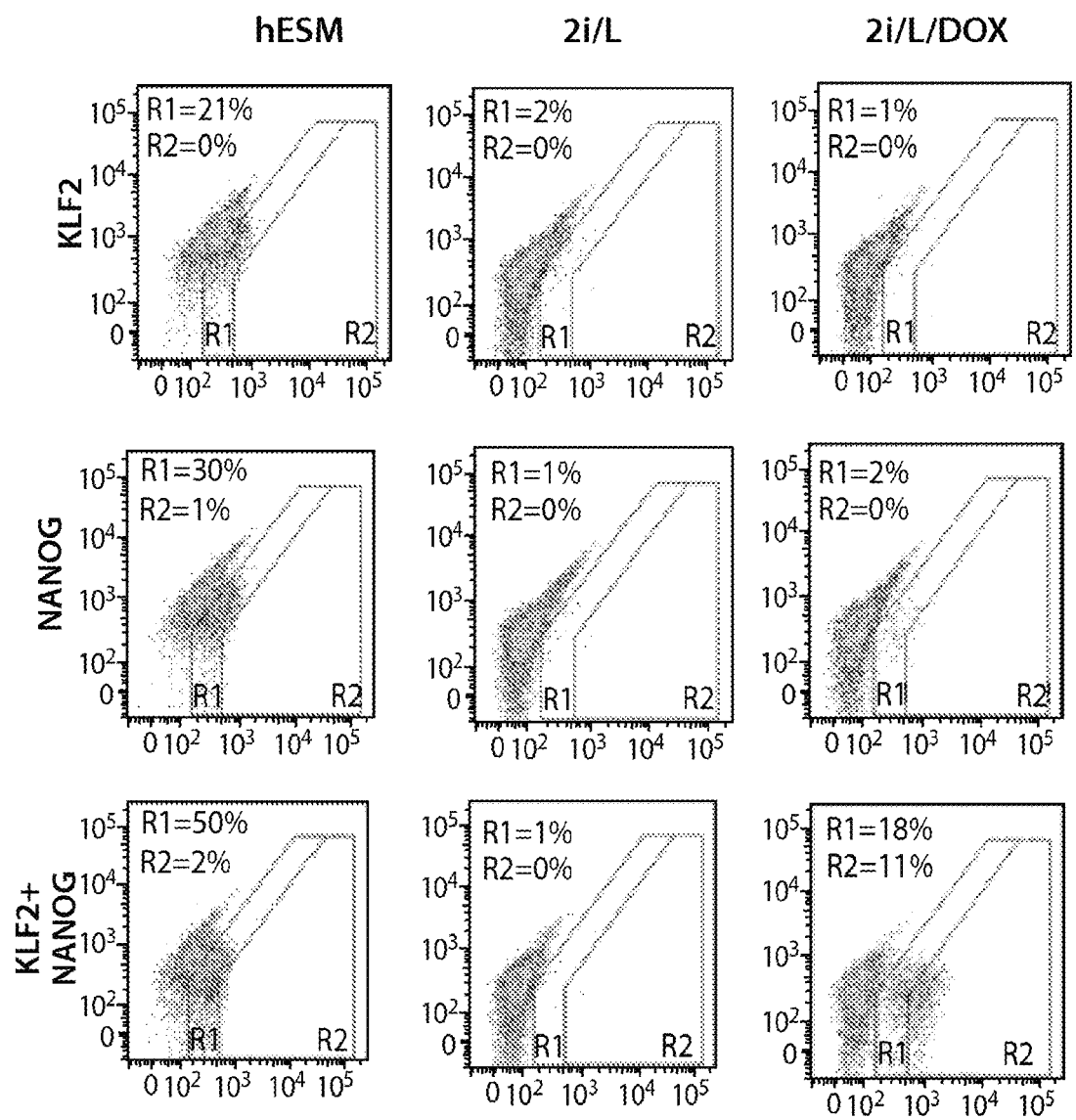
Figure 1F:
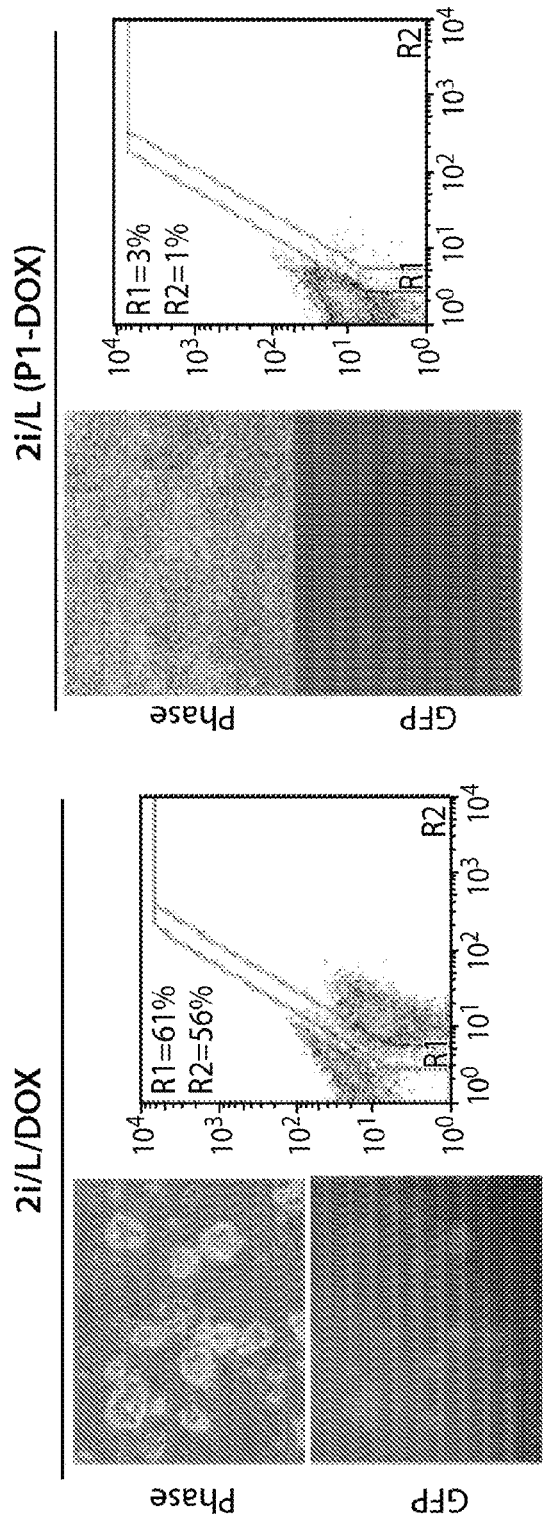
Figure 1G:
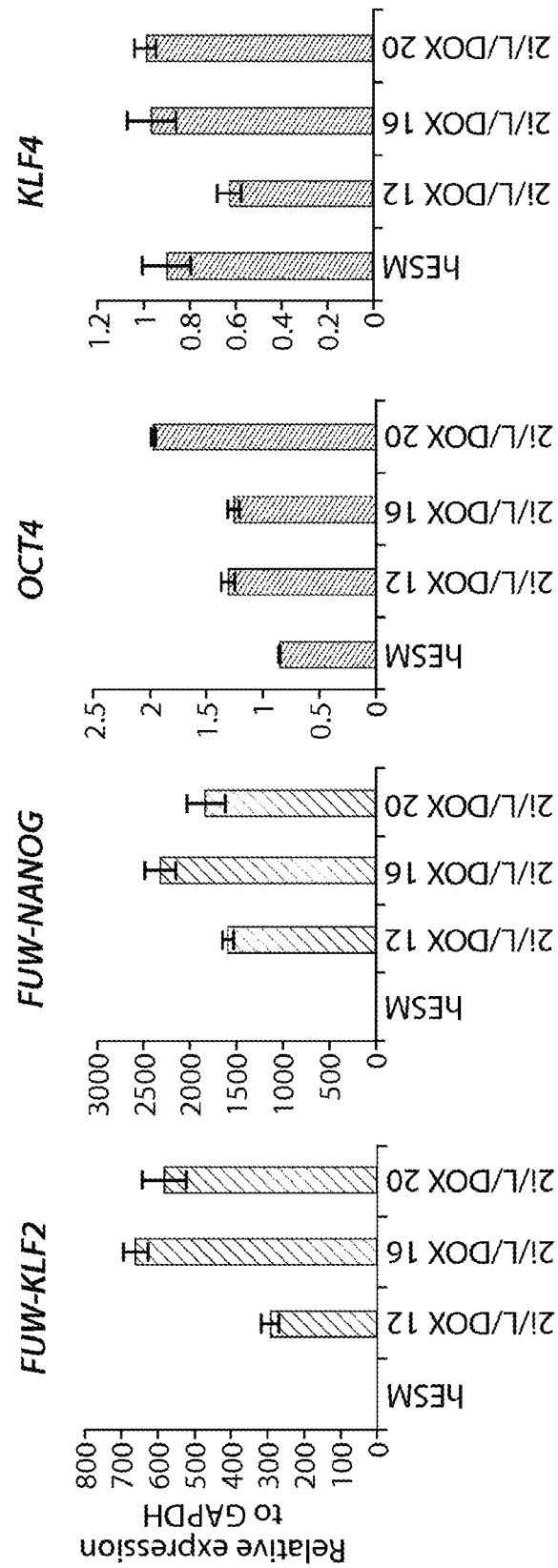
Figure 8B:
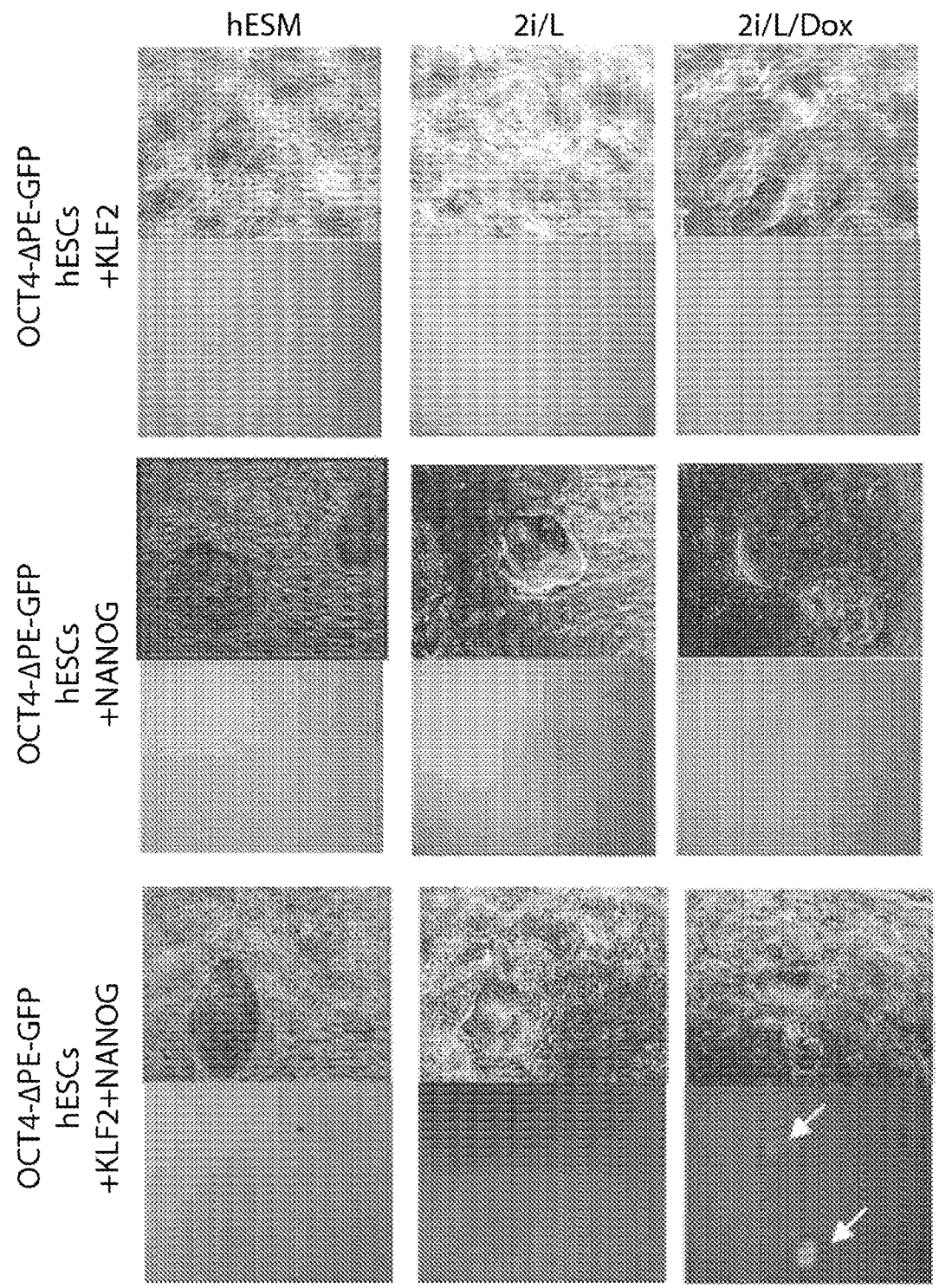

It was investigated whether overexpression of transcription factors specific to naïve pluripotency together with the application of serum-free 2i/L culture conditions would result in augmented OCT4-ΔPE-GFP activity. For this reason the transcription factors KLF2 and NANOG were overexpressed using doxycycline (DOX) inducible lentiviral expression vectors. Compared to its family members Klf4 and Klf5, Klf2 has enhanced capability to induce naïve pluripotency in mouse EpiSCs (Hall et al., 2009). In addition, the homeodomain transcription factor Nanog is critical for the establishment of naïve pluripotency (Silva et al., 2009) and can revert EpiSCs to the naïve state in the absence of kinase inhibition (Theunissen et al., 2011). Consistent with the potent effects of these factors in the mouse system, combined overexpression of KLF2 and NANOG in primed human ESCs resulted in increased OCT4-ΔPE-GFP reporter levels in a fraction of cells (FIG. 1E and FIG. 8B). The appearance of high OCT4-ΔPE-GFP+ cells was strictly dependent on the expression of both factors, and could only be observed in presence of 2i/L/DOX. GFP+ colonies were clonally expanded on a mouse embryonic fibroblast (MEF) feeder layers in the presence of 2i/L/DOX, while retaining a dome-like colony morphology and pluripotency gene expression (FIG. 1F and FIG. 1G). Strikingly, withdrawal of DOX-dependent KLF2 and NANOG expression resulted in the rapid loss of colony morphology, appearance of differentiated cells and shutdown of OCT4-ΔPE-GFP reporter activity within 7 days (FIG. 1F, Right). Thus, 2i/L culture conditions are insufficient to maintain the self-renewal of OCT4-ΔPE-GFP+ cells after withdrawal of exogenous factor expression. The rapid downregulation of naïve reporter activity provides a defined time window in which to screen for small molecules that support the maintenance of a putative naïve human pluripotent state.

Figure 1H:
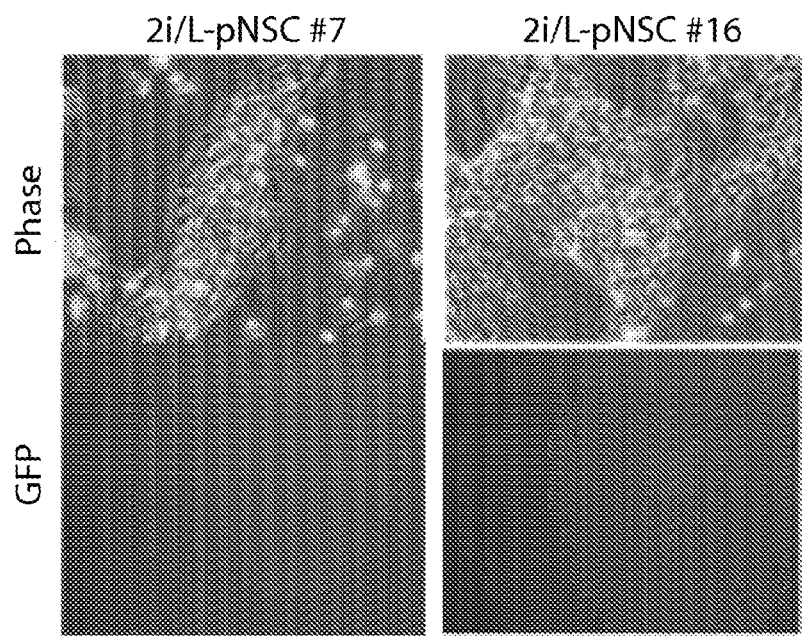
Figure 1I:
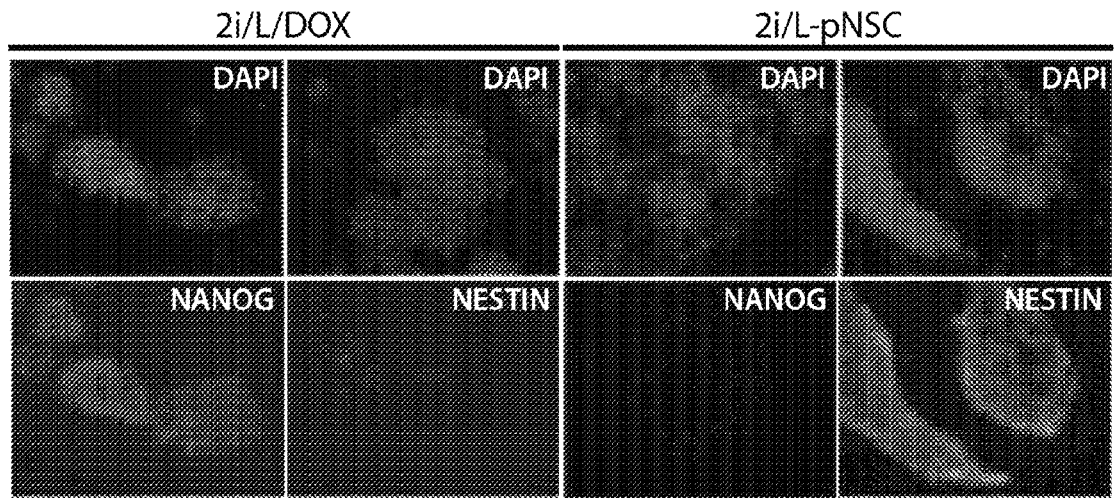
Figure 1J:
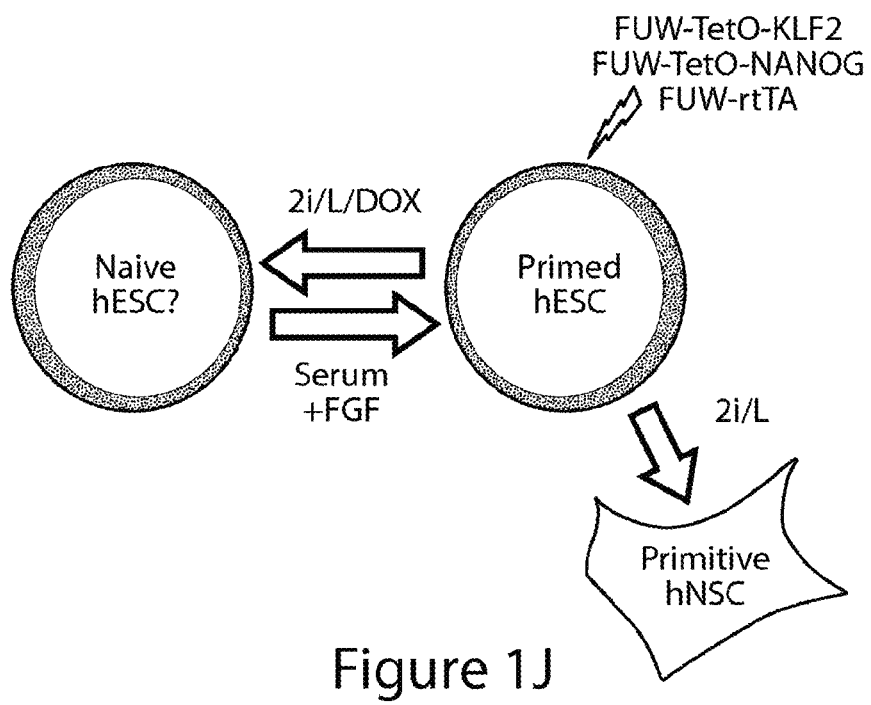
Figure 8C:
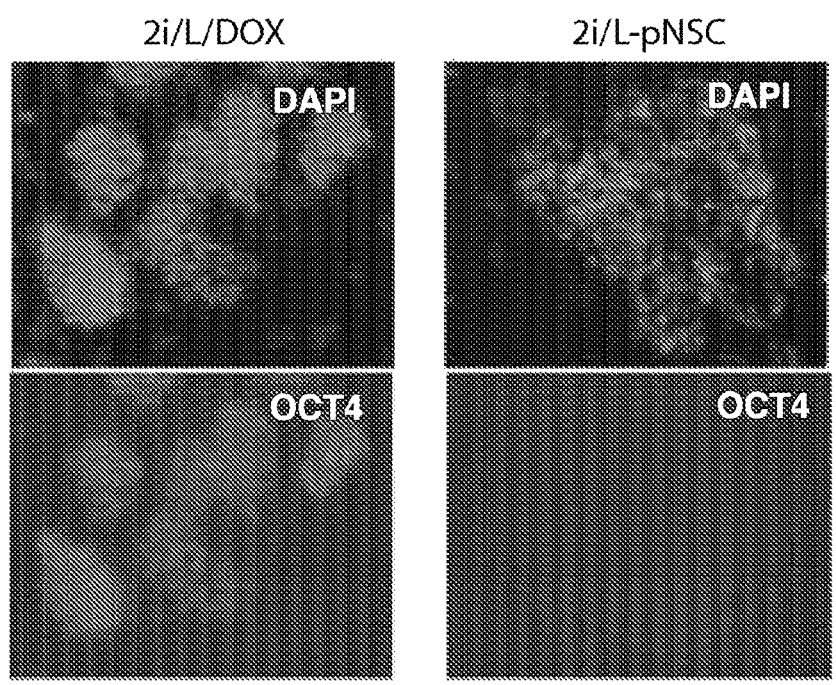
Figure 8D:
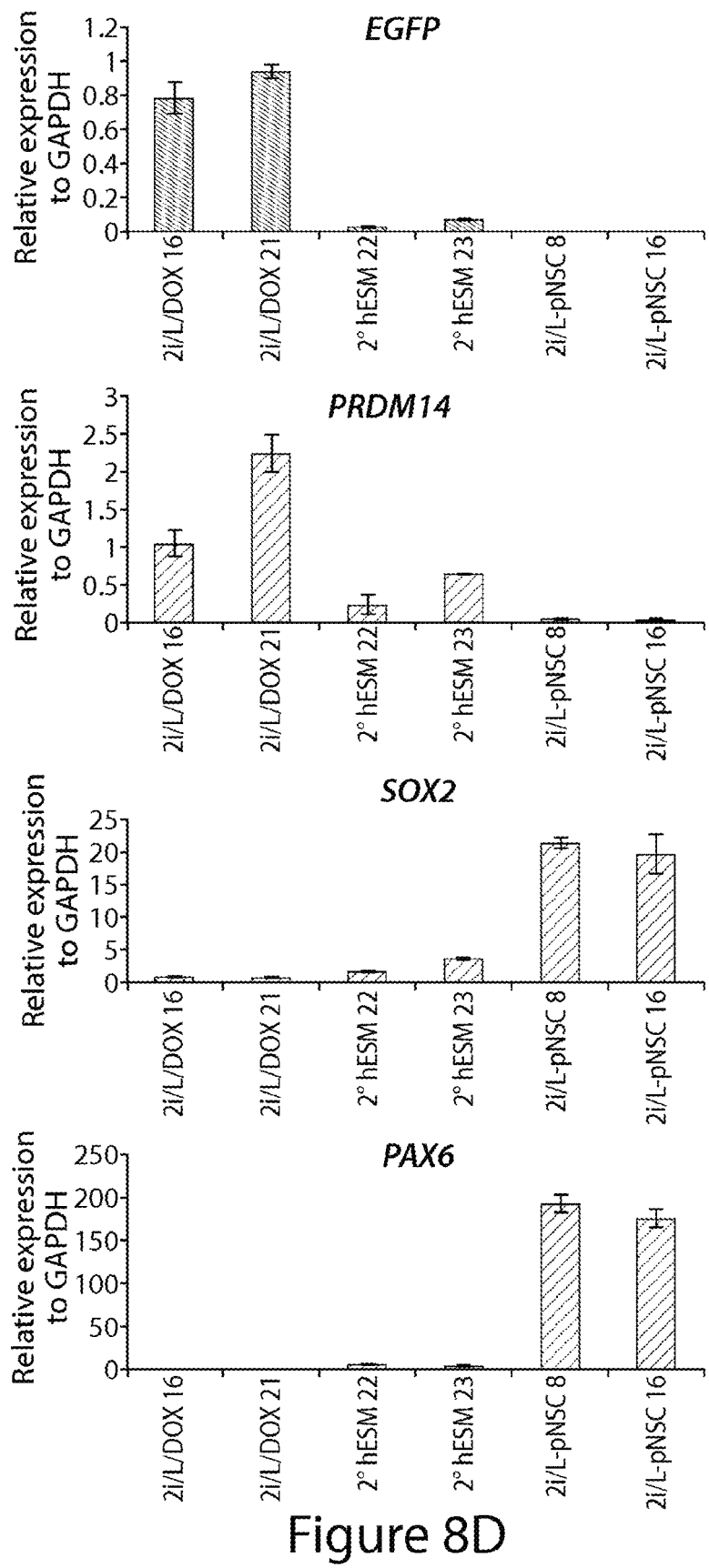

The inability to maintain OCT4-ΔPE-GFP activity in 2i/L led us to further investigate the consequences of these culture conditions when applied directly to conventional human ESCs in the absence of transgene expression. In the mouse system dual MEK and GSK3 inhibition is thought to consolidate the ground state and eliminate EpiSCs and other differentiated phenotypes that cannot survive under these minimal conditions (Silva and Smith, 2008). In contrast, rapid expansion in serum-free 2i/L was observed of initially dome-shaped human ESC colonies that assumed a neural morphology upon further passaging (FIG. 1H). Flow cytometric analysis revealed that weak levels of OCT4-ΔPE-GFP detected in primed human ESCs completely disappeared in 2i/L alone (FIG. 1E). Consistent with the morphological change, the loss of OCT4 and NANOG expression and upregulation of NESTIN and PAX6 expression in primed human ESCs expanded in serum-free 2i/L medium was observed (FIG. 1I and FIG. 8C-D). These observations are in agreement with a report that 2i/L treatment induces differentiation of human ESCs into primitive neural stem cells (Hirano et al., 2012). We conclude that 2i/L conditions do not interfere with expansion of differentiated cell types in human cells to the same extent as in the mouse system and are consequently insufficient for stabilizing naïve human pluripotency (FIG. 1J).

Figure 2A:
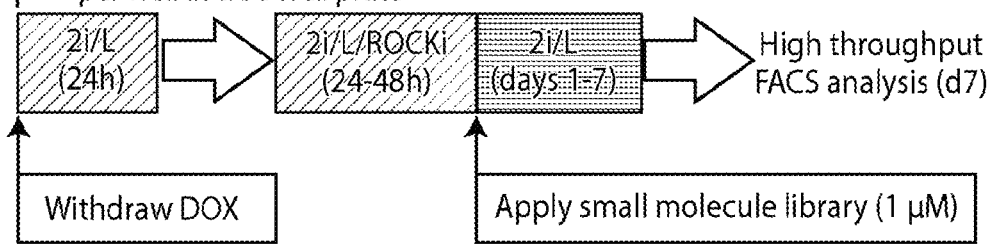
FIGS. 2A-2H show the identification of small molecules that maintain OCT4-ΔPE-GFP activity after transgene withdrawal.
Figure 2A:
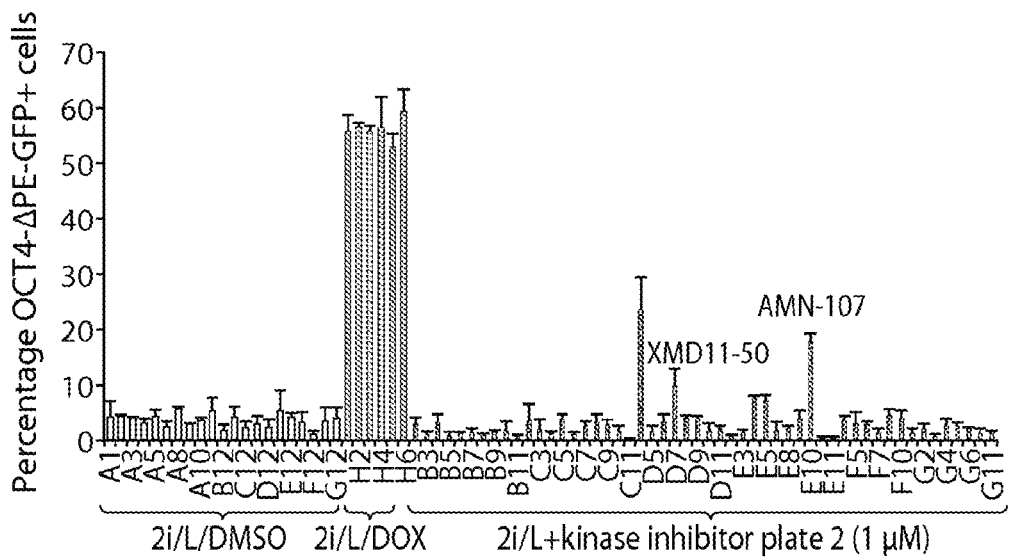
Figure 2B:
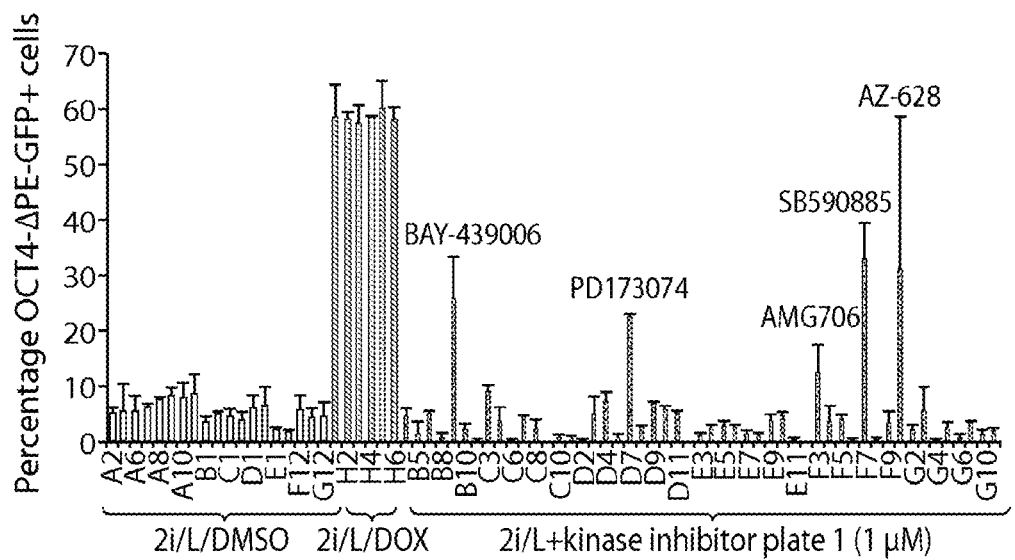
Figure 2B:
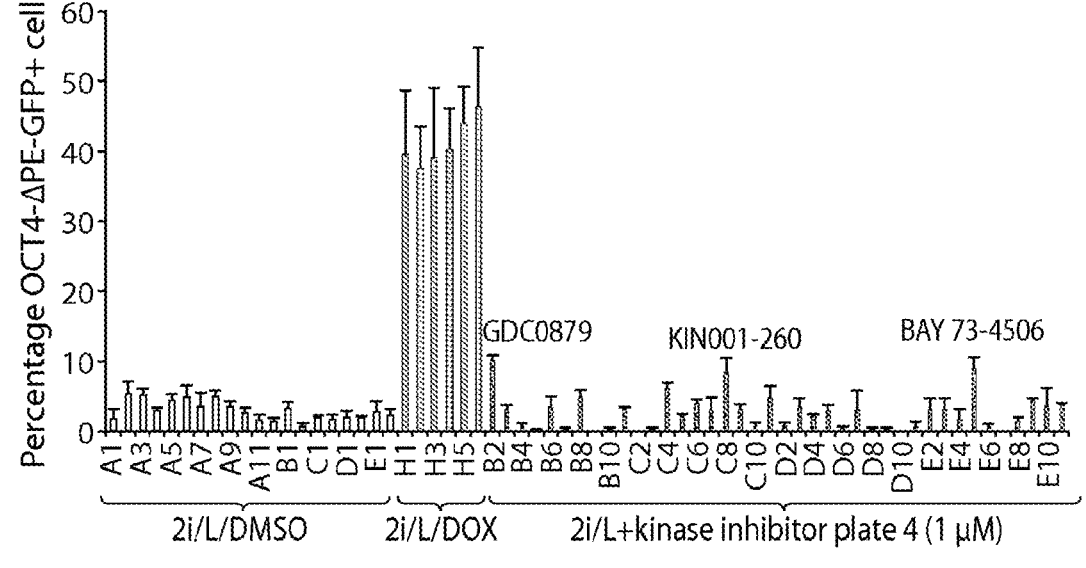
Figure 2D:
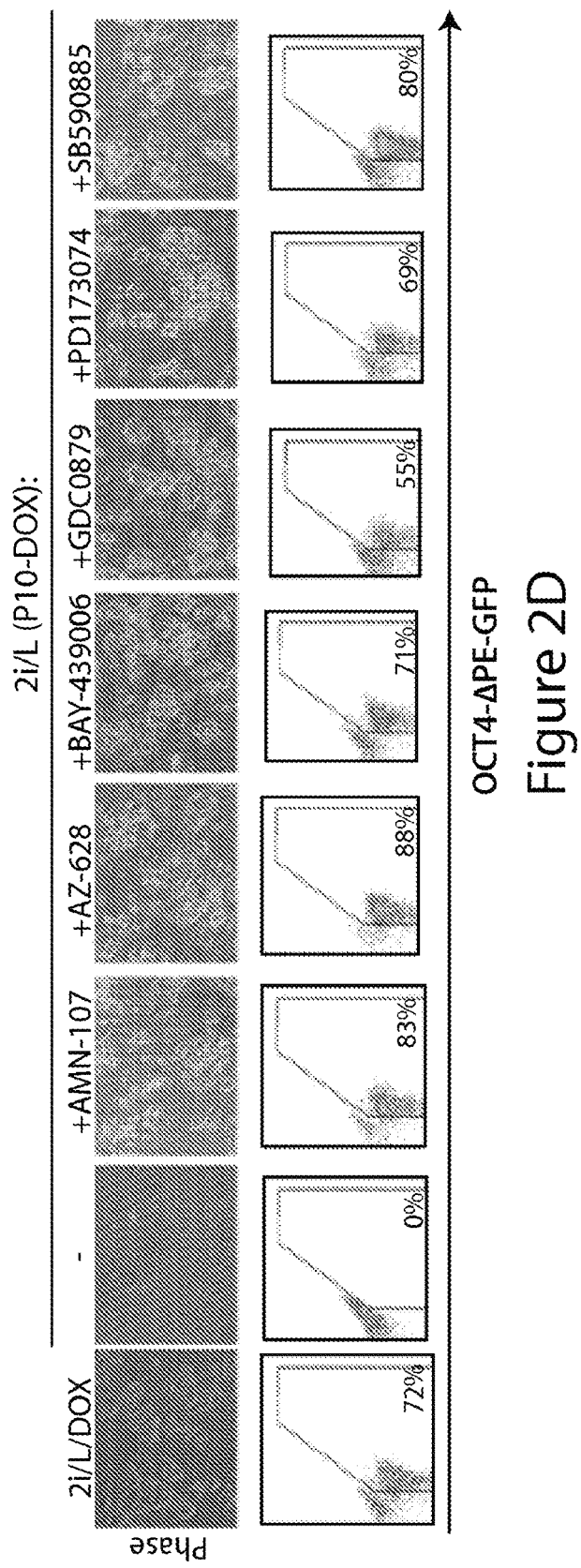
Figure 2E:
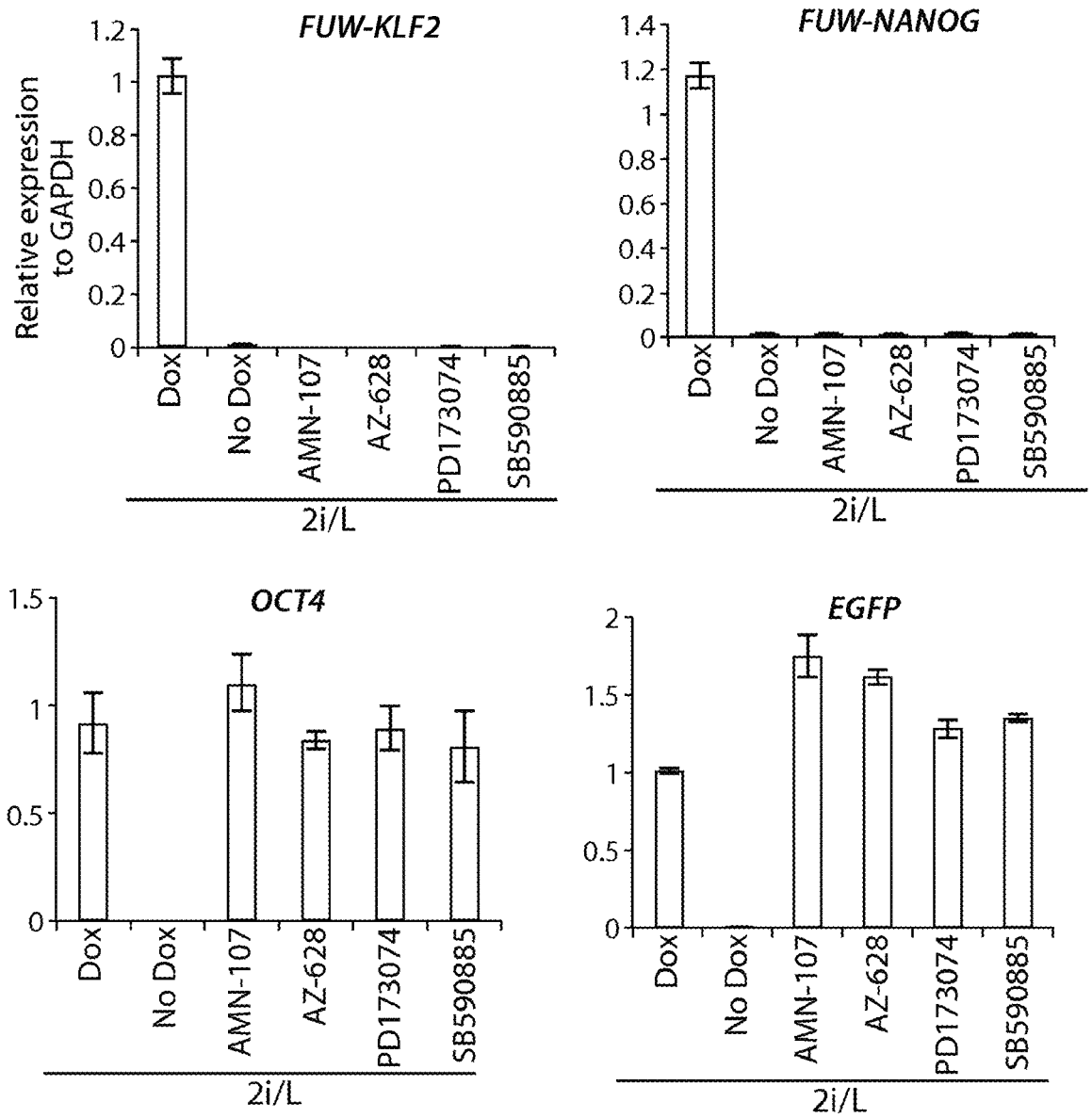
Figure 2F:
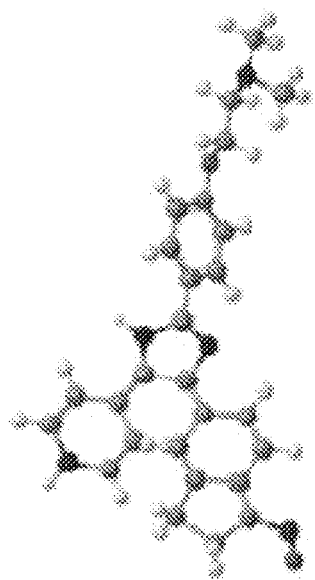
Figure 2G:
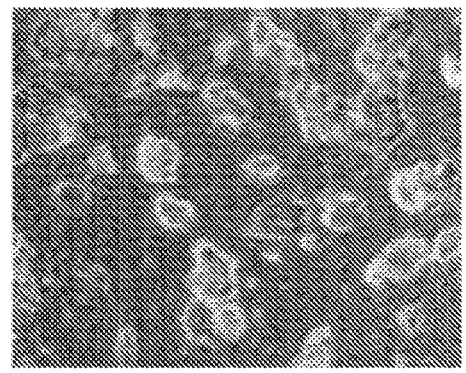
Figure 2G:
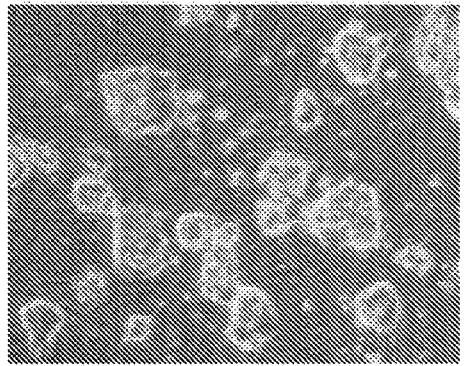
Figure 2H:
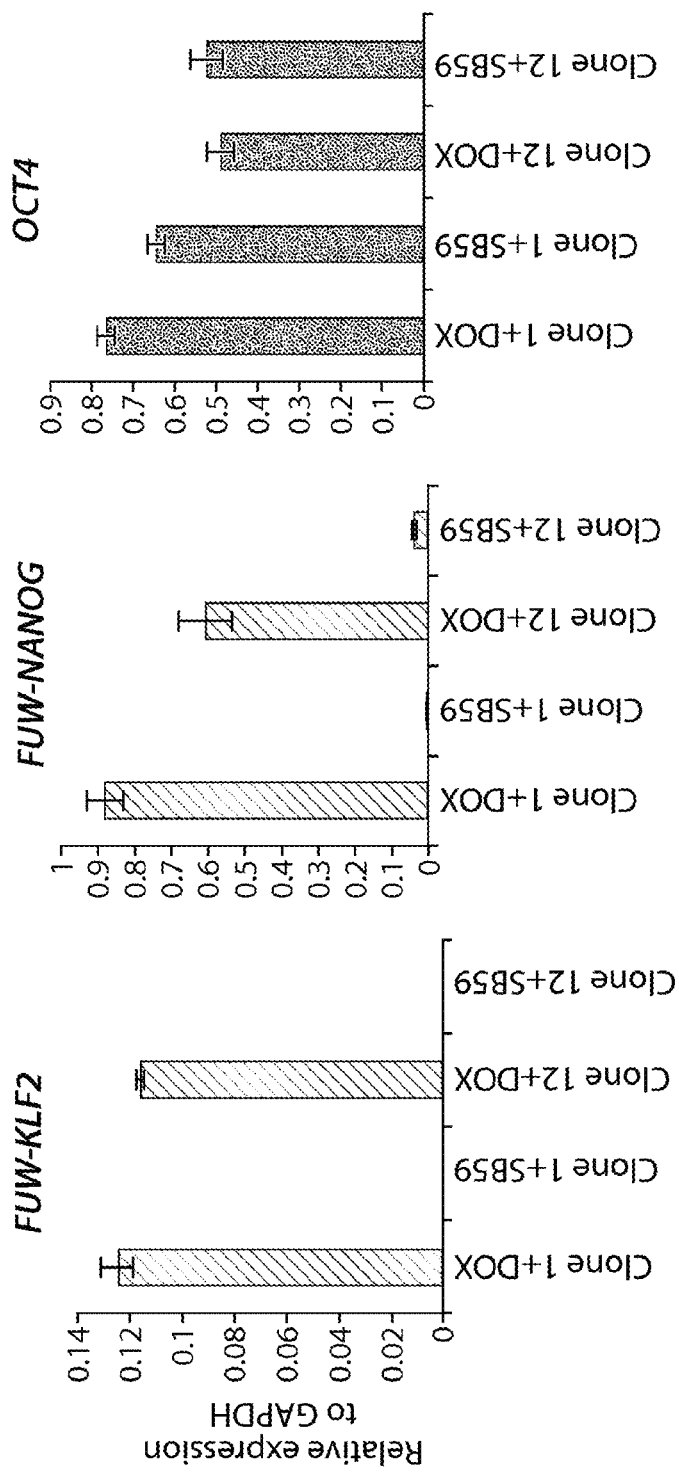
Figure 9A:
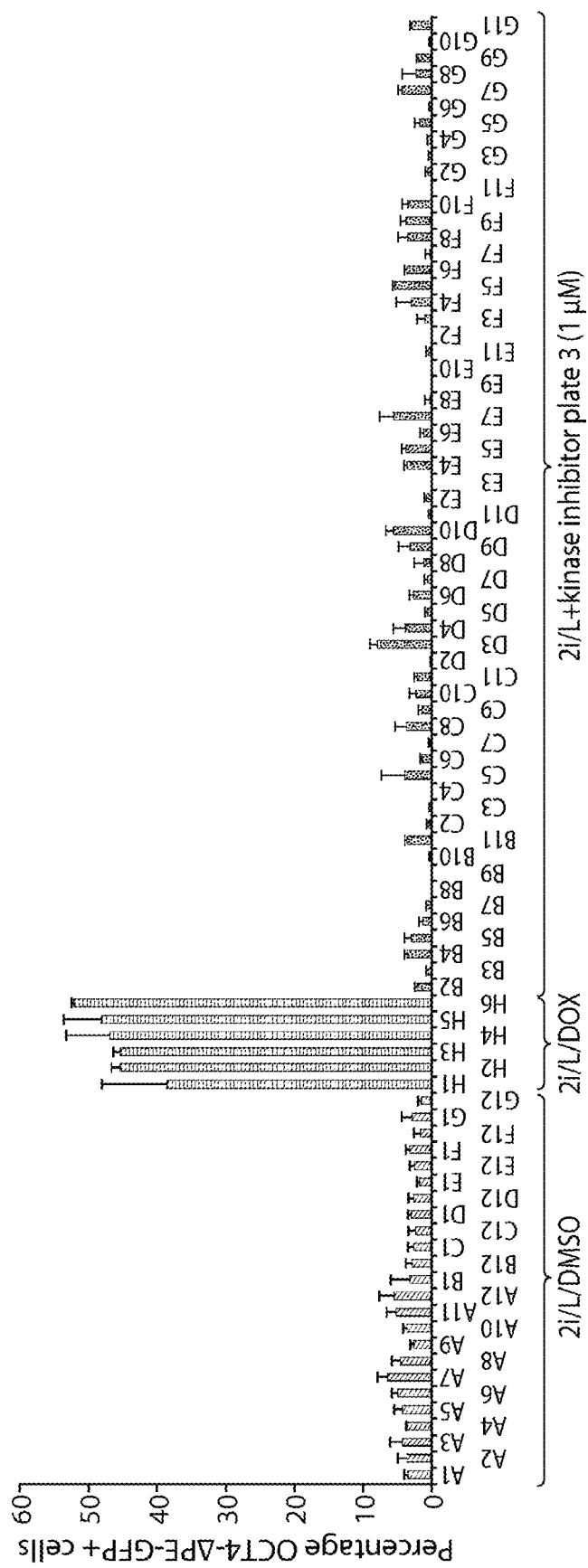
FIGS. 9A-9C show the identification of small molecules that maintain OCT4-ΔPE-GFP activity after transgene withdrawal (associated with FIG. 2).
Figure 9B:
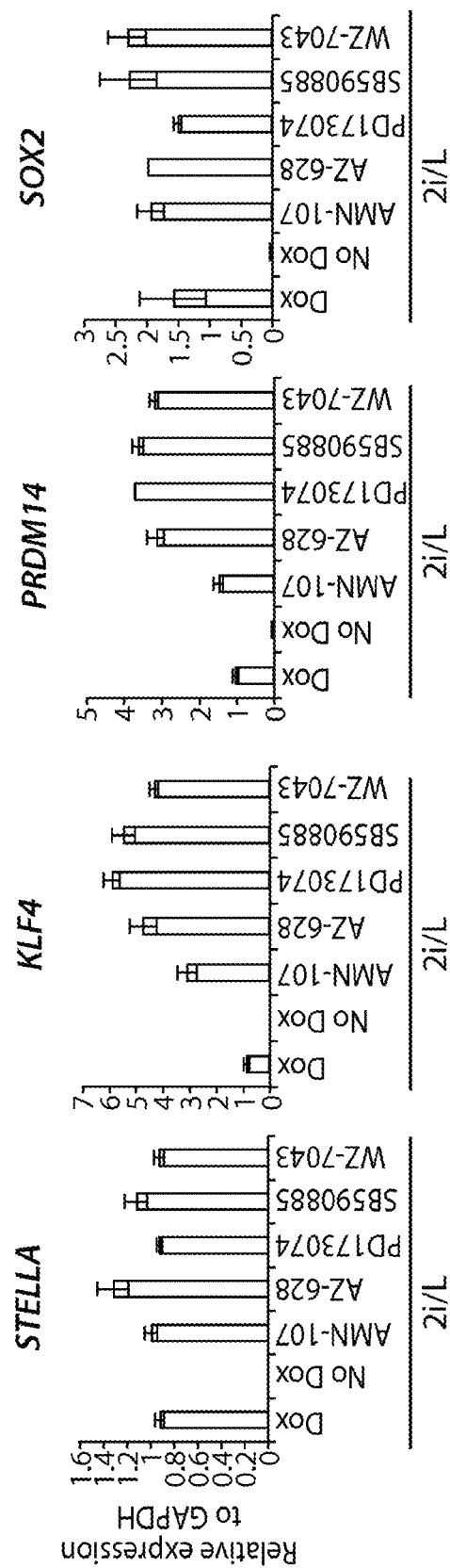

Identification of Compounds that Maintain Naïve Reporter Activity Upon Transgene Withdrawal To identify compounds that sustain OCT4-ΔPE-GFP activity in the absence of KLF2 and NANOG expression, a kinase inhibitor library was screened in the presence of 2i/L for a period of 7 days after DOX withdrawal in 96 well format (FIG. 2A). This screen identified 10 different hit compounds that partially rescued the proportion of GFP+ cells when assayed by high-throughput FACS analysis (FIG. 2B-C and FIG. 9A). Notable among these hits were four separate inhibitors of BRAF and four inhibitors of upstream receptor tyrosine kinases (RTKs), including DDR1, VEGFR1 and FGFR1. A validation experiment was then performed in 6 well format by withdrawing DOX and culturing the cells in 2i/L supplemented with each hit compound for up to 10 passages (FIG. 2D). Nearly all hit compounds maintained a proportion of GFP+ cells similar to that observed with DOX. However, the BRAF inhibitor SB590885 preserved the best colony morphology and proliferation. In contrast, treatment with the FGF receptor inhibitor PD173074 or pan-RTK inhibitor WZ-4-145 resulted in maintenance of OCT4-ΔPE-GFP activity in colonies with a disorganized morphology. Gene expression analysis 5 passages after DOX withdrawal confirmed the absence of KLF2 and NANOG transgene expression and retention of endogenous OCT4 and GFP transcripts (FIG. 2E and FIG. 9B). To validate these findings in an independent system DOX-inducible KLF2 and NANOG transgenes were introduced in a line of wild-type WIBR3 human ESCs. Upon application of DOX and 2i/L, dome-shaped colonies appeared that could be expanded clonally. After DOX withdrawal these lines were maintained in 2i/L/SB590885 while retaining both colony morphology and the expression of endogenous OCT4 (FIG. 2F-H). Thus, high-throughput chemical screening identified a number of kinase inhibitors, most notably the BRAF inhibitor SB590885, that synergize with 2i/L to maintain OCT4-ΔPE-GFP reporter activity and pluripotency gene expression in human ESCs after removal of exogenous KLF2 and NANOG expression.

Figure 3A:
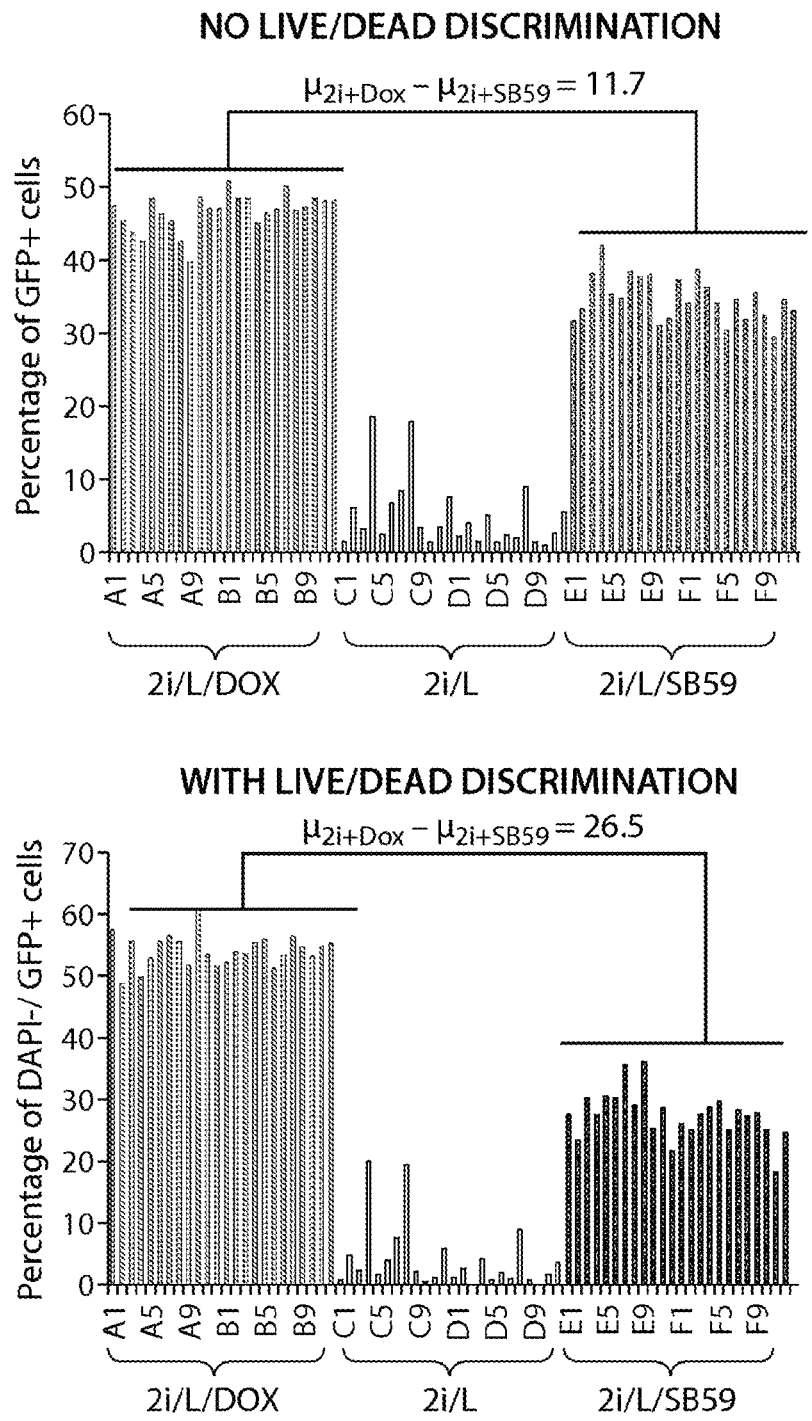
FIGS. 3A-3H show the optimization of medium for maintaining viable OCT4-ΔPE-GFP+ cells.
Figure 3B:
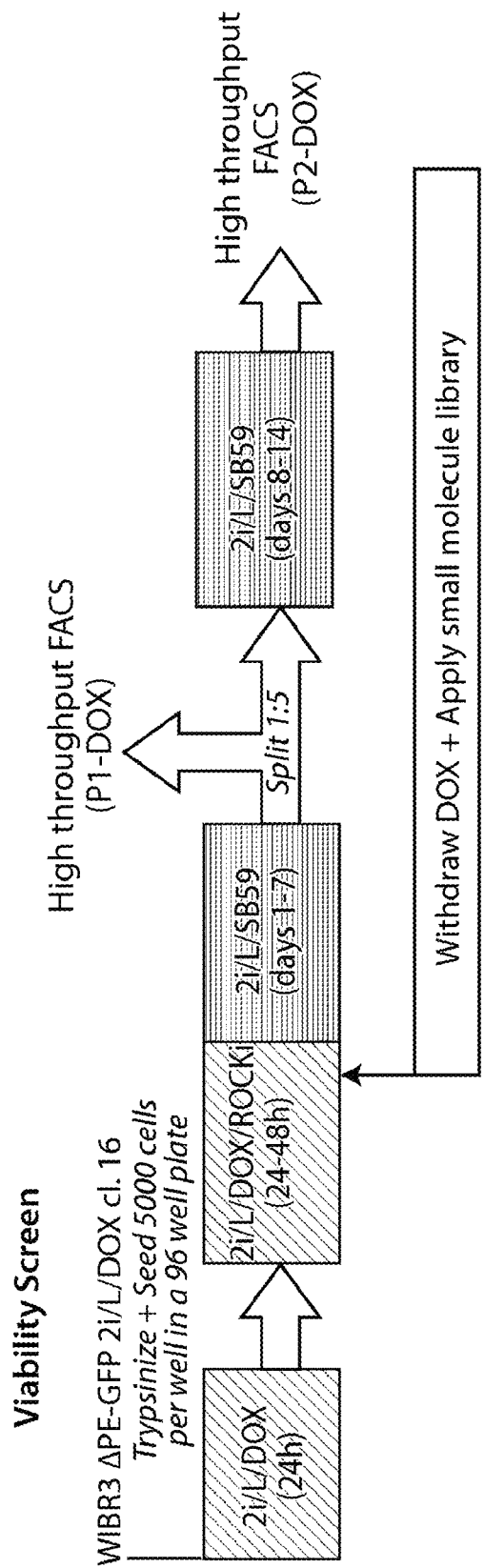
Figure 3C:
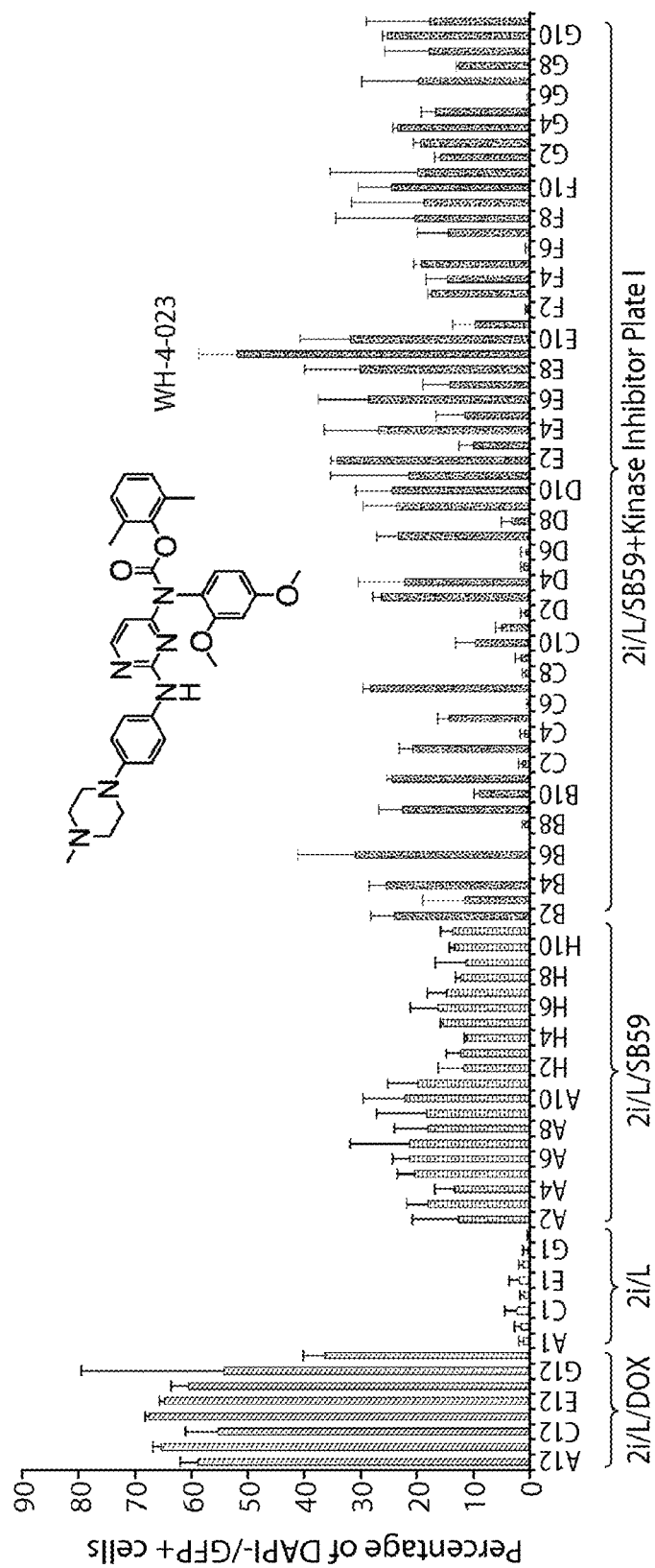
Figure 3D:
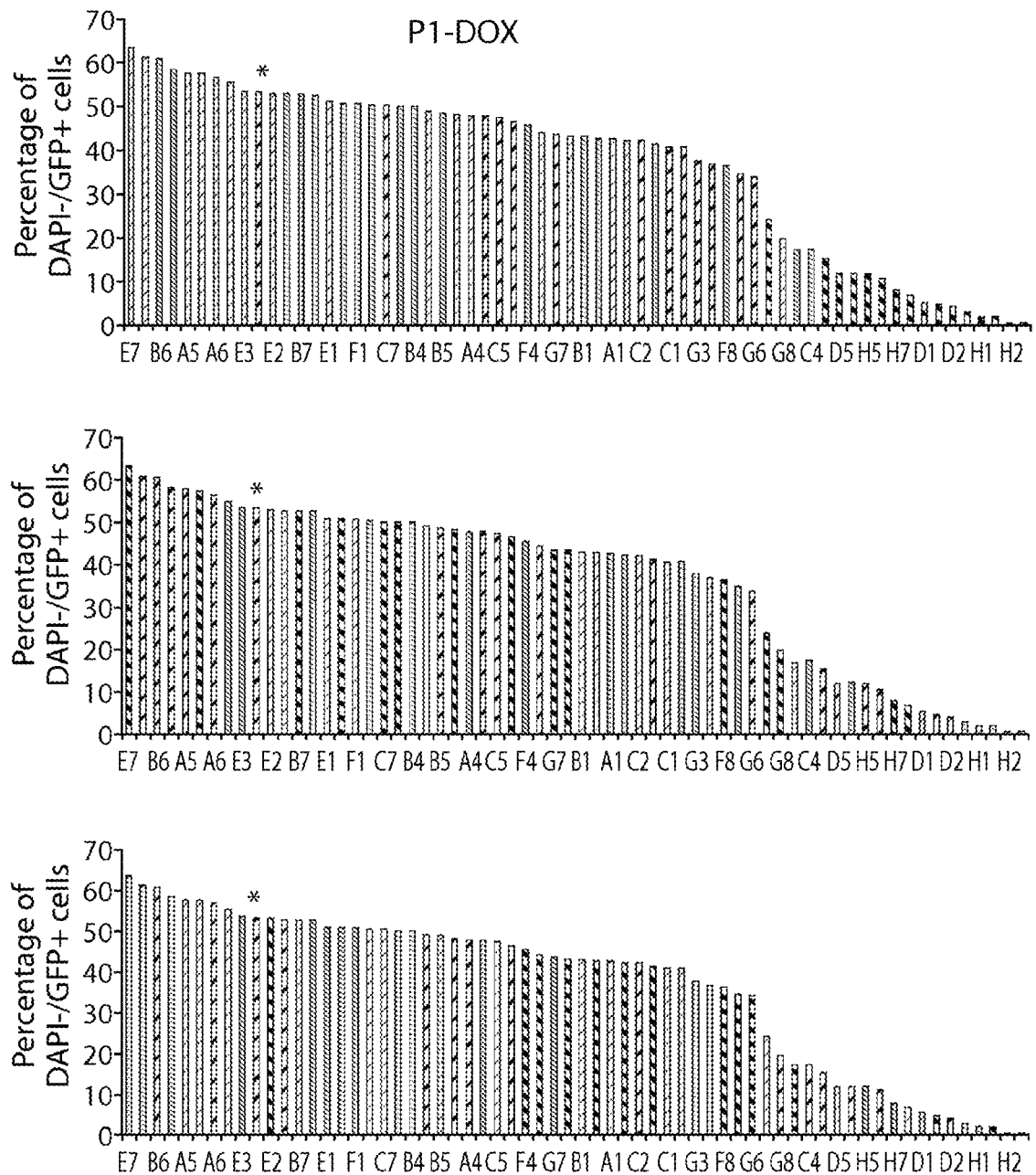
Figure 3E:
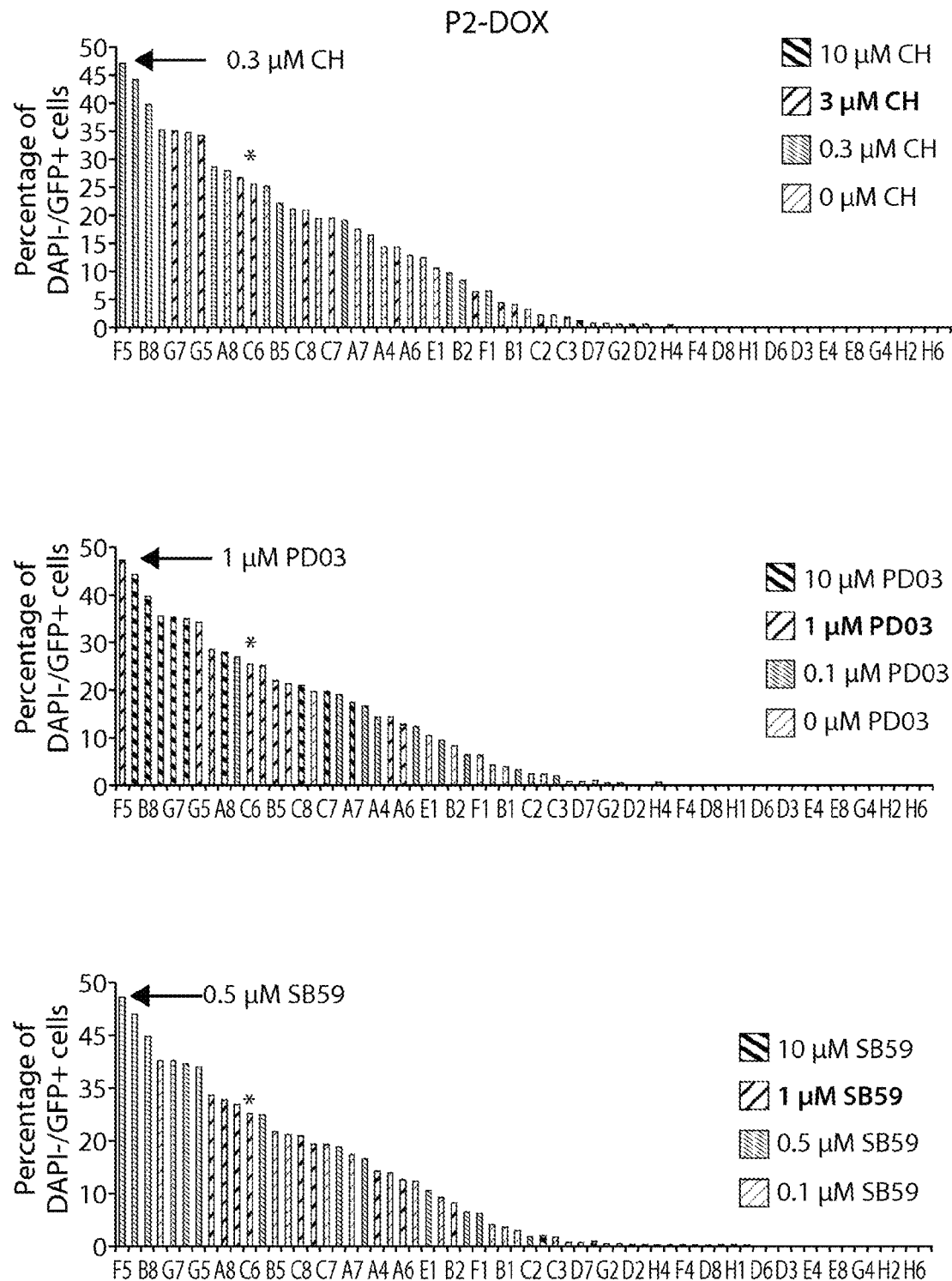
Figure 9C:
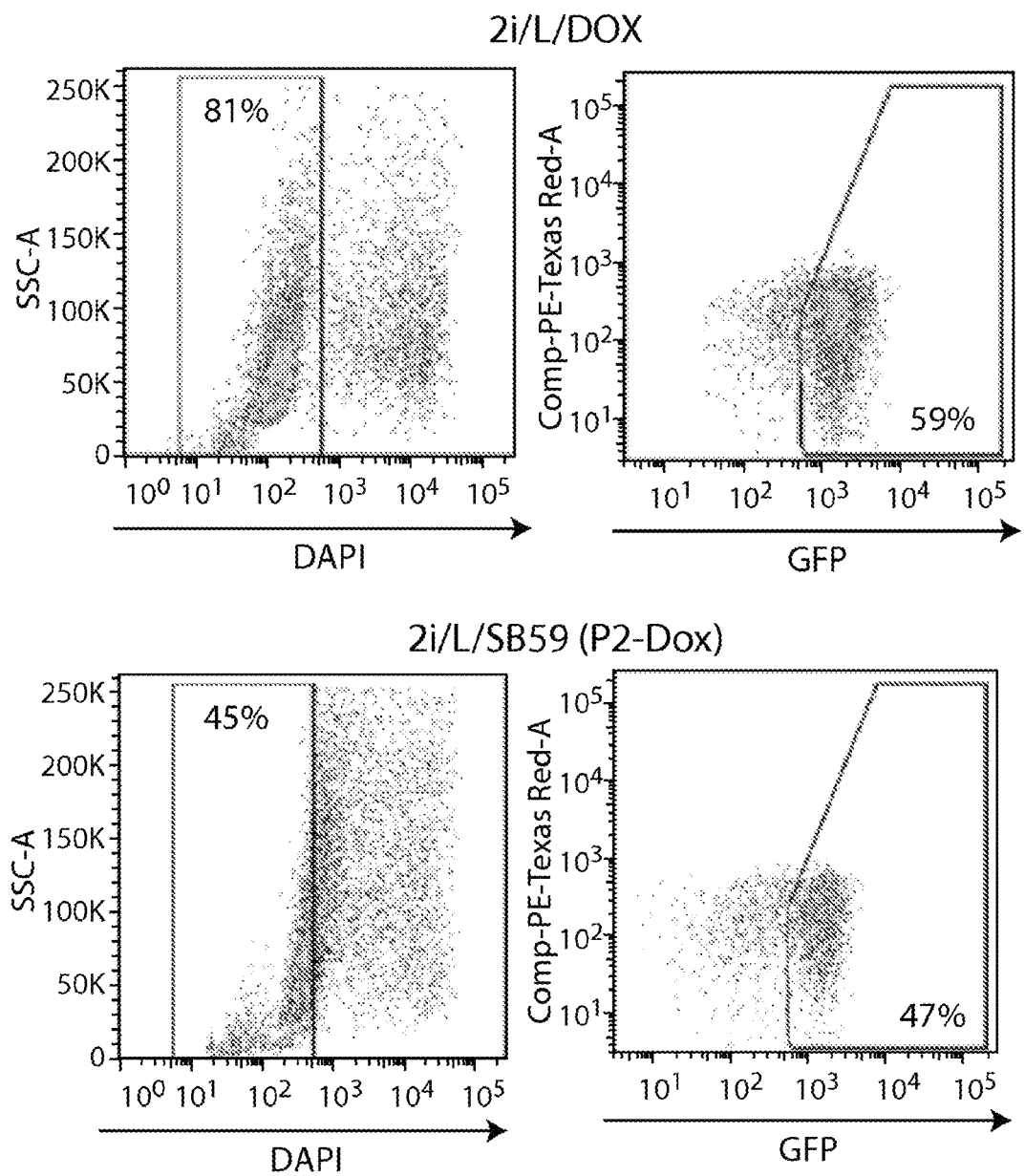

Using a FACS-based live/dead discrimination assay it was determined that cells maintained in 2i/L/SB590885 had reduced viability (FIG. 9C). This led us to consider whether other small molecules could cooperate with 2i/L/SB590885 to improve the fraction of viable GFP+ cells. Inclusion of a live/dead assay enhanced the resolution of the 96 well high-throughput FACS analysis, allowing for more sensitive discrimination between the proportion of viable OCT4-ΔPE-GFP+ cells cultured in 2i/L/DOX vs. 2i/L/SB590885 (FIG. 3A). This viability assay was included in a modified screen in which GFP+ cells were cultured for two passages after DOX withdrawal in 2i/L/SB590885 supplemented with the kinase inhibitor library (FIG. 3B-C and FIG. 10A). This screen identified several hit compounds that improved the fraction of viable GFP+ cells, including the LCK/SRC inhibitor WH-4-023 (FIG. 10B). A titration of the concentrations of PD0325901, CHIR99021 and SB590885 was also performed during two passages after DOX withdrawal followed by high-throughput FACS analysis (FIG. 3D). A significant improvement was observed in the proportion of viable GFP+ cells using a concentration of 1 μM PD0325901, 0.3 μM CHIR99021 and 0.5 μM SB590885. Notably, lower concentrations of CHIR99021 improved the proportion of viable GFP+ cells, whereas higher concentrations of CHIR99021 had an opposite effect. This is reminiscent of recent evidence that lowered GSK3 inhibition reduces differentiation and enhances the self-renewal of rat ESCs (Meek et al., 2013).

Figure 3F:
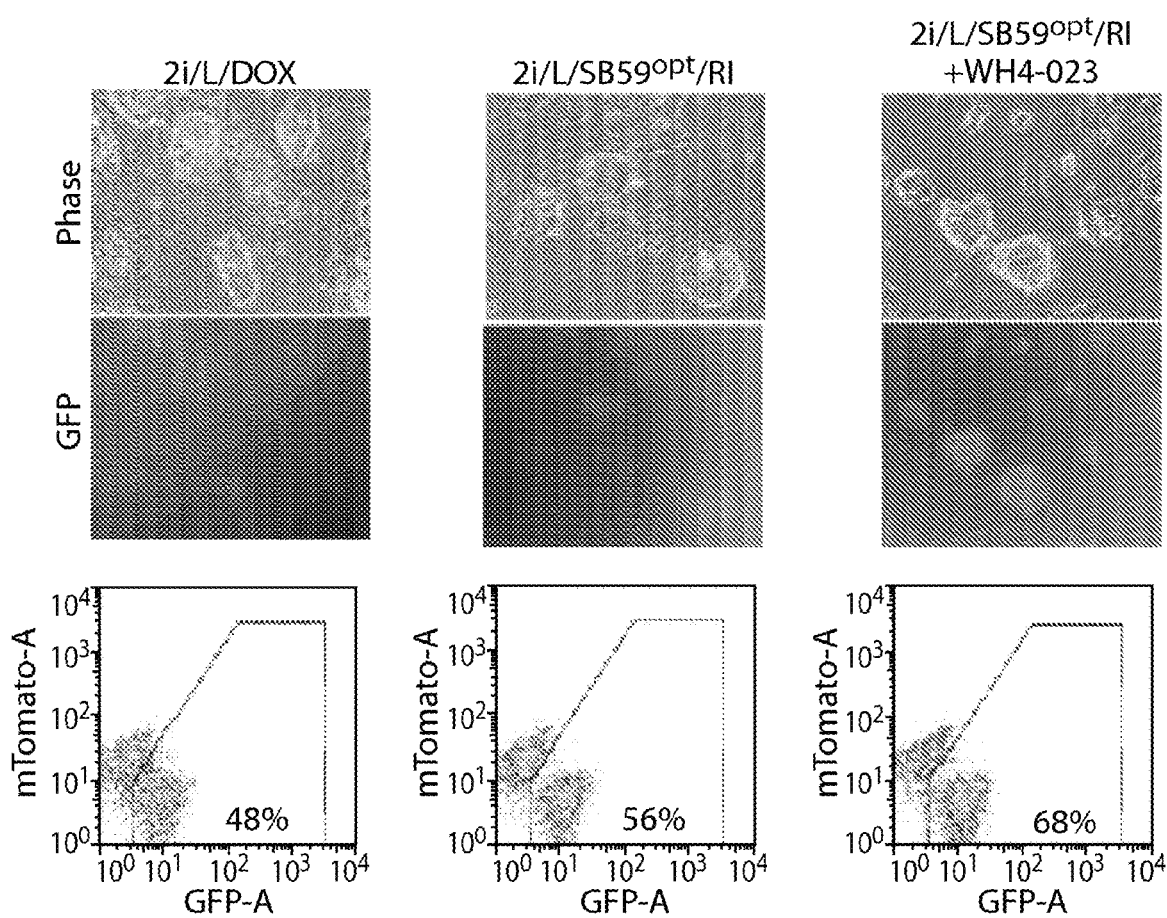
Figure 3G:
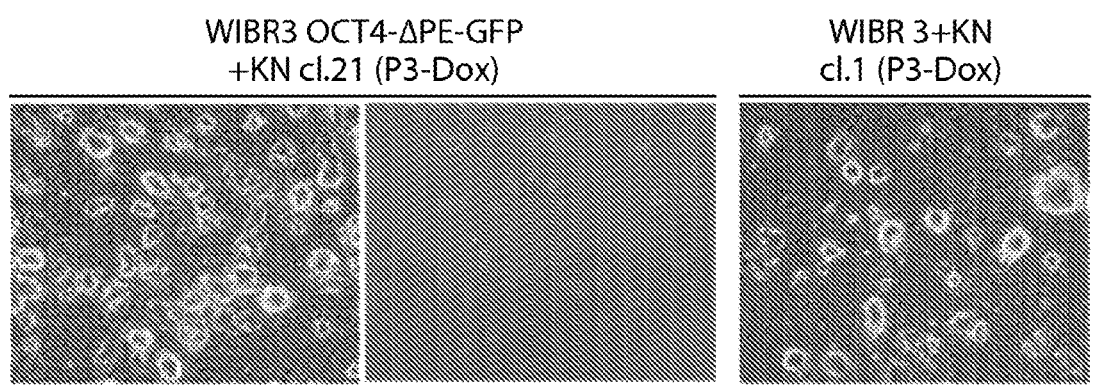
Figure 3H:
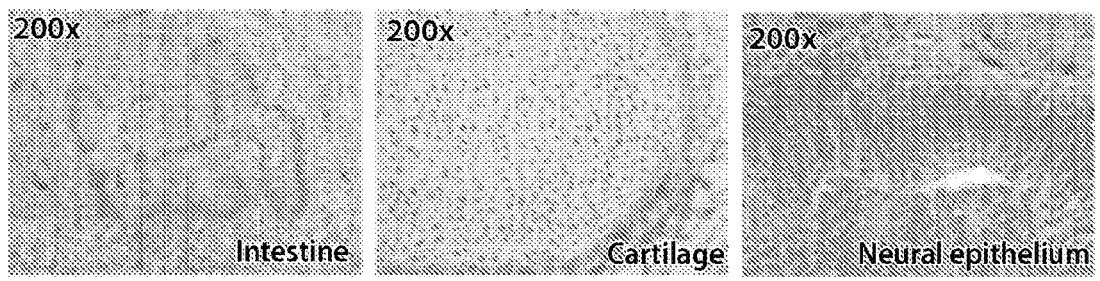

The proportion of viable OCT4-ΔPE-GFP+ cells after DOX withdrawal was further improved by combining optimized concentrations of PD0325901, CHIR99021 and SB590885 with 1 μM WH-4-023 (FIG. 3F). The ROCK inhibitor Y-27632, which improved the proportion of viable GFP+ cells, was also included (FIG. 10C). Finally, improved morphology upon long-term culture was observed without DOX by replacing CHIR99021 with an alternative GSK3 inhibitor, IM12 (FIG. 3G and FIG. 10D). Pluripotency of putative naïve human ESCs maintained under these conditions was confirmed by generation of high-grade teratomas including tissues representing all three germ layers after subcutaneous injection in NOD/SCID mice (FIG. 3H). In summary, a combination of five compounds have been provided, including inhibitors of MEK, GSK3, BRAF, ROCK and SRC, that supports the expansion of viable OCT4-ΔPE-GFP+ human pluripotent cells after removal of exogenous transcription factor expression.

Derivation of Genetically Unmodified Naïve Human ESCs in 5i/L

Figure 4A:
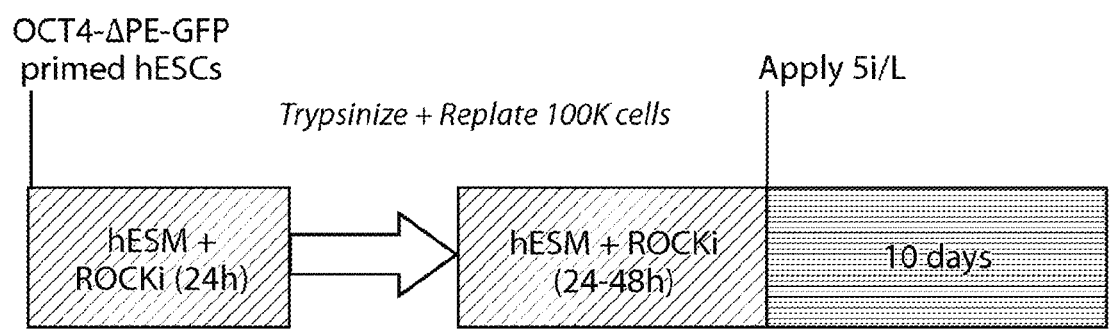
FIGS. 4A-4G show the direct conversion of conventional human ESCs to naïve pluripotency in 5i/L.
Figure 4B:
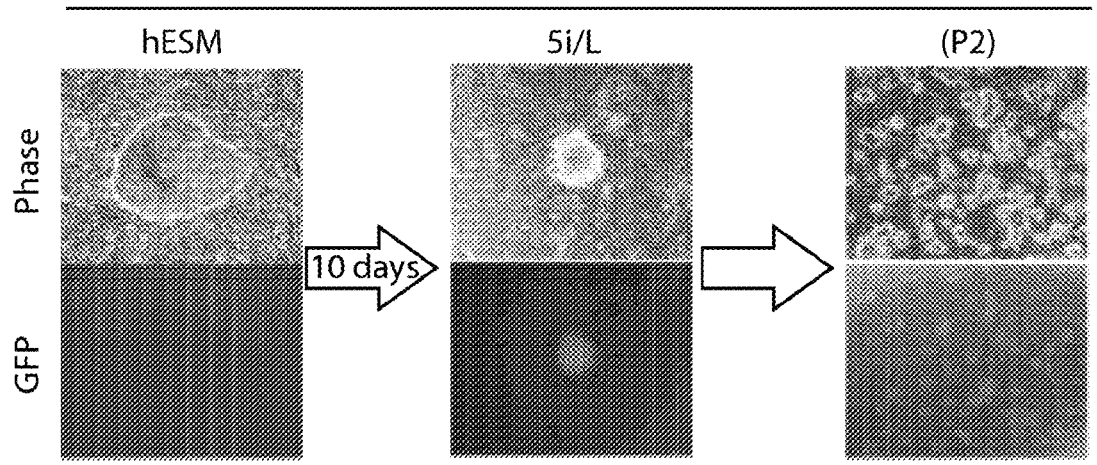
Figure 4C:
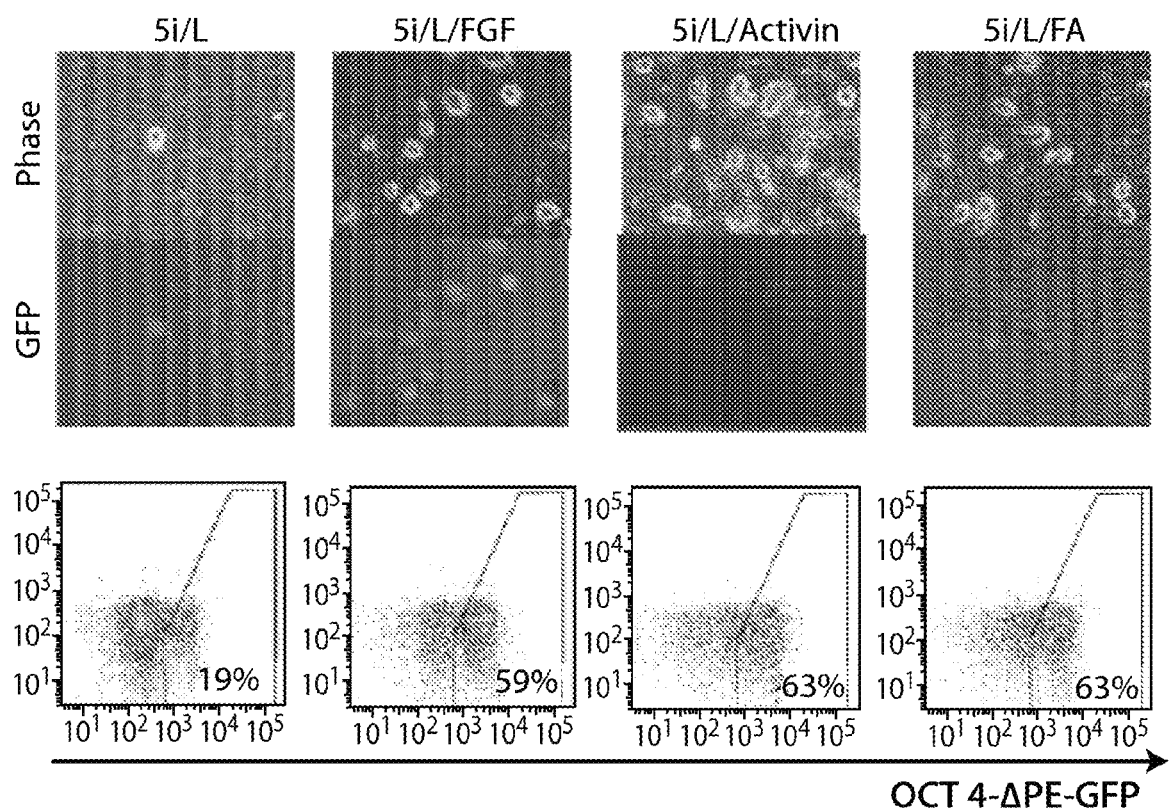
Figure 4D:
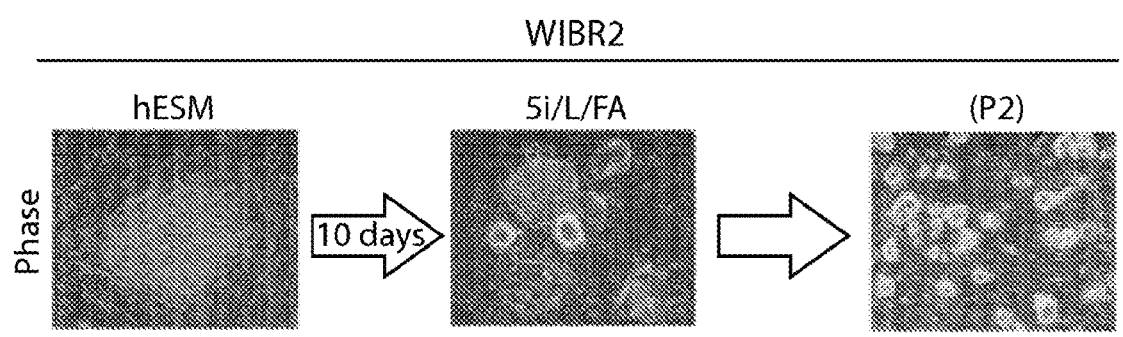
Figure 4E:
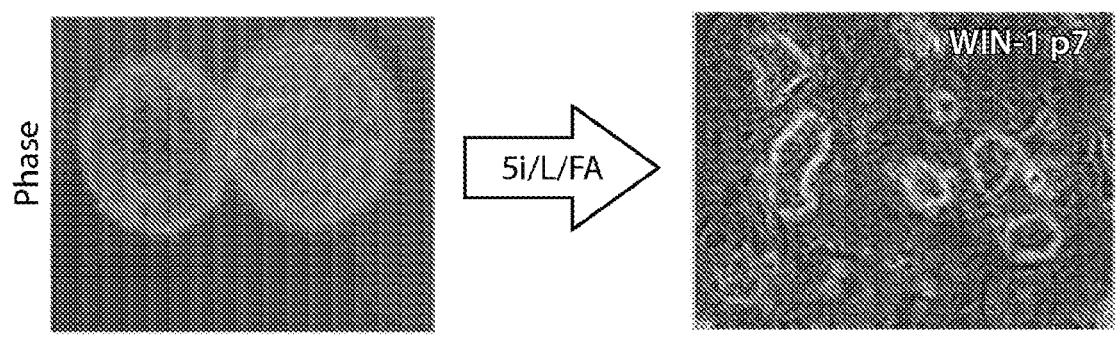

The consequences of applying the optimized 5i/L medium to conventional human ESCs was investigated in the absence of ectopic factor expression. Not surprisingly, this highly selective inhibitor cocktail generated widespread cell death within 2 days of treatment. However, the emergence of a small number of dome-shaped colonies was observed within 10 days that were positive for the OCT4-ΔPE-GFP reporter allele (FIG. 4B). In addition, these colonies were efficiently isolated and clonally expanded after dissociation in trypsin (FIG. 4B). The appearance of these OCT4-ΔPE-GFP+ cells using the optimized chemical conditions suggested that genetic manipulation, such as overexpression of KLF2 and NANOG, may be dispensable for driving primed human ESCs to the naïve state. However, the slow and inefficient kinetics of this chemical conversion event led us to consider whether providing additional growth factor support might boost the efficiency of naïve cell induction. Provision of 5i/L supplemented with FGF and Activin A (5i/L/FA) enhanced the kinetics of OCT4-ΔPE-GFP induction (FIG. 4C), and enabled conversion of wild-type WIBR2 primed human ESCs into a cell state with identical morphology and normal karyotype (FIG. 4D and FIG. 11A). Given the selective nature of the 5i culture regimen, it is speculated that additional growth factor support prolongs the time window during which primed human ESCs are amenable to convert to the naïve state. Consideration was taken toward culture conditions and if they would support the direct derivation of novel ESC lines from human blastocysts. Application of 5i/L/FA to human blastocyst outgrowths resulted in the establishment of a human ESC line with a similar dome-shaped colony morphology and normal karyotype (FIG. 4E and FIG. 11B). Hence, 5i/L/FA promotes induction of OCT4-ΔPE-GFP activity in the absence of reprogramming transgenes, and the derivation of putative naïve human ESCs directly from blastocysts.

Figure 4F:
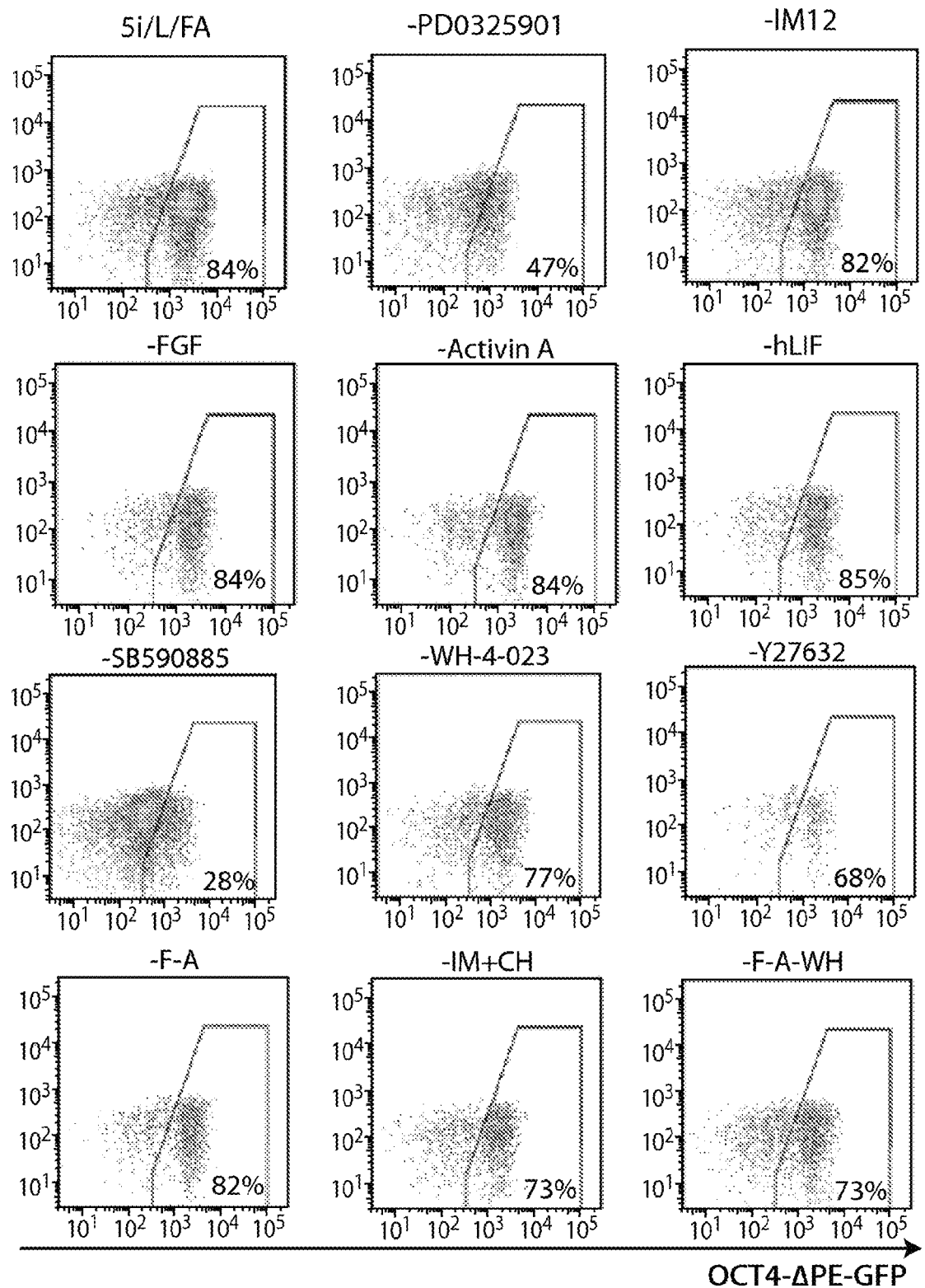
Figure 4G:
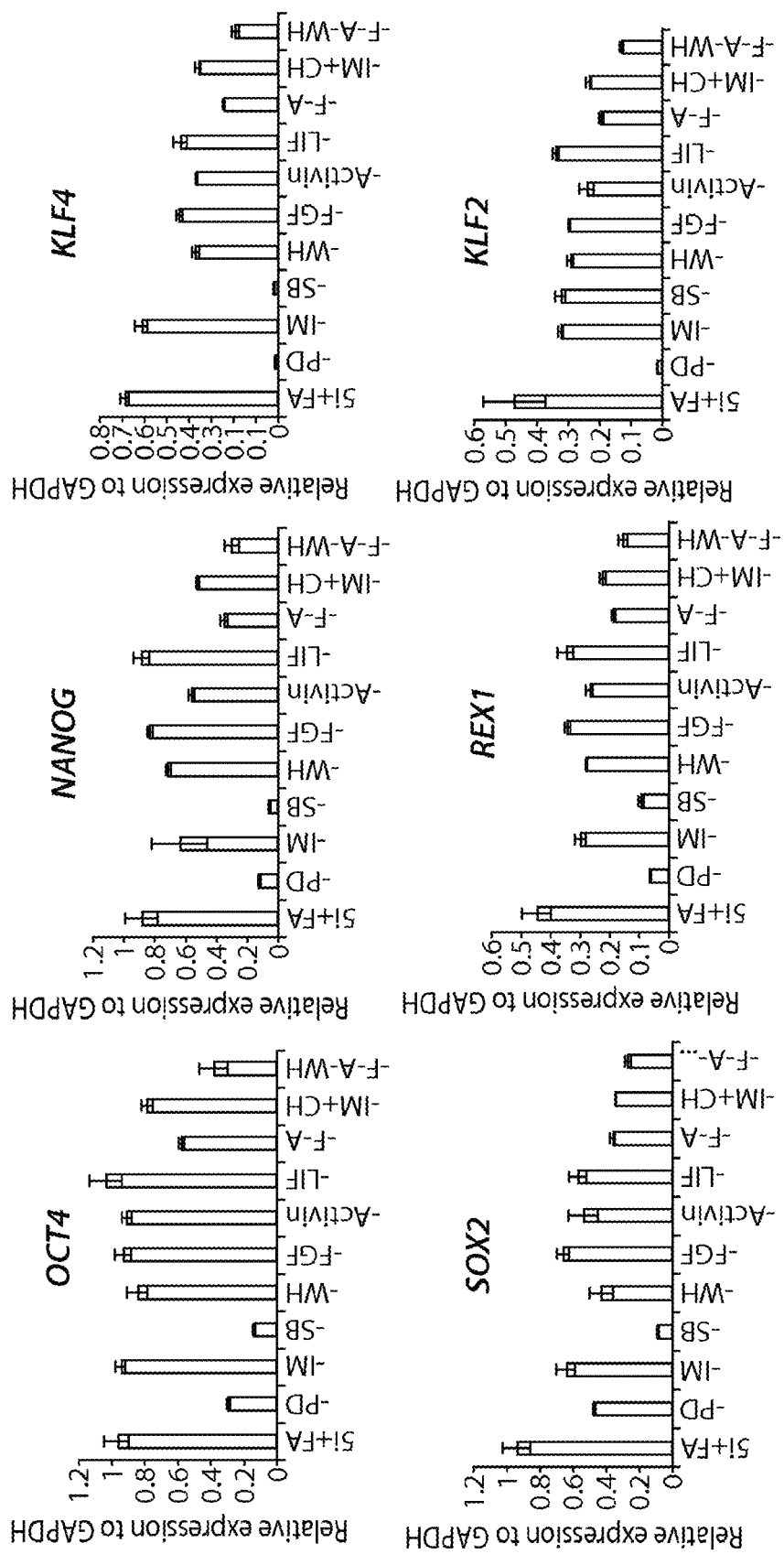

To investigate the relative contribution of individual components in 5i/L/FA medium, single kinase inhibitors or growth factors were removed from a clonal line of OCT4-ΔPE-GFP+ cells derived in the absence of transgenes. Withdrawal of the MEK inhibitor PD0325901 or BRAF inhibitor SB590885 resulted in the rapid and widespread loss of colony morphology (FIG. 11C), OCT4-ΔPE-GFP reporter activity (FIG. 4F) and pluripotency gene expression (FIG. 4G). Withdrawal of the SRC inhibitor WH-4-023 caused a change in morphology (FIG. 11C) and slight reduction in OCT4-ΔPE-GFP reporter activity (FIG. 4F). In addition, withdrawal of the ROCK inhibitor Y-27632 caused a significant reduction in proliferation (FIG. 11C). On the other hand, withdrawal of FGF had no apparent effect by any of the parameters examined, which is consistent with this growth factor being involved in the maintenance of primed pluripotency. Similarly, withdrawal of Activin A did not cause a reduction in OCT4-ΔPE-GFP activity (FIG. 4F). However, more differentiation and reduced expression was observed of pluripotency genes when FGF and Activin A were removed together (FIG. 4G and FIG. 11C). Surprisingly, reporter activity and pluripotency gene expression were unaffected by the removal of either GSK3 inhibition or hLIF (FIG. 4F-G). Therefore, the maintenance of OCT4-ΔPE-GFP reporter activity is dependent primarily on MEK inhibition and BRAF inhibition, while robust proliferation of GFP+ cells requires ROCK inhibition. Recombinant FGF enhances the induction of naïve reporter activity, but can be omitted in established GFP+ cells.

Evaluation of Alternative Culture Systems for Naïve Human Pluripotency

Figure 5B:
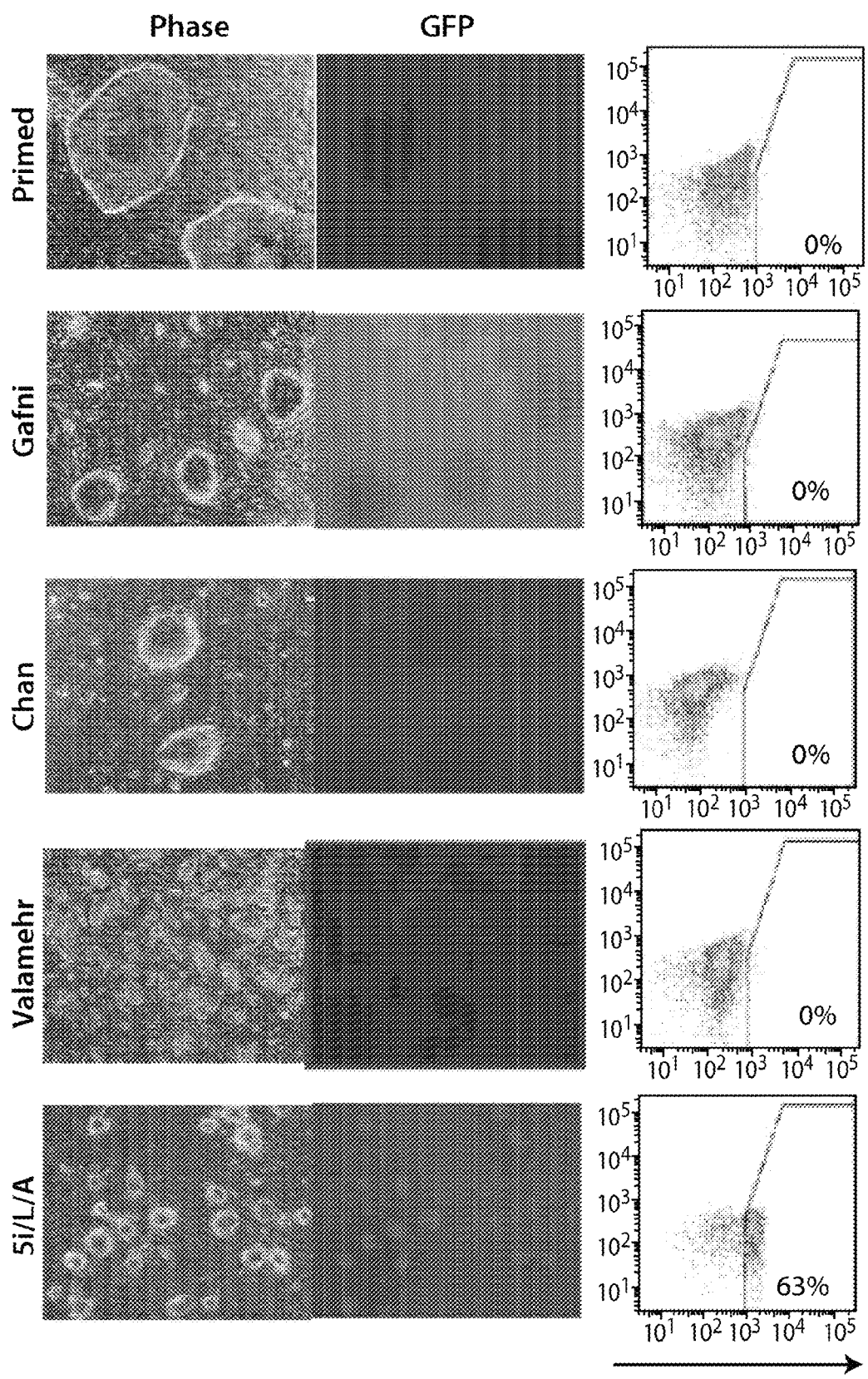
Figure 5C:
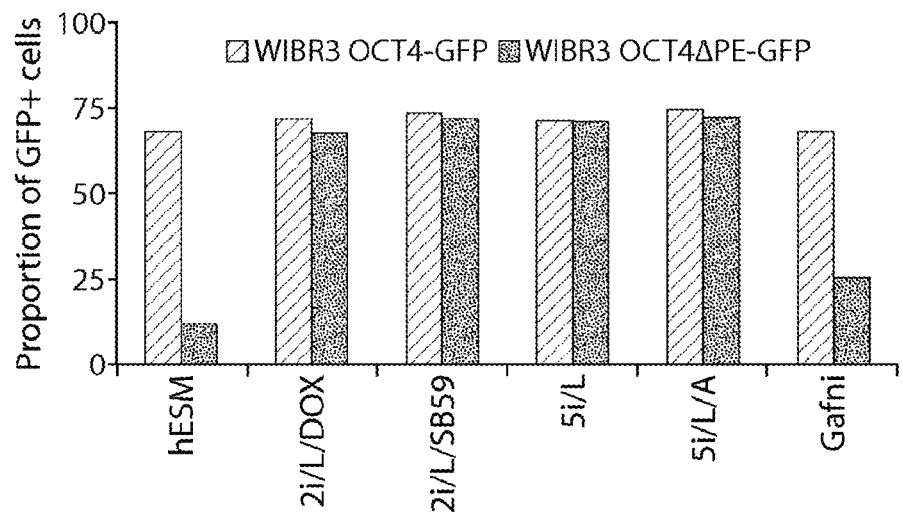

Recently, several groups reported alternative conditions for inducing a naïve pluripotent state in conventional human ESCs (Chan et al., 2013; Gafni et al., 2013; Valamehr et al., 2014; Ware et al., 2014). Comparison of the culture components in these studies with the media shows both commonalities and differences (FIG. 5A). All previously published protocols for naïve human pluripotency include 2i. Another ubiquitous component is FGF, which is added either as a recombinant protein (Gafni et al., 2013; Valamehr et al., 2014; Ware et al., 2014) or present at high levels in mTesr basal medium (Chan et al., 2013). However, the use of additional FGF-Raf-Erk inhibitors, the primary hits from the kinase inhibitor screen, was not previously reported. Furthermore, while these studies considered various criteria for defining naïve human pluripotency, endogenous OCT4 distal enhancer activity was not assessed. Therefore, it was examined whether previously published culture conditions for naïve human pluripotency could activate the reporter system. Remarkably, increased levels of OCT4-ΔPE-GFP activity were exclusively observed upon application of 5i/L/A (FIG. 5B). Whereas the naïve conditions described in Gafni et al. (2013) were capable of maintaining regular OCT4-GFP reporter activity after removal of KLF2 and NANOG expression, these conditions did not maintain OCT4-ΔPE-GFP activity (FIG. 5C). This result is consistent with the observation that none of six JNK inhibitors and seven p38 MAP kinase inhibitors present in the kinase inhibitor library showed ability to maintain OCT4-ΔPE-GFP activity after withdrawal of KLF2 and NANOG expression (FIG. 2B and FIG. 9A). These findings suggest that the combination of kinase inhibitors induces a novel and distinct state of human pluripotency.

Figure 5D:
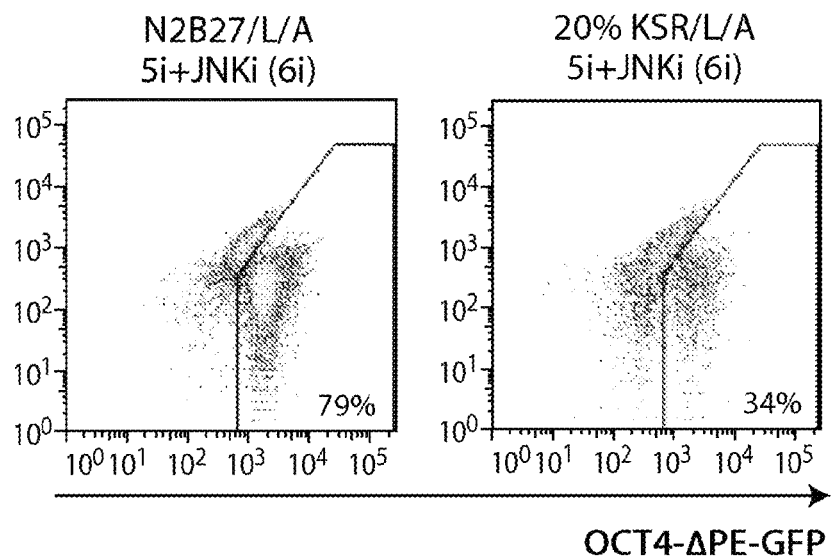
Figure 5E:
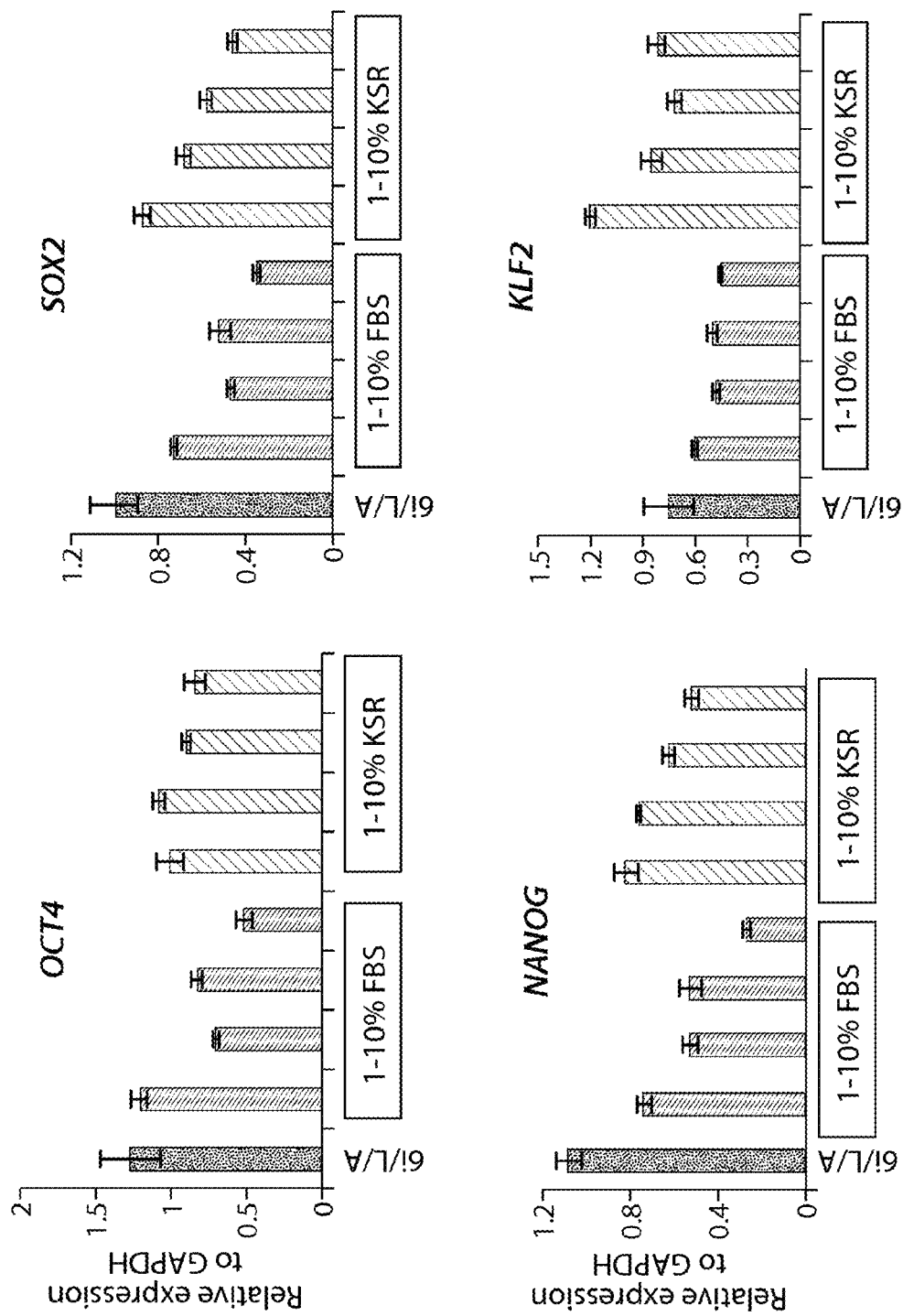
Figure 5F:
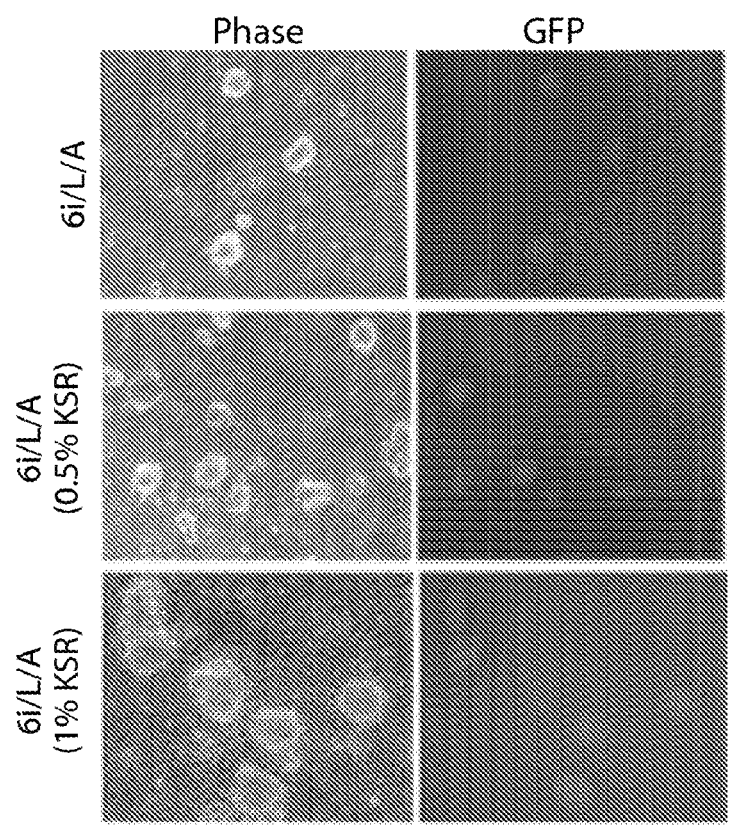

The kinase inhibitors reported by Hanna and colleagues may have an additive effect in combination with the 5i/L/A medium. Inclusion of the JNK inhibitor SP600125 and/or p38 MAP kinase inhibitor BIRB796 did not affect the proportion of OCT4-ΔPE-GFP+ cells (FIG. 12A). However, an increase in expression of KLF4 and KLF2 was observed upon addition of SP600125 (FIG. 12B). A beneficial effect was not observed when adding insulin (FIG. 12A and FIG. 5C). Another difference between the naïve human studies reported to date is the use of 20% knock-out serum replacement (KSR) or Albumax-containing medium (Gafni et al., 2013; Valamehr et al., 2014; Ware et al., 2014) vs. serum-free N2B27 medium (this study). The consequences of applying the inhibitor cocktail in the presence of 20% KSR was therefore investigated. Remarkably, this switch in basal medium resulted in the rapid attenuation of OCT4-ΔPE-GFP signal concomitant with morphological changes (FIG. 5D and FIG. 12C). Hence, a high concentration of KSR appears to be detrimental to naïve reporter activity, independent of additional kinase inhibition. In fact, a reduction in pluripotency gene expression was observed upon provision of KSR or FBS at concentrations >5% (FIG. 5E). However, including 0.5-1% KSR in combination with 5i/L, JNKi and Activin A (6i/L/A) enhanced the efficiency of OCT4-ΔPE-GFP induction from the primed state (FIG. 5F). It is concluded that the induction and maintenance of OCT4-ΔPE-GFP+ human ESCs is highly sensitive to the choice of basal medium.

Molecular Characterization of Naïve Human Pluripotency

Figure 6A:
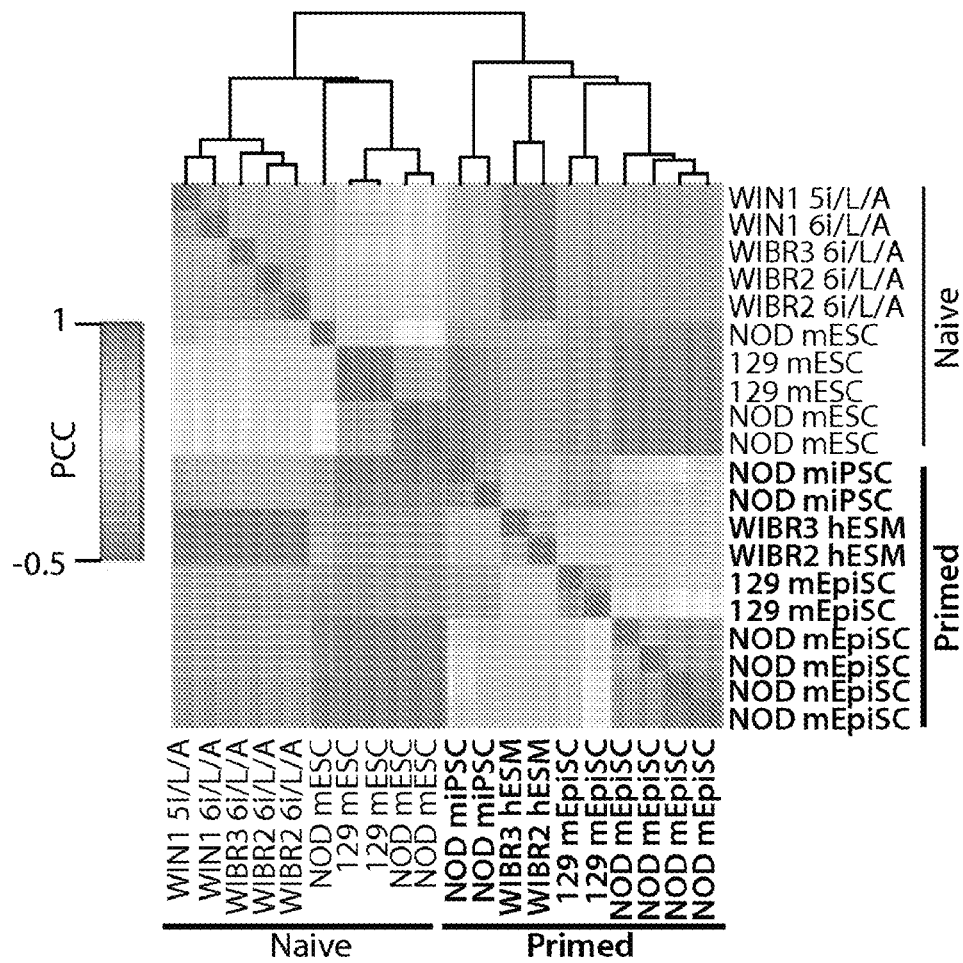
FIGS. 6A-6H show the transcriptional profiling of naïve human ESCs in 5i/L/A.
Figure 6B:
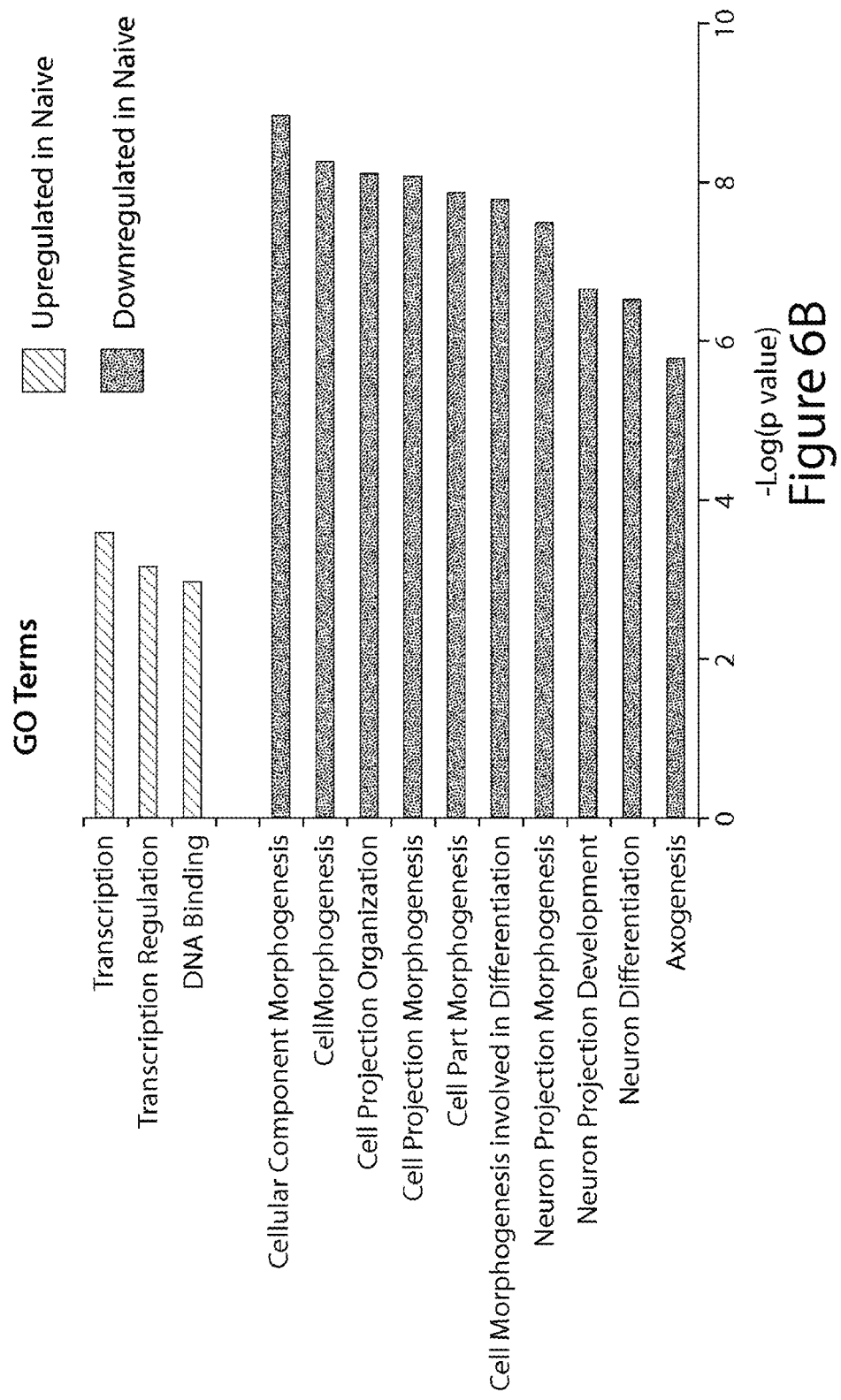
Figure 6C:
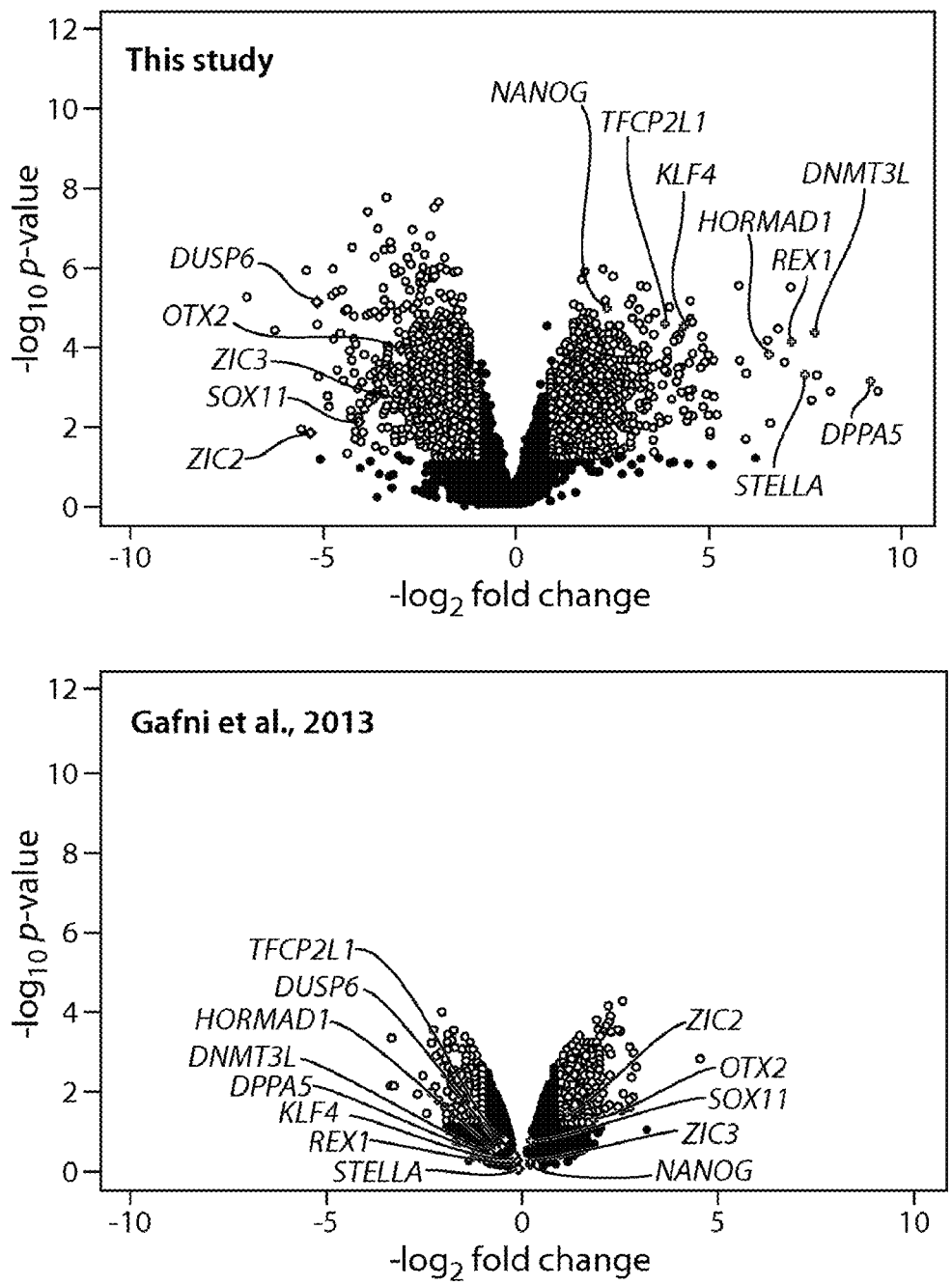
Figure 6D:
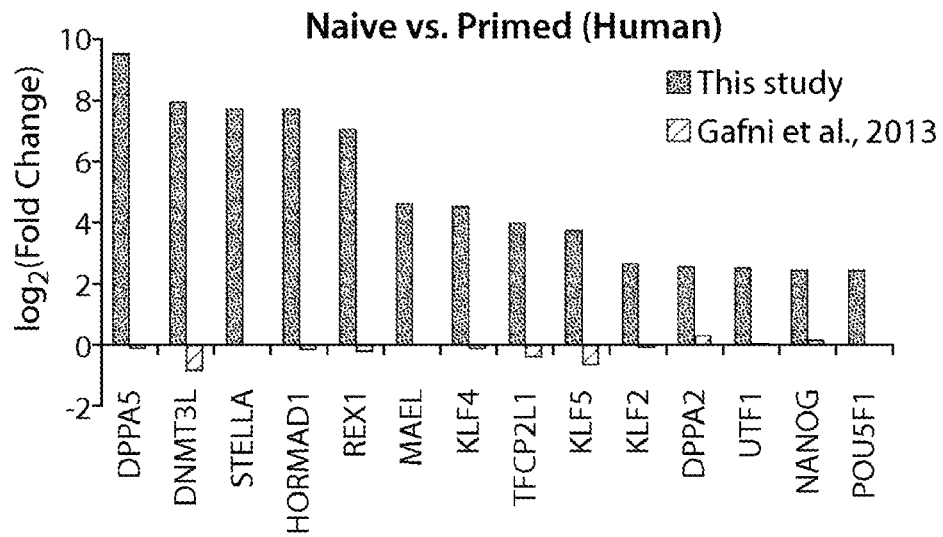
Figure 6E:
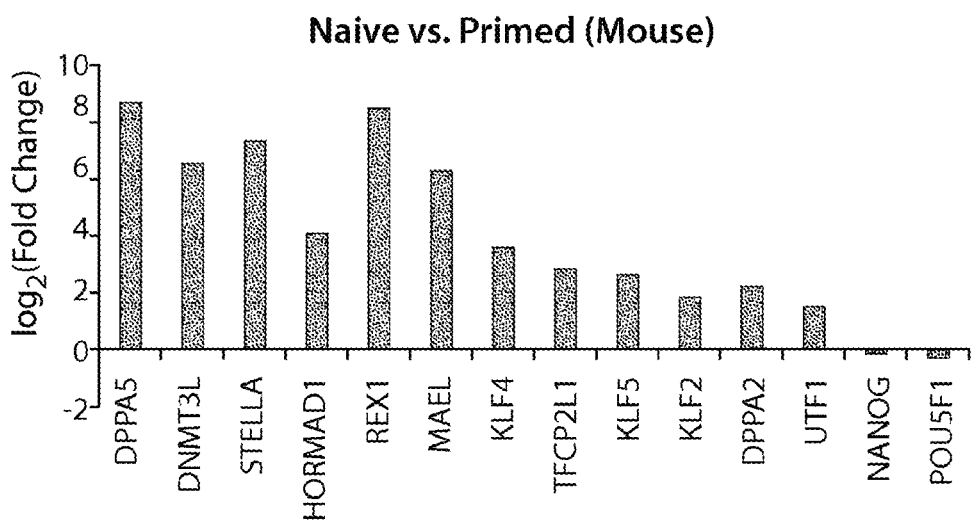
Figure 6F:
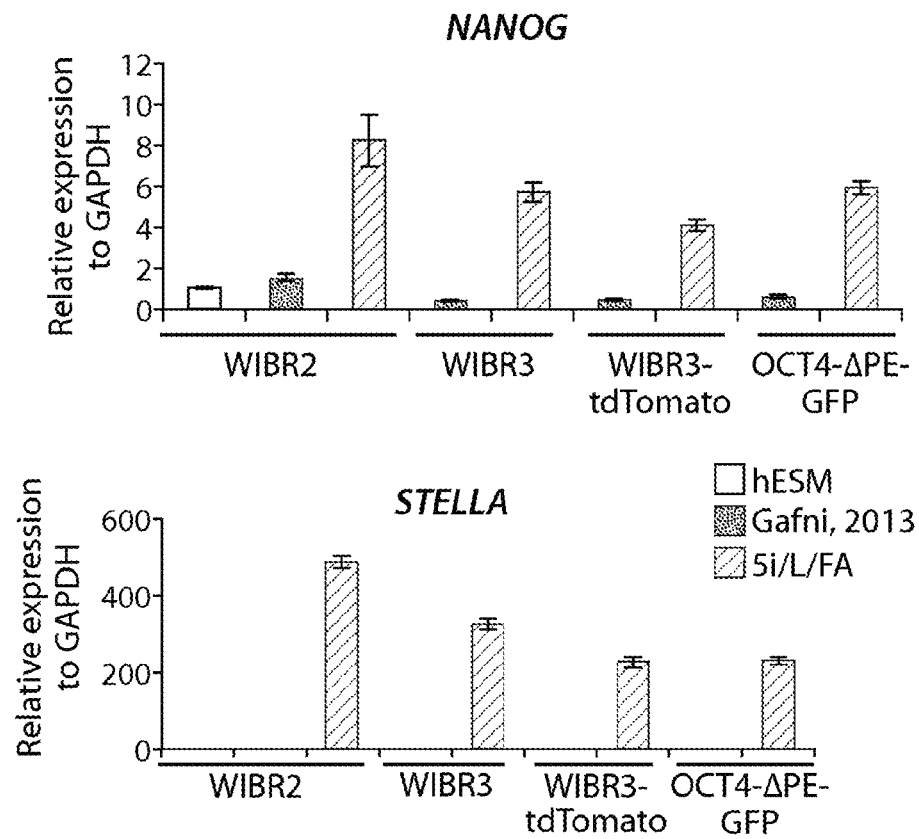

To characterize the gene expression profile of naïve human ESCs derived under the conditions, RNA was collected from WIBR2 and WIBR3 human ESCs cultured in primed medium or 6i/L/A, and embryo-derived naïve WIN1 cells cultured in 5i/L/A or 6i/L/A. Expression analysis on Affymetrix arrays were then performed using RNA spike-in normalization (Loven et al., 2012). Cross-species gene expression comparison demonstrated that primed WIBR2 and WIBR3 human ESCs clustered with primed mouse EpiSCs, while naïve human ESCs cultured in 5i/L/A or 6i/L/A clustered with naïve mouse ESCs (FIG. 6A). The naïve human ESC samples clustered together closely, and addition of the JNK inhibitor had little impact on overall gene expression in the naïve state (FIG. 6A). The most upregulated gene ontology (GO) categories in the naïve state were associated with transcriptional control, while the most down-regulated categories were implicated in neural differentiation and cell adhesion (FIG. 6B). Comparison with the gene expression data published by Gafni et al. (2013) indicated that the conditions for naïve human pluripotency induce greater transcriptional differences with the primed state (FIG. 6C). In particular, 3238 differentially expressed genes (DEGs) were observed compared to primed human ESCs, whereas Gafni et al. reported 831 DEGs (where $\log_2$ fold change >1 and <−1 & p<0.05). Intriguingly, the naïve human ESCs exhibited marked downregulation of the transcription factors OTX2 and ZIC2/3, which were recently shown to direct Oct4 to primed state-specific enhancer sites in mouse EpiSCs (Buecker et al., 2014). In contrast, these transcription factors were slightly upregulated in the naïve human ESCs reported by Gafni et al. (2013). The list of differentially expressed genes was examined for presence of bona fide markers of naïve pluripotency. A number of transcription factors typically associated with the self-renewal and pluripotency of mouse ESCs ranked among the most highly upregulated genes in 5i/L/A or 6i/LIA, including DPPA5, DPPA3 (also known as STELLA), DPPA2, REX1, KLF4, KLF5, TFCP2L1, and NANOG (FIG. 6D-E). Expression of these factors was largely unaffected in the conditions for naïve human pluripotency described by Gafni et al. (2013) (FIG. 6D). Upregulation of transcripts specific to naïve pluripotency under the conditions was confirmed by qRT-PCR (FIG. 6F and FIG. 13A). A recent single cell RNA-Seq analysis revealed that these markers of naïve pluripotency were highly upregulated at the morula and epiblast stages of human pre-implantation development compared to conventional (primed) human ESCs (Yan et al., 2013) (FIG. 13B). This suggests that 5i/L/A culture re-establishes an early pre-implantation epiblast-specific gene expression signature that is lost during derivation of human ESCs under conventional conditions. Hence, the conditions induce a unique transcriptional profile in human ESCs, characterized by upregulation of naïve-specific transcription factors and suppression of neural differentiation genes.

Figure 6G:
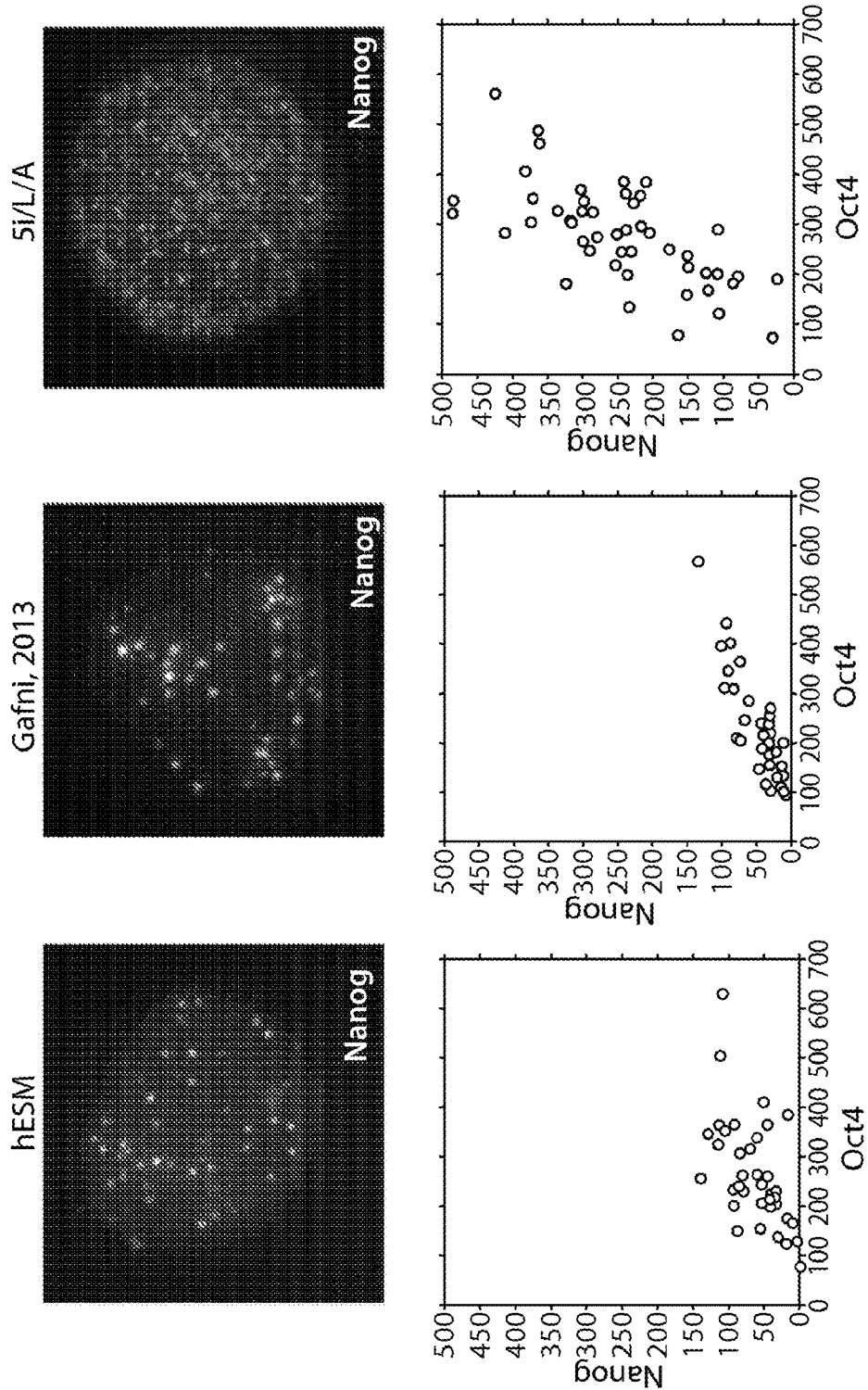
Figure 6H:
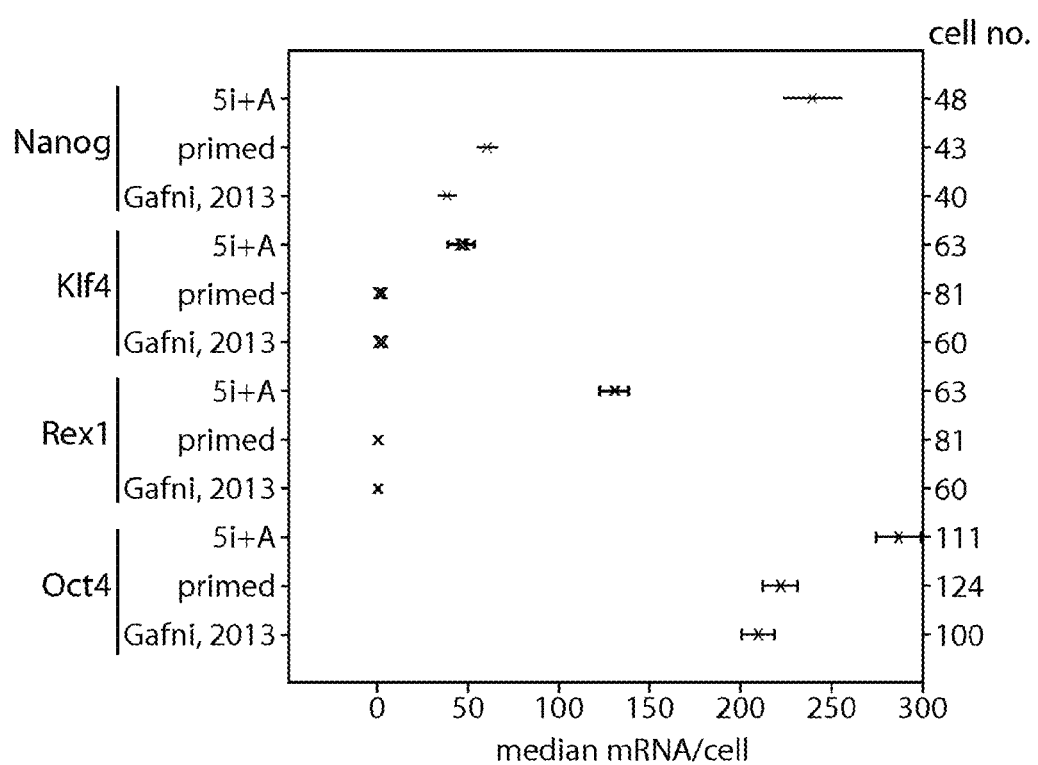

A defining feature of ground state pluripotency in the mouse system is that transcriptional regulators such as Nanog are expressed homogeneously (Wray et al., 2010). In contrast, human ESCs under conventional conditions are known to exhibit significant variability in gene expression at the single cell level (Hough et al., 2009). It was therefore investigated whether human ESCs cultured under the conditions are more homogeneous with respect to expression of NANOG by single molecule (sm) RNA FISH analysis. The mean number of OCT4 mRNAs per cell was approximately similar between WIBR2 human ESCs in primed medium, the naïve medium of Gafni et al. (2013), and 5i/L/A (FIG. 6G). As expected from array and qRT-PCR analyses (FIG. 6D and FIG. 6F), the mean number of NANOG mRNAs per cell was significantly higher in 5i/L/A (FIG. 6G-H). Intriguingly, 5i/L/A culture also resulted in reduced cell-to-cell variability in NANOG expression (FIG. 13C). Thus, the increased expression level of NANOG in 5i/L/A does not arise from a subset of cells, but is uniform across the population. It was also confirmed by RNA FISH that single cells cultured in 5i/L/A express significantly higher numbers of KLF4 and REX1 mRNAs (FIG. 6H).

Figure 7A:
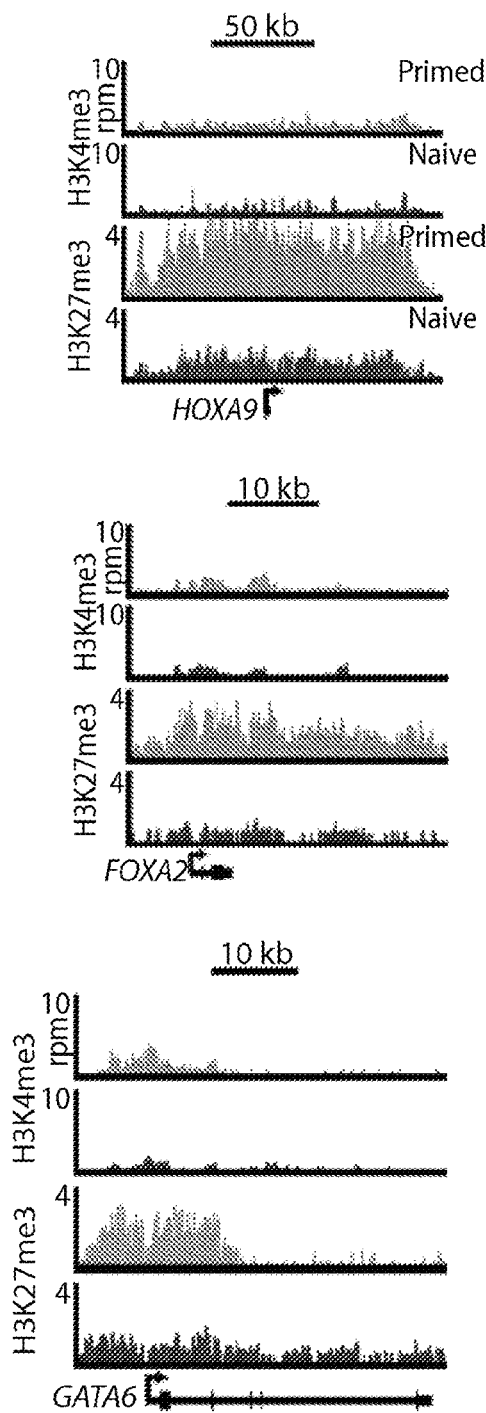
FIGS. 7A-7G show the chromatin landscape of naïve human pluripotency.
Figure 7B:
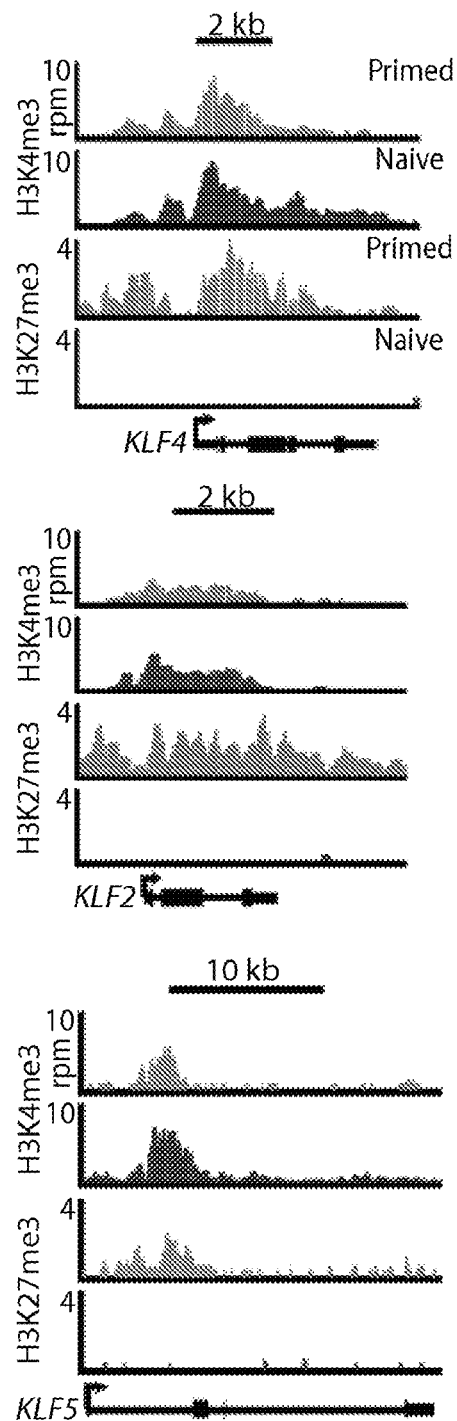
Figure 7C:
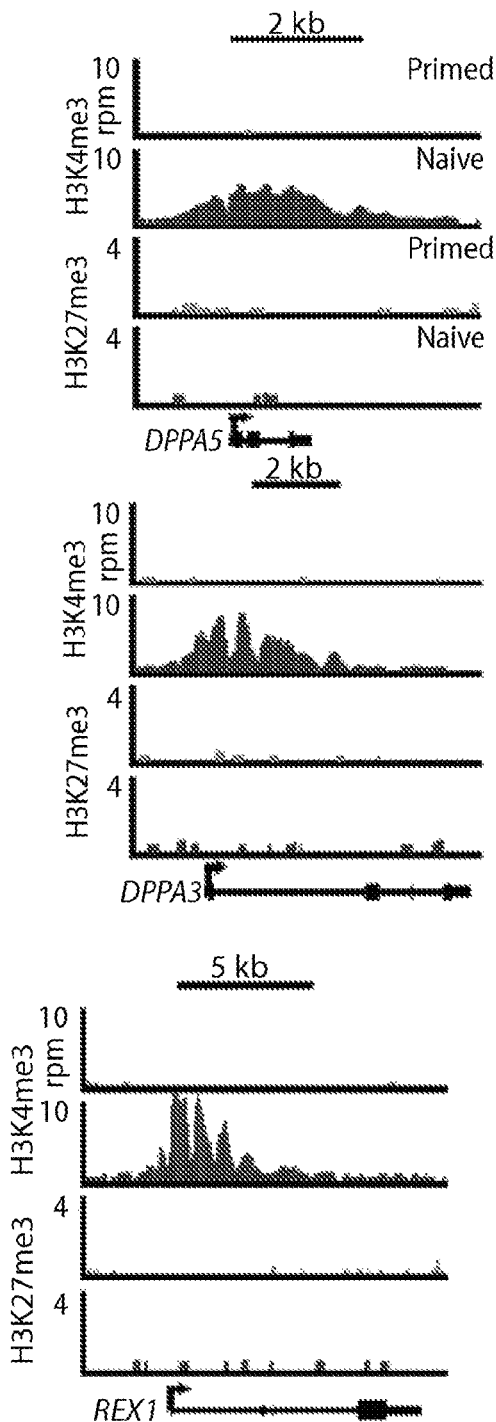
Figure 7D:
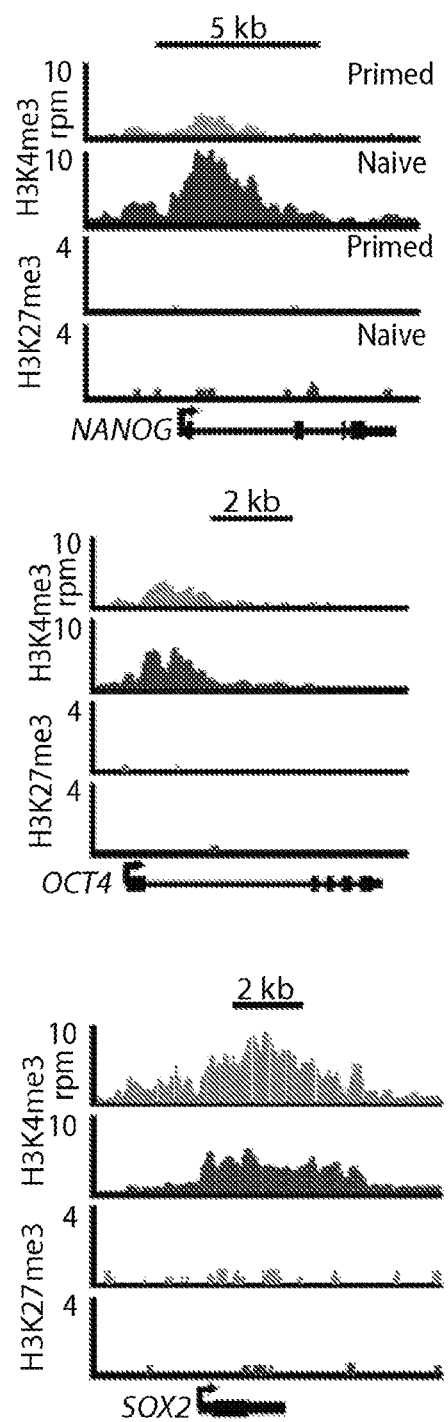
Figure 7E:
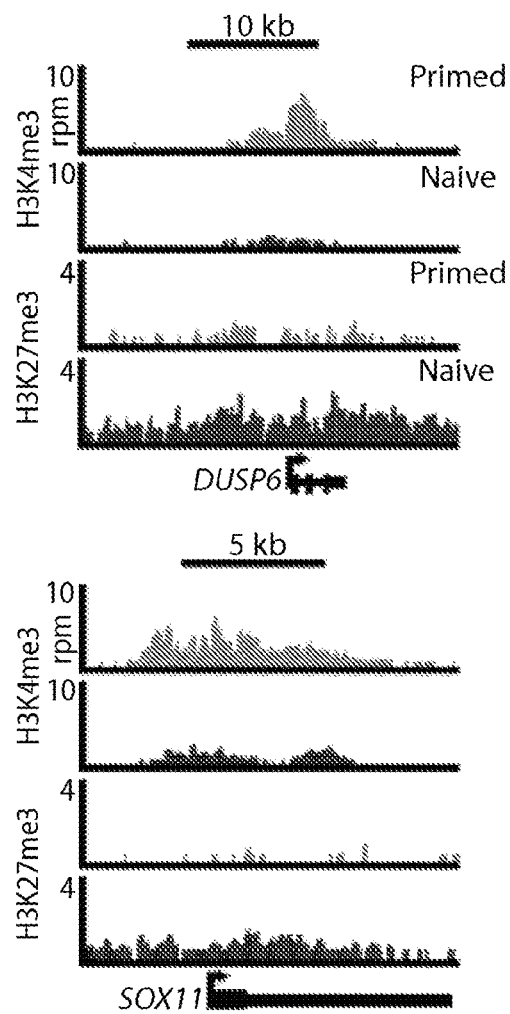
Figure 7F:
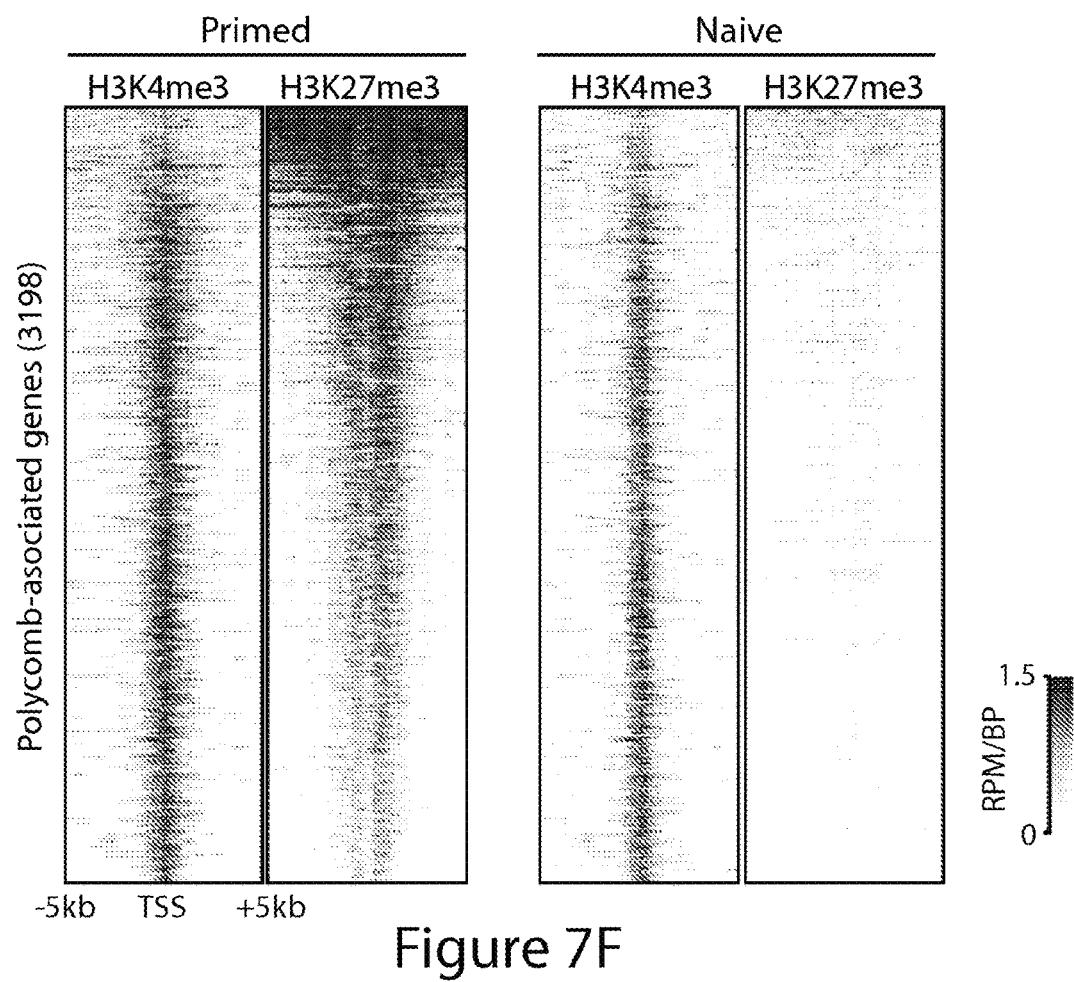
Figure 7G:
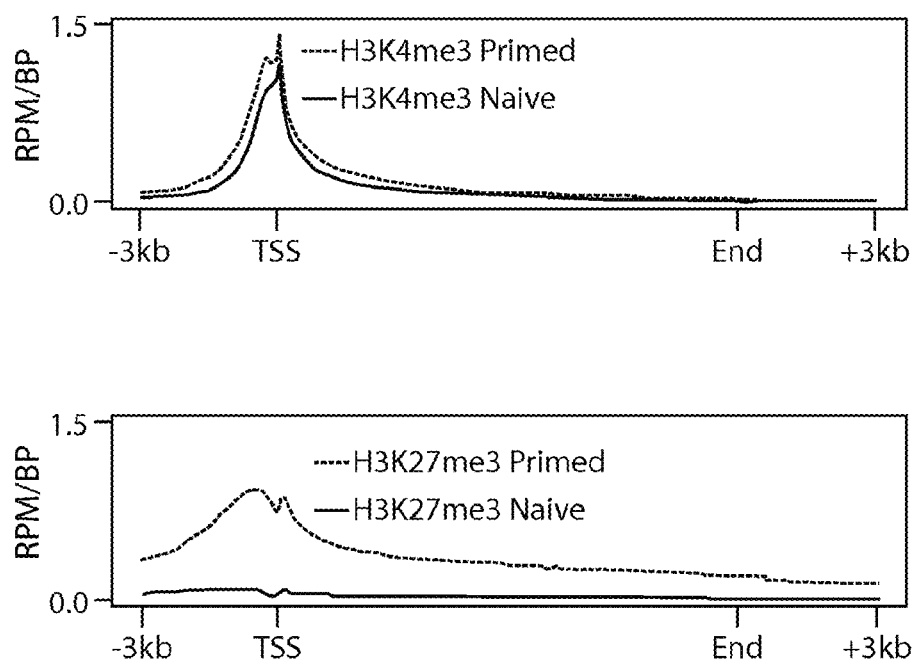

Chromatin immunoprecipitation was performed followed by DNA sequencing (ChIP-Seq) analysis to determine the genome-wide distribution of the activation-associated marker, trimethylation of histone 3 lysine 4 (H3K4me3) and the transcriptional-silencing-associated marker, trimethylation of histone 3 lysine 27 (H3K27me3). Developmental genes with bivalent domains marked by the presence of both H3K4me3 and H3K27me3 in the primed state, such as HOXA9, FOXA2, GATA6 and NKX2.5, exhibited a reduced H3K27me3 signal in the naïve state (FIG. 7A). The histone methylation profile at loci encoding naïve-specific pluripotency regulators was then examined. KLF2, KLF4 and KLF5 were bivalent in the primed state, but almost entirely lost the H3K27me3 mark in the naïve state (FIG. 7B). Other markers of ground state pluripotency that are highly upregulated in the system, such as DPPA5, DPPA3 and REX1, acquired H3K4me3 signal during conversion from primed to naïve pluripotency (FIG. 7C). The core pluripotency determinants OCT4, SOX2 and NANOG were marked exclusively by H3K4me3 in naïve and primed human ESCs (FIG. 7D). However, a slightly higher H3K4me3 signal was observed at the NANOG promoter in the naïve state, consistent with increased transcription (FIG. 6A). Finally, while H3K27me3 was generally depleted from promoter regions in the naïve state, some genes that were strongly down-regulated acquired H3K27me3 signal (FIG. 7E). Consistent with observations in naïve pluripotent mouse ESCs (Marks et al., 2012), H3K27me3 was strongly reduced at the transcriptional start site (TSS) of Polycomb group target genes in human ESCs cultured in 6i/L/A (FIG. 7F-G). It is concluded that the conversion from primed to naïve human pluripotency is accompanied by the dynamic rearrangement of activating and repressive histone modifications. In particular, transcriptional upregulation of specific regulators of ground state pluripotency is associated with the gain of H3K4me3 or loss of H3K27me3 in a locus-specific manner.

Developmental Potential of Human ESCs in 5i/L/A

The classical assay for pluripotency of human ESCs and iPSCs is to examine teratomas formed after subcutaneous injection in NOD/SCID mice. Naïve human ESCs converted under the optimized conditions contributed to high-grade teratomas containing tissues representing all three germ layers, regardless of the presence of FGF and Activin in the medium (FIG. 14A). As the practical utility of human pluripotent stem cells resides mainly in the capacity to differentiate into defined lineages in vitro, the suitability of naïve human ESCs in directed differentiation was also investigated. For this purpose human ESCs derived from WIBR2 and WIBR3 primed cells in 5i/L/A were subjected to a five-step protocol for hepatic differentiation (Si-Tayeb et al., 2010). Hepatocytes positive for the mature markers AFP and HNF4a were generated from both lines of naïve ESCs (FIG. 14B).

In the mouse system, naïve ESCs are functionally distinguished by the capability to colonize the embryo and contribute to chimeric animals. In contrast, primed EpiSCs contribute only very inefficiently to chimeras (Brons et al., 2007; Tesar et al., 2007). Hanna and colleagues reported that human ESCs cultured in the presence of 2i, hLIF, JNK inhibition, p38 inhibition, FGF and TGFβ contributed robustly to interspecies chimeric embryos after injection into mouse morulae (Gafni et al., 2013). This assay would provide a defining functional read-out for naïve human pluripotency. Therefore, a reproduction this experiment was attempted using human ESCs containing constitutive GFP and tdTomato transgenes in the AAVS1 locus. In total, 860 embryos (8-cell, morula and blastocyst stages) were injected with GFP and tdTomato-labeled human ESCs cultured in 5i/L/A. 436 embryos were also injected with C1-AAVS1-GFP cells provided by the Hanna laboratory, which were cultured using the conditions reported by Gafni et al. (2013). Only a fraction of embryos (43-45%) were recovered from both experimental groups at E10.5, suggesting that the majority of embryos had been reabsorbed. No fluorescent signal was detected by microscopy in any embryos recovered at E10.5 (FIG. 14). Thus, contribution of human ESCs in 5i/L/A or the medium of Gafni et al. (2013) to interspecies chimeras is currently too inefficient for detection by standard visual inspection. The development of novel optical clearing methods may facilitate the investigation of low-contribution interspecies chimerism in the future.

The proliferation of naïve human embryonic stem cells was found to be enhanced by the reduction or removal of GSK3 inhibition. A transgene-dependent naïve human embryonic stem (ES) cell line, a subclone of WIBR3, was used to titrate different concentrations of inhibitors in 5i/L/A (see Theunissen et al., Cell Stem Cell, 2014). The cell line used is dependent on Doxycycline (DOX) to maintain the expression of two lentiviral transgenes, KLF2 and NANOG. Flow cytometry revealed that proportion of cells positive for the OCT4-ΔPE-GFP reporter in 2i/L/DOX was approximately 60% (FIG. 15A). The cell line was karyotyped, and showed a normal (46, XX) karyotype. A titration assay was performed to determine the optimal concentrations of small molecule inhibitors to maintain naïve human DES cells. The cells were subject to sequential passaging by single cell dissociation at low density (1:10) under four conditions: 2i/L, 5i/L/A, t5i/L/A (0.2 µM GSK3 inhibitor IM12) and 4i/L/A (removal of GSK3 inhibitor IM12). Flow cytometry demonstrated that the two latter conditions showed higher proportions of cells positive for the OCT4-ΔPE-GFP reporter (FIG. 15B). Quantitative RT-PCR was performed, and it confirmed the downregulation of exogenous KLF2 and NANOG transgenes and the primed marker VIMENTIN, as well as the upregulation of naïve markers, including KLF4, REX1 and STELLA in t5i/L/A and 4i/L/A (FIG. 15C).

The proliferation of naïve human ES cells in the presence of different Wnt signal modulators was quantified after the withdrawal of DOX from the transgene-dependent cell line described above. In a six-well plate, $1 \times 10^5$ cells were seeded per well and cells were dissociated and re-seeded at a 1:5 density for three successive passages. Cell numbers at successive passages were recorded under six conditions (n=2 per group): 2i/L/DOX (control), 2i/L, 5i/L/A, 4i/L/A (removal of GSK3 inhibitor IM12), 4i/L/A+CHIR99021 (1 µM), and 4i/L/A+IWR1 (2.5 µM). The proliferation was significantly elevated in 4i/L/A compared to 5i/L/A at passages 2 and 3 (FIG. 16). Replacing IM12 with an alternative GSK3 inhibitor, CHIR99021, or addition of the Wnt inhibitor, IWR1, did not further stimulate the proliferation of naïve human cells, demonstrating that the reduction or removal of GSK3 inhibitors further enhances human ES cell proliferation.

The induction of naïve human pluripotency in 5i/L/A or 4i/L/A is associated with X chromosome reactivation. Using TALEN-mediated targeting of both alleles of the X-linked MECP2 gene, a fluorescent reporter system for the X chromosome status of human ES cells was established (FIG. 17A). Conversion of the naïve state in 5i/L/A or 4i/L/A (-IM12) results in activation of the tdTomato-labeled allele and GFP activity is maintained, regardless of whether the starting color is tdTomato-positive (FIG. 17C) or GFP-positive (FIG. 17B). Therefore, the induction of naïve human pluripotency results from a switch toward biallelic expression of X-linked genes.

Discussion

The morphological, molecular and functional similarity between human ESCs and mouse post-implantation epiblast-derived EpiSCs has prompted widespread interest in capturing the equivalent of a naïve pluripotent stem cell in humans. At the outset of this study, it was considered that the identification of putative naïve human ESCs would be greatly facilitated by the availability of a selective reporter system. In the mouse, enhancer-specific regulation of Oct4 expression is a defining molecular distinction between ESCs and EpiSCs in vitro (Brons et al., 2007; Tesar et al., 2007), and between the ICM and post-implantation epiblast in vivo (Yeom et al., 1996). The primed-specific PE from an OCT4-GFP allele were deleted using TALEN-mediated genome editing in human ESCs (Hockemeyer et al., 2011). The observation that OCT4-GFP expression was down-regulated following PE removal demonstrated that this reporter behaves as expected in the primed state. Conversely, OCT4-ΔPE-GFP activity was strongly induced by combined overexpression of KLF2 and NANOG. A systematic approach was then taken to screen a diverse collection of 230 kinase inhibitors for the capacity to maintain OCT4-ΔPE-GFP activity after removal of ectopic KLF2 and NANOG expression. Through iterative screening a combination of five kinase inhibitors were identified that maintained viable GFP-positive cells upon transgene withdrawal. Moreover, this kinase inhibitor cocktail was capable of inducing OCT4-ΔPE-GFP activity when applied directly to conventional (primed) human ESCs in the complete absence of reprogramming factors.

Previous studies describing the isolation of naïve human ESCs also reported transgene-free interconversion from primed to naïve pluripotency (Chan et al., 2013; Gafni et al., 2013; Valamehr et al., 2014; Ware et al., 2014). However, these published protocols did not induce OCT4-ΔPE-GFP activity. This finding was surprising given that Gafni et al. (2013) reported activation of luciferase and BAC reporter constructs under the control of the DE of human OCT4, while Ware et al. (2014) observed increased DNaseI hypersensitivity at the DE in human ESCs derived in 2i and FGF. Thus, the activation of the DE of endogenous OCT4 may represent a more stringent criterion for the naïve pluripotent state. A difference in the kinetics of conversion was noticed using previously reported protocols: whereas the emergence of naïve colonies under the conditions is a relatively protracted process (ca. 10 days) that occurs after widespread cell death, the application of previously described naïve conditions was accompanied with little cell death and rapid expansion in primed human ESCs. The slow kinetics of conversion observed in 5i/L/A are consistent with a reprogramming event towards a novel cellular state, rather than adaptation to an identity closer to conventional (primed) human ESCs. Thus, the observations suggest that the chemical screens used in this study have identified a distinct and novel state of human pluripotency.

There are several important differences in the selection of inhibitors, growth factors and basal medium between this protocol and previously reported protocols for capturing naïve human pluripotency. First, the primary screen for maintenance of OCT4-ΔPE-GFP activity identified a number of inhibitors of BRAF and upstream RTKs, including VEGFR1/2, FGFR1 and EGFR. These targets were not previously implicated in the establishment of naïve human pluripotency. The requirement for further inhibition of FGF-Ras-MEK signaling contrasts with the dependence on FGF signaling reported in the published protocols. In the mouse system, independence of FGF signaling is considered to be a hallmark of ground state pluripotent cells, which are primed for commitment by auto-inductive Fgf4/Erk signaling (Silva and Smith, 2008). While recombinant FGF facilitated the conversion of primed human ESCs into OCT4-ΔPE-GFP-positive cells, the removal of FGF did not affect reporter activity or pluripotency gene expression in established OCT4-ΔPE-GFP-positive cells.

Unlike previous approaches for capturing transgene-independent naïve human ESCs, the protocol uses serum-free N2B27 basal medium. This basal medium was originally used in neural differentiation, but was subsequently adapted by the Smith laboratory to develop fully defined conditions for self-renewal of mouse ESCs in combination with LIF and BMP4 (Ying et al., 2003) or 2i (Ying et al., 2008). Maintenance of OCT4-ΔPE-GFP activity is highly sensitive to the choice of basal medium: addition of as little as 5% FBS or KSR resulted in attenuation of the GFP signal concomitant with a reduction in pluripotency gene expression. However, a low percentage (<1%) of KSR improved the kinetics of inducing GFP-positive cells from the primed state. Thus, previously proposed basal media for naïve human ESCs do not appear to support the maintenance of OCT4-ΔPE-GFP reporter activity.

Transcriptional profiling of human ESCs cultured in 5i/L/A and primed human ESCs indicated that the conditions induce a dramatic upregulation in the expression of transcription factors typically associated with naïve pluripotency, suggesting that induction of endogenous OCT4-ΔPE-GFP activity correlates with a broader expression signature of the naïve state. Intriguingly, many of the top-ranked differentially expressed genes were also enriched during human pre-implantation development, specifically at the morula and epiblast stages, in comparison to conventional human ESCs (Yan et al., 2013). These transcripts include several factors that possess the capability to instate the naïve pluripotent program in mouse EpiSCs, such as KLF4 (Guo et al., 2009), NANOG (Silva et al., 2009), and TFCP2L1 (Martello et al., 2013; Ye et al., 2013). The latter gene is of particular interest as it was identified as the main effector downstream of LIF-STAT3 signaling in naïve mouse ESCs. Induction of TFCP2L1 provides a rationale for the surprising observation that withdrawal of hLIF does not affect OCT4-ΔPE-GFP activity or pluripotency gene expression in the naïve human ESCs. Strong upregulation of REX1 and STELLA were also observed, both of which are used as reporters of ground state pluripotency in the mouse system (Hayashi et al., 2008; Marks et al., 2012). Of further interest is that the conditions for naïve human pluripotency induced significant downregulation of OTX2 and ZIC2/3, which drive primed-specific enhancer binding of Oct4 in mouse EpiSCs (Buecker et al., 2013). In contrast, these transcription factors were upregulated in the naïve human ESCs reported by Gafni et al. (2013), while typical markers of naïve pluripotency such as NANOG, KLF2, KLF4, STELLA, REX1 and TFCP2L1 were not induced.

Human ESCs can be expanded in the presence of 2i and various additional inhibitors and growth factors while maintaining a dome-shaped morphology and expression of some pluripotency genes (Gafni et al., 2013; Valamehr et al., 2014; Ware et al., 2014). These protocols offer practical advantages, including enhanced proliferation and single cell cloning, which benefit applications such as gene targeting. As such, these studies facilitate the application of human iPSCs in disease modeling and regenerative medicine. The state of pluripotency defined here is based on activation of the endogenous OCT4-ΔPE-GFP allele along with a transcriptional and epigenomic profile that closely resembles naïve mouse pluripotency, and is distinct from previously reported naïve human ESCs.

REFERENCES

Bao, S., Tang, F., Li, X., Hayashi, K., Gillich, A., Lao, K., and Surani, M. A. (2009). Epigenetic reversion of post-implantation epiblast to pluripotent embryonic stem cells. Nature 461, 1292-1295.

Brons, I. G., Smithers, L. E., Trotter, M. W., Rugg-Gunn, P., Sun, B., Chuva de Sousa Lopes, S. M., Howlett, S. K., Clarkson, A., Ahrlund-Richter, L., Pedersen, R. A., et al. (2007). Derivation of pluripotent epiblast stem cells from mammalian embryos. Nature 448, 191-195.

Chan, Y. S., Goke, J., Ng, J. H., Lu, X., Gonzales, K. A., Tan, C. P., Tng, W. Q., Hong, Z. Z., Lim, Y. S., and Ng, H. H. (2013). Induction of a human pluripotent state with distinct regulatory circuitry that resembles preimplantation epiblast. Cell stem cell 13, 663-675.

Chen, Y., Blair, K., and Smith, A. (2013). Robust Self-Renewal of Rat Embryonic Stem Cells Requires Fine-Tuning of Glycogen Synthase Kinase-3 Inhibition. Stem cell reports 1, 209-217.

Gafni, O., Weinberger, L., Mansour, A. A., Manor, Y. S., Chomsky, E., Ben-Yosef, D., Kalma, Y., Viukov, S., Maza, I., Zviran, A., et al. (2013). Derivation of novel human ground state naïve pluripotent stem cells. Nature 504, 282-286.

Guo, G., Yang, J., Nichols, J., Hall, J. S., Eyres, I., Mansfield, W., and Smith, A. (2009). Klf4 reverts developmentally programmed restriction of ground state pluripotency. Development 136, 1063-1069.

Hall, J., Guo, G., Wray, J., Eyres, I., Nichols, J., Grotewold, L., Morfopoulou, S., Humphreys, P., Mansfield, W., Walker, R., et al. (2009). Oct4 and LIF/Stat3 additively induce Kruppel factors to sustain embryonic stem cell self-renewal. Cell stem cell 5, 597-609.

Hanna, J., Cheng, A. W., Saha, K., Kim, J., Lengner, C. J., Soldner, F., Cassady, J. P., Muffat, J., Carey, B. W., and Jaenisch, R. (2010a). Human embryonic stem cells with biological and epigenetic characteristics similar to those of mouse ESCs. Proc Natl Acad Sci USA 107, 9222-9227.

Hanna, J., Markoulaki, S., Mitalipova, M., Cheng, A. W., Cassady, J. P., Staerk, J., Carey, B. W., Lengner, C. J., Foreman, R., Love, J., et al. (2009). Metastable pluripotent states in NOD-mouse-derived ESCs. Cell stem cell 4, 513-524.

Hanna, J. H., Saha, K., and Jaenisch, R. (2010b). Pluripotency and cellular reprogramming: facts, hypotheses, unresolved issues. Cell 143, 508-525.

Hayashi, K., Lopes, S. M., Tang, F., and Surani, M. A. (2008). Dynamic equilibrium and heterogeneity of mouse pluripotent stem cells with distinct functional and epigenetic states. Cell stem cell 3, 391-401.

Hirano, K., Nagata, S., Yamaguchi, S., Nakagawa, M., Okita, K., Kotera, H., Ainscough, J., and Tada, T. (2012). Human and mouse induced pluripotent stem cells are differentially reprogrammed in response to kinase inhibitors. Stem cells and development 21, 1287-1298.

Hockemeyer, D., Wang, H., Kiani, S., Lai, C. S., Gao, Q., Cassady, J. P., Cost, G. J., Zhang, L., Santiago, Y., Miller, J. C., et al. (2011). Genetic engineering of human pluripotent cells using TALE nucleases. Nat Biotechnol 29, 731-734.

Hough, S. R., Laslett, A. L., Grimmond, S. B., Kolle, G., and Pera, M. F. (2009). A continuum of cell states spans pluripotency and lineage commitment in human embryonic stem cells. PLoS One 4, e7708.

Loven, J., Orlando, D. A., Sigova, A. A., Lin, C. Y., Rahl, P. B., Burge, C. B., Levens, D. L., Lee, T. I., and Young, R. A. (2012). Revisiting global gene expression analysis. Cell 151, 476-482.

Marks, H., Kalkan, T., Menafra, R., Denissov, S., Jones, K., Hofemeister, H., Nichols, J., Kranz, A., Stewart, A. F., Smith, A., et al. (2012). The transcriptional and epigenomic foundations of ground state pluripotency. Cell 149, 590-604.

Martello, G., Bertone, P., and Smith, A. (2013). Identification of the missing pluripotency mediator downstream of leukaemia inhibitory factor. The EMBO journal 32, 2561-2574.

Meek, S., Wei, J., Sutherland, L., Nilges, B., Buehr, M., Tomlinson, S. R., Thomson, A. J., and Burdon, T. (2013). Tuning of beta-catenin Activity is Required to Stabilise Self-renewal of Rat Embryonic Stem Cells. Stem cells.

Melichar, H., Li, O., Ross, J., Haber, H., Cado, D., Nolla, H., Robey, E. A., and Winoto, A. (2011). Comparative study of hematopoietic differentiation between human embryonic stem cell lines. PLoS One 6, e19854.

Najm, F. J., Chenoweth, J. G., Anderson, P. D., Nadeau, J. H., Redline, R. W., McKay, R. D., and Tesar, P. J. (2011). Isolation of epiblast stem cells from preimplantation mouse embryos. Cell stem cell 8, 318-325.

Nichols, J., and Smith, A. (2009). Naïve and primed pluripotent states. Cell stem cell 4, 487-492.

Osafune, K., Caron, L., Borowiak, M., Martinez, R. J., Fitz-Gerald, C. S., Sato, Y., Cowan, C. A., Chien, K. R., and Melton, D. A. (2008). Marked differences in differentiation propensity among human embryonic stem cell lines. Nat Biotechnol 26, 313-315.

Si-Tayeb, K., Noto, F. K., Nagaoka, M., Li, J., Battle, M. A., Duris, C., North, P. E., Dalton, S., and Duncan, S. A. (2010). Highly efficient generation of human hepatocyte-like cells from induced pluripotent stem cells. Hepatology 51, 297-305.

Silva, J., Barrandon, O., Nichols, J., Kawaguchi, J., Theunissen, T. W., and Smith, A. (2008). Promotion of reprogramming to ground state pluripotency by signal inhibition. PLoS biology 6, e253.

Silva, J., Nichols, J., Theunissen, T. W., Guo, G., van Oosten, A. L., Barrandon, O., Wray, J., Yamanaka, S., Chambers, I., and Smith, A. (2009). Nanog is the gateway to the pluripotent ground state. Cell 138, 722-737.

Silva, J., and Smith, A. (2008). Capturing pluripotency. Cell 132, 532-536.

Tesar, P. J., Chenoweth, J. G., Brook, F. A., Davies, T. J., Evans, E. P., Mack, D. L., Gardner, R. L., and McKay, R. D. (2007). New cell lines from mouse epiblast share defining features with human embryonic stem cells. Nature 448, 196-199.

Theunissen, T. W., van Oosten, A. L., Castelo-Branco, G., Hall, J., Smith, A., and Silva, J. C. (2011). Nanog overcomes reprogramming barriers and induces pluripotency in minimal conditions. Current biology: CB 21, 65-71.

Valamehr, B., Robinson, M., Abujarour, R., Rezner, B., Vranceanu, F., Le, T., Medcalf, A., Lee, T. T., Fitch, M., Robbins, D., et al. (2014). Platform for Induction and Maintenance of Transgene-free hiPSCs Resembling Ground State Pluripotent Stem Cells. Stem cell reports 2, 366-381.

Wang, W., Yang, J., Liu, H., Lu, D., Chen, X., Zenonos, Z., Campos, L. S., Rad, R., Guo, G., Zhang, S., et al. (2011). Rapid and efficient reprogramming of somatic cells to induced pluripotent stem cells by retinoic acid receptor gamma and liver receptor homolog 1. Proc Natl Acad Sci USA 108, 18283-18288.

Ware, C. B., Nelson, A. M., Mecham, B., Hesson, J., Zhou, W., Jonlin, E. C., Jimenez-Caliani, A. J., Deng, X., Cavanaugh, C., Cook, S., et al. (2014). Derivation of naïve human embryonic stem cells. Proc Natl Acad Sci USA 111, 4484-4489.

Wray, J., Kalkan, T., and Smith, A. G. (2010). The ground state of pluripotency. Biochemical Society transactions 38, 1027-1032.

Yan, L., Yang, M., Guo, H., Yang, L., Wu, J., Li, R., Liu, P., Lian, Y., Zheng, X., Yan, J., et al. (2013). Single-cell RNA-Seq profiling of human preimplantation embryos and embryonic stem cells. Nature structural & molecular biology 20, 1131-1139.

Ye, S., Li, P., Tong, C., and Ying, Q. L. (2013). Embryonic stem cell self-renewal pathways converge on the transcription factor Tfcp2l1. The EMBO journal 32, 2548-2560.

Yeom, Y. I., Fuhrmann, G., Ovitt, C. E., Brehm, A., Ohbo, K., Gross, M., Hubner, K., and Scholer, H. R. (1996). Germline regulatory element of Oct-4 specific for the totipotent cycle of embryonal cells. Development 122, 881-894.

Ying, Q. L., Nichols, J., Chambers, I., and Smith, A. (2003). BMP induction of Id proteins suppresses differentiation and sustains embryonic stem cell self-renewal in collaboration with STAT3. Cell 115, 281-292.

Ying, Q. L., Wray, J., Nichols, J., Batlle-Morera, L., Doble, B., Woodgett, J., Cohen, P., and Smith, A. (2008). The ground state of embryonic stem cell self-renewal. Nature 453, 519-523.

Brambrink, T., Foreman, R., Welstead, G. G., Lengner, C. J., Wernig, M., Suh, H., and Jaenisch, R. (2008). Sequential expression of pluripotency markers during direct reprogramming of mouse somatic cells. Cell stem cell 2, 151-159.

Costa, M., Dottori, M., Sourris, K., Jamshidi, P., Hatzistavrou, T., Davis, R., Azzola, L., Jackson, S., Lim, S., Pera, M., et al. (2007). A method for genetic modification of human embryonic stem cells using electroporation. Nat Protoc 2, 792-796.

Faddah, D. A., Wang, H., Cheng, A. W., Katz, Y., Buganim, Y., and Jaenisch, R. (2013). Single-cell analysis reveals that expression of nanog is biallelic and equally variable as that of other pluripotency factors in mouse ESCs. Cell stem cell 13, 23-29.

Hockemeyer, D., Soldner, F., Cook, E. G., Gao, Q., Mitalipova, M., and Jaenisch, R. (2008). A drug-inducible system for direct reprogramming of human somatic cells to pluripotency. Cell stem cell 3, 346-353.

Itzkovitz, S., Lyubimova, A., Blat, I. C., Maynard, M., van Es, J., Lees, J., Jacks, T., Clevers, H., and van Oudenaarden, A. (2011). Single-molecule transcript counting of stem-cell markers in the mouse intestine. Nat Cell Biol 14, 106-114.

Lengner, C. J., Gimelbrant, A. A., Erwin, J. A., Cheng, A. W., Guenther, M. G., Welstead, G. G., Alagappan, R., Frampton, G. M., Xu, P., Muffat, J., et al. (2010). Derivation of pre-X inactivation human embryonic stem cells under physiological oxygen concentrations. Cell 141, 872-883.

Raj, A., Rifkin, S. A., Andersen, E., and van Oudenaarden, A. (2010). Variability in gene expression underlies incomplete penetrance. Nature 463, 913-918.

Raj, A., van den Bogaard, P., Rifkin, S. A., van Oudenaarden, A., and Tyagi, S. (2008). Imaging individual mRNA molecules using multiple singly labeled probes. Nat Methods 5, 877-879.

Soldner, F., Hockemeyer, D., Beard, C., Gao, Q., Bell, G. W., Cook, E. G., Hargus, G., Blak, A., Cooper, O., Mitalipova, M., et al. (2009). Parkinson's disease patient-derived induced pluripotent stem cells free of viral reprogramming factors. Cell 136, 964-977.

Soldner, F., Laganiere, J., Cheng, A. W., Hockemeyer, D., Gao, Q., Alagappan, R., Khurana, V., Golbe, L. I., Myers, R. H., Lindquist, S., et al. (2011). Generation of isogenic pluripotent stem cells differing exclusively at two early onset Parkinson point mutations. Cell 146, 318-331.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A method for changing the pluripotency state of a human cell to a more naïve state, the method comprising:

culturing a pluripotent human stem cell in a medium comprising N2B27 supplemented with:

(i) 1 μM

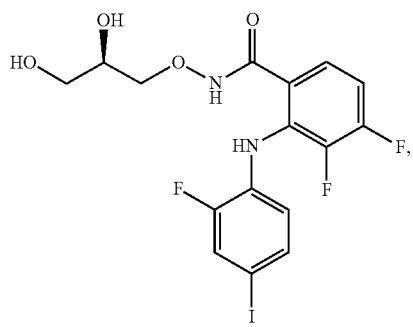

(PD0325901)

(ii) 0.5 μM

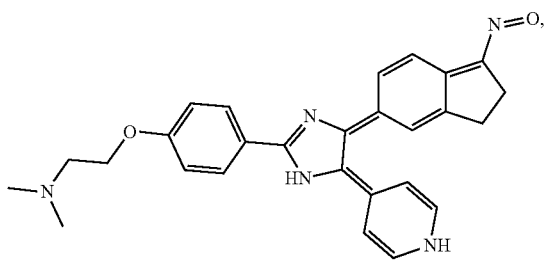

(SB590885)

(iii) 1 μM

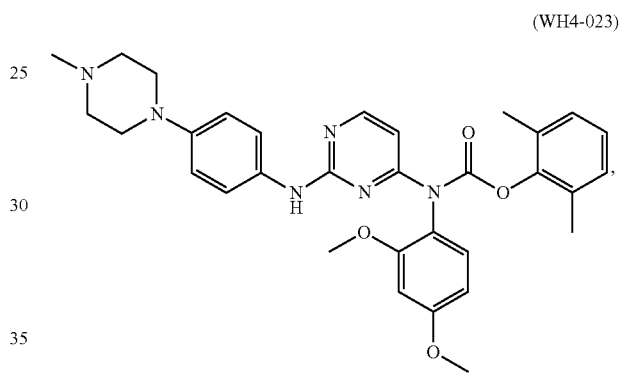

(WH4-023)

(iv) 10 μM

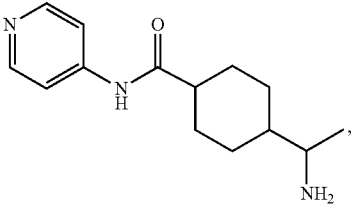

(Y-27632)

(v) 1 μM

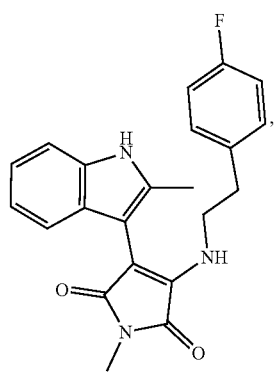

(IM-12)

(vi) 20 ng/mL Activin A, and (vii) 20 ng/mL recombinant human leukemia inhibitory factor; and maintaining the cell in culture under conditions suitable and a time sufficient to convert the pluripotency state of the cell to a more naïve state, wherein the more naïve state cell (i) exhibits OCT4 distal enhancer activity, (ii) upregulates TFCP2L1, REX1, and STELLA, and/or (iii) downregulates OTX2 and ZIC2/3 when compared to before the pluripotent stem cell is cultured in the medium.

2. The method of claim 1, wherein the cell is a human embryonic stem cell.

3. The method of claim 1, wherein the cell is a human induced pluripotent stem cell (iPS cell).

4. The method of claim 1, wherein the cell is not cultured and maintained in the presence of a JNK inhibitor.

5. The method of claim 1, wherein the more naïve state cell exhibits OCT4 distal enhancer activity when compared to before the pluripotent stem cell is cultured in the medium.

6. The method of claim 1, wherein the more naïve state cell upregulates TFCP2L1, REX1, and STELLA when compared to before the pluripotent stem cell is cultured in the medium.

7. The method of claim 1, wherein the more naïve state cell downregulates OTX2 and ZIC2/3 when compared to before the pluripotent stem cell is cultured in the medium.

* * * * *

SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
gcagaaggcc tcagcaccta                                              20

<210> SEQ ID NO 2
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 2
aggttcccag tcgggttca                                               19

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

```
<400> SEQUENCE: 3
gctcgagaag gatgtggtcc                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4
cgttgtgcat agtcgctgct                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
cactgcccct ctcacacatg                                              20

<210> SEQ ID NO 6
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 6
tcccatttcc ctcgtttttc t                                            21

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
gttactgggc ggagttcgta                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8
tgaagtggct tggtgtcttg                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9
gatggggtct gtgactggat                                              20

<210> SEQ ID NO 10
```

```
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
cccccaactc acggatataa                                                    20

<210> SEQ ID NO 11
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 11
cgagatccct ccaaaatcaa                                                    20

<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 12
atccacagtc ttctgggtgg                                                    20

<210> SEQ ID NO 13
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 13
ggaatgtggg aaagcgttcg t                                                  21

<210> SEQ ID NO 14
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 14
ccgtgtggat gcgcacgt                                                      18

<210> SEQ ID NO 15
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 15
tgagccttca ggtcacagag                                                    20

<210> SEQ ID NO 16
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 16
```

```
atttcctatc gcccttgtcc                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 17
agaacggcat caaggtgaac                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 18
tgctcaggta gtggttgtcg                                               20

<210> SEQ ID NO 19
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 19
gattttgctg ggttggtttt t                                             21

<210> SEQ ID NO 20
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 20
ccacatagcg taaaaggagc a                                             21

<210> SEQ ID NO 21
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 21
gctggggaag gccttaatgt                                               20

<210> SEQ ID NO 22
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 22
ccacatagcg taaaaggagc a                                             21

<210> SEQ ID NO 23
<211> LENGTH: 20
<212> TYPE: DNA
```

```
<213> ORGANISM: Artificial Sequence
<220> FEATURE:
<223> OTHER INFORMATION: Synthetic Polynucleotide

<400> SEQUENCE: 23
ctttgcttgg gaaatccgag                                         20

<210> SEQ ID NO 24
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 24
agccaggttg cgaagaactc                                         20
```